(12) United States Patent
Altman et al.

(10) Patent No.: US 11,660,372 B2
(45) Date of Patent: *May 30, 2023

(54) SILK-HYALURONIC ACID BASED TISSUE FILLERS AND METHODS OF USING THE SAME

(71) Applicant: EVOLVED BY NATURE, INC., Medford, MA (US)

(72) Inventors: Gregory H. Altman, Providence, RI (US); Peng Xu, Lexington, MA (US); Erlei Jin, Peabody, MA (US)

(73) Assignee: EVOLVED BY NATURE, INC., Medford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/592,312

(22) Filed: Feb. 3, 2022

(65) Prior Publication Data
US 2022/0193304 A1    Jun. 23, 2022

Related U.S. Application Data

(63) Continuation of application No. 16/626,081, filed as application No. PCT/US2018/039574 on Jun. 26, 2018.

(60) Provisional application No. 62/641,095, filed on Mar. 9, 2018, provisional application No. 62/525,131, filed on Jun. 26, 2017.

(51) Int. Cl.
*A61L 27/26* (2006.01)
*A61L 27/52* (2006.01)

(52) U.S. Cl.
CPC .............. *A61L 27/26* (2013.01); *A61L 27/52* (2013.01); *A61L 2300/402* (2013.01); *A61L 2400/06* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 6,630,457 B1 | 10/2003 | Aeschlimann et al. | |
| 8,357,795 B2 | 1/2013 | Lebreton | |
| 9,187,538 B2* | 11/2015 | Altman | A61K 8/735 |
| 9,511,012 B2* | 12/2016 | Altman | A61K 8/042 |
| 9,517,191 B2* | 12/2016 | Altman | A61K 8/987 |
| 9,522,107 B2* | 12/2016 | Altman | A61K 8/922 |
| 9,522,108 B2* | 12/2016 | Altman | A61K 8/64 |
| 9,545,369 B2* | 1/2017 | Altman | A45D 33/00 |
| 10,154,951 B2 | 12/2018 | Pavlovic et al. | |
| 10,166,177 B2 | 1/2019 | Altman et al. | |
| 10,588,843 B2* | 3/2020 | Altman | A61K 8/9794 |
| 10,610,478 B2* | 4/2020 | Altman | A61K 8/922 |
| 10,987,294 B2* | 4/2021 | Altman | A45D 33/00 |
| 2004/0170590 A1 | 9/2004 | Fahnestock et al. | |
| 2004/0191199 A1 | 9/2004 | Mougin | |
| 2004/0219630 A1 | 11/2004 | Tsubouchi | |
| 2004/0265260 A1 | 12/2004 | Tsubouchi et al. | |
| 2009/0036403 A1 | 2/2009 | Stroumpoulis et al. | |
| 2010/0028438 A1 | 2/2010 | Lebreton | |
| 2010/0215957 A1 | 8/2010 | Tajima | |
| 2011/0129531 A1 | 6/2011 | Collette et al. | |
| 2011/0189292 A1 | 8/2011 | Lebreton et al. | |
| 2012/0004673 A1 | 1/2012 | Noishiki | |
| 2012/0301441 A1 | 11/2012 | Karperien et al. | |
| 2014/0023688 A1 | 1/2014 | Budijono et al. | |
| 2014/0235554 A1 | 8/2014 | Lawrence et al. | |
| 2014/0314817 A1* | 10/2014 | Leisk | A61L 27/56 424/93.1 |
| 2014/0315828 A1 | 10/2014 | Pavlovic et al. | |
| 2015/0064147 A1 | 3/2015 | Pollock et al. | |
| 2015/0079012 A1 | 3/2015 | Bellas et al. | |
| 2015/0093340 A1 | 4/2015 | Altman et al. | |
| 2015/0094269 A1 | 4/2015 | Altman et al. | |
| 2016/0022559 A1 | 1/2016 | Altman et al. | |
| 2016/0193106 A1 | 7/2016 | Wagner et al. | |
| 2016/0193293 A1 | 7/2016 | Nishi et al. | |
| 2016/0263228 A1 | 9/2016 | Kluge et al. | |
| 2017/0136145 A1 | 5/2017 | Liu et al. | |
| 2018/0008522 A1 | 1/2018 | Altman et al. | |
| 2018/0055971 A1 | 3/2018 | Yu et al. | |
| 2018/0272030 A1 | 9/2018 | Brown | |
| 2018/0280274 A1 | 10/2018 | Altman et al. | |
| 2019/0070088 A1 | 3/2019 | Altman et al. | |
| 2020/0147262 A1 | 5/2020 | Wei et al. | |
| 2020/0188268 A1 | 6/2020 | Altman et al. | |
| 2020/0188269 A1 | 6/2020 | Altman et al. | |

FOREIGN PATENT DOCUMENTS

| | | |
|---|---|---|
| CN | 102170855 A | 8/2011 |
| CN | 102836465 A | 12/2012 |
| CN | 102850468 A | 1/2013 |
| CN | 104105474 A | 10/2014 |
| CN | 104998302 A | 10/2015 |
| CN | 106492279 A | 3/2017 |
| CN | 107619481 A | 1/2018 |
| CN | 107880282 A | 4/2018 |
| CN | 111263646 A | 6/2020 |
| JP | 2014515307 A | 6/2014 |
| SG | 11201913229 P | 1/2019 |
| WO | 2004067575 A1 | 8/2004 |
| WO | 2010015901 A1 | 2/2010 |
| WO | 2012167079 A2 | 12/2012 |
| WO | 2013040242 A2 | 3/2013 |
| WO | 2013159101 A1 | 10/2013 |
| WO | 2014055895 A1 | 4/2014 |
| WO | 2014176158 A1 | 10/2014 |
| WO | 2014189780 A2 | 11/2014 |
| WO | 2016176633 A1 | 11/2016 |

(Continued)

OTHER PUBLICATIONS

Motta et al. "Stabilization of Bombyx mori silk fibroin/sericin films by crosslinknig with PEG-DE 600 and genipin" J. Bioactive and Compatible Polymers 26:130-143. (Year: 2011).*

(Continued)

*Primary Examiner* — Sudhakar Katakam
*Assistant Examiner* — Zachary J Miknis
(74) *Attorney, Agent, or Firm* — Morgan, Lewis & Bockius LLP

(57) ABSTRACT

Hyaluronic acid and silk protein fragments based tissue fillers and methods of using the same are provided herein.

14 Claims, 55 Drawing Sheets

(56) References Cited

FOREIGN PATENT DOCUMENTS

| WO | 2016180904 A1 | 11/2016 |
|---|---|---|
| WO | 2018039496 A1 | 3/2018 |
| WO | 2018121510 A1 | 7/2018 |
| WO | 2019005848 A1 | 1/2019 |
| WO | 2020132331 A1 | 6/2020 |

OTHER PUBLICATIONS

Extended European Search Report for European Patent Application No. 18823073, dated Mar. 15, 2021.
Office Action for Chinese Patent Application No. 201880055268.1, dated Oct. 19, 2021 (with translation).
Office Action for Israeli Patent Application No. 271692, dated Nov. 4, 2021 (with translation).
Written Opinion and Search Report for Singapore Patent Application No. 11201913229P, dated May 31, 2021.
International Search Report and Written Opinion for International Patent Application No. PCT/US2018/039574, dated Sep. 7, 2018.
International Search Report and Written Opinion for International Patent Application No. PCT/US2019/067617, dated Feb. 20, 2020.
Ballin et al., "Long-term efficacy, safety and durability of Juvéderm® XC," Clinical, Cosmetic and Investigational Dermatology, Aug. 2, 2013, vol. 6, pp. 183-189.
Smith et al., "Hyaluronic acid dermal fillers: can adjunctive lidocaine improve patient satisfaction without decreasing efficacy or duration?" Patient Preference and Adherence, Mar. 14, 2011, vol. 5, pp. 133-139.
Office Action for Eurasian Patent Application No. 202090145, dated Oct. 20, 2021 (with translation).
Extended European Search Report for European Application No. 19901148.7 dated Sep. 16, 2022, 7 pages.
First substantive examination for related Colombian Application NC2020-0000774 (Office Action 10848), dated Jul. 11, 2022, 7 pages.
Search Report for related Brazilian Application No. BR112019027687-4 dated May 9, 2002, 4 pages.
Second Office Action for related Chinese Application No. 201880055268.1 dated Jun. 23, 2022, 12 pages.
Official Action for related Ukrainian Application No. a202000401 dated May 10, 2022, 4 pages.
Notice of Reasons for Rejection for related Japanese Application No. JP 2020-520437 dated Jul. 26, 2022, 4 pages.
Official Action for related Eurasian Application No. 202090145, dated Jul. 29, 2022, 2 pages.
Office Action for Chinese Patent Application No. 201880055268.1 (Based on PCT/US2018/039574) dated Dec. 2, 2022.
Gu Qisheng, Alginate Based Biomedical Materials and Clinical Medicine, p. 219, Shanghai: Shanghai Scientific & Technical Publishers, Apr. 2015.
Office Action and Search Report for Chinese Patent Application No. 201980092428.4 (Based on PCT/US2019/067617) dated Dec. 29, 2022.
Technical Report and Written Opinion for Brazilian Patent Application No. BR 11 2019 027687-4 (Based on PCT/US2018/039574) dated Dec. 23, 2022.
Search Report and Written Opinion for Singapore Patent Application No. 11202106411Q (Based on PCT/US2019/067617) dated Jan. 4, 2023.
Office Action for Eurasian Patent Application No. 202191718 (Based on PCT/US2019/067617) dated Nov. 17, 2022.
Office Action for Colombian Patent Application No. NC2020/0000774 dated Jan. 31, 2023.
Technical Examination Report for Brazilian Patent Application No. BR 12 2022 016694-6 dated Feb. 10, 2023 (English).
Extended Search Report for European Patent Application No. 22197284.7 dated Mar. 7, 2023.
First Examination Report for Indian Patent Application No. 202017003291 dated Mar. 3, 2023.
Foss et al. "Silk Fibroin/Hyaluronic Acid 3D Matrices for Cartilage Tissue Engineering." Biomacromolecules 14.1 (2013): 38-47.
Lee et al. (2016). "Hyaluronic acid hydrogels cross-linked by polyethylene glycol diglycidyl ether (PEGDE) for long-lasting dermal filler applications." Front. Bioeng. Biotechnol. Conference Abstract: 10th World Biomaterials Congress.
Samal et al. "Ultrasound Sonication Effects on Silk Fibroin Protein." Macromolecular Journals (2013).
Tavsanli et al. "Preparation and fracture process of high strength hyaluronic acid hydrogels cross-linked by ethylene glycol diglycidyl ether", Reactive and Functional Polymers, vol. 109, (2016) pp. 42-51.
Zhang, Qiang, et al. "Silk fibroin/hyaluronic acid porous scaffold for dermal wound healing." Fibers and Polymers 18 (2017): 1056-1063.

* cited by examiner

Lithium Bromide and Sodium Carbonate Concentration in Silk Protein Solution

| Sample ID | Sample Description | Average Concentration of $Na_2CO_3$ (ppm) | Average Concentration of LiBr (ppm) |
|---|---|---|---|
| A | TFF 5kDa | 32.13 | 90.85 |
| B | TFF 10 kDa | 42.91 | 107 |
| C | TFF 10 kDa | 49.06 | 78.55 |
| D | STI 1(TFF-10-0019) | 2.17 | 129.07 |
| E | STI 2(TFF-10-0033) | 2.63 | 196.2 |
| F | STI 3(TFF-10-0034) | 4.18 | 248.93 |

Method: 100C extraction for 60 min, 60C rinse, 100C LiBr in 100 °C oven for 60 min. Note that TFF could be run for longer and/or at different flow rates (as varied between A-C and D-F) to alter ppm of $Na_2CO_3$ and LiBr.

FIG. 3

Lithium Bromide and Sodium Carbonate content in Silk Protein Solution

| Sample ID | Solution Volume Equivalent to (X) Films | Sample Weight (mg) | Concentration | |
|---|---|---|---|---|
| | | | Na2CO3 | LiBr |
| 1 | 6 | 0.171 | ND | ND |
| 2 | 8 | 0.228 | ND | ND |
| 3 | 10 | 0.285 | ND | ND |
| 4 | 12 | 0.342 | ND | ND |
| 5 | Neat | - | ND | ND |

*ND=None Detected

Method: 100 °C boil for 60 min, 60C rinse, LiBr in 60 °C oven for 4-6 hours

FIG. 4

Molecular Weights of Silk Protein Solutions

| Sample ID | Sample Description | Mn | Mw | Polydispersity (PD) (Mw/Mn) |
|---|---|---|---|---|
| A | TFF 5kDa | 14,497 | 33,874 | 2.3366 |
| B | TFF 10 kDa | 14,542 | 33,455 | 2.3006 |
| C | TFF 10 kDa | 14,972 | 34,026 | 2.2726 |
| D | Silk protein solution in water | 12,055 | 26,531 | 2.2008 |

Method:
TFF: 100 °C extraction for 60 min, 60 °C rinse, 100 °C LiBr in 100 °C oven for 60 min.
Silk Protein: 100 °C extraction for 20 min, RT rinse, LiBr in 60 °C oven for 4-6 hours

FIG. 5

| Sample | LiBr (M) | Avg MW | PD |
|---|---|---|---|
| STI 1(TFF-10-0019) | 9.3 | 15727 | 2.033 |
| STI 2(TFF-10-0033) | 9.3 | 24587 | 2.3669 |
| STI 3(TFF-10-0034) | 9.3 | 25273 | 2.338 |
| STI 9.3 M avg | | 21862 | 2.25 |
| STI 1(TFF-10-0031) | ~7.5 | 29645 | 3.0868 |
| STI 2(TFF-10-0030) | ~7.5 | 26856 | 2.9748 |
| STI 7.5M avg | | 28250.5 | 3.0308 |

* TFF-10-0019 from 2.25 g extraction / 35 g dissolution

* TFF-10-0034 from 100 g extraction / 17-35 g dissolution

* TFF-10-0033 from 100 g extraction / 100 g dissolution

FIG. 8

SILK-HYALURONIC ACID BASED TISSUE FILLERS AND METHODS OF USING THE SAME

CROSS-REFERENCE TO RELATED APPLICATIONS

This application is a Continuation of U.S. patent application Ser. No. 16/626,081, filed Dec. 23, 2019, which is a U.S. National Phase Application under 35 U.S.C. § 371 of International Application PCT/US18/39574, filed Jun. 26, 2018, which claims the benefit of U.S. Provisional Patent Applications Nos. 62/525,131, filed on Jun. 26, 2017, and 62/641,095, filed on Mar. 9, 2018, which are incorporated by reference herein in their entireties.

BACKGROUND OF THE INVENTION

Silk is a natural polymer produced by a variety of insects and spiders. Silk comprises a filament core protein, silk fibroin, and a glue-like coating consisting of a non-filamentous protein, sericin. Silk has been historically studied for use in the medical field. Hyaluronic acid (hyaluronan) is a glycosaminoglycan that is distributed throughout the body and is found in connective and epithelial tissues. Due to its biocompatibility and structural benefits, it is a useful component in medical devices and implantable materials.

Soft tissues of the human body owe their structures in part to an extracellular matrix that includes collagen, elastin, and glycosaminoglycan. Soft tissue defects may occur, which distort, deform, or otherwise alters soft tissue structures. Such structure may be restored through the use of tissue fillers that may be deposited at the defect site remedy the defect. For example, tissue fillers may be placed at the site of a facial wrinkle to remedy the wrinkle.

However, new tissue fillers are needed in the field that remedy a number of tissue defects while providing tunable properties, which may allow for tailoring of the tissue filler to the specific tissue defect.

SUMMARY OF THE INVENTION

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum: and an active agent selected from the group consisting of an enzyme inhibitor, an anesthetic agent, a medicinal neurotoxin, an antioxidant, an anti-infective agent, an anti-inflammatory agent, an ultraviolet (UV) light blocking agent, a dye, a hormone, an immunosuppressant, and an anti-inflammatory agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent. In some embodiments, the glycosaminoglycan is hyaluronic acid (HA). In some embodiments, the % w/w amount of cross-linked HA relative to the total amount of HA is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of cross-linking of the cross-linked HA is between about 1% and about 100%. In some embodiments, the degree of cross-linking of the cross-linked HA is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of cross-linking of the cross-linked HA is between about 1% and about 15%. In some embodiments, the degree of cross-linking of the cross-linked HA is one or more of about 1%, about 2%, about 3%, about 4%, about 5%, about 6%, about 7%, about 8%, about 9%, about 10%, about 11%, about 12%, about 13%, about 14%, and about 15%.

In some embodiments, the cross-linked HA comprises a cross-linking moiety comprising a polyethylene glycol (PEG) chain. In some embodiments, the cross-linking agent and/or the cross-linking precursor comprises an epoxy group. In some embodiments, cross-linking is obtained using a cross-linking agent, a cross-linking precursor, or an activating agent selected from the group consisting of a polyepoxy linker, a diepoxy linker, a polyepoxy-PEG, a diepoxy-PEG, a polyglycidyl-PEG, a diglycidyl-PEG, a poly acrylate PEG, a diacrylate PEG, 1,4-bis(2,3-epoxypropoxy)butane, 1,4-bisglycidyloxybutane, divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMIDA), 1-(2,3-epoxypropyl)-2,3-epoxycyclohexane, a carbodiimide, and any combinations thereof. In some embodiments, cross-linking is obtained using a polyfunctional epoxy compound selected from the group consisting of 1,4-butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylolpropane polyglycidyl ether, pentaerythritol polyglycidyl ether, and sorbitol polyglycidyl ether. In some embodiments, cross-linking is obtained using a cross-linking agent and/or a cross-linking precursor selected from the group consisting of polyethylene glycol diglycidyl ether, diepoxy PEG, PEG diglycidyl ether, polyoxyethylene bis-glycidyl ether, PEGDE, and PEGDGE. In some embodiments, cross-linking is obtained using polyethylene glycol diglycidyl ether having an average $M_n$ of about 500, about 1000, about 2000, or about 6000. In some embodiments, cross-linking is obtained using polyethylene glycol diglycidyl ether having from 2 to 25 ethylene glycol groups. In some embodiments, cross-linking is obtained using a cross-linking agent and/or a cross-linking precursor selected from the group consisting of a polyepoxy silk fibroin linker, a diepoxy silk fibroin linker, a polyepoxy silk fibroin fragment linker, a diepoxy silk fibroin fragment linker, a polyglycidyl silk fibroin linker, a diglycidyl silk fibroin linker, a polyglycidyl silk fibroin fragment linker, and a diglycidyl silk fibroin fragment linker.

In some embodiments, the invention relates to a tissue filler further comprising an organic compound and/or an inorganic compound. In some embodiments, the inorganic compound comprises calcium hydroxyapatite. In some embodiments, the calcium hydroxyapatite is formulated as particles having a diameter between about 1 µm and about 100 µm, between about 1 µm and about 10 µm, between about 2 µm and about 12 µm, between about 3 µm and about 10 µm, between about 4 µm and about 15 µm, between about 8 µm and about 12 µm, between about 5 µm and about 10 µm, between about 6 µm and about 12 µm, between about 7 µm and about 20 µm, between about 9 µm and about 18 µm, or between about 10 µm and about 25 µm. In some embodiments, the concentration of calcium hydroxyapatite is between about 0.001% and about 5%. In some embodiments, the concentration of calcium hydroxyapatite is about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, or about 0.02%. In some embodiments, the concentration of calcium hydroxyapatite is about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, or about 2%. In some embodiments, the organic compound comprises an amino acid selected from the group consisting of glycine, L-proline, alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine.

In some embodiments, the invention relates to a tissue filler comprising HA, wherein the HA is obtained from *Streptococcus* bacteria, or from *Bacillus subtilis* bacteria.

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent. In some embodiments, the anesthetic agent is lidocaine. In some embodiments, the concentration of anesthetic agent in the tissue filler is from about 0.001% to about 5%. In some embodiments, the concentration of lidocaine in the tissue filler is about 0.3%.

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent; wherein the tissue filler is a gel. In some embodiments, the tissue filler is a hydrogel. In some embodiments, the tissue filler further comprises water. In some embodiments, the total concentration of HA in the tissue filler is from about 10 mg/mL to about 50 mg/mL. In some embodiments, the total concentration of HA in the tissue filler is about 15 mg/mL, about 16 mg/mL, 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In some embodiments, the concentration of cross linked HA in the tissue filler is from about 10 mg/mL to about 50 mg/mL. In some embodiments, the concentration of cross linked HA in the tissue filler is about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL.

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent; the tissue filler comprising silk protein or silk protein fragments (SPF). In some embodiments, the silk protein is silk fibroin. In some embodiments, the silk protein is silk fibroin substantially devoid of sericin. In some embodiments, the SPF have an average weight average molecular weight ranging from about 1 kDa to about 250 kDa. In some embodiments, the SPF have an average weight average molecular weight ranging from about 5 kDa to about 150 kDa. In some embodiments, the SPF have an average weight average molecular weight ranging from about 6 kDa to about 17 kDa. In some embodiments, the SPF have an average weight average molecular weight ranging from about 17 kDa to about 39 kDa. In some embodiments, the SPF have an average weight average molecular weight ranging from about 39 kDa to about 80 kDa. In some embodiments, the SPF have low molecular weight. In some embodiments, the SPF have medium molecular weight. In some embodiments, the SPF have high molecular weight. In some embodiments, the silk protein fragments (SPF) have a polydispersity of between about 1.5 and about 3.0. In some embodiments, the SPF have a degree of crystallinity of up to 60%. In some embodiments, a portion of the SPF are cross-linked. In some embodiments, the % w/w amount of cross-linked SPF relative to the total amount of SPF is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 400%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of cross-linking of the cross-linked SPF is between about 1% and about 100%. In some embodiments, the degree of cross-linking of the cross-linked SPF is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of cross-linking of the cross-linked SPF is between about 1% and about 15%. In some embodiments, the degree of cross-linking of the cross-linked SPF is one or more of about 1%, about 2%, about 3%, about 4%, about 5%, about 6%, about 7%, about 8%, about 9%, about 10%, about 11%, about 12%, about 13%, about 14%, and about 15%.

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent; the tissue filler comprising silk protein or silk protein fragments (SPF), wherein a portion of the SPF are cross-linked. In some embodiments, the cross-linked SPF comprises a cross-linking moiety comprising an alkane or alkyl chain, and/or an ether group. In some embodiments, the cross-linked SPF comprises a cross-linking moiety comprising a polyethylene glycol (PEG) chain. In some embodiments, the cross-linked SPF comprises a cross-linking moiety comprising a secondary alcohol. In some embodiments, cross-linking is obtained using a cross-linking agent, a cross-linking precursor, or an activating agent. In some embodiments, the cross-linking agent and/or the cross-linking precursor comprises an epoxy group. In some embodiments, cross-linking is obtained using a cross-linking agent, a cross-linking precursor, or an activating agent selected from the group consisting of a polyepoxy linker, a diepoxy linker, a polyepoxy-PEG, a diepoxy-PEG, a polyglycidyl-PEG, a diglycidyl-PEG, a poly acrylate PEG, a diacrylate PEG, 1,4-bis(2,3-epoxypropoxy)butane, 1,4-bisglycidyloxybutane, divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, a carbodiimide, and any combinations thereof. In some embodiments, cross-linking is obtained using a polyfunctional epoxy compound selected from the group consisting of 1,4-butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylolpropane polyglycidyl ether, pentaerythritol polyglycidyl ether, and sorbitol polyglycidyl ether. In some embodiments, cross-linking is obtained using a cross-linking agent and/or a cross-linking precursor selected from the group consisting of polyethylene glycol diglycidyl ether, diepoxy PEG, PEG diglycidyl ether, polyoxyethylene bis-glycidyl ether, PEGDE, and PEGDGE. In some embodiments, cross-linking is obtained using polyethylene glycol diglycidyl ether having an average $M_n$ of about 500, about 1000, about 2000, or about 6000. In some embodiments, cross-linking is obtained using polyethylene glycol diglycidyl ether having from 2 to 25 ethylene glycol groups. In some embodiments, cross-linking is obtained using a cross-linking agent and/or a cross-linking precursor selected from the group consisting of a polyepoxy silk fibroin linker, a diepoxy silk fibroin linker, a polyepoxy silk fibroin fragment linker, a diepoxy silk fibroin fragment linker, a polyglycidyl silk fibroin linker, a diglycidyl silk fibroin linker, a polyglycidyl silk fibroin fragment linker, and a diglycidyl silk fibroin fragment linker. In some embodiments, a portion of SPF is cross linked to HA. In some embodiments, a portion of the SPF are cross-linked to SPF. In some embodiments, the tissue filler is a gel. In some embodiments, the tissue filler is a hydrogel. In some embodiments, the tissue filler further comprises water. In some embodiments, the total concentration of SPF in the tissue filler is from about 0.1 mg/mL to about 15 mg/mL. In some embodiments, the total concentration of SPF in the tissue filler is about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, or about 15 mg/mL. In some embodiments, the concentration of cross linked SPF in the tissue filler is from about 0.1 mg/mL to about 15 mg/mL. In some embodiments, the concentration of cross linked SPF in the tissue filler is about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, or about 15 mg/mL.

In one embodiment, the invention relates to a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent; the tissue filler optionally comprising silk protein or silk protein fragments (SPF), wherein a portion of the SPF are cross-linked. In some embodiments, the tissue filler is a dermal filler. In some embodiments, the tissue filler is biodegradable. In some embodiments, the tissue filler is injectable. In some embodiments, the tissue filler has a storage modulus (G') of from about 25 Pa to about 1500 Pa. In some embodiments, the tissue filler has a storage modulus (G') of about 25 Pa, about 26 Pa, about 27 Pa, about 28 Pa, about 29 Pa, about 30 Pa, about 31 Pa, about 32 Pa, about 33 Pa, about 34 Pa, about 35 Pa, about 36 Pa, about 37 Pa, about 38 Pa, about 39 Pa, about 40 Pa, about 41 Pa, about 42 Pa, about 43 Pa, about 44 Pa, about 45 Pa, about 46 Pa, about 47 Pa, about 48 Pa, about 49 Pa, about 50 Pa, about 51 Pa, about 52 Pa, about 53 Pa, about 54 Pa, about 55 Pa, about 56 Pa, about 57 Pa, about 58 Pa, about 59 Pa, about 60 Pa, about 61 Pa, about 62 Pa, about 63 Pa, about 64 Pa, about 65 Pa, about 66 Pa, about 67 Pa, about 68 Pa, about 69 Pa, about 70 Pa, about 71 Pa, about 72 Pa, about 73 Pa, about 74 Pa, about 75 Pa, about 76 Pa, about 77 Pa, about 78 Pa, about 79 Pa, about 80 Pa, about 81 Pa, about 82 Pa, about 83 Pa, about 84 Pa, about 85 Pa, about 86 Pa, about 87 Pa, about 88 Pa, about 89 Pa, about 90 Pa, about 91 Pa, about 92 Pa, about 93 Pa, about 94 Pa, about 95 Pa, about 96 Pa, about 97 Pa, about 98 Pa, about 99 Pa, about 100 Pa, about 101 Pa, about 102 Pa, about 103 Pa, about 104 Pa, about 105 Pa, about 106 Pa, about 107 Pa, about 108 Pa, about 109 Pa, about 110 Pa, about 111 Pa, about 112 Pa, about 113 Pa, about 114 Pa, about 115 Pa, about 116 Pa, about 117 Pa, about 118 Pa, about 119 Pa, about 120 Pa, about 121 Pa, about 122 Pa, about 123 Pa, about 124 Pa, or about 125 Pa. In some embodiments, herein G' is measured by means of an oscillatory stress of about 0.1 to about 10 Hz. In some embodiments, G' is measured by means of an oscillatory stress of about 1 Hz. In some embodiments, G' is measured by means of an oscillatory stress of about 5 Hz. In some embodiments, G' is measured by means of an oscillatory stress of about 10 Hz. In some embodiments, the tissue filler has a complex viscosity from about 1 Pa·s to about 10 Pa·s. In some embodiments, the tissue filler has a complex viscosity of about 1 Pa·s, about 1.5 Pa·s, about 2 Pa·s, about 2.5 Pa·s, about 3 Pa·s, about 3.5 Pa·s, about 4 Pa·s, about 4.5 Pa·s, about 5 Pa·s, about 5.5 Pa·s, about 6 Pa·s, about 6.5 Pa·s, about 7 Pa·s, about 7.5 Pa·s, about 8 Pa·s, about 8.5 Pa·s, about 9 Pa·s, about 9.5 Pa·s, or about 10 Pa·s. In some embodiments, the complex viscosity is measured by means of an oscillatory stress of about 0.1 to about 10 Hz. In some embodiments, the complex viscosity is measured by means of an oscillatory stress of about 1 Hz. In some embodiments, the complex viscosity is measured by means of an oscillatory stress of about 5 Hz.

In one embodiment, the invention relates to a method of treating a condition in a subject in need thereof, and/or a method of cosmetic treatment in a subject in need thereof, the method comprising administering to the subject a therapeutically effective amount of a biocompatible tissue filler comprising: a glycosaminoglycan selected from the group consisting of hyaluronic acid (HA), carboxymethyl cellulose (CMC), starch, alginate, chondroitin-4-sulfate, chondroitin-6-sulfate, xanthan gum, chitosan, pectin, agar, carrageenan, and guar gum; and an anesthetic agent; wherein a portion of the glycosaminoglycan is cross-linked by cross-linking moieties comprising one or more of an alkane or alkyl chain, an ether group, and a secondary alcohol; and wherein cross-linking is obtained using a cross-linking agent, a cross-linking precursor, or an activating agent; the tissue filler optionally comprising silk protein or silk protein fragments (SPF), wherein a portion of the SPF are cross-linked. In some embodiments, the condition is a skin condition. In some embodiments, the skin condition is selected from the group consisting of skin dehydration, lack of skin elasticity, skin roughness, lack of skin tautness, a skin stretch line, a skin stretch mark, skin paleness, a dermal divot, a sunken cheek, a thin lip, a retro-orbital defect, a facial fold, and a wrinkle. In some embodiments the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection. In some embodiments, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months. In some embodiments, administration of the tissue filler to the subject results in a reduced inflammatory response compared to the inflammatory response induced by a control tissue filler comprising a polysaccharide and lidocaine, wherein the control tissue filler does not include silk protein fragments (SPF). In some embodiments, administration of the tissue filler to the subject results in increased collagen production compared to the collagen production induced by a control tissue filler comprising a polysaccharide and lidocaine, wherein the control tissue filler does not include silk protein fragments (SPF).

In one embodiment, the invention relates to a biocompatible tissue filler including silk protein fragments (SPF) having a polydispersity of between about 1.5 and about 3.0, and a polysaccharide. In some embodiments, the polysaccharide is hyaluronic acid (HA). In an embodiment, the invention includes tissue fillers that may be prepared from silk and hyaluronic acid.

In some embodiments, the invention relates to a biocompatible tissue filler including silk protein fragments (SPF) with an average molecular weight ranging from about 1 kDa to about 250 kDa. In some embodiments, the invention relates to a biocompatible tissue filler including silk protein fragments (SPF) with an average molecular weight ranging from about 5 kDa to about 150 kDa. In some embodiments, the SPF have an average molecular weight ranging from about 6 kDa to about 17 kDa. In some embodiments, the SPF have an average molecular weight ranging from about 17 kDa to about 39 kDa. In some embodiments, the SPF have an average molecular weight ranging from about 39 kDa to about 80 kDa. In some embodiments, the SPF have an average molecular weight ranging from about 80 kDa to about 150 kDa.

In some embodiments, the invention relates to a biocompatible tissue filler including silk protein fragments (SPF) which are up to about 0% to 100% cross-linked with SPF. In some embodiments, the SPF were cross-linked to SPF using cross-linking agents such as BDDE, or one of the other cross-linking agents described herein. In some embodiments, the degree of cross-linking is up to about 100%.

In one embodiment, the invention relates to a biocompatible tissue filler including silk protein fragments (SPF) having a polydispersity of between about 1.5 and about 3.0, and hyaluronic acid (HA), wherein up to about 0% to 100% of the SPF are cross-linked to SPF, and the SPF were cross-linked to SPF using a cross-linking agent such as BDDE, or one of the other cross-linking agents described herein, and the SPF degree of cross-linking is up to about 100%.

In one embodiment, the invention relates to a biocompatible tissue filler including silk protein fragments (SPF) having a polydispersity of between about 1.5 and about 3.0, and hyaluronic acid (HA), wherein up to 100% of HA is cross-linked to HA using a cross-linking agent such as BDDE, or one of the other cross-linking agents described herein. In some embodiments, up to about 100% of the SPF are cross-linked to SPF, wherein the SPF were cross-linked to SPF using a cross-linking agent such as BDDE, or one of the other cross-linking agents described herein, and the SPF degree of cross-linking is up to about 100%.

In one embodiment, the invention relates to a biocompatible tissue filler including silk protein fragments (SPF) having a polydispersity of between about 1.5 and about 3.0, and hyaluronic acid (HA), wherein 0% to 100% of HA is non-cross-linked. In some embodiments, up to about 100% of the SPF are cross-linked, wherein the SPF were cross-linked using a cross-linking agent such as BDDE, or one of the other cross-linking agents described herein, and the SPF degree of cross-linking is up to about 100%. In some embodiments, all of the HA is non-cross-linked.

In one embodiment, the invention relates to a biocompatible tissue filler including silk protein fragments (SPF) having a polydispersity of between about 1.5 and about 3.0, and hyaluronic acid (HA), wherein 0% to 100% of SPF is cross-linked to HA. In some embodiments, the SPF and HA were cross-linked using a cross-linking agent such as BDDE, or one of the cross-linking agents described herein. In some embodiments, the degree of SPF-HA cross-linking is up to about 100%. In some embodiments, up to 100% of HA is cross-linked to HA. In some embodiments, HA was cross-linked to HA using a cross-linking agent such as BDDE, or one of the cross-linking agents described herein. In some embodiments, at least 0.1% of HA is non-cross-linked. In some embodiments, all of the HA is non-cross-linked.

In one embodiment, the invention relates to a biocompatible tissue filler including silk protein fragments (SPF) having a polydispersity of between about 1.5 and about 3.0, and hyaluronic acid (HA), wherein at least 0.1% of HA is non-cross-linked. In some embodiments, up to about 100% of the SPF are cross-linked, wherein the SPF were cross-linked using a cross-linking agent such as BDDE, or one of the other cross-linking agents described herein, and the SPF degree of cross-linking is up to about 100%. In some embodiments, all of the HA is non-cross-linked.

In one embodiment, the invention relates to a biocompatible tissue filler including silk protein fragments (SPF) having a polydispersity of between about 1.5 and about 3.0, and hyaluronic acid (HA), wherein at least 0.1% of SPF is cross-linked to HA. In some embodiments, the SPF and HA were cross-linked using a cross-linking agent such as BDDE, or one of the cross-linking agents described herein. In some embodiments, the degree of SPF-HA cross-linking is up to about 100%. In some embodiments, up to 100% of HA is cross-linked to HA. In some embodiments, HA was cross-linked to HA using a cross-linking agent such as BDDE, or one of the cross-linking agents described herein. In some embodiments, at least 0.1% of HA is non-cross-linked. In some embodiments, all of the HA is non-cross-linked.

In one embodiment, the invention relates to a biocompatible tissue filler including silk protein fragments (SPF) having a polydispersity of between about 1.5 and about 3.0, and a polysaccharide, wherein the SPF are substantially devoid of sericin.

In one embodiment, the invention relates to a biocompatible gel tissue filler including silk protein fragments (SPF) having a polydispersity of between about 1.5 and about 3.0, and a polysaccharide.

In one embodiment, the invention relates to a biocompatible hydrogel tissue filler including silk protein fragments (SPF) having a polydispersity of between about 1.5 and about 3.0, and a polysaccharide In one embodiment, the invention relates to a biocompatible tissue filler including silk protein fragments (SPF) having a polydispersity of between about 1.5 and about 3.0, a polysaccharide, and water.

In one embodiment, the invention relates to a biocompatible tissue filler including silk protein fragments (SPF) having a polydispersity of between about 1.5 and about 3.0, and a polysaccharide, wherein SPF have a degree of crystallinity of about 0% to about 60%.

In one embodiment, the invention relates to a biocompatible tissue filler including silk protein fragments (SPF) having a polydispersity of between about 1.5 and about 3.0, and a polysaccharide, and further including an active agent. In some embodiments, the active agent can be an enzyme inhibitor, an anesthetic agent, a medicinal neurotoxin, an antioxidant, an anti-infective agent, vasodilators, a reflective agent, an anti-inflammatory agent, an ultraviolet (UV) light blocking agent, a dye, a hormone, an immunosuppressant, or an anti-inflammatory agent. In one embodiment, the anesthetic agent is lidocaine.

In one embodiment, the invention relates to an injectable biocompatible tissue filler including silk protein fragments (SPF) having a polydispersity of between about 1.5 and about 3.0, and a polysaccharide.

In one embodiment, the invention relates to a biocompatible tissue filler including silk protein fragments (SPF) having a polydispersity of between about 1.5 and about 3.0, and a polysaccharide. In some embodiments, G' is measured by means of an oscillatory stress of about 0.1 to about 10 Hz. In one embodiment, G' is measured by means of an oscillatory stress of about 1 Hz.

In one embodiment, the invention relates to a method of making a biocompatible tissue filler including silk protein fragments (SPF) having a polydispersity of between about 1.5 and about 3.0, and a polysaccharide, the method including providing an SPF solution, and adding to the solution a gelation enhancer, which may be any proton donating species.

In one embodiment, the invention relates to a method of making a biocompatible tissue filler including silk protein fragments (SPF) having a polydispersity of between about 1.5 and about 3.0, and a polysaccharide, the method including providing an SPF solution, and subjecting the solution to mechanical excitation.

In one embodiment, the invention relates to a method of treating a condition in a subject in need thereof, the method including administering to the subject a therapeutically effective amount of a biocompatible tissue filler including silk protein fragments (SPF) having a polydispersity of between about 1.5 and about 3.0, and a polysaccharide. In some embodiments, the condition is a skin condition. In some embodiments, the skin condition can be skin dehydration, lack of skin elasticity, skin roughness, lack of skin tautness, a skin stretch line, a skin stretch mark, skin paleness, a dermal divot, a sunken cheek, sunken temple, a thin lip, a retro-orbital defect, a facial fold, or a wrinkle.

In one embodiment, the invention relates to a method of cosmetic treatment in a subject in need thereof, the method including administering to the subject an effective amount of a biocompatible tissue filler including silk protein fragments (SPF) having a polydispersity of between about 1.5 and about 3.0, and a polysaccharide.

In some embodiments, the methods of the invention include administering a biocompatible tissue filler including silk protein fragments (SPF) having a polydispersity of between about 1.5 and about 3.0, and a polysaccharide, into a dermal region of a subject.

In one embodiment, a method of the invention including administering a biocompatible tissue filler including silk protein fragments (SPF) having a polydispersity of between about 1.5 and about 3.0, and a polysaccharide, can be an augmentation, a reconstruction, treating a disease, treating a disorder, correcting a defect or imperfection of a body part, region or area.

In one embodiment, a method of the invention including administering a biocompatible tissue filler including silk protein fragments (SPF) having a polydispersity of between about 1.5 and about 3.0, and a polysaccharide, can be a facial augmentation, a facial reconstruction, treating a facial disease, treating a facial disorder, treating a facial defect, or treating a facial imperfection.

In one embodiment, a biocompatible tissue filler including silk protein fragments (SPF) having a polydispersity of between about 1.5 and about 3.0, and a polysaccharide, administered according to a method of the invention, resists biodegradation, bioabsorption, and/or bioresorption, for at least about 3 days after administration.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water.

In some embodiments, the % w/w amount of cross-linked SPF relative to the total amount of SPF is up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the degree of cross-linking of SPF is up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the % w/w amount of cross-linked HA relative to the total amount of HA is up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the degree of cross-linking of HA is up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, cross-linking is obtained using a cross-linking agent, a cross-linking precursor, or an activating agent. In some embodiments, the cross-linking agent and/or the crosslinking precursor comprise an epoxy group. In some embodiments, the SPF are substantially devoid of sericin.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, cross-linking is obtained using a cross-linking agent, a cross-linking precursor, or an activating agent. In some embodiments, the cross-linking agent and/or the cross-linking precursor comprise an epoxy group. In some embodiments, the SPF are substantially devoid of sericin.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, cross-linking is obtained using a cross-linking agent, a cross-linking precursor, or an activating agent selected from the group consisting of 1,4-bis(2,3-epoxypropoxy)butane, 1,4-bisglycidyloxybutane, divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, a carbodiimide, and any combinations thereof. In some embodiments, the SPF are substantially devoid of sericin.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, cross-linking is obtained using a cross-linking agent, a cross-linking precursor, or an activating agent selected from the group consisting of 1,4-bis(2,3-epoxypropoxy)butane, 1,4-bisglycidyloxybutane, divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, a carbodiimide, and any combinations thereof. In some embodiments, the SPF are substantially devoid of sericin.

In one embodiment, the invention relates to a biocompatible tissue filler gel, e.g., a dermal filler gel, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the gel further comprises water.

In one embodiment, the invention relates to a biocompatible tissue filler gel, e.g., a dermal filler gel, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the gel further comprises water.

In one embodiment, the invention relates to a biocompatible tissue filler hydrogel, e.g., a dermal filler hydrogel, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the hydrogel further comprises water.

In one embodiment, the invention relates to a biocompatible tissue filler hydrogel, e.g., a dermal filler hydrogel, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the hydrogel further comprises water.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF have a degree of crystallinity of up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, or more than 60%.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF have a degree of crystallinity of up to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, or more than 60%.

In one embodiment, the invention relates to a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of crosslinking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the tissue filler further comprises an active agent. In some embodiments, the active agent is selected from the group consisting of an enzyme inhibitor, an anesthetic agent, a medicinal neurotoxin, an antioxidant, an anti-infective agents, an anti-inflammatory agent, an ultraviolet (UV) light blocking agent, a dye, a hormone, an immunosuppressant, and an anti-inflammatory agent. In some embodiments, the anesthetic agent is lidocaine.

In one embodiment, the invention relates to a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the tissue filler further comprises an active agent. In some embodiments, the active agent is selected from the group consisting of an enzyme inhibitor, an anesthetic agent, a medicinal neurotoxin, an antioxidant, an anti-infective agent, an anti-inflammatory agent, an ultraviolet (UV) light blocking agent, a dye, a hormone, an immunosuppressant, and an anti-inflammatory agent. In some embodiments, the anesthetic agent is lidocaine.

In one embodiment, the invention relates to a biocompatible injectable tissue filler, e.g., an injectable dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA).

In one embodiment, the invention relates to a biocompatible injectable tissue filler, e.g., an injectable dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA).

In one embodiment, the invention relates to a biocompatible tissue filler having a storage modulus (G') of from about 50 Pa to about 1500 Pa, e.g., a dermal filler having a storage modulus (G') of from about 50 Pa to about 1500 Pa, the filler including silk protein fragments (SPF) having a polydispersity of between about 1.5 and about 3.0, and a polysaccharide, the SPF having an average weight average molecular weight ranging from about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, G' is measured by means of an oscillatory stress of about 0.1 to about 10 Hz. In some embodiments, G' is measured by means of an oscillatory stress of about 1 Hz.

In one embodiment, the invention relates to a biocompatible tissue filler having a storage modulus (G') of from about 50 Pa to about 1500 Pa, e.g., a dermal filler having a storage modulus (G') of from about 50 Pa to about 1500 Pa, the filler including silk protein fragments (SPF) having a polydispersity of between about 1.5 and about 3.0, and a polysaccharide, the SPF having low molecular weight, medium molecular weight, or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, cross-linking includes chemical bond cross-linking. In some embodiments, a portion of cross-linking is zero-length cross-linking. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, G' is measured by means of an oscillatory stress of about 0.1 to about 10 Hz. In some embodiments, G' is measured by means of an oscillatory stress of about 1 Hz.

In some embodiments, the invention relates to a method of making a biocompatible tissue filler. e.g., a dermal filler, including silk protein fragments (SPF) having a polydispersity of between about 1.5 and about 3.0, and a polysaccharide, the method including providing a composition comprising SPF and a polysaccharide, and adding to the solution a cross-linking agent, a cross-linking precursor, an activating agent, or a gelation enhancer, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, the tissue filler further comprises water.

In some embodiments, the invention relates to a method of making a biocompatible tissue filler, e.g., a dermal filler, including silk protein fragments (SPF) having a polydispersity of between about 1.5 and about 3.0, and a polysaccharide, the method including providing a composition comprising SPF and a polysaccharide, and adding to the solution a cross-linking agent, a cross-linking precursor, an activating agent, or a gelation enhancer, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water.

In some embodiments, the invention relates to a method of treating a condition in a subject in need thereof, e.g., a skin condition, the method comprising administering to the subject a therapeutically effective amount of a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water. In some embodiments, the skin condition is selected from the group consisting of skin dehydration, lack of skin elasticity, skin roughness, lack of skin tautness, a skin stretch line, a skin stretch mark, skin paleness, a dermal divot, a sunken cheek, a thin lip, a retro-orbital defect, a facial fold, and a wrinkle. In some embodiments, the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection. In some embodiments, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months.

In some embodiments, the invention relates to a method of treating a condition in a subject in need thereof, e.g., a skin condition, the method comprising administering to the subject a therapeutically effective amount of a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water. In some embodiments, the skin condition is selected from the group consisting of skin dehydration, lack of skin elasticity, skin roughness, lack of skin tautness, a skin stretch line, a skin stretch mark, skin paleness, a dermal divot, a sunken cheek, a thin lip, a retro-orbital defect, a facial fold, and a wrinkle. In some embodiments, the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection. In some embodiments, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months.

In some embodiments, the invention relates to a method of cosmetic treatment in a subject in need thereof, the method comprising administering to the subject an effective amount of a biocompatible tissue filler, e.g., a dermal filler, including silk protein fragments (SPF) having a polydispersity of between about 1.5 and about 3.0, and a polysaccharide, the SPF having an average weight average molecular weight ranging from about 1 kDa to about 250 kDa, about 5 kDa to about 150 kDa, from about 6 kDa to about 17 kDa, from about 17 kDa to about 39 kDa, or from about 39 kDa to about 80 kDa. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water. In some embodiments, the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection. In some embodiments, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months.

In some embodiments, the invention relates to a method of cosmetic treatment in a subject in need thereof, the method comprising administering to the subject an effective amount of a biocompatible tissue filler, e.g., a dermal filler, including silk protein fragments (SPF) having a polydispersity of between about 1.5 and about 3.0, and a polysaccharide, the SPF having low molecular weight, medium molecular weight, and/or high molecular weight. In some embodiments, the tissue filler is biodegradable. In some embodiments, a portion of SPF are cross-linked. In some embodiments, a portion of the SPF are cross-linked to polysaccharide. In some embodiments, a portion of the SPF are cross-linked to SPF. In some embodiments, a portion of the polysaccharide is cross-linked to polysaccharide. In some embodiments, the tissue filler further includes cross-linking moieties, e.g., epoxy derived cross-linking moieties. In some embodiments, a portion of cross-linking is auto-cross-linking. In some embodiments, the portion of cross-linked SPF is up to about 100%. In some embodiments, the portion of cross-linked polysaccharide is up to about 100%. In some embodiments, the polysaccharide is hyaluronic acid (HA). In some embodiments, the SPF are substantially devoid of sericin. In some embodiments, tissue filler further comprises water. In some embodiments, the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection. In some embodiments, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months.

In some embodiments, the invention relates to a biocompatible tissue filler, comprising hyaluronic acid (HA) and an anesthetic agent, wherein a portion of the HA is modified by one or more linker moieties comprising one or more of an alkane or alkyl chain, an ether group, and a secondary alcohol, wherein the linker moieties are attached to the HA at one end of the linker. In some embodiments, modification is obtained using a cross-linking agent, a cross-linking precursor, or an activating agent. In some embodiments, the HA in the tissue filler has a degree of modification (MoD) of about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14.7%, about 14.8%, about 14.9%, about 15.0%, about 15.1%, about 15.2%, about 15.3%, about 15.4%, about 15.5%, about 15.6%, about 15.7%, about 15.8%, about 15.9%, about 16.0%, about 16.1%, about 16.2%, about 16.3%, about 16.4%, about 16.5%, about 16.6%, about 16.7%, about 16.8%, about 16.9%, about 17.0%, about 17.1%, about 17.2%, about 17.3%, about 17.4%, about 17.5%, about 17.6%, about 17.7%, about 17.8%, about 17.9%, about 18.0%, about 18.1%, about 18.2%, about 18.3%, about 18.4%, about 18.5%, about 18.6%, about 18.7%, about 18.8%, about 18.9%, about 19.0%, about 19.1%, about 19.2%, about 19.3%, about 19.4%, about 19.5%, about 19.6%, about 19.7%, about 19.8%, about 19.9%, or about 20.0%. In some embodiments, the % w/w amount of modified HA relative to the total amount of HA in the tissue filler is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%.

In some embodiments, the modified HA includes cross-linked HA, wherein the degree of cross-linking of the cross-linked HA is between about 1% and about 100%. In some embodiments, the degree of cross-linking of the cross-linked HA is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of cross-linking of the cross-linked HA is between about 1% and about 15%.

In some embodiments, the modified or cross-linked HA comprises a linker or cross-linking moiety comprising a polyethylene glycol (PEG) chain. In some embodiments, the cross-linking agent and/or the cross-linking precursor comprises an epoxy group. In some embodiments, modification or cross-linking is obtained using a cross-linking agent, a cross-linking precursor, or an activating agent selected from the group consisting of a polyepoxy linker, a diepoxy linker, a polyepoxy-PEG, a diepoxy-PEG, a polyglycidyl-PEG, a diglycidyl-PEG, a poly acrylate PEG, a diacrylate PEG, 1,4-bis(2,3-epoxypropoxy)butane, 1,4-bisglycidyloxybutane, divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, a carbodiimide, and any combinations thereof. In some embodiments, modification or cross-linking is obtained using a polyfunctional epoxy compound selected from the group consisting of 1,4-butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylolpropane polyglycidyl ether, pentaerythritol polyglycidyl ether, and sorbitol polyglycidyl ether. In some embodiments, modification or cross-linking is obtained using a cross-linking agent and/or a cross-linking precursor selected from the group consisting of polyethylene glycol diglycidyl ether, diepoxy PEG, PEG diglycidyl ether, polyoxyethylene bis-glycidyl ether, PEGDE, and PEGDGE. In some embodiments, modification or cross-linking is obtained using polyethylene glycol diglycidyl ether having an average $M_n$ of about 500, about 1000, about 2000, or about 6000. In some embodiments, modification or cross-linking is obtained using polyethylene glycol diglycidyl ether having from about 2 to about 25 ethylene glycol groups. In some embodiments, modification or cross-linking is obtained using a cross-linking agent and/or a cross-linking precursor selected from the group consisting of a polyepoxy silk fibroin linker, a diepoxy silk fibroin linker, a polyepoxy silk fibroin fragment linker, a diepoxy silk fibroin fragment linker, a polyglycidyl silk fibroin linker, a diglycidyl silk fibroin linker, a polyglycidyl silk fibroin fragment linker, and a diglycidyl silk fibroin fragment linker.

In some embodiments, the tissue filler further includes an organic compound and/or an inorganic compound. In some embodiments, the inorganic compound comprises calcium hydroxyapatite. In some embodiments, the calcium hydroxyapatite is formulated as particles having a diameter between about 1 µm and about 100 µm, between about 1 µm and about 10 µm, between about 2 µm and about 12 µm, between about 3 µm and about 10 µm, between about 4 µm and about 15 µm, between about 8 µm and about 12 µm, between about 5 µm and about 10 µm, between about 6 µm and about 12 µm, between about 7 µm and about 20 µm, between about 9 µm and about 18 µm, or between about 10 µm and about µm. In some embodiments, the concentration of calcium hydroxyapatite is between about 0.001% and about 5%. In some embodiments, the concentration of calcium hydroxyapatite is about 0.001%, about 0.002%, about 0.003%, about 0.004%, about 0.005%, about 0.006%, about 0.007%, about 0.008%, about 0.009%, about 0.01%, about 0.011%, about 0.012%, about 0.013%, about 0.014%, about 0.015%, about 0.016%, about 0.017%, about 0.018%, about 0.019%, or about 0.02%. In some embodiments, the concentration of calcium hydroxyapatite is about 0.05%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, or about 2%. In some embodiments, the organic compound comprises an amino acid selected from the group consisting of glycine, L-proline, alanine, arginine, asparagine, aspartic acid, cysteine, glutamic acid, glutamine, histidine, isoleucine, leucine, lysine, methionine, phenylalanine, proline, serine, threonine, tryptophan, tyrosine, and valine.

In some embodiments, the HA is obtained from *Streptococcus* bacteria, or from *Bacillus subtilis* bacteria. In some embodiments, the active agent is lidocaine. In some embodiments, the concentration of active agent in the tissue filler is from about 0.001% to about 5%. In some embodiments, the concentration of lidocaine in the tissue filler is about 0.3%.

In some embodiments, the tissue filler disclosed herein is a gel. In some embodiments, the tissue filler is a hydrogel. In some embodiments, the tissue filler further comprises water. In some embodiments, the total concentration of HA in the tissue filler is from about 10 mg/mL to about 50 mg/mL. In some embodiments, the total concentration of HA in the tissue filler is about 15 mg/mL, about 16 mg/mL, 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL. In some embodiments, the concentration of modified or cross linked HA in the tissue filler is from about 10 mg/mL to about 50 mg/mL. In some embodiments, the concentration of modified or cross linked HA in the tissue filler is about 15 mg/mL, about 16 mg/mL, about 17 mg/mL, about 18 mg/mL, about 19 mg/mL, about 20 mg/mL, about 21 mg/mL, about 22 mg/mL, about 23 mg/mL, about 24 mg/mL, about 25 mg/mL, about 26 mg/mL, about 27 mg/mL, about 28 mg/mL, about 29 mg/mL, or about 30 mg/mL.

In some embodiments, the tissue filler disclosed further includes silk protein or silk protein fragments (SPF). In some embodiments, the silk protein is silk fibroin. In some embodiments, the silk protein is silk fibroin substantially devoid of sericin. In some embodiments, the SPF have an average weight average molecular weight ranging from about 1 kDa to about 250 kDa. In some embodiments, the SPF have an average weight average molecular weight ranging from about 5 kDa to about 150 kDa. In some embodiments, the SPF have an average weight average molecular weight ranging from about 6 kDa to about 17 kDa. In some embodiments, the SPF have an average weight average molecular weight ranging from about 17 kDa to about 39 kDa. In some embodiments, the SPF have an average weight average molecular weight ranging from about 39 kDa to about 80 kDa. In some embodiments, the SPF have low molecular weight. In some embodiments, the SPF have medium molecular weight. In some embodiments, the SPF have high molecular weight. In some embodiments, the silk protein fragments (SPF) have a polydispersity of between about 1.5 and about 3.0. In some embodiments, the SPF have a degree of crystallinity of up to 60%.

In some embodiments, the invention relates to a tissue filler including HA and SPF, wherein a portion of the SPF are modified or cross-linked. In some embodiments, the % w/w amount of modified or cross-linked SPF relative to the total amount of SPF is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of modification or cross-linking of the modified or cross-linked SPF is between about 1% and about 100%. In some embodiments, the degree of modification or cross-linking of the modified or cross-linked SPF is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the degree of modification or cross-linking of the modified or cross-linked SPF is between about 1% and about 15%. In some embodiments, the degree of modification or cross-linking of the modified or cross-linked SPF is one or more of about 1%, about 2%, about 3%, about 4%, about 5%, about 6%, about 7%, about 8%, about 9%, about 10%, about 11%, about 12%, about 13%, about 14%, and about 15%.

In some embodiments, the modified or cross-linked SPF comprises a linker or cross-linking moiety comprising an alkane or alkyl chain, and/or an ether group, wherein the linker or cross-linking moiety is attached to the SPF at one end of the linker or cross-linking moiety. In some embodiments, the modified or cross-linked SPF comprises a linker or cross-linking moiety comprising a polyethylene glycol (PEG) chain. In some embodiments, the modified or cross-linked SPF comprises a linker or cross-linking moiety comprising a secondary alcohol. In some embodiments, modification or cross-linking is obtained using a modification or cross-linking agent, a modification or cross-linking precursor, or an activating agent. In some embodiments, the modification or cross-linking agent and/or the modification or cross-linking precursor comprises an epoxy group. In some embodiments, modification or cross-linking is obtained using a modification or cross-linking agent, a modification or cross-linking precursor, or an activating agent selected from the group consisting of a polyepoxy linker, a diepoxy linker, a polyepoxy-PEG, a diepoxy-PEG, a polyglycidyl-PEG, a diglycidyl-PEG, a poly acrylate PEG, a diacrylate PEG, 1,4-bis(2,3-epoxypropoxy)butane, 1,4-bisglycidyloxybutane, divinyl sulfone (DVS), 1,4-butanediol diglycidyl ether (BDDE). UV light, glutaraldehyde, 1,2-bis(2,3-epoxypropoxy)ethylene (EGDGE), 1,2,7,8-diepoxyoctane (DEO), biscarbodiimide (BCDI), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, a carbodiimide, and any combinations thereof. In some embodiments, modification or cross-linking is obtained using a polyfunctional epoxy compound selected from the group consisting of 1,4-butanediol diglycidyl ether (BDDE), ethylene glycol diglycidyl ether (EGDGE), 1,6-hexanediol diglycidyl ether, polyethylene glycol diglycidyl ether, polypropylene glycol diglycidyl ether, polytetramethylene glycol diglycidyl ether, neopentyl glycol diglycidyl ether, polyglycerol polyglycidyl ether, diglycerol polyglycidyl ether, glycerol polyglycidyl ether, tri-methylolpropane polyglycidyl ether, pentaerythritol polyglycidyl ether, and sorbitol polyglycidyl ether.

In some embodiments, modification or cross-linking is obtained using a modification or cross-linking agent and/or a modification or cross-linking precursor selected from the group consisting of polyethylene glycol diglycidyl ether, diepoxy PEG, PEG diglycidyl ether, polyoxyethylene bis-glycidyl ether, PEGDE, and PEGDGE. In some embodiments, the modification or cross-linking is obtained using polyethylene glycol diglycidyl ether having an average $M_n$ of about 500, about 1000, about 2000, or about 6000. In some embodiments, modification or cross-linking is obtained using polyethylene glycol diglycidyl ether having from about 2 to about 25 ethylene glycol groups. In some embodiments, modification or cross-linking is obtained using a modification or cross-linking agent and/or a modification or cross-linking precursor selected from the group consisting of a polyepoxy silk fibroin linker, a diepoxy silk fibroin linker, a polyepoxy silk fibroin fragment linker, a diepoxy silk fibroin fragment linker, a polyglycidyl silk fibroin linker, a diglycidyl silk fibroin linker, a polyglycidyl silk fibroin fragment linker, and a diglycidyl silk fibroin fragment linker.

In some embodiments, the invention relates to a tissue filler including HA and SPF, wherein a portion of SPF is cross linked to HA. In some embodiments, the invention relates to a tissue filler including HA and SPF, wherein a portion of the SPF are cross-linked to SPF. In some embodiments, the tissue filler is a gel. In some embodiments, the tissue filler is a hydrogel. In some embodiments, the tissue filler further comprises water. In some embodiments, the total concentration of SPF in the tissue filler is from about 0.1 mg/mL to about 15 mg/mL. In some embodiments, the total concentration of SPF in the tissue filler is about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mg/mL, about 12 mg/mL, about 12.5 mg/mL, about 13 mg/mL, about 13.5 mg/mL, about 14 mg/mL, about 14.5 mg/mL, or about 15 mg/mL. In some embodiments, the concentration of modified or cross linked SPF in the tissue filler is from about 0.1 mg/mL to about 15 mg/mL. In some embodiments, the concentration of modified or cross linked SPF in the tissue filler is about 0.1 mg/mL, about 0.5 mg/mL, about 1 mg/mL, about 1.5 mg/mL, about 2 mg/mL, about 2.5 mg/mL, about 3 mg/mL, about 3.5 mg/mL, about 4 mg/mL, about 4.5 mg/mL, about 5 mg/mL, about 5.5 mg/mL, about 6 mg/mL, about 6.5 mg/mL, about 7 mg/mL, about 7.5 mg/mL, about 8 mg/mL, about 8.5 mg/mL, about 9 mg/mL, about 9.5 mg/mL, about 10 mg/mL, about 10.5 mg/mL, about 11 mg/mL, about 11.5 mng/mL, about 12 mg/mL, about 12.5 mg/mL, about 13 mg/mL, about 13.5 mg/mL, about 14 mg/mL, about 14.5 mg/mL, or about 15 mg/mL.

In some embodiments, the invention relates to a tissue filler including modified or cross-linked HA, and/or modified or cross-linked SPF, wherein the tissue filler is a dermal filler. In some embodiments, the tissue filler is biodegradable. In some embodiments, the tissue filler is injectable. In some embodiments, the tissue filler has a storage modulus (G) of from about 25 Pa to about 1500 Pa. In some embodiments, the tissue filler has a storage modulus (G') of about 25 Pa, about 26 Pa, about 27 Pa, about 28 Pa, about 29 Pa, about 30 Pa, about 31 Pa, about 32 Pa, about 33 Pa, about 34 Pa, about 35 Pa, about 36 Pa, about 37 Pa, about 38 Pa, about 39 Pa, about 40 Pa, about 41 Pa, about 42 Pa, about 43 Pa, about 44 Pa, about 45 Pa, about 46 Pa, about 47 Pa, about 48 Pa, about 49 Pa, about 50 Pa, about 51 Pa, about 52 Pa, about 53 Pa, about 54 Pa, about 55 Pa, about 56 Pa, about 57 Pa, about 58 Pa, about 59 Pa, about 60 Pa, about 61 Pa, about 62 Pa, about 63 Pa, about 64 Pa, about 65 Pa, about 66 Pa, about 67 Pa, about 68 Pa, about 69 Pa, about 70 Pa, about 71 Pa, about 72 Pa, about 73 Pa, about 74 Pa, about 75 Pa, about 76 Pa, about 77 Pa, about 78 Pa, about 79 Pa, about 80 Pa, about 81 Pa, about 82 Pa, about 83 Pa, about 84 Pa, about 85 Pa, about 86 Pa, about 87 Pa, about 88 Pa, about 89 Pa, about 90 Pa, about 91 Pa, about 92 Pa, about 93 Pa, about 94 Pa, about 95 Pa, about 96 Pa, about 97 Pa, about 98 Pa, about 99 Pa, about 100 Pa, about 101 Pa, about 102 Pa, about 103 Pa, about 104 Pa, about 105 Pa, about 106 Pa, about 107 Pa, about 108 Pa, about 109 Pa, about 110 Pa, about 111 Pa, about 112 Pa, about 113 Pa, about 114 Pa, about 115 Pa, about 116 Pa, about 117 Pa, about 118 Pa, about 119 Pa, about 120 Pa, about 121 Pa, about 122 Pa, about 123 Pa, about 124 Pa, or about 125 Pa.

In some embodiments, G' is measured by means of an oscillatory stress of about 0.1 to about 10 Hz. In some embodiments, G' is measured by means of an oscillatory stress of about 1 Hz. In some embodiments, G' is measured by means of an oscillatory stress of about 5 Hz. In some embodiments, G' is measured by means of an oscillatory stress of about 10 Hz. In some embodiments, the tissue filler has a complex viscosity from about 1 Pa·s to about 10 Pa·s. In some embodiments, the tissue filler has a complex viscosity of about 1 Pa·s, about 1.5 Pa·s, about 2 Pa·s, about 2.5 Pa·s, about 3 Pa·s, about 3.5 Pa·s, about 4 Pa·s, about 4.5 Pa·s, about 5 Pa's, about 5.5 Pa·s, about 6 Pa·s, about 6.5 Pa·s, about 7 Pa·s, about 7.5 Pa·s, about 8 Pa·s, about 8.5 Pa·s, about 9 Pa·s, about 9.5 Pa·s, or about 10 Pa·s. In some embodiments, the complex viscosity is measured by means of an oscillatory stress of about 0.1 to about 10 Hz. In some embodiments, the complex viscosity is measured by means of an oscillatory stress of about 1 Hz. In some embodiments, the complex viscosity is measured by means of an oscillatory stress of about 5 Hz.

In some embodiments, the invention relates to a method of treating a condition in a subject in need thereof, comprising administering to the subject a therapeutically effective amount of a tissue filler including modified or cross-linked HA, and/or modified or cross-linked SPF. In some embodiments, the condition is a skin condition. In some embodiments, the skin condition is selected from the group consisting of skin dehydration, lack of skin elasticity, skin roughness, lack of skin tautness, a skin stretch line, a skin stretch mark, skin paleness, a dermal divot, a sunken cheek, a thin lip, a retro-orbital defect, a facial fold, and a wrinkle.

In some embodiments, the invention relates to a method of cosmetic treatment in a subject in need thereof, comprising administering to the subject an effective amount of a tissue filler including modified or cross-linked HA, and/or modified or cross-linked SPF. In some embodiments, the tissue filler is administered into a dermal region of the subject. In some embodiments, the method is an augmentation, a reconstruction, treating a disease, treating a disorder, correcting a defect or imperfection of a body part, region or area. In some embodiments, the method is a facial augmentation, a facial reconstruction, treating a facial disease, treating a facial disorder, treating a facial defect, or treating a facial imperfection.

In some embodiments of the methods described herein, the tissue filler resists biodegradation, bioerosion, bioabsorption, and/or bioresorption, for at least about 3 days, about 7 days, about 14 days, about 21 days, about 28 days, about 1 month, about 2 months, about 3 months, about 4 months, about 5 months, or about 6 months. In some embodiments of the methods described herein, administration of the tissue filler to the subject results in a reduced inflammatory response compared to the inflammatory response induced by a control tissue filler comprising a polysaccharide and lidocaine, wherein the control tissue filler does not include silk protein fragments (SPF).

In some embodiments of the methods described herein, administration of the tissue filler to the subject results in increased collagen production compared to the collagen production induced by a control tissue filler comprising a polysaccharide and lidocaine, wherein the control tissue filler does not include silk protein fragments (SPF).

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 3 is a table summarizing the LiBr and Sodium Carbonate ($Na_2CO_3$) concentration in silk protein solutions of the present disclosure.

FIG. 4 is a table summarizing the LiBr and $Na_2CO_3$ concentration in silk protein solutions of the present disclosure.

FIG. 5 is a table summarizing the Molecular Weights of silk protein solutions of the present disclosure.

FIG. 8 is a table summarizing the Molecular Weights of silk dissolved from different concentrations of LiBr and from different extraction and dissolution sizes.

FIG. 47A: mixed HA cross-linked at 100 gm/ml, and FIG. 47B: single MW HA cross-linked at 25 mg/ml.

FIG. 48A: mixed HA cross-linked at 100 mg/ml, and FIG. 48B: single MW HA cross-linked at 25 mg/ml.

Figure 1:
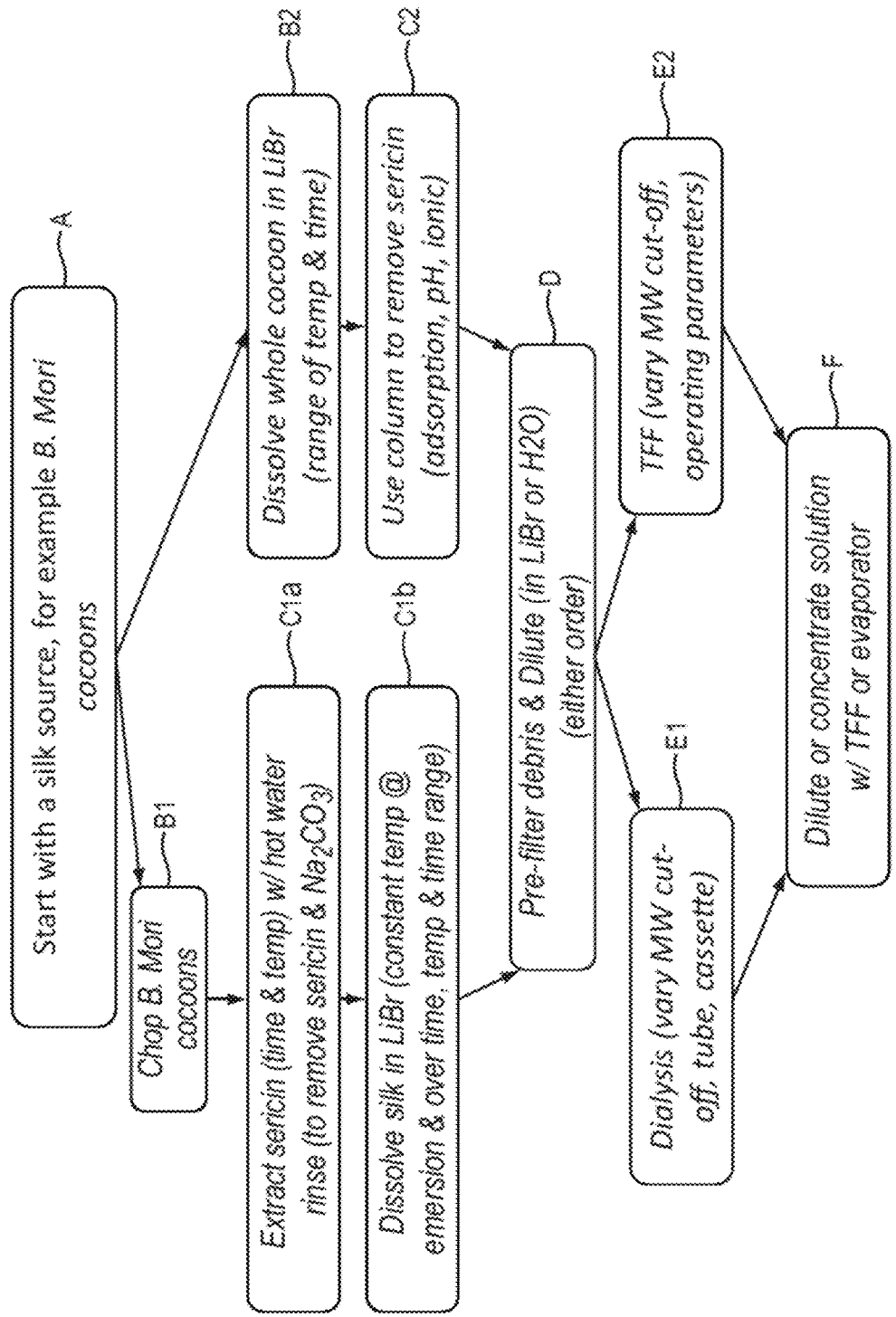
FIG. 1 is a flow chart showing various embodiments for producing pure silk fibroin-based protein fragments (SPFs) of the present disclosure.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Disclosed herein are tissue fillers that include silk protein fragments (SPF). In some embodiments, the tissue fillers are prepared from compositions described herein that may include SPF and hyaluronic acid (HA). In some embodiments, the tissue fillers described herein may be dermal fillers.

In some embodiments, the dermal fillers are made by a process described herein by using HA having a MW of between about 5 kDa and about 5 MDa, between about 100 kDa and about 4 MDa, or between about 500 kDa and about 3 MDa. In some embodiments, the dermal fillers are made by a process described herein by using HA having a MW of about 50 kDa, about 100 kDa, about 150 kDa, about 200 kDa, about 250 kDa, about 300 kDa, about 350 kDa, about 400 kDa, about 450 kDa, about 500 kDa, about 550 kDa, about 600 kDa, about 650 kDa, about 700 kDa, about 750 kDa, about 800 kDa, about 850 kDa, about 900 kDa, about 950 kDa, about 1000 kDa, about 1050 kDa, about 1100 kDa, about 1150 kDa, about 1200 kDa, about 1250 kDa, about 1300 kDa, about 1350 kDa, about 1400 kDa, about 1450 kDa, about 1500 kDa, about 1550 kDa, about 1600 kDa, about 1650 kDa, about 1700 kDa, about 1750 kDa, about 1800 kDa, about 1850 kDa, about 1900 kDa, about 1950 kDa, about 2000 kDa, about 2050 kDa, about 2100 kDa, about 2150 kDa, about 2200 kDa, about 2250 kDa, about 2300 kDa, about 2350 kDa, about 2400 kDa, about 2450 kDa, about 2500 kDa, about 2550 kDa, about 2600 kDa, about 2650 kDa, about 2700 kDa, about 2750 kDa, about 2800 kDa, about 2850 kDa, about 2900 kDa, about 2950 kDa, about 3000 kDa, about 3050 kDa, about 3100 kDa, about 3150 kDa, about 3200 kDa, about 3250 kDa, about 3300 kDa, about 3350 kDa, about 3400 kDa, about 3450 kDa, about 3500 kDa, about 3550 kDa, about 3600 kDa, about 3650 kDa, about 3700 kDa, about 3750 kDa, about 3800 kDa, about 3850 kDa, about 3900 kDa, about 3950 kDa, or about 4000 kDa. Any of the above MW of HA can be mixed with any other of the above MW of HA, in any possible proportion. In some embodiments, a dermal filler is made by mixing a high MW HA can be mixed with a low MW HA, where the high MW HA is in a proportion of about 0.01%, or about 0.1%, or about 0.2%, or about 0.3%, or about 0.4%, or about 0.5%, or about 0.6%, or about 0.7%, or about 0.8%, or about 0.9%, or about 1%, or about 2%, or about 3%, or about 4%, or about 5%, or about 6%, or about 7%, or about 8%, or about 9%, or about 10%, or about 11%, or about 12%, or about 13%, or about 14%, or about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%, or about 36%, or about 37%, or about 38%, or about 39%, or about 40%, or about 41%, or about 42%, or about 43%, or about 44%, or about 45%, or about 46%, or about 47%, or about 48%, or about 49%, or about 50%, or about 51%, or about 52%, or about 53%, or about 54%, or about 55%, or about 56%, or about 57%, or about 58%, or about 59%, or about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%, or about 99.5%, or about 99.9%.

In some embodiments, the dermal fillers are made by a process described herein by using silk SPF having a MW between about 5 kDa and about 35 kDa. In some embodiments, the dermal fillers are made by a process described herein by using silk SPF having a MW of about 5 kDa, or about 6 kDa, or about 7 kDa, or about 8 kDa, or about 9 kDa, or about 10 kDa, or about 11 kDa, or about 12 kDa, or about 13 kDa, or about 14 kDa, or about 15 kDa, or about 16 kDa, or about 17 kDa, or about 19 kDa, or about 19 kDa, or about 20 kDa, or about 21 kDa, or about 22 kDa, or about 23 kDa, or about 24 kDa, or about 25 kDa, or about 26 kDa, or about 27 kDa, or about 28 kDa, or about 29 kDa, or about 30 kDa.

In some embodiments, the dermal fillers are made by a process described herein by using an initial concentration of HA of about 80 mg/ml, or about 81 mg/ml, or about 82 mg, ml, or about 83 mg/ml, or about 84 mg/ml, or about 85 mg/ml, or about 86 mg/ml, or about 87 mg/ml, or about 88 mg/ml, or about 89 mg/ml, or about 90 mg/ml, or about 91 mg/ml, or about 92 mg/ml, or about 93 mg/ml, or about 94 mg/ml, or about 95 mg/ml, or about 96 mg/ml, or about 97 mg/ml, or about 98 mg/ml, or about 99 mg/ml, or about 100 mg/ml, or about 101 mg/ml, or about 102 mg/ml, or about 103 mg/ml, or about 104 mg/ml, or about 105 mg/ml, or about 106 mg/ml, or about 107 mg/ml, or about 108 mg/ml, or about 109 mg/ml, or about 110 mg/ml, or about 111 mg/ml, or about 112 mg/ml, or about 113 mg/ml, or about 114 mg/ml, or about 115 mg/ml, or about 116 mg/ml, or about 117 mg/ml, or about 118 mg/ml, or about 119 mg/ml, or about 120 mg/ml, or higher.

In some embodiments, the dermal fillers described herein have a silk SPF concentration of about 0.1%, or about 0.2%, or about 0.3%, or about 0.4%, or about 0.5%, or about 0.6%, or about 0.7%, or about 0.8%, or about 0.9%, or about 1%, or about 1.1%, or about 1.2%, or about 1.3%, or about 1.4%, or about 1.5%, or about 1.6%, or about 1.7%, or about 1.8%, or about 1.9%, or about 2%, or about 2.1%, or about 2.2%, or about 2.3%, or about 2.4%, or about 2.5%, or about 2.6%, or about 2.7%, or about 2.8%, or about 2.9%, or about 3%, or about 3.1%, or about 3.2%, or about 3.3%, or about 3.4%, or about 3.5%, or about 3.6%, or about 3.7%, or about 3.8%, or about 3.9%, or about 4%, or about 4.1%, or about 4.2%, or about 4.3%, or about 4.4%, or about 4.5%, or about 4.6%, or about 4.7%, or about 4.8%, or about 4.9%, or about 5% of total HA and silk SPF.

In some embodiments, the dermal fillers are made by a process described herein by using a PEGDE cross-linker having a Mn of about 100, about 200, about 300, about 400, about 500, about 600, about 700, about 800, about 900, about 1000, about 1100, or about 1200.

In some embodiments, the dermal fillers are made by a process described herein by using reaction conditions including a cross-linking step at about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., or about 55° C. In some embodiments, the dermal fillers are made by a process described herein by using reaction conditions including a cross-linking step of about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes, about 60 minutes, about 61 minutes, about 62 minutes, about 63 minutes, about 64 minutes, or about 65 minutes.

In some embodiments, the dermal fillers include free HA, for example un-cross-linked HA. In some embodiments, the dermal fillers include about 0.1%, or about 0.2%, or about 0.3%, or about 0.4%, or about 0.5%, or about 0.6%, or about 0.7%, or about 0.8%, or about 0.9%, or about 1%, or about 1.1%, or about 1.2%, or about 1.3%, or about 1.4%, or about 1.5%, or about 1.6%, or about 1.7%, or about 1.8%, or about 1.9%, or about 2%, or about 2.1%, or about 2.2%, or about 2.3%, or about 2.4%, or about 2.5%, or about 2.6%, or about 2.7%, or about 2.8%, or about 2.9%, or about 3%, or about 3.1%, or about 3.2%, or about 3.3%, or about 3.4%, or about 3.5%, or about 3.6%, or about 3.7%, or about 3.8%, or about 3.9%, or about 4%, or about 4.1%, or about 4.2%, or about 4.3%, or about 4.4%, or about 4.5%, or about 4.6%, or about 4.7%, or about 4.8%, or about 4.9%, or about 5%, or about 5.1%, or about 5.2%, or about 5.3%, or about 5.4%, or about 5.5%, or about 5.6%, or about 5.7%, or about 5.8%, or about 5.9%, or about 6%, or about 6.1%, or about 6.2%, or about 6.3%, or about 6.4%, or about 6.5%, or about 6.6%, or about 6.7%, or about 6.8%, or about 6.9%, or about 7%, or about 7.1%, or about 7.2%, or about 7.3%, or about 7.4%, or about 7.5%, or about 7.6%, or about 7.7%, or about 7.8%, or about 7.9%, or about 8%, or about 8.1%, or about 8.2%, or about 8.3%, or about 8.4%, or about 8.5%, or about 8.6%, or about 8.7%, or about 8.8%, or about 8.9%, or about 9%, or about 9.1%, or about 9.2%, or about 9.3%, or about 9.4%, or about 9.5%, or about 9.6%, or about 9.7%, or about 9.8%, or about 9.9%, or about 10% of total HA (cross-linked HA and un-cross-linked HA). In some embodiments, the dermal fillers do not include free HA.

In some embodiments, the dermal fillers include HA at about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26/mg/ml, about 27 mg/ml, about 28 mg/ml, about 29 mg/ml, or about 30 mg/ml.

In some embodiments, the dermal fillers have a MoD of about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14.7%, about 14.8%, about 14.9%, about 15.0%, about 15.1%, about 15.2%, about 15.3%, about 15.4%, about 15.5%, about 15.6%, about 15.7%, about 15.8%, about 15.9%, about 16.0%, about 16.1%, about 16.2%, about 16.3%, about 16.4%, about 16.5%, about 16.6%, about 16.7%, about 16.8%, about 16.9%, about 17.0%, about 17.1%, about 17.2%, about 17.3%, about 17.4%, about 17.5%, about 17.6%, about 17.7%, about 17.8%, about 17.9%, about 18.0%, about 18.1%, about 18.2%, about 18.3%, about 18.4%, about 18.5%, about 18.6%, about 18.7%, about 18.8%, about 18.9%, about 19.0%, about 19.1%, about 19.2%, about 19.3%, about 19.4%, about 19.5%, about 19.6%, about 19.7%, about 19.8%, about 19.9%, or about 20.0%.

In some embodiments, the dermal fillers have an injection force of about 5 N, about 6 N, about 7 N, about 8 N, about 9 N, about 10 N, about 11 N, about 12 N, about 13 N, about 14 N, about 15 N, about 16 N, about 17 N, about 18 N, about 19 N, about 20 N, about 21 N, about 22 N, about 23 N, about 24 N, or about 25 N. In some embodiments, the injection force relate to injection through a 30 G needle.

The tissue fillers provided herein include compositions further including one or more components such as SPF, for example cross-linked SPF and/or non-cross-linked SPF, hyaluronic acid, for example cross-linked HA and/or non-cross-linked HA. As used herein, cross-linked SPF refers to SPF which is cross-linked with an identical or non-identical SPF. Cross-linked SPF can also be referred to as homo-cross-linked SPF. As used herein, cross-linked HA refers to HA which is cross-linked with an identical or non-identical HA. Cross-linked HA can also be referred to as homo-cross-linked HA. The tissue fillers provided herein can also include SPF cross-linked to HA, and/or HA cross-linked to SPF. SPF cross-linked to HA, and/or HA cross-linked to SPF, can also be referred to as cross-linked SPF-HA, or hetero-cross-linked SPF-HA.

In some embodiments, the compositions of the invention are monophasic. In some embodiments, the compositions of the invention are biphasic, or multiphasic. In some embodiments, the compositions of the invention include a non-cross-linked polymeric phase, for example non-cross-linked SPF, and/or non-cross-linked HA. In some embodiments, the compositions of the invention include a cross-linked phase, for example cross-linked SPF, and/or cross-linked HA. In some embodiments, the compositions of the invention include a liquid phase, for example water, and/or an aqueous solution. In some embodiments, the aqueous solution can include SPF. In some embodiments, the aqueous phase can include HA. In some embodiments, the liquid phase may include a non-cross-linked polymer such as non-cross-linked HA and/or non-cross-linked SPF.

In some embodiments, a composition of the invention comprises a carrier phase. As such, the disclosed compositions can be monophasic or multiphasic compositions. As used herein, the term "carrier phase" is synonymous with "carrier" and refers to a material used to increase fluidity of a hydrogel. A carrier is advantageously a physiologically-acceptable carrier and may include one or more conventional excipients useful in pharmaceutical compositions. As used herein, the term "a physiologically-acceptable carrier" refers to a carrier in accord with, or characteristic of, the normal functioning of a living organism. As such, administration of a composition comprising a hydrogel and a carrier has substantially no long term or permanent detrimental effect when administered to a mammal. The present tissue fillers include a carrier where a major of the volume is water or saline. However, other useful carriers include any physiologically tolerable material which improves upon extrudability or intrudability of the hydrogel through a needle or into a target host environment. Potential carriers could include but are not limited to physiological buffer solutions, serum, other protein solutions, gels composed of polymers including proteins, glycoproteins, proteoglycans, or polysaccharides. Any of the indicated potential carriers may be either naturally derived, wholly synthetic, or combinations of thereof.

In one embodiment, a composition provided herein includes one or more of modified SPF, cross-linked SPF, non-cross-linked SPF, modified HA, cross-linked HA, non-cross-linked HA, homo-cross-linked SPF, homo-cross-linked HA, and hetero-cross-linked SPF-HA.

In some embodiments, the compositions provided herein include cross-linked SPF and non-cross-linked SPF. In some embodiments, the compositions provided herein include cross-linked SPF and non-cross-linked HA. In some embodiments, the compositions provided herein include cross-linked SPF and cross-linked HA. In some embodiments, the compositions provided herein include cross-linked SPF and cross-linked SPF-HA.

In some embodiments, the compositions provided herein include non-cross-linked SPF and non-cross-linked HA. In some embodiments, the compositions provided herein include non-cross-linked SPF and cross-linked HA. In some embodiments, the compositions provided herein include non-cross-linked SPF and cross-linked SPF-HA.

In some embodiments, the compositions provided herein include cross-linked SPF, non-cross-linked SPF, and non-cross-linked HA. In some embodiments, the compositions provided herein include cross-linked SPF, non-cross-linked SPF, and cross-linked HA. In some embodiments, the compositions provided herein include cross-linked SPF, non-cross-linked SPF, and cross-linked SPF-HA.

In some embodiments, the compositions provided herein include cross-linked SPF, cross-linked HA, and non-cross-linked HA. In some embodiments, the compositions provided herein include cross-linked SPF, cross-linked HA, and cross-linked SPF-HA. In some embodiments, the compositions provided herein include cross-linked SPF, non-cross-linked HA, and cross-linked SPF-HA.

In some embodiments, the compositions provided herein include non-cross-linked SPF, cross-linked HA, and non-cross-linked HA. In some embodiments, the compositions provided herein include non-cross-linked SPF, cross-linked HA, and cross-linked SPF-HA. In some embodiments, the compositions provided herein include non-cross-linked SPF, non-cross-linked HA, and cross-linked SPF-HA.

In some embodiments, the compositions provided herein include cross-linked SPF, non-cross-linked SPF, cross-linked HA, and non-cross-linked HA. In some embodiments, the compositions provided herein include cross-linked SPF, non-cross-linked SPF, cross-linked HA, and cross-linked SPF-HA. In some embodiments, the compositions provided herein include cross-linked SPF, non-cross-linked SPF, non-cross-linked HA, and cross-linked SPF-HA.

In some embodiments, the compositions provided herein include cross-linked SPF, cross-linked HA, non-cross-linked HA, and cross-linked SPF-HA. In some embodiments, the compositions provided herein include non-cross-linked SPF, cross-linked HA, non-cross-linked HA, and cross-linked SPF-HA.

In some embodiments, the compositions provided herein include cross-linked SPF, non-cross-linked SPF, cross-linked HA, non-cross-linked HA, and cross-linked SPF-HA.

In some embodiments, the compositions provided herein include cross-linked SPF. In some embodiments, the compositions provided herein include SPF and hyaluronic acids (HA). In one aspect, the SPF/HA based compositions described herein include HA cross-linked moieties. In some embodiments, the compositions include SPF-HA cross linked moieties. In some embodiments, the compositions include non-cross linked HA. In some embodiments, the compositions may include non-cross linked SPF. In some embodiments, the compositions may include at least one additional agent. In some embodiments, the compositions include cross-linked SPF-SPF, SPF-HA, and or HA-HA, with variable stability, resulting in compositions of various degrees of bio absorbability, and/or bioresorbability.

In some embodiments, the HA is cross-linked into a matrix. In some embodiments, the HA matrix encapsulates or semi-encapsulates one or more SPF. In some embodiments, the HA is cross-linked with one or more SPF.

In some embodiments, the tissue fillers, or portions thereof, are biocompatible, biodegradable, bioabsorbable, bioresorbable, or a combination thereof. In some embodiments, the tissue fillers provided herein include a fluid component, for example a single fluid or a solution including substantially one or more fluids. In some embodiments, the tissue fillers include water or an aqueous solution. In some embodiments, the tissue fillers are injectable, implantable, or deliverable under the skin by any means known in the art such as, for example, following surgical resection of the tissue. In some embodiments, the compositions are dermal fillers. In some embodiments, the compositions are sterile.

In some embodiments, the tissue fillers described herein may include about 1% (w/w) SPF and about 0.3% (w/w) lidocaine.

Provided herein are methods of manufacturing compositions including silk protein fragments (SPFs) and hyaluronic acid (HA), methods of delivery of compositions including SPF and HA, and methods of treatment using compositions including SPF and HA.

Definitions

As used herein, the term "fibroin" includes silkworm fibroin, insect or spider silk protein, or recombinant silk fibroin. In an embodiment, fibroin is obtained from *Bombyx mori*.

As used herein, the terms "substantially sericin free" or "substantially devoid of sericin" refer to silk fibers in which a majority of the sericin protein has been removed, and/or SPF made from silk fibers in which a majority of the sericin protein has been removed. In an embodiment, silk fibroin and SPF that are substantially devoid of sericin refers to silk fibroin and SPF having between about 0.01% (w/w) and about 10.0% (w/w) sericin. In an embodiment, silk fibroin and SPF that are substantially devoid of sericin refers to silk fibroin and SPF having between about 0.01% (w/w) and about 9.0% (w/w) sericin. In an embodiment, silk fibroin and SPF that are substantially devoid of sericin refers to silk fibroin and SPF having between about 0.01% (w/w) and about 8.0% (w/w) sericin. In an embodiment, silk fibroin and SPF that are substantially devoid of sericin refers to silk fibroin and SPF having between about 0.01% (w/w) and about 7.0% (w/w) sericin. In an embodiment, silk fibroin and SPF that are substantially devoid of sericin refers to silk fibroin and SPF having between about 0.01% (w/w) and about 6.0% (w/w) sericin. In an embodiment, silk fibroin and SPF that are substantially devoid of sericin refers to silk fibroin and SPF having between about 0.01% (w/w) and about 5.0% (w/w) sericin. In an embodiment, silk fibroin and SPF that are substantially devoid of sericin refers to silk fibroin and SPF having between about 0% (w/w) and about 4.0% (w/w) sericin. In an embodiment, silk fibroin and SPF that are substantially devoid of sericin refers to silk fibroin and SPF having between about 0.05% (w/w) and about 4.0% (w/w) sericin. In an embodiment, silk fibroin and SPF that are substantially devoid of sericin refers to silk fibroin and SPF having between about 0.1% (w/w) and about 4.0% (w/w) sericin. In an embodiment, silk fibroin and SPF that are substantially devoid of sericin refers to silk fibroin and SPF having between about 0.5% (w/w) and about 4.0% (w/w) sericin. In an embodiment, silk fibroin and SPF that are substantially devoid of sericin refers to silk fibroin and SPF having between about 1.0% (w/w) and about 4.0% (w/w) sericin. In an embodiment, silk fibroin and SPF that are substantially devoid of sericin refers to silk fibroin and SPF having between about 1.5% (w/w) and about 4.0%

(w/w) sericin. In an embodiment, silk fibroin and SPF that are substantially devoid of sericin refers to silk fibroin and SPF having between about 2.0% (w/w) and about 4.0% (w/w) sericin. In an embodiment, silk fibroin and SPF that are substantially devoid of sericin refers to silk fibroin and SPF having between about 2.5% (w/w) and about 4.0% (w/w) sericin. In an embodiment, silk fibroin and SPF that are substantially devoid of sericin refers to silk fibroin and SPF having a sericin content between about 0.01% (w/w) and about 0.1% (w/w). In an embodiment, silk fibroin and SPF that are substantially devoid of sericin refers to silk fibroin and SPF having a sericin content below about 0.1% (w/w). In an embodiment, silk fibroin and SPF that are substantially devoid of sericin refers to silk fibroin and SPF having a sericin content below about 0.05% (w/w). In an embodiment, when a silk source is added to a boiling (100° C.) aqueous solution of sodium carbonate for a treatment time of between about 30 minutes to about 60 minutes, a degumming loss of about 26 wt. % to about 31 wt. % is obtained.

As used herein, the term "substantially homogeneous" may refer to pure silk fibroin-based protein fragments that are distributed in a normal distribution about an identified molecular weight. As used herein, the term "substantially homogeneous" may refer to an even distribution of an additive, for example lidocaine, throughout a composition of the present disclosure.

As used herein, the term "substantially free of inorganic residuals" means that the composition exhibits residuals of 0.1% (w/w) or less. In an embodiment, substantially free of inorganic residuals refers to a composition that exhibits residuals of 0.05% (w/w) or less. In an embodiment, substantially free of inorganic residuals refers to a composition that exhibits residuals of 0.01% (w/w) or less. In an embodiment, the amount of inorganic residuals is between 0 ppm ("non-detectable" or "ND") and 1000 ppm. In an embodiment, the amount of inorganic residuals is ND to about 500 ppm. In an embodiment, the amount of inorganic residuals is ND to about 400 ppm. In an embodiment, the amount of inorganic residuals is ND to about 300 ppm. In an embodiment, the amount of inorganic residuals is ND to about 200 ppm. In an embodiment, the amount of inorganic residuals is ND to about 100 ppm. In an embodiment, the amount of inorganic residuals is between 10 ppm and 1000 ppm.

As used herein, the term "substantially free of organic residuals" means that the composition exhibits residuals of 0.1% (w/w) or less. In an embodiment, substantially free of organic residuals refers to a composition that exhibits residuals of 0.05% (w/w) or less. In an embodiment, substantially free of organic residuals refers to a composition that exhibits residuals of 0.01% (w/w) or less. In an embodiment, the amount of organic residuals is between 0 ppm ("non-detectable" or "ND") and 1000 ppm. In an embodiment, the amount of organic residuals is ND to about 500 ppm. In an embodiment, the amount of organic residuals is ND to about 400 ppm. In an embodiment, the amount of organic residuals is ND to about 300 ppm. In an embodiment, the amount of organic residuals is ND to about 200 ppm. In an embodiment, the amount of organic residuals is ND to about 100 ppm. In an embodiment, the amount of organic residuals is between 10 ppm and 1000 ppm.

As used herein, the term "non-cross-linked" refers to a lack of intermolecular bonds joining individual matrix polymer molecules, macromolecules, and/or monomer chains. As such, a non-cross-linked matrix polymer is not linked to any other matrix polymer by an intermolecular bond.

Tissue fillers, compositions, or portions thereof, of the present disclosure exhibit "biocompatibility" or are "biocompatible" meaning that the compositions are compatible with living tissue or a living system by not being substantially toxic, injurious, or physiologically reactive and not causing immunological rejection. The term "biocompatible" encompasses the terms "bioabsorbable," "bioresorbable," and "biodegradable," which are defined herein.

Tissue fillers, compositions, or portions thereof, of the present disclosure may be "bioabsorbable," "bioresorbable," and/or "biodegradable". As used herein, the terms "bioabsorbable" refers to materials or substances that dissipate upon implantation within a body, independent of which mechanisms by which dissipation can occur, such as dissolution, degradation, absorption and excretion. As used herein, the term "bioresorbable" means capable of being absorbed by the body. As used herein, the term "biodegradable" refers to materials which can decompose under physiological conditions into byproducts. Such physiological conditions include, for example, hydrolysis (decomposition via hydrolytic cleavage), enzymatic catalysis (enzymatic degradation), mechanical interactions, and the like. As used herein, the term "biodegradable" also encompasses the term "bioresorbable", which describes a material or substance that decomposes under physiological conditions to break down to products that undergo bioresorption into the host-organism, namely, become metabolites of the biochemical systems of the host organism. As used herein, the terms "bioresorbable" and "bioresorption" encompass processes such as cell-mediated degradation, enzymatic degradation and/or hydrolytic degradation of the bioresorbable polymer, and/or elimination of the bioresorbable polymer from living tissue as will be appreciated by the person skilled in the art. In some embodiments, the SPF-HA compositions and materials described herein may be biocompatible, bioresorbable, bioabsorbable, and/or biodegradable.

Where the tissue fillers described herein are biodegradable or bioresorbable, they may resist biodegradation or bioresorption for at least about 1 day, or at least about 2 days, or at least about 3 days, or at least about 4 days, at least about 5 days, or at least about 10 days, or at least about 15 days, or at least about 20 days, or at least about 25 days, or at least about 30 days, or at least about 35 days, or at least about 40 days, or at least about 45 days, or at least about 50 days, or at least about 60 days, or at least about 70 days, or at least about 80 days, or at least about 90 days, or at least about 100 days, or at least about 110 days, or at least about 120 days, or at least about 130 days, or at least about 140 days, or at least about 140 days, or at least about 150 days, or at least about 160 days, or at least about 170 days, or at least about 180 days, or at least about 190 days, or at least about 200 days, or at least about 250 days, or at least about 300 days, or at least about 1 year, or at least about 2 years or they may resist biodegradation for less than about 5 days, or at most about 10 days, or at most about 15 days, or at most about 20 days, or at most about 25 days, or at most about 30 days, or at most about 35 days, or at most about 40 days, or at most about 45 days, or at most about 50 days, or at most about 60 days, or at most about 70 days, or at most about 80 days, or at most about 90 days, or at most about 100 days, or at most about 110 days, or at most about 120 days, or at most about 130 days, or at most about 140 days, or at most about 140 days, or at most about 150 days, or at most about 160 days, or at most about 170 days, or at most about 180 days, or at most about 190 days, or at most about 200 days, or at most about 250 days, or at most about 300 days, or at most about 1 year, or at most about 2 years.

Where the tissue fillers described herein are bioabsorbable they may resist bioabsorption for at least about 1 day, or at least about 2 days, or at least about 3 days, or at least about 4 days, at least about 5 days, or at least about 10 days, or at least about 15 days, or at least about 20 days, or at least about 25 days, or at least about 30 days, or at least about 35 days, or at least about 40 days, or at least about 45 days, or at least about 50 days, or at least about 60 days, or at least about 70 days, or at least about 80 days, or at least about 90 days, or at least about 100 days, or at least about 110 days, or at least about 120 days, or at least about 130 days, or at least about 140 days, or at least about 140 days, or at least about 150 days, or at least about 160 days, or at least about 170 days, or at least about 180 days, or at least about 190 days, or at least about 200 days, or at least about 250 days, or at least about 300 days, or at least about 1 year, or at least about 2 years or they may resist bioabsorption for less than about 5 days, or at most about 10 days, or at most about 15 days, or at most about 20 days, or at most about 25 days, or at most about 30 days, or at most about 35 days, or at most about 40 days, or at most about 45 days, or at most about 50 days, or at most about 60 days, or at most about 70 days, or at most about 80 days, or at most about 90 days, or at most about 100 days, or at most about 110 days, or at most about 120 days, or at most about 130 days, or at most about 140 days, or at most about 140 days, or at most about 150 days, or at most about 160 days, or at most about 170 days, or at most about 180 days, or at most about 190 days, or at most about 200 days, or at most about 250 days, or at most about 300 days, or at most about 1 year, or at most about 2 years.

As described herein, the degree of biodegradation, bioabsorption, and bioresorption may be modified and/or controlled by, for example, adding one or more agents to compositions described herein that retard biodegradation, bioabsorption, and/or bioresorption. In addition, the degree of biodegradation, bioabsorption, and bioresorption may be modified and/or controlled by increasing or decreasing the degree of polymeric cross-linking present in the polymeric materials described herein. For example, the rate of biodegradation, bioabsorption, and/or bioresorption of the compositions described here may be increased by reducing the amount of crosslinking in the polymeric materials described herein. Alternatively, the rate of biodegradation, bioabsorption, and/or bioresorption of the tissue fillers and compositions described here may be decreased by increasing the amount of crosslinking in the polymeric materials described herein.

Tissue fillers and compositions of the present disclosure are "hypoallergenic" meaning that they are relatively unlikely to cause an allergic reaction. Such hypoallergenicity can be evidenced by participants topically applying compositions of the present disclosure on their skin for an extended period of time. In an embodiment, the extended period of time is about 3 days. In an embodiment, the extended period of time is about 7 days. In an embodiment, the extended period of time is about 14 days. In an embodiment, the extended period of time is about 21 days. In an embodiment, the extended period of time is about 30 days. In an embodiment, the extended period of time is selected from the group consisting of about 1 month, about 2 months, about 3 months, about 4 months, about 5 months, about 6 months, about 7 months, about 8 months, about 9 months, about 10 months, about 11 months, about 12 months, and indefinitely.

As used herein, "low molecular weight" silk refers to silk protein fragments having a molecular weight in a range of about 5 kDa to about 20 kDa. In some embodiments, a target low molecular weight for certain silk protein fragments may be about 11 kDa.

As used herein, "medium molecular weight" silk refers to silk protein fragments having a molecular weight in a range of about 20 kDa to about 55 kDa. In some embodiments, a target low molecular weight for certain silk protein fragments may be about 40 kDa.

As used herein, "high molecular weight" silk refers to silk protein fragments having a molecular weight in a range of about 55 kDa to about 150 kDa. In some embodiments, a target low molecular weight for certain silk protein fragments may be about 100 kDa to about 145 kDa.

In some embodiments, the molecular weights described herein, e.g., low molecular weight SPF, medium molecular weight SPF, high molecular weight SPF, may be converted to the approximate number of amino acids contained within the respective natural or recombinant proteins, such as natural or recombinant silk proteins, as would be understood by a person having ordinary skill in the art. For example, the average weight of an amino acid may be about 110 daltons, i.e., 110 g/mol. Therefore, in some embodiments, dividing the molecular weight of a linear protein by 110 daltons may be used to approximate the number of amino acid residues contained therein.

As used herein, the term "polydispersity" refers to a measure of the distribution of molecular mass in a given polymer sample. Polydispersity may be calculated by dividing the weight average molecular weight (Mw) by the number average molecular weight (Mn). As used herein, the term "weight average molecular weight" (Mw) generally refers to a molecular weight measurement that depends on the contributions of polymer molecules according to their sizes. The weight average molecular weight may be defined by the formula:

$$Mw = \frac{\Sigma N_i M_i^2}{\Sigma N_i M_i},$$

where $M_i$ is the molecular weight of a chain and $N_i$ is the number of chains of that molecular weight. As used herein, the term "number average molecular weight" (Mn) generally refers to a molecular weight measurement that is calculated by dividing the total weight of all the polymer molecules in a sample with the total number of polymer molecules in the sample. The number average molecular weight may be defined by the formula:

$$Mn = \frac{\Sigma N_i M_i}{\Sigma N_i},$$

where $M_i$ is the molecular weight of a chain and $N_i$ is the number of chains of that molecular weight. For example, a monodisperse polymer, where all polymer chains are equal has a polydispersity (Mw/Mn) of 1. In general, molecular weight averages may be determined by gel permeation chromatography (GPC) and size exclusion chromatography (SEC). The larger the polydispersity index, the broader the molecular weight.

As used herein, the term "tissue filler" refers broadly a material that may be provided in and about soft tissue to add volume, add support, or otherwise treat a soft tissue deficiency. The term "tissue filler" also encompasses dermal fillers; however, the term "dermal filler" should not be construed as imposing any limitations as to the location and type of delivery of such filler. Nevertheless, dermal fillers described herein may generally encompass the use and delivery of such dermal fillers at multiple levels beneath the dermis. As used herein, the term "soft tissue" may refer to those tissues that connect, support, or surround other structures and organs of the body. For example, soft tissues described herein may include, without limitation, skin, dermal tissues, subdermal tissues, cutaneous tissues, subcutaneous tissues, intradural tissue, muscles, tendons, ligaments, fibrous tissues, fat, blood vessels and arteries, nerves, and synovial (intradermal) tissues.

As used herein, the term "epoxy derived cross-linker" refers to a molecular bridge between two moieties in the same or separate polymer chains, which is obtained by employing a cross-linking precursor including an epoxide group, for example 1,4-butanediol diglycidyl ether (BDDE), polyethylene glycol diglycidyl ether (PEGDE, or PEGDGE), or a silk fibroin or silk fibroin fragment polyepoxy linker. Without wishing to be bound by any particular theory, by reacting with a reactive center in a polymer chain, including in the side chain of the polymer, the epoxide ring opens to form a secondary alcohol and a new bond (Scheme 1). Reactive groups include, but are not limited to, nucleophilic groups such as carboxylic groups, amino groups, or hydroxyl groups.

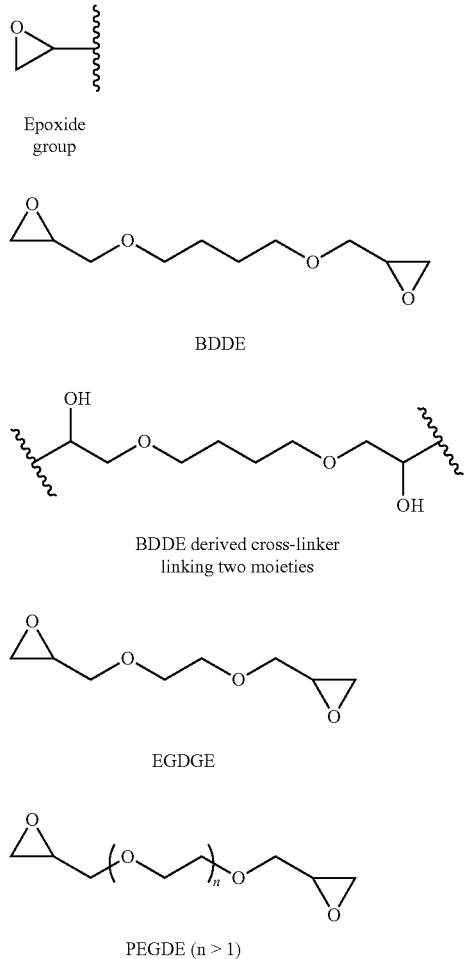

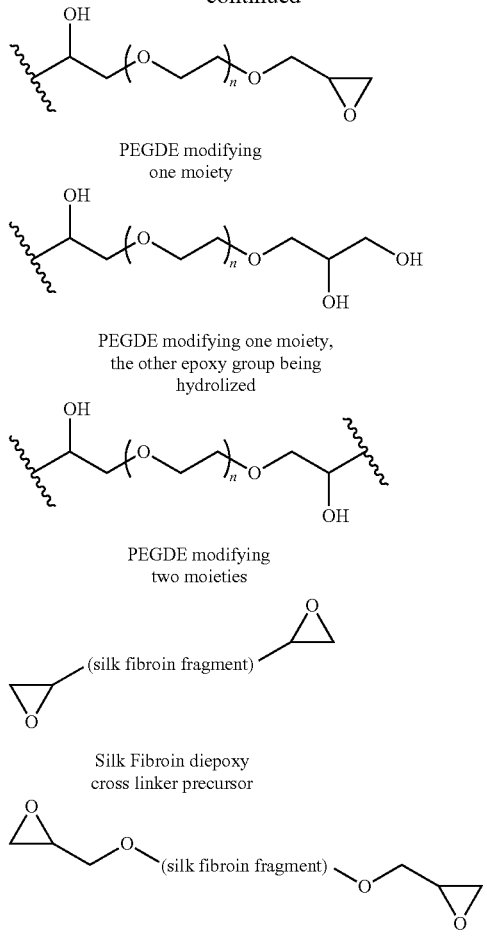

As used herein, "auto cross-linking" refers to either a) cross-linking between two strands of polymers of similar chemical nature, for example cross-linking between two strands of hyaluronic acid, or cross-linking between two strands of SPFs, or b) cross-linking between cross-linking groups on the same polymers strand to create a cyclic ester (lactone), a cyclic amide, a cyclic construct including a cross-linking moiety, or the like, for example cross-linking between two groups on the same strand of hyaluronic acid, or cross-linking between two groups on the same SPF strand.

As used herein, "zero-length cross linking," and/or "cross-linking including a bond," and/or "cross-linking using an activating agent," refers to cross-linking between two groups on either separate polymer strands, or the same polymer strand, where the groups react directly with each other, and no additional cross-linking moiety is inserted between them. Cross-linking between a carboxylic acid group and an amine or alcohol, where one of the groups is activated by an activating agent, for example a carbodiimide, is an example of zero-length cross-linking.

As used herein, the "Tyndall effect," and/or "tyndalling," is an adverse event occurring in some patients administered with tissue fillers. Tyndall effect is characterized by the appearance of a blue discoloration at the skin site where a tissue filler had been injected, which represents visible dermal filler composition seen through the translucent epidermis. The Tyndall effect can be seen when light-scattering particulate-matter is dispersed in an otherwise-light-transmitting medium, when the cross-section of particles is in a specific range, usually somewhat below or near the wavelength of visible light. Under the Tyndall effect, longer-wavelength light (e.g., red) is transmitted to a greater degree through the medium, while shorter-wavelength light (e.g., blue) is reflected to a greater degree via scattering, giving the overall impression that the medium is colored blue.

Silk Protein Fragments

In some embodiments, the silk protein-based compositions and silk protein fragments, or methods of producing the same, may include those described in U.S. Patent Application Publication Nos. 2015/00933340, 2015/0094269, 2016/0193130, 2016/0022560, 2016/0022561, 2016/0022562, 2016/0022563, and 2016/0222579, 2016/0281294, and U.S. Pat. Nos. 9,187,538, 9,522,107, 9,517,191, 9,522,108, 9,511,012, and 9,545,369, the entirety of which are incorporated herein by reference.

As used herein, silk protein fragments (SPFs) refer generally to a mixture, composition, or population of peptides and/or proteins originating from silk. In some embodiments, SPFs are produced as substantially pure and highly scalable SPF mixture solutions that may be used across multiple industries for a variety of applications. The solutions are generated from raw pure intact silk protein material and processed in order to remove any sericin and achieve the desired weight average molecular weight (MW) and polydispersity of the fragment mixture. Select method parameters may be altered to achieve distinct final silk protein fragment characteristics depending upon the intended use. The resulting final fragment solution is pure silk protein fragments and water with PPM to non-detectable levels of process contaminants, levels acceptable in the pharmaceutical, medical and consumer cosmetic markets. The concentration, size and polydispersity of silk protein fragments in the solution may further be altered depending upon the desired use and performance requirements. In an embodiment, the pure silk fibroin-based protein fragments in the solution are substantially devoid of sericin, have an average weight average molecular weight ranging from about 1 kDa to about 250 kDa, and have a polydispersity ranging from about 1.5 and about 3.0. In an embodiment, the pure silk fibroin-based protein fragments in the solution are substantially devoid of sericin, have an average weight average molecular weight ranging from about 5 kDa to about 150 kDa, and have a polydispersity ranging from about 1.5 and about 3.0. In an embodiment, the pure silk fibroin-based protein fragments in the solution are substantially devoid of sericin, have an average weight average molecular weight ranging from about 6 kDa to about 17 kDa, and have a polydispersity ranging from about 1.5 and about 3.0. In an embodiment, the pure silk fibroin-based protein fragments in the solution are substantially devoid of sericin, have an average weight average molecular weight ranging from about 17 kDa to about 39 kDa, and have a polydispersity ranging from about 1.5 and about 3.0. In an embodiment, the pure silk fibroin-based protein fragments in the solution are substantially devoid of sericin, have an average weight average molecular weight ranging from about 39 kDa to about 80 kDa, and have a polydispersity ranging from about 1.5 and about 3.0. In an embodiment, the pure silk fibroin-based protein fragments in the solution are substantially devoid of sericin, have an average weight average molecular weight ranging from about 80 kDa to about 150 kDa, and have a polydispersity ranging from about 1.5 and about 3.0.

In an embodiment, the silk protein fragments described herein may be prepared in a solution or as a solid, whereby the solid is suspended in a physiological solution (e.g., water, saline, and the like) or a gel of HA, as described herein. In some embodiments, the silk protein fragments described herein may be prepared in liposomes or microspheres before depositing the same in a gel of HA.

In an embodiment, the silk solutions of the present disclosure may be used to generate the tissue filler compositions described herein. In an embodiment, the solutions may be used to generate gels that may be homogenized with HA and additional agents to prepare the tissue fillers described herein. Depending on the silk solution utilized and the methods for casting the films or gels, various properties are achieved.

In some embodiments, the percent SPF content, by weight, in the tissue fillers described herein is at least 0.01%, or at least 0.1%, or at least 0.2%, or at least 0.3%, or at least 0.4%, or at least 0.5%, or at least 0.6%, or at least 0.7%, or at least 0.8%, or at least 0.9%, or at least 1%, or at least 2%, or at least 3%, or at least 4%, or at least 5%, or at least 6%, or at least 7%, or at least 8%, or at least 9%, or at least 10%, or at least 11%, or at least 12%, or at least 13%, or at least 14%, or at least 15%, or at least 16%, or at least 17%, or at least 18%, or at least 19%, or at least 20%, or at least 21%, or at least 22%, or at least 23%, or at least 24%, or at least 25%, or at least 26%, or at least 27%, or at least 28%, or at least 29%, or at least 30%, or at least 31%, or at least 32%, or at least 33%, or at least 34%, or at least 35%, or at least 36%, or at least 37%, or at least 38%, or at least 39%, or at least 40%, or at least 41%, or at least 42%, or at least 43%, or at least 44%, or at least 45%, or at least 46%, or at least 47%, or at least 48%, or at least 49%, or at least 50%, or at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.5%, or at least 99.9%.

In some embodiments, the percent SPF content, by weight, in the tissue fillers described herein is at most 0.01%, or at most 0.1%, or at most 0.2%, or at most 0.3%, or at most 0.4%, or at most 0.5%, or at most 0.6%, or at most 0.7%, or at most 0.8%, or at most 0.9%, or at most 1%, or at most 2%, or at most 3%, or at most 4%, or at most 5%, or at most 6%, or at most 7%, or at most 8%, or at most 9%, or at most 10%, or at most 11%, or at most 12%, or at most 13%, or at most 14%, or at most 15%, or at most 16%, or at most 17%, or at most 18%, or at most 19%, or at most 20%, or at most 21%, or at most 22%, or at most 23%, or at most 24%, or at most 25%, or at most 26%, or at most 27%, or at most 28%, or at most 29%, or at most 30%, or at most 31%, or at most 32%, or at most 33%, or at most 34%, or at most 35%, or at most 36%, or at most 37%, or at most 38%, or at most 39%, or at most 40%, or at most 41%, or at most 42%, or at most 43%, or at most 44%, or at most 45%, or at most 46%, or at most 47%, or at most 48%, or at most 49%, or at most 50%, or at most 51%, or at most 52%, or at most 53%, or at most 54%, or at most 55%, or at most 56%, or at most 57%, or at most 58%, or at most 59%, or at most 60%, or at most 61%, or at most 62%, or at most 63%, or at most 64%, or at most 65%, or at most 66%, or at most 67%, or at most 68%, or at most 69%, or at most 70%, or at most 71%, or at most 72%, or at most 73%, or at most 74%, or at most 75%, or at most 76%, or at most 77%, or at most 78%, or at most 79%, or at most 80%, or at most 81%, or at most 82%, or at most 83%, or at most 84%, or at most 85%, or at most 86%, or at most 87%, or at most 88%, or at most 89%, or at most 90%, or at most 91%, or at most 92%, or at most 93%, or at most 94%, or at most 95%, or at most 96%, or at most 97%, or at most 98%, or at most 990%, or at most 99.5%, or at most 99.9%.

In some embodiments, the percent SPF content, by weight, in the tissue fillers described herein is about 0.01%, or about 0.1%, or about 0.2%, or about 0.3%, or about 0.4%, or about 0.5%, or about 0.6%, or about 0.7%, or about 0.8%, or about 0.9%, or about 1%, or about 2%, or about 3%, or about 4%, or about 5%, or about 6%, or about 7%, or about 8%, or about 9%, or about 10%, or about 11%, or about 12%, or about 13%, or about 14%, or about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%, or about 36%, or about 37%, or about 38%, or about 39%, or about 40%, or about 41%, or about 42%, or about 43%, or about 44%, or about 45%, or about 46%, or about 47%, or about 48%, or about 49%, or about 50%, or about 51%, or about 52%, or about 53%, or about 54%, or about 55%, or about 56%, or about 57%, or about 58%, or about 59%, or about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%, or about 99.5%, or about 99.9%.

In some embodiments, the percent SPF content, by weight, in the tissue fillers described herein is between about 0.01% to about 100%, or about 0.01% to about 99.9%, or about 0.01% to about 75%; or between about 0.1% to about 95%, or about 1% to about 95%, or about 10% to about 95%; or between about 0.1% to about 1%, or about 0.1% to about 2%, or about 0.1% to about 3%, or about 0.1% to about 4%, or about 0.1% to about 5%, or about 0.1% to about 6%, or about 0.1% to about 7%, or about 0.1% to about 8%, or about 0.1% to about 9%, or about 0.1% to about 10%, or about 0.1% to about 11%, or about 0.1% to about 12%, or about 0.1% to about 13%, or about 0.1% to about 14%, or about 0.1% to about 15%, or about 0.1% to about 16%, or about 0.1% to about 17%, or about 0.1% to about 18%, or about 0.1% to about 19%, or about 0.1% to about 20%, or about 0.1% to about 21%, or about 0.1% to about 22%, or about 0.1% to about 23%, or about 0.1% to about 24%, or about 0.1% to about 25%; or between about 1% to about 2%, or about 1% to about 3%, or about 1% to about 4%, or about 1% to about 5%, or about 1% to about 6%, or about 1% to about 7%, or about 1% to about 8%, or about 1% to about 9%, or about 1% to about 10%, or about 1% to about 11%, or about 1% to about 12%, or about 1% to about 13%, or about 1% to about 14%, or about 1% to about 15%, or about 1% to about 16%, or about 1% to about 17%, or about 1% to about 18%, or about 1% to about 19%, or about 1% to about 20%, or about 1% to about 21%, or about 1% to about 22%, or about 1% to about 23%, or about 1% to about 24%, or about 1% to about 25%; or between about 10% to about 20%, or about 10% to about 25%, or about 10% to about 30%, or about 10% to about 35%, or about 10% to about 40%, or about 10% to about 45%, or about 10% to about 50%, or about 10% to about 55%, or about 10% to about 60%, or about 10% to about 65%, or about 10% to about 70%, or about 10% to about 75%, or about 10% to about 80%, or about 10% to about 85%, or about 10% to about 90%, or about 10% to about 100%.

The SPF described herein can have a variety of mechanical and physical properties depending on the degree of crystallinity of the SPF peptides and/or proteins. In an embodiment, an SPF composition of the present disclosure is not soluble in an aqueous solution due to the crystallinity of the protein. In an embodiment, an SPF composition of the present disclosure is soluble in an aqueous solution. In an embodiment, the SPFs of a composition of the present disclosure include a crystalline portion of about two-thirds and an amorphous region of about one-third. In an embodiment, the SPFs of a composition of the present disclosure include a crystalline portion of about one-half and an amorphous region of about one-half. In an embodiment, the SPFs of a composition of the present disclosure include a 99% crystalline portion and a 1% amorphous region. In an embodiment, the SPFs of a composition of the present disclosure include a 95% crystalline portion and a 5% amorphous region. In an embodiment, the SPFs of a composition of the present disclosure include a 90% crystalline portion and a 10% amorphous region. In an embodiment, the SPFs of a composition of the present disclosure include a 85% crystalline portion and a 15% amorphous region. In an embodiment, the SPFs of a composition of the present disclosure include a 80% crystalline portion and a 20% amorphous region. In an embodiment, the SPFs of a composition of the present disclosure include a 75% crystalline portion and a 25% amorphous region. In an embodiment, the SPFs of a composition of the present disclosure include a 70% crystalline portion and a 30% amorphous region. In an embodiment, the SPFs of a composition of the present disclosure include a 65% crystalline portion and a 35% amorphous region. In an embodiment, the SPFs of a composition of the present disclosure include a 60% crystalline portion and a 40% amorphous region. In an embodiment, the SPFs of a composition of the present disclosure include a 50% crystalline portion and a 50% amorphous region. In an embodiment, the SPFs of a composition of the present disclosure include a 40% crystalline portion and a 60% amorphous region. In an embodiment, the SPFs of a composition of the present disclosure include a 35% crystalline portion and a 65% amorphous region. In an embodiment, the SPFs of a composition of the present disclosure include a 30% crystalline portion and a 70% amorphous region. In an embodiment, the SPFs of a composition of the present disclosure include a 25% crystalline portion and a 75% amorphous region. In an embodiment, the SPFs of a composition of the present disclosure include a 20% crystalline portion and a 80% amorphous region. In an embodiment, the SPFs of a composition of the present disclosure include a 15% crystalline portion and a 85% amorphous region. In an embodiment, the SPFs of a composition of the present disclosure include a 10% crystalline portion and a 90% amorphous region. In an embodiment, the SPFs of a composition of the present disclosure include a 5% crystalline portion and a 90% amorphous region. In an embodiment, the SPFs of a composition of the present disclosure include a 1% crystalline portion and a 99% amorphous region.

In some embodiments, the physical and mechanical properties of the SPF vary with the degree of presence in the SPF composition of α-helix and/or random coil regions. In some embodiments, an SPF hydrogel disclosed herein has a protein structure that is substantially-free of α-helix and random coil regions. In aspects of these embodiments, a hydrogel has a protein structure including, e.g., about 5% α-helix and random coil regions, about 10% α-helix and random coil regions, about 15% α-helix and random coil regions, about 20% α-helix and random coil regions, about 25% α-helix and random coil regions, about 30% α-helix and random coil regions, about 35% α-helix and random coil regions, about 40% α-helix and random coil regions, about 45% α-helix and random coil regions, or about 50% α-helix and random coil regions. In other aspects of these embodiments, a hydrogel has a protein structure including, e.g., at most 5% α-helix and random coil regions, at most 10% α-helix and random coil regions, at most 15% α-helix and random coil regions, at most 20% α-helix and random coil regions, at most 25% α-helix and random coil regions, at most 30% α-helix and random coil regions, at most 35% α-helix and random coil regions, at most 40% α-helix and random coil regions, at most 45% α-helix and random coil regions, or at most 50% α-helix and random coil regions. In yet other aspects of these embodiments, a hydrogel has a protein structure including, e.g., about 5% to about 10% α-helix and random coil regions, about 5% to about 15% α-helix and random coil regions, about 5% to about 20% α-helix and random coil regions, about 5% to about 25% α-helix and random coil regions, about 5% to about 30% α-helix and random coil regions, about 5% to about 40% α-helix and random coil regions, about 5% to about 50% α-helix and random coil regions, about 10% to about 20% α-helix and random coil regions, about 10% to about 30% α-helix and random coil regions, about 15% to about 25% α-helix and random coil regions, about 15% to about 30% α-helix and random coil regions, or about 15% to about 35% α-helix and random coil regions.

In some embodiments, SPF solution compositions of the present disclosure have shelf stability, i.e., they will not slowly or spontaneously gel when stored in an aqueous solution and there, without apparent aggregation of fragments and/or increase in molecular weight over time, from 10 days to 3 years depending on storage conditions, percent silk, and number of shipments and shipment conditions. Additionally, pH may be altered to extend shelf-life and/or support shipping conditions by preventing premature folding and aggregation of the silk. In an embodiment, a SPF solution composition of the present disclosure has a shelf stability for up to 2 weeks at room temperature (RT). In an embodiment, a SPF solution composition of the present disclosure has a shelf stability for up to 4 weeks at RT. In an embodiment, a SPF solution composition of the present disclosure has a shelf stability for up to 6 weeks at RT. In an embodiment, a SPF solution composition of the present disclosure has a shelf stability for up to 8 weeks at RT. In an embodiment, a SPF solution composition of the present disclosure has a shelf stability for up to 10 weeks at RT. In an embodiment, a SPF solution composition of the present disclosure has a shelf stability for up to 12 weeks at RT. In an embodiment, a SPF solution composition of the present disclosure has a shelf stability ranging from about 4 weeks to about 52 weeks at RT. Table 1 below shows shelf stability test results for embodiments of SPF compositions of the present disclosure.

TABLE 1

Shelf Stability of SPF Compositions of the Present Disclosure

| % Silk | Temperature | Time to Gelation |
| --- | --- | --- |
| 2 | RT | 4 weeks |
| 2 | 4° C. | >9 weeks |
| 4 | RT | 4 weeks |
| 4 | 4° C. | >9 weeks |
| 6 | RT | 2 weeks |
| 6 | 4° C. | >9 weeks |

A known additive such as a vitamin (e.g., vitamin C) can be added to a SPF solution composition of the present disclosure to create a gel that is stable from 10 days to 3 years at room temperature (RT). Both examples, a SPF composition and the same with an additive, can be lyophilized for enhanced storage control ranging from 10 days to 10 years depending on storage and shipment conditions. The lyophilized silk powder can also be used as a raw ingredient in the medical, consumer, and electronic markets. Additionally, lyophilized silk powder can be resuspended in water, HFIP, or organic solution following storage to create silk solutions of varying concentrations, including higher concentration solutions than those produced initially. In another embodiment, the silk fibroin-based protein fragments are dried using a rototherm evaporator or other methods known in the art for creating a dry protein form containing less than 10% water by mass.

The SPFs used in the tissue fillers and methods disclosed herein can be manipulated and incorporated in various ways, for example in the form of a solution, which may be combined with other materials (e.g., HA) to prepare the tissue filler compositions described herein. Following are non-limiting examples of suitable ranges for various parameters in and for preparation of the silk solutions of the present disclosure. The silk solutions of the present disclosure may include one or more, but not necessarily all, of these parameters and may be prepared using various combinations of ranges of such parameters.

In an embodiment, the percent silk in the solution is less than 30%. In an embodiment, the percent silk in the solution is less than 25%. In an embodiment, the percent silk in the solution is less than 20%. In an embodiment, the percent silk in the solution is less than 19%. In an embodiment, the percent silk in the solution is less than 18%. In an embodiment, the percent silk in the solution is less than 17%. In an embodiment, the percent silk in the solution is less than 16%. In an embodiment, the percent silk in the solution is less than 15%. In an embodiment, the percent silk in the solution is less than 14%. In an embodiment, the percent silk in the solution is less than 13%. In an embodiment, the percent silk in the solution is less than 12%. In an embodiment, the percent silk in the solution is less than 11%. In an embodiment, the percent silk in the solution is less than 10%. In an embodiment, the percent silk in the solution is less than 9%. In an embodiment, the percent silk in the solution is less than 8%. In an embodiment, the percent silk in the solution is less than 7%. In an embodiment, the percent silk in the solution is less than 6%. In an embodiment, the percent silk in the solution is less than 5%. In an embodiment, the percent silk in the solution is less than 4%. In an embodiment, the percent silk in the solution is less than 3%. In an embodiment, the percent silk in the solution is less than 2%. In an embodiment, the percent silk in the solution is less than 1%. In an embodiment, the percent silk in the solution is less than 0.9%. In an embodiment, the percent silk in the solution is less than 0.8%. In an embodiment, the percent silk in the solution is less than 0.7%. In an embodiment, the percent silk in the solution is less than 0.6%. In an embodiment, the percent silk in the solution is less than 0.5%. In an embodiment, the percent silk in the solution is less than 0.4%. In an embodiment, the percent silk in the solution is less than 0.3%. In an embodiment, the percent silk in the solution is less than 0.2%. In an embodiment, the percent silk in the solution is less than 0.1%. In an embodiment, the percent silk in the solution is greater than 0.1%. In an embodiment, the percent silk in the solution is greater than 0.2%. In an embodiment, the percent silk in the solution is greater than 0.3%. In an embodiment, the percent silk in the solution is greater than 0.4%. In an embodiment, the percent silk in the solution is greater than 0.5%. In an embodiment, the percent silk in the solution is greater than 0.6%. In an embodiment, the percent silk in the solution is greater than 0.7%. In an embodiment, the percent silk in the solution is greater than 0.8%. In an embodiment, the percent silk in the solution is greater than 0.9%. In an embodiment, the percent silk in the solution is greater than 1%. In an embodiment, the percent silk in the solution is greater than 2%. In an embodiment, the percent silk in the solution is greater than 3%. In an embodiment, the percent silk in the solution is greater than 4%. In an embodiment, the percent silk in the solution is greater than 5%. In an embodiment, the percent silk in the solution is greater than 6%. In an embodiment, the percent silk in the solution is greater than 7%. In an embodiment, the percent silk in the solution is greater than 8%. In an embodiment, the percent silk in the solution is greater than 9%. In an embodiment, the percent silk in the solution is greater than 10%. In an embodiment, the percent silk in the solution is greater than 11%. In an embodiment, the percent silk in the solution is greater than 12%. In an embodiment, the percent silk in the solution is greater than 13%. In an embodiment, the percent silk in the solution is greater than 14%. In an embodiment, the percent silk in the solution is greater than 15%. In an embodiment, die percent silk in the solution is greater than 16%. In an embodiment, the percent silk in the solution is greater than 17%. In an embodiment, the percent silk in the solution is greater than 18%. In an embodiment, the percent silk in the solution is greater than 19%. In an embodiment, the percent silk in the solution is greater than 20%. In an embodiment, die percent silk in the solution is greater than 25%. In an embodiment, the percent silk in the solution is between 0.1% and 30%. In an embodiment, the percent silk in the solution is between 0.1% and 25%. In an embodiment, the percent silk in the solution is between 0.1% and 20%. In an embodiment, the percent silk in the solution is between 0.1% and 15%. In an embodiment, the percent silk in the solution is between 0.1% and 10%. In an embodiment, the percent silk in the solution is between 0.1% and 9%. In an embodiment, the percent silk in the solution is between 0.1% and 8%. In an embodiment, the percent silk in the solution is between 0.1% and 7%. In an embodiment, the percent silk in the solution is between 0.1% and 6.5%. In an embodiment, the percent silk in the solution is between 0.1% and 6%. In an embodiment, the percent silk in the solution is between 0.1% and 5.5%. In an embodiment, the percent silk in the solution is between 0.1% and 5%. In an embodiment, the percent silk in the solution is between 0.1% and 4.5%. In an embodiment, the percent silk in the solution is between 0.1% and 4%. In an embodiment, the percent silk in the solution is between 0.1% and 3.5%. In an embodiment, the percent silk in the solution is between 0.1% and 3%. In an embodiment, the percent silk in the solution is between 0.1% and 2.5%. In an embodiment, the percent silk in the solution is between 0.1% and 2.0%. In an embodiment, the percent silk in the solution is between 0.1% and 2.4%. In an embodiment, the percent silk in the solution is between 0.5% and 5%. In an embodiment, the percent silk in the solution is between 0.5% and 4.5%. In an embodiment, the percent silk in the solution is between 0.5% and 4%. In an embodiment, the percent silk in the solution is between 0.5% and 3.5%. In an embodiment, the percent silk in the solution is between 0.5% and 3%. In an embodiment, the percent silk in the solution is between 0.5% and 2.5%. In an embodiment, the percent silk in the solution is between 1 and 4%. In an embodiment, the percent silk in the solution is between 1 and 3.5%. In an embodiment, the percent silk in the solution is between 1 and 3%. In an embodiment, the percent silk in the solution is between 1 and 2.5%. In an embodiment, the percent silk in the solution is between 1 and 2.4%. In an embodiment, the percent silk in the solution is between 1 and 2%. In an embodiment, the percent silk in the solution is between 20% and 30%. In an embodiment, the percent silk in the solution is between 0.1% and 6%. In an embodiment, the percent silk in the solution is between 6% and 10%. In an embodiment, the percent silk in the solution is between 6% and 8%. In an embodiment, the percent silk in the solution is between 6% and 9%. In an embodiment, the percent silk in the solution is between 10% and 20%. In an embodiment, the percent silk in the solution is between 11% and 19%. In an embodiment, the percent silk in the solution is between 12% and 18%. In an embodiment, the percent silk in the solution is between 13% and 17%. In an embodiment, the percent silk in the solution is between 14% and 16%.

In an embodiment, the silk compositions described herein may be combined with HA to form a tissue filler composition. In an embodiment, the percent silk in the tissue filler composition by weight is less than 30%. In an embodiment, the percent silk in the tissue filler composition by weight is less than 25%. In an embodiment, the percent silk in the tissue filler composition by weight is less than 20%. In an embodiment, the percent silk in the tissue filler composition by weight is less than 19%. In an embodiment, the percent silk in the tissue filler composition by weight is less than 18%. In an embodiment, the percent silk in the tissue filler composition by weight is less than 17%. In an embodiment, the percent silk in the tissue filler composition by weight is less than 16%. In an embodiment, the percent silk in the tissue filler composition by weight is less than 15%. In an embodiment, the percent silk in the tissue filler composition by weight is less than 14%. In an embodiment, the percent silk in the tissue filler composition by weight is less than 13%. In an embodiment, the percent silk in the tissue filler composition by weight is less than 12%. In an embodiment, the percent silk in the tissue filler composition by weight is less than 11%. In an embodiment, the percent silk in the tissue filler composition by weight is less than 10%. In an embodiment, the percent silk in the tissue filler composition by weight is less than 9%. In an embodiment, the percent silk in the tissue filler composition by weight is less than 8%. In an embodiment, the percent silk in the tissue filler composition by weight is less than 7%. In an embodiment, the percent silk in the tissue filler composition by weight is less than 6%. In an embodiment, the percent silk in the tissue filler composition by weight is less than 5%. In an embodiment, the percent silk in the tissue filler composition by weight is less than 4%. In an embodiment, the percent silk in the tissue filler composition by weight is less than 3%. In an embodiment, the percent silk in the tissue filler composition by weight is less than 2%. In an embodiment, the percent silk in the tissue filler composition by weight is less than 1%. In an embodiment, the percent silk in the tissue filler composition by weight is less than 0.9%. In an embodiment, the percent silk in the tissue filler composition by weight is less than 0.8%. In an embodiment, the percent silk in the tissue filler composition by weight is less than 0.7%. In an embodiment, the percent silk in the tissue filler composition by weight is less than 0.6%. In an embodiment, the percent silk in the tissue filler composition by weight is less than 0.5%. In an embodiment, the percent silk in the tissue filler composition by weight is less than 0.4%. In an embodiment, the percent silk in the tissue filler composition by weight is less than 0.3%. In an embodiment, the percent silk in the tissue filler composition by weight is less than 0.2%. In an embodiment, the percent silk in the tissue filler composition by weight is less than 0.1%. In an embodiment, the percent silk in the tissue filler composition by weight is greater than 0.1%. In an embodiment, the percent silk in the tissue filler composition by weight is greater than 0.2%. In an embodiment, the percent silk in the tissue filler composition by weight is greater than 0.3%. In an embodiment, the percent silk in the tissue filler composition by weight is greater than 0.4%. In an embodiment, the percent silk in the tissue filler composition by weight is greater than 0.5%. In an embodiment, the percent silk in the tissue filler composition by weight is greater than 0.6%. In an embodiment, the percent silk in the tissue filler composition by weight is greater than 0.7%. In an embodiment, the percent silk in the tissue filler composition by weight is greater than 0.8%. In an embodiment, the percent silk in the tissue filler composition by weight is greater than 0.9%. In an embodiment, the percent silk in the tissue filler composition by weight is greater than 1%. In an embodiment, the percent silk in the tissue filler composition by weight is greater than 2%. In an embodiment, the percent silk in the tissue filler composition by weight is greater than 3%. In an embodiment, the percent silk in the tissue filler composition by weight is greater than 4%. In an embodiment, the percent silk in the tissue filler composition by weight is greater than 5%. In an embodiment, the percent silk in the tissue filler composition by weight is greater than 6%. In an embodiment, the percent silk in the tissue filler composition by weight is greater than 7%. In an embodiment, the percent silk in the tissue filler composition by weight is greater than 8%. In an embodiment, the percent silk in the tissue filler composition by weight is greater than 9%. In an embodiment, the percent silk in the tissue filler composition by weight is greater than 10%. In an embodiment, the percent silk in the tissue filler composition by weight is greater than 11%. In an embodiment, the percent silk in the tissue filler composition by weight is greater than 12%. In an embodiment, the percent silk in the tissue filler composition by weight is greater than 13%. In an embodiment, the percent silk in the tissue filler composition by weight is greater than 14%. In an embodiment, the percent silk in the tissue filler composition by weight is greater than 15%. In an embodiment, the percent silk in the tissue filler composition by weight is greater than 16%. In an embodiment, the percent silk in the tissue filler composition by weight is greater than 17%. In an embodiment, the percent silk in the tissue filler composition by weight is greater than 18%. In an embodiment, the percent silk in the tissue filler composition by weight is greater than 19%. In an embodiment, the percent silk in the tissue filler composition by weight is greater than 20%. In an embodiment, the percent silk in the tissue filler composition by weight is greater than 25%. In an embodiment, the percent silk in the tissue filler composition by weight is between 0.1% and 30%. In an embodiment, the percent silk in the tissue filler composition by weight is between 0.1% and 25%. In an embodiment, the percent silk in the tissue filler composition by weight is between 0.1% and 20%. In an embodiment, the percent silk in the tissue filler composition by weight is between 0.1% and 15%. In an embodiment, the percent silk in the tissue filler composition by weight is between 0.1% and 10%. In an embodiment, the percent silk in the tissue filler composition by weight is between 0.1% and 9%. In an embodiment, the percent silk in the tissue filler composition by weight is between 0.1% and 8%. In an embodiment, the percent silk in the tissue filler composition by weight is between 0.1% and 7%. In an embodiment, the percent silk in the tissue filler composition by weight is between 0.1% and 6.5%. In an embodiment, the percent silk in the tissue filler composition by weight is between 0.1% and 6%. In an embodiment, the percent silk in the tissue filler composition by weight is between 0.1% and 5.5%. In an embodiment, the percent silk in the tissue filler composition by weight is between 0.1% and 5%. In an embodiment, the percent silk in the tissue filler composition by weight is between 0.1% and 4.5%. In an embodiment, the percent silk in the tissue filler composition by weight is between 0.1% and 4%. In an embodiment, the percent silk in the tissue filler composition by weight is between 0.1% and 3.5%. In an embodiment, the percent silk in the tissue filler composition by weight is between 0.1% and 3%. In an embodiment, the percent silk in the tissue filler composition by weight is between 0.1% and 2.5%. In an embodiment, the percent silk in the tissue filler composition by weight is between 0.1% and 2.0%. In an embodiment, the percent silk in the tissue filler composition by weight is between 0.1% and 2.4%. In an embodiment, the percent silk in the tissue filler composition by weight is between 0.5% and 5%. In an embodiment, the percent silk in the tissue filler composition by weight is between 0.5% and 4.5%. In an embodiment, the percent silk in the tissue filler composition by weight is between 0.5% and 4%. In an embodiment, the percent silk in the tissue filler composition by weight is between 0.5% and 3.5%. In an embodiment, the percent silk in the tissue filler composition by weight is between 0.5% and 3%. In an embodiment, the percent silk in the tissue filler composition by weight is between 0.5% and 2.5%. In an embodiment, the percent silk in the tissue filler composition by weight is between 1 and 4%. In an embodiment, the percent silk in the tissue filler composition by weight is between 1 and 3.5%. In an embodiment, the percent silk in the tissue filler composition by weight is between 1 and 3%. In an embodiment, the percent silk in the tissue filler composition by weight is between 1 and 2.5%. In an embodiment, the percent silk in the tissue filler composition by weight is between 1 and 2.4%. In an embodiment, the percent silk in the tissue filler composition by weight is between 1 and 2%. In an embodiment, the percent silk in the tissue filler composition by weight is between 20% and 30%. In an embodiment, the percent silk in the tissue filler composition by weight is between 0.1% and 6%. In an embodiment, the percent silk in the tissue filler composition by weight is between 6% and 10%. In an embodiment, the percent silk in the tissue filler composition by weight is between 6% and 8%. In an embodiment, the percent silk in the tissue filler composition by weight is between 6% and 9%. In an embodiment, the percent silk in the tissue filler composition by weight is between 10% and 20%. In an embodiment, the percent silk in the tissue filler composition by weight is between 11% and 19%. In an embodiment, the percent silk in the tissue filler composition by weight is between 12% and 18%. In an embodiment, the percent silk in the tissue filler composition by weight is between 13% and 17%. In an embodiment, the percent silk in the tissue filler composition by weight is between 14% and 16%.

In an embodiment, the percent sericin in the solution or tissue filler composition is non-detectable to 30%. In an embodiment, the percent sericin in the solution or tissue filler composition is non-detectable to 5%. In an embodiment, the percent sericin in the solution or tissue filler composition is 1%. In an embodiment, the percent sericin in the solution or tissue filler composition is 2%. In an embodiment, the percent sericin in the solution or tissue filler composition is 3%. In an embodiment, the percent sericin in the solution or tissue filler composition is 4%. In an embodiment, the percent sericin in the solution or tissue filler composition is 5%. In an embodiment, the percent sericin in the solution or tissue filler composition is 10%. In an embodiment, the percent sericin in the solution or tissue filler composition is 30%.

In an embodiment, the stability of the LiBr-silk fragment solution is 0 to 1 year. In an embodiment, the stability of the LiBr-silk fragment solution is 0 to 2 years. In an embodiment, the stability of the LiBr-silk fragment solution is 0 to 3 years. In an embodiment, the stability of the LiBr-silk fragment solution is 0 to 4 years. In an embodiment, the stability of the LiBr-silk fragment solution is 0 to 5 years. In an embodiment, the stability of the LiBr-silk fragment solution is 1 to 2 years. In an embodiment, the stability of the LiBr-silk fragment solution is 1 to 3 years. In an embodiment, the stability of the LiBr-silk fragment solution is 1 to 4 years. In an embodiment, the stability of the LiBr-silk fragment solution is 1 to 5 years. In an embodiment, the stability of the LiBr-silk fragment solution is 2 to 3 years. In an embodiment, the stability of the LiBr-silk fragment solution is 2 to 4 years. In an embodiment, the stability of the LiBr-silk fragment solution is 2 to 5 years. In an embodiment, the stability of the LiBr-silk fragment solution is 3 to 4 years. In an embodiment, the stability of the LiBr-silk fragment solution is 3 to 5 years. In an embodiment, the stability of the LiBr-silk fragment solution is 4 to 5 years.

In an embodiment, the stability of a silk-fibroin based protein fragment compositions that may be included in the tissue fillers of the present disclosure is 10 days to 6 months. In an embodiment, the stability of a silk-fibroin based protein fragment compositions that may be included in the tissue fillers of the present disclosure is 6 months to 12 months. In an embodiment, the stability of a silk-fibroin based protein fragment compositions that may be included in the tissue fillers of the present disclosure is 12 months to 18 months. In an embodiment, the stability of a silk-fibroin based protein fragment compositions that may be included in the tissue fillers of the present disclosure is 18 months to 24 months. In an embodiment, the stability of a silk-fibroin based protein fragment compositions that may be included in the tissue fillers of the present disclosure is 24 months to 30 months. In an embodiment, the stability of a silk-fibroin based protein fragment compositions that may be included in the tissue fillers of the present disclosure is 30 months to 36 months. In an embodiment, the stability of a silk-fibroin based protein fragment compositions that may be included in the tissue fillers of the present disclosure is 36 months to 48 months. In an embodiment, the stability of a silk-fibroin based protein fragment compositions that may be included in the tissue fillers of the present disclosure is 48 months to 60 months.

In an embodiment, silk fibroin-based protein fragments incorporated into the tissue fillers described herein have having an average weight average molecular weight ranging from 1 kDa to 250 kDa. In an embodiment, silk fibroin-based protein fragments incorporated into the tissue fillers described herein have having an average weight average molecular weight ranging from 5 kDa to 150 kDa. In an embodiment, silk fibroin-based protein fragments incorporated into the tissue fillers described herein have having an average weight average molecular weight ranging from 1 kDa to 6 kDa. In an embodiment, silk fibroin-based protein fragments incorporated into the tissue fillers described herein have an average weight average molecular weight ranging from 6 kDa to 17 kDa. In an embodiment, silk fibroin-based protein fragments incorporated into the tissue fillers described herein have an average weight average molecular weight ranging from 17 kDa to 39 kDa. In an embodiment, silk fibroin-based protein fragments incorporated into the tissue fillers described herein have an average weight average molecular weight ranging from 39 kDa to 80 kDa. In an embodiment, silk fibroin-based protein fragments incorporated into the tissue fillers described herein have an average weight average molecular weight ranging from 80 kDa to 150 kDa.

In an embodiment, silk fibroin-based protein fragments incorporated into the tissue fillers described herein have an average weight average molecular weight ranging from 1 kDa to 250 kDa. In an embodiment, silk fibroin-based protein fragments incorporated into the tissue fillers described herein have an average weight average molecular weight ranging from 1 kDa to 240 kDa. In an embodiment, silk fibroin-based protein fragments incorporated into the tissue fillers described herein have an average weight average molecular weight ranging from 1 kDa to 230 kDa. In an embodiment, silk fibroin-based protein fragments incorporated into the tissue fillers described herein have an average weight average molecular weight ranging from 1 kDa to 220 kDa. In an embodiment, silk fibroin-based protein fragments incorporated into the tissue fillers described herein have an average weight average molecular weight ranging from 1 kDa to 210 kDa. In an embodiment, silk fibroin-based protein fragments incorporated into the tissue fillers described herein have an average weight average molecular weight ranging from 1 kDa to 200 kDa. In an embodiment, silk fibroin-based protein fragments incorporated into the tissue fillers described herein have an average weight average molecular weight ranging from 1 kDa to 190 kDa. In an embodiment, silk fibroin-based protein fragments incorporated into the tissue fillers described herein have an average weight average molecular weight ranging from 1 kDa to 180 kDa. In an embodiment, silk fibroin-based protein fragments incorporated into the tissue fillers described herein have an average weight average molecular weight ranging from 1 kDa to 170 kDa. In an embodiment, silk fibroin-based protein fragments incorporated into the tissue fillers described herein have an average weight average molecular weight ranging from 1 kDa to 160 kDa. In an embodiment, silk fibroin-based protein fragments incorporated into the tissue fillers described herein have an average weight average molecular weight ranging from 1 kDa to 150 kDa. In an embodiment, silk fibroin-based protein fragments incorporated into the tissue fillers described herein have an average weight average molecular weight ranging from 1 kDa to 140 kDa. In an embodiment, silk fibroin-based protein fragments incorporated into the tissue fillers described herein have an average weight average molecular weight ranging from 1 kDa to 130 kDa. In an embodiment, silk fibroin-based protein fragments incorporated into the tissue fillers described herein have an average weight average molecular weight ranging from 1 kDa to 120 kDa. In an embodiment, silk fibroin-based protein fragments incorporated into the tissue fillers described herein have an average weight average molecular weight ranging from 1 kDa to 110 kDa. In an embodiment, silk fibroin-based protein fragments incorporated into the tissue fillers described herein have an average weight average molecular weight ranging from 1 kDa to 100 kDa. In an embodiment, silk fibroin-based protein fragments incorporated into the tissue fillers described herein have an average weight average molecular weight ranging from 1 kDa to 90 kDa. In an embodiment, silk fibroin-based protein fragments incorporated into the tissue fillers described herein have an average weight average molecular weight ranging from 1 kDa to 80 kDa. In an embodiment, silk fibroin-based protein fragments incorporated into the tissue fillers described herein have an average weight average molecular weight ranging from 1 kDa to 70 kDa. In an embodiment, silk fibroin-based protein fragments incorporated into the tissue fillers described herein have an average weight average molecular weight ranging from 1 kDa to 60 kDa. In an embodiment, silk fibroin-based protein fragments incorporated into the tissue fillers described herein have an average weight average molecular weight ranging from 1 kDa to 50 kDa. In an embodiment, silk fibroin-based protein fragments incorporated into the tissue fillers described herein have an average weight average molecular weight ranging from 1 kDa to 40 kDa. In an embodiment, silk fibroin-based protein fragments incorporated into the tissue fillers described herein have an average weight average molecular weight ranging from 1 kDa to 30 kDa. In an embodiment, silk fibroin-based protein fragments incorporated into the tissue fillers described herein have an average weight average molecular weight ranging from 1 kDa to 20 kDa. In an embodiment, silk fibroin-based protein fragments incorporated into the tissue fillers described herein have an average weight average molecular weight ranging from 1 kDa to 10 kDa.

In an embodiment, silk fibroin-based protein fragments incorporated into the tissue fillers described herein have an average weight average molecular weight ranging from 1 to 5 kDa. In an embodiment, silk fibroin-based protein fragments incorporated into the tissue fillers described herein have an average weight average molecular weight ranging from 5 to 10 kDa. In an embodiment, silk fibroin-based protein fragments incorporated into the tissue fillers described herein have an average weight average molecular weight ranging from 10 to 15 kDa. In an embodiment, silk fibroin-based protein fragments incorporated into the tissue fillers described herein have an average weight average molecular weight ranging from 15 to 20 kDa. In an embodiment, silk fibroin-based protein fragments incorporated into the tissue fillers described herein have an average weight average molecular weight ranging from 20 to 25 kDa. In an embodiment, silk fibroin-based protein fragments incorporated into the tissue fillers described herein have an average weight average molecular weight ranging from 25 to 30 kDa. In an embodiment, silk fibroin-based protein fragments incorporated into the tissue fillers described herein have an average weight average molecular weight ranging from 30 to 35 kDa. In an embodiment, silk fibroin-based protein fragments incorporated into the tissue fillers described herein have an average weight average molecular weight ranging from 35 to 40 kDa. In an embodiment, silk fibroin-based protein fragments incorporated into the tissue fillers described herein have an average weight average molecular weight ranging from 40 to 45 kDa. In an embodiment, silk fibroin-based protein fragments incorporated into the tissue fillers described herein have an average weight average molecular weight ranging from 45 to 50 kDa. In an embodiment, silk fibroin-based protein fragments incorporated into the tissue fillers described herein have an average weight average molecular weight ranging from 50 to 55 kDa. In an embodiment, silk fibroin-based protein fragments incorporated into the tissue fillers described herein have an average weight average molecular weight ranging from 55 to 60 kDa. In an embodiment, silk fibroin-based protein fragments incorporated into the tissue fillers described herein have an average weight average molecular weight ranging from 60 to 65 kDa. In an embodiment, silk fibroin-based protein fragments incorporated into the tissue fillers described herein have an average weight average molecular weight ranging from 65 to 70 kDa. In an embodiment, silk fibroin-based protein fragments incorporated into the tissue fillers described herein have an average weight average molecular weight ranging from 70 to 75 kDa. In an embodiment, silk fibroin-based protein fragments incorporated into the tissue fillers described herein have an average weight average molecular weight ranging from 75 to 80 kDa. In an embodiment, silk fibroin-based protein fragments incorporated into the tissue fillers described herein have an average weight average molecular weight ranging from 80 to 85 kDa. In an embodiment, silk fibroin-based protein fragments incorporated into the tissue fillers described herein have an average weight average molecular weight ranging from 85 to 90 kDa. In an embodiment, silk fibroin-based protein fragments incorporated into the tissue fillers described herein have an average weight average molecular weight ranging from 90 to 95 kDa. In an embodiment, silk fibroin-based protein fragments incorporated into the tissue fillers described herein have an average weight average molecular weight ranging from 95 to 100 kDa. In an embodiment, silk fibroin-based protein fragments incorporated into the tissue fillers described herein have an average weight average molecular weight ranging from 100 to 105 kDa. In an embodiment, silk fibroin-based protein fragments incorporated into the tissue fillers described herein have an average weight average molecular weight ranging from 105 to 110 kDa. In an embodiment, silk fibroin-based protein fragments incorporated into the tissue fillers described herein have an average weight average molecular weight ranging from 110 to 115 kDa. In an embodiment, silk fibroin-based protein fragments incorporated into the tissue fillers described herein have an average weight average molecular weight ranging from 115 to 120 kDa. In an embodiment, silk fibroin-based protein fragments incorporated into the tissue fillers described herein have an average weight average molecular weight ranging from 120 to 125 kDa. In an embodiment, silk fibroin-based protein fragments incorporated into the tissue fillers described herein have an average weight average molecular weight ranging from 125 to 130 kDa. In an embodiment, silk fibroin-based protein fragments incorporated into the tissue fillers described herein have an average weight average molecular weight ranging from 130 to 135 kDa. In an embodiment, silk fibroin-based protein fragments incorporated into the tissue fillers described herein have an average weight average molecular weight ranging from 135 to 140 kDa. In an embodiment, silk fibroin-based protein fragments incorporated into the tissue fillers described herein have an average weight average molecular weight ranging from 140 to 145 kDa. In an embodiment, silk fibroin-based protein fragments incorporated into the tissue fillers described herein have an average weight average molecular weight ranging from 145 to 150 kDa. In an embodiment, silk fibroin-based protein fragments incorporated into the tissue fillers described herein have an average weight average molecular weight ranging from 150 to 155 kDa. In an embodiment, silk fibroin-based protein fragments incorporated into the tissue fillers described herein have an average weight average molecular weight ranging from 155 to 160 kDa. In an embodiment, silk fibroin-based protein fragments incorporated into the tissue fillers described herein have an average weight average molecular weight ranging from 160 to 165 kDa. In an embodiment, silk fibroin-based protein fragments incorporated into the tissue fillers described herein have an average weight average molecular weight ranging from 165 to 170 kDa. In an embodiment, silk fibroin-based protein fragments incorporated into the tissue fillers described herein have an average weight average molecular weight ranging from 170 to 175 kDa. In an embodiment, silk fibroin-based protein fragments incorporated into the tissue fillers described herein have an average weight average molecular weight ranging from 175 to 180 kDa. In an embodiment, silk fibroin-based protein fragments incorporated into the tissue fillers described herein have an average weight average molecular weight ranging from 180 to 185 kDa. In an embodiment, silk fibroin-based protein fragments incorporated into the tissue fillers described herein have an average weight average molecular weight ranging from 185 to 190 kDa. In an embodiment, silk fibroin-based protein fragments incorporated into the tissue fillers described herein have an average weight average molecular weight ranging from 190 to 195 kDa. In an embodiment, silk fibroin-based protein fragments incorporated into the tissue fillers described herein have an average weight average molecular weight ranging from 195 to 200 kDa. In an embodiment, silk fibroin-based protein fragments incorporated into the tissue fillers described herein have an average weight average molecular weight ranging from 200 to 205 kDa. In an embodiment, silk fibroin-based protein fragments incorporated into the tissue fillers described herein have having an average weight average molecular weight ranging from 205 to 210 kDa. In an embodiment, silk fibroin-based protein fragments incorporated into the tissue fillers described herein have an average weight average molecular weight ranging from 210 to 215 kDa. In an embodiment, silk fibroin-based protein fragments incorporated into the tissue fillers described herein have an average weight average molecular weight ranging from 215 to 220 kDa. In an embodiment, silk fibroin-based protein fragments incorporated into the tissue fillers described herein have an average weight average molecular weight ranging from 220 to 225 kDa. In an embodiment, silk fibroin-based protein fragments incorporated into the tissue fillers described herein have an average weight average molecular weight ranging from 225 to 230 kDa. In an embodiment, silk fibroin-based protein fragments incorporated into the tissue fillers described herein have an average weight average molecular weight ranging from 230 to 235 kDa. In an embodiment, silk fibroin-based protein fragments incorporated into the tissue fillers described herein have an average weight average molecular weight ranging from 235 to 240 kDa. In an embodiment, silk fibroin-based protein fragments incorporated into the tissue fillers described herein have an average weight average molecular weight ranging from 240 to 245 kDa. In an embodiment, silk fibroin-based protein fragments incorporated into the tissue fillers described herein have an average weight average molecular weight ranging from 245 to 250 kDa. In an embodiment, silk fibroin-based protein fragments incorporated into the tissue fillers described herein have an average weight average molecular weight ranging from 250 to 255 kDa. In an embodiment, silk fibroin-based protein fragments incorporated into the tissue fillers described herein have an average weight average molecular weight ranging from 255 to 260 kDa. In an embodiment, silk fibroin-based protein fragments incorporated into the tissue fillers described herein have an average weight average molecular weight ranging from 260 to 265 kDa. In an embodiment, silk fibroin-based protein fragments incorporated into the tissue fillers described herein have an average weight average molecular weight ranging from 265 to 270 kDa. In an embodiment, silk fibroin-based protein fragments incorporated into the tissue fillers described herein have an average weight average molecular weight ranging from 270 to 275 kDa. In an embodiment, silk fibroin-based protein fragments incorporated into the tissue fillers described herein have an average weight average molecular weight ranging from 275 to 280 kDa. In an embodiment, silk fibroin-based protein fragments incorporated into the tissue fillers described herein have an average weight average molecular weight ranging from 280 to 285 kDa. In an embodiment, silk fibroin-based protein fragments incorporated into the tissue fillers described herein have an average weight average molecular weight ranging from 285 to 290 kDa. In an embodiment, silk fibroin-based protein fragments incorporated into the tissue fillers described herein have an average weight average molecular weight ranging from 290 to 295 kDa. In an embodiment, silk fibroin-based protein fragments incorporated into the tissue fillers described herein have an average weight average molecular weight ranging from 295 to 300 kDa. In an embodiment, silk fibroin-based protein fragments incorporated into the tissue fillers described herein have an average weight average molecular weight ranging from 300 to 305 kDa. In an embodiment, silk fibroin-based protein fragments incorporated into the tissue fillers described herein have an average weight average molecular weight ranging from 305 to 310 kDa. In an embodiment, silk fibroin-based protein fragments incorporated into the tissue fillers described herein have an average weight average molecular weight ranging from 310 to 315 kDa. In an embodiment, silk fibroin-based protein fragments incorporated into the tissue fillers described herein have an average weight average molecular weight ranging from 315 to 320 kDa. In an embodiment, silk fibroin-based protein fragments incorporated into the tissue fillers described herein have an average weight average molecular weight ranging from 320 to 325 kDa. In an embodiment, silk fibroin-based protein fragments incorporated into the tissue fillers described herein have an average weight average molecular weight ranging from 325 to 330 kDa. In an embodiment, silk fibroin-based protein fragments incorporated into the tissue fillers described herein have an average weight average molecular weight ranging from 330 to 335 kDa. In an embodiment, silk fibroin-based protein fragments incorporated into the tissue fillers described herein have an average weight average molecular weight ranging from 35 to 340 kDa. In an embodiment, silk fibroin-based protein fragments incorporated into the tissue fillers described herein have an average weight average molecular weight ranging from 340 to 345 kDa. In an embodiment, silk fibroin-based protein fragments incorporated into the tissue fillers described herein have an average weight average molecular weight ranging from 345 to 350 kDa.

In an embodiment, the tissue fillers described herein may include silk protein comprising one or more of low molecular weight silk, medium molecular weight silk, and high molecular weight silk.

In an embodiment, the tissue fillers described herein may include silk protein comprising one or more of low molecular weight silk, medium molecular weight silk, and high molecular weight silk. In an embodiment, the tissue fillers described herein may include silk protein comprising low molecular weight silk and medium molecular weight silk. In an embodiment, the tissue fillers described herein may include silk protein comprising low molecular weight silk and high molecular weight silk. In an embodiment, the tissue fillers described herein may include silk protein comprising medium molecular weight silk and high molecular weight silk. In an embodiment, the tissue fillers described herein may include silk protein comprising low molecular weight silk, medium molecular weight silk, and high molecular weight silk.

In an embodiment, the tissue fillers described herein may include silk protein comprising low molecular weight silk and medium molecular weight silk. In some embodiments, the w/w ratio between low molecular weight silk and medium molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and medium molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and medium molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99. In an embodiment, the w/w ratio between low molecular weight silk and medium molecular weight silk is about 9:1, about 8:1, about 7:1, about 6:1, about 5:1, about 4:1, about 3:1, about 2:1, or about 1:1. In an embodiment, the w/w ratio between low molecular weight silk and medium molecular weight silk is about 1:9, about 1:8, about 1:7, about 1:6, about 1:5, about 1:4, about 1:3, about 1:2, or about 1:1.

In an embodiment, the tissue fillers described herein may include silk protein comprising low molecular weight silk and high molecular weight silk. In some embodiments, the w/w ratio between low molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between low molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between low molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the tissue fillers described herein may include silk protein comprising medium molecular weight silk and high molecular weight silk. In some embodiments, the w/w ratio between medium molecular weight silk and high molecular weight silk is between about 99:1 to about 1:99, between about 95:5 to about 5:95, between about 90:10 to about 10:90, between about 75:25 to about 25:75, between about 65:35 to about 35:65, or between about 55:45 to about 45:55. In some embodiments, the w/w ratio between medium molecular weight silk and high molecular weight silk is between about 99:1 to about 55:45, between about 95:5 to about 45:55, between about 90:10 to about 35:65, between about 75:25 to about 15:85, between about 65:35 to about 10:90, or between about 55:45 to about 1:99. In an embodiment, the w/w ratio between medium molecular weight silk and high molecular weight silk is about 99:1, about 98:2, about 97:3, about 96:4, about 95:5, about 94:6, about 93:7, about 92:8, about 91:9, about 90:10, about 89:11, about 88:12, about 87:13, about 86:14, about 85:15, about 84:16, about 83:17, about 82:18, about 81:19, about 80:20, about 79:21, about 78:22, about 77:23, about 76:24, about 75:25, about 74:26, about 73:27, about 72:28, about 71:29, about 70:30, about 69:31, about 68:32, about 67:33, about 66:34, about 65:35, about 64:36, about 63:37, about 62:38, about 61:39, about 60:40, about 59:41, about 58:42, about 57:43, about 56:44, about 55:45, about 54:46, about 53:47, about 52:48, about 51:49, about 50:50, about 49:51, about 48:52, about 47:53, about 46:54, about 45:55, about 44:56, about 43:57, about 42:58, about 41:59, about 40:60, about 39:61, about 38:62, about 37:63, about 36:64, about 35:65, about 34:66, about 33:67, about 32:68, about 31:69, about 30:70, about 29:71, about 28:72, about 27:73, about 26:74, about 25:75, about 24:76, about 23:77, about 22:78, about 21:79, about 20:80, about 19:81, about 18:82, about 17:83, about 16:84, about 15:85, about 14:86, about 13:87, about 12:88, about 11:89, about 10:90, about 9:91, about 8:92, about 7:93, about 6:94, about 5:95, about 4:96, about 3:97, about 2:98, or about 1:99.

In an embodiment, the tissue fillers described herein may include silk protein comprising low molecular weight silk, medium molecular weight silk, and high molecular weight silk. In an embodiment, the w/w ratio between low molecular weight silk, medium molecular weight silk, and high molecular weight silk is about 1:1:8, 1:2:7, 1:3:6, 1:4:5, 1:5:4, 1:6:3, 1:7:2, 1:8:1, 2:1:7, 2:2:6, 2:3:5, 2:4:4, 2:5:3, 2:6:2, 2:7:1, 3:1:6, 3:2:5, 3:3:4, 3:4:3, 3:5:2, 3:6:1, 4:1:5, 4:2:4, 4:3:3, 4:4:2, 4:5:1, 5:1:4, 5:2:3, 5:3:2, 5:4:1, 6:1:3, 6:2:2, 6:3:1, 7:1:2, 7:2:1, or 8:1:1. In an embodiment, the w/w ratio between low molecular weight silk, medium molecular weight silk, and high molecular weight silk is about 3:0.1:0.9, 3:0.2:0.8, 3:0.3:0.7, 3:0.4:0.6, 3:0.5:0.5, 3:0.6:0.4, 3:0.7:0.3, 3:0.8:0.2, or 3:0.9:0.1.

In an embodiment, silk fibroin-based protein fragments incorporated into the tissue fillers described herein have a polydispersity ranging from about 1 to about 5.0. In an embodiment, silk fibroin-based protein fragments incorporated into the tissue fillers described herein have a polydispersity ranging from about 1.5 to about 3.0. In an embodiment, silk fibroin-based protein fragments incorporated into the tissue fillers described herein have a polydispersity ranging from about 1 to about 1.5. In an embodiment, silk fibroin-based protein fragments incorporated into the tissue fillers described herein have a polydispersity ranging from about 1.5 to about 2.0. In an embodiment, silk fibroin-based protein fragments incorporated into the tissue fillers described herein have a polydispersity ranging from about 2.0 to about 2.5. In an embodiment, a composition of the present disclosure having pure silk fibroin-based protein fragments, has a polydispersity ranging from about is 2.0 to about 3.0. In an embodiment, a composition of the present disclosure having pure silk fibroin-based protein fragments, has a polydispersity ranging from about is 2.5 to about 3.0.

In an embodiment, a tissue filler described herein that includes SPF has non-detectable levels of LiBr residuals. In an embodiment, the amount of the LiBr residuals in a tissue filler described herein that includes SPF is between 10 ppm and 1000 ppm. In an embodiment, the amount of the LiBr residuals in a tissue filler described herein that includes SPF is between 10 ppm and 300 ppm. In an embodiment, the amount of the LiBr residuals in a tissue filler described herein that includes SPF is less than 25 ppm. In an embodiment, the amount of the LiBr residuals in a tissue filler described herein that includes SPF is less than 50 ppm. In an embodiment, the amount of the LiBr residuals in a tissue filler described herein that includes SPF is less than 75 ppm. In an embodiment, the amount of the LiBr residuals in a tissue filler described herein that includes SPF is less than 100 ppm. In an embodiment, the amount of the LiBr residuals in a tissue filler described herein that includes SPF is less than 200 ppm. In an embodiment, the amount of the LiBr residuals in a tissue filler described herein that includes SPF is less than 300 ppm. In an embodiment, the amount of the LiBr residuals in a tissue filler described herein that includes SPF is less than 400 ppm. In an embodiment, the amount of the LiBr residuals in a tissue filler described herein that includes SPF is less than 500 ppm. In an embodiment, the amount of the LiBr residuals in a tissue filler described herein that includes SPF is less than 600 ppm. In an embodiment, the amount of the LiBr residuals in a tissue filler described herein that includes SPF is less than 700 ppm. In an embodiment, the amount of the LiBr residuals in a tissue filler described herein that includes SPF is less than 800 ppm. In an embodiment, the amount of the LiBr residuals in a tissue filler described herein that includes SPF is less than 900 ppm. In an embodiment, the amount of the LiBr residuals in a tissue filler described herein that includes SPF is less than 1000 ppm. In an embodiment, the amount of the LiBr residuals in a tissue filler described herein that includes SPF is non-detectable to 500 ppm. In an embodiment, the amount of the LiBr residuals in a tissue filler described herein that includes SPF is non-detectable to 450 ppm. In an embodiment, the amount of the LiBr residuals in a tissue filler described herein that includes SPF is non-detectable to 400 ppm. In an embodiment, the amount of the LiBr residuals in a tissue filler described herein that includes SPF is non-detectable to 350 ppm. In an embodiment, the amount of the LiBr residuals in a tissue filler described herein that includes SPF is non-detectable to 300 ppm. In an embodiment, the amount of the LiBr residuals in a tissue filler described herein that includes SPF is non-detectable to 250 ppm. In an embodiment, the amount of the LiBr residuals in a tissue filler described herein that includes SPF is non-detectable to 200 ppm. In an embodiment, the amount of the LiBr residuals in a tissue filler described herein that includes SPF is non-detectable to 150 ppm. In an embodiment, the amount of the LiBr residuals in a tissue filler described herein that includes SPF is non-detectable to 100 ppm. In an embodiment, the amount of the LiBr residuals in a tissue filler described herein that includes SPF is 100 ppm to 200 ppm. In an embodiment, the amount of the LiBr residuals in a tissue filler described herein that includes SPF is 200 ppm to 300 ppm. In an embodiment, the amount of the LiBr residuals in a tissue filler described herein that includes SPF is 300 ppm to 400 ppm. In an embodiment, the amount of the LiBr residuals in a tissue filler described herein that includes SPF is 400 ppm to 500 ppm.

In an embodiment, a tissue filler described herein that includes SPF having pure silk fibroin-based protein fragments, has non-detectable levels of $Na_2CO_3$ residuals. In an embodiment, the amount of the $Na_2CO_3$ residuals in a tissue filler described herein that includes SPF is less than 100 ppm. In an embodiment, the amount of the $Na_2CO_3$ residuals in a tissue filler described herein that includes SPF is less than 200 ppm. In an embodiment, the amount of the $Na_2CO_3$ residuals in a tissue filler described herein that includes SPF is less than 300 ppm. In an embodiment, the amount of the $Na_2CO_3$ residuals in a tissue filler described herein that includes SPF is less than 400 ppm. In an embodiment, the amount of the $Na_2CO_3$ residuals in a tissue filler described herein that includes SPF is less than 500 ppm. In an embodiment, the amount of the $Na_2CO_3$ residuals in a tissue filler described herein that includes SPF is less than 600 ppm. In an embodiment, the amount of the $Na_2CO_3$ residuals in a tissue filler described herein that includes SPF is less than 700 ppm. In an embodiment, the amount of the $Na_2CO_3$ residuals in a tissue filler described herein that includes SPF is less than 800 ppm. In an embodiment, the amount of the $Na_2CO_3$ residuals in a tissue filler described herein that includes SPF is less than 900 ppm. In an embodiment, the amount of the $Na_2CO_3$ residuals in a tissue filler described herein that includes SPF is less than 1000 ppm. In an embodiment, the amount of the $Na_2CO_3$ residuals in a tissue filler described herein that includes SPF is non-detectable to 500 ppm. In an embodiment, the amount of the $Na_2CO_3$ residuals in a tissue filler described herein that includes SPF is non-detectable to 450 ppm. In an embodiment, the amount of the $Na_2CO_3$ residuals in a tissue filler described herein that includes SPF is non-detectable to 400 ppm. In an embodiment, the amount of the $Na_2CO_3$ residuals in a tissue filler described herein that includes SPF is non-detectable to 350 ppm. In an embodiment, the amount of the $Na_2CO_3$ residuals in a tissue filler described herein that includes SPF is non-detectable to 300 ppm. In an embodiment, the amount of the $Na_2CO_3$ residuals in a tissue filler described herein that includes SPF is non-detectable to 250 ppm. In an embodiment, the amount of the $Na_2CO_3$ residuals in a tissue filler described herein that includes SPF is non-detectable to 200 ppm. In an embodiment, the amount of the $Na_2CO_3$ residuals in a tissue filler described herein that includes SPF is non-detectable to 150 ppm. In an embodiment, the amount of the $Na_2CO_3$ residuals in a tissue filler described herein that includes SPF is non-detectable to 100 ppm. In an embodiment, the amount of the $Na_2CO_3$ residuals in a tissue filler described herein that includes SPF is 100 ppm to 200 ppm. In an embodiment, the amount of the $Na_2CO_3$ residuals in a tissue filler described herein that includes SPF is 200 ppm to 300 ppm. In an embodiment, the amount of the $Na_2CO_3$ residuals in a tissue filler described herein that includes SPF is 300 ppm to 400 ppm. In an embodiment, the amount of the $Na_2CO_3$ residuals in a tissue filler described herein that includes SPF is 400 ppm to 500 ppm.

In an embodiment, the water solubility of pure silk fibroin-based protein fragments of the present disclosure is 50 to 100%. In an embodiment, the water solubility of pure silk fibroin-based protein fragments of the present disclosure is 60 to 100%. In an embodiment, the water solubility of pure silk fibroin-based protein fragments of the present disclosure is 70 to 100%. In an embodiment, the water solubility of pure silk fibroin-based protein fragments of the present disclosure is 80 to 100%. In an embodiment, the water solubility is 90 to 100%. In an embodiment, the silk fibroin-based fragments of the present disclosure are non-soluble in aqueous solutions.

In an embodiment, the solubility of pure silk fibroin-based protein fragments of the present disclosure in organic solutions is 50 to 100%. In an embodiment, the solubility of pure silk fibroin-based protein fragments of the present disclosure in organic solutions is 60 to 100%. In an embodiment, the solubility of pure silk fibroin-based protein fragments of the present disclosure in organic solutions is 70 to 100%. In an embodiment, the solubility of pure silk fibroin-based protein fragments of the present disclosure in organic solutions is 80 to 100%. In an embodiment, the solubility of pure silk fibroin-based protein fragments of the present disclosure in organic solutions is 90 to 100%. In an embodiment, the silk fibroin-based fragments of the present disclosure are non-soluble in organic solutions.

Figure 6:
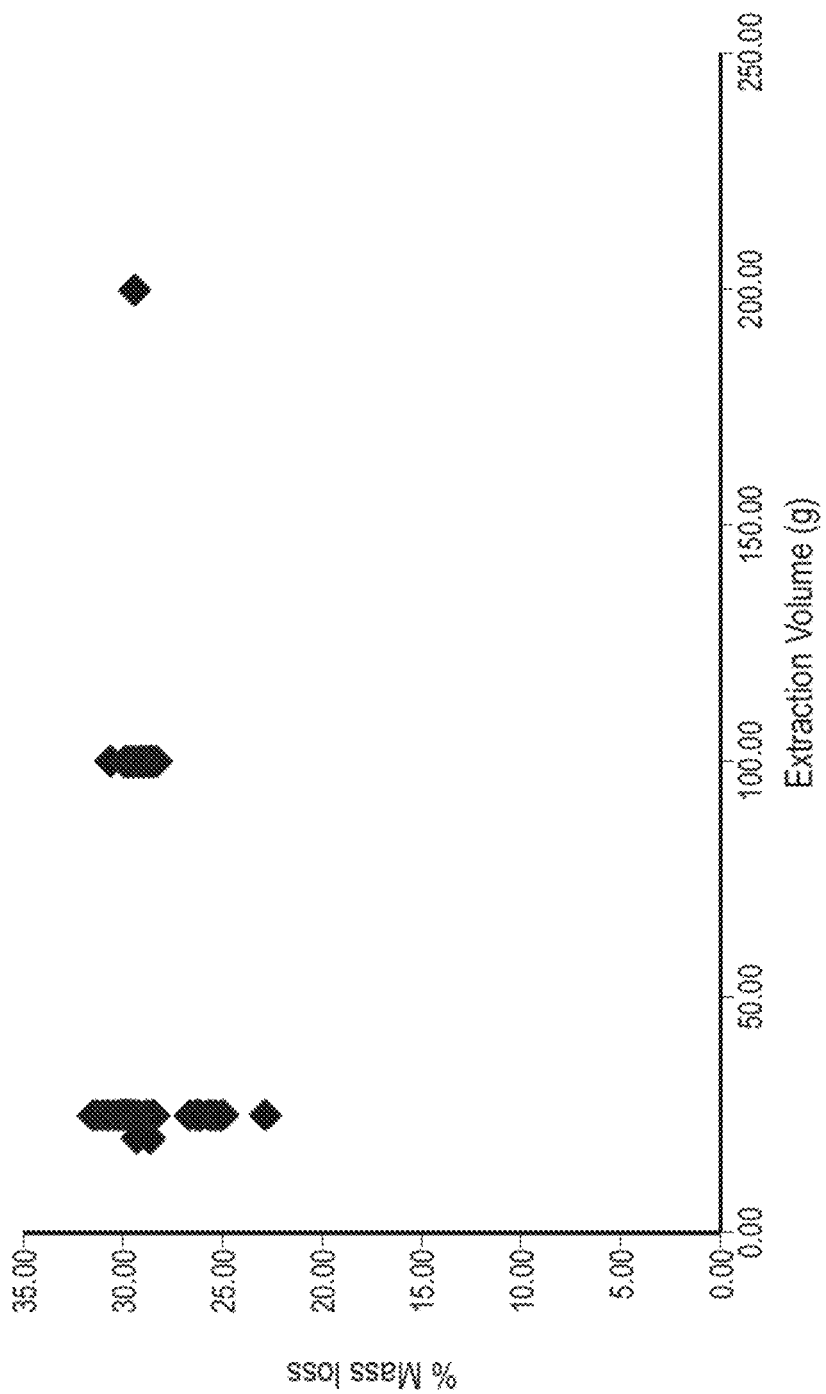
FIGS. 6 and 7 are graphs representing the effect of extraction volume on % mass loss.
Figure 7:
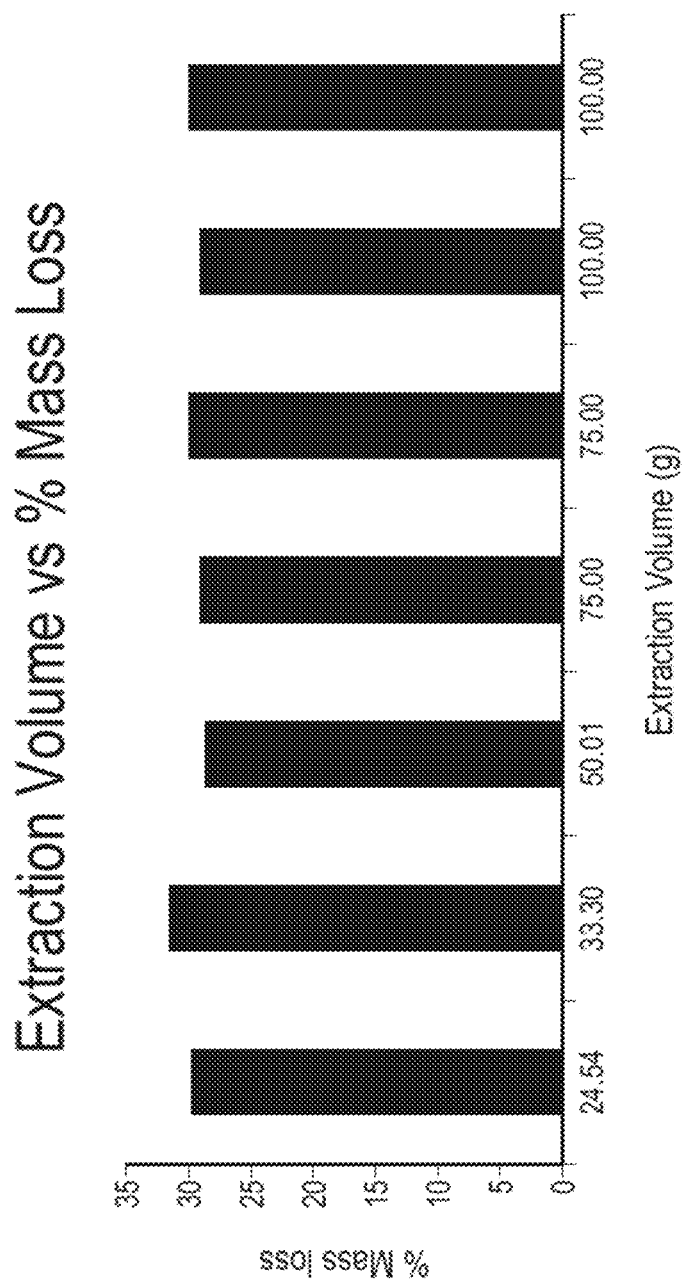
Figure 9:
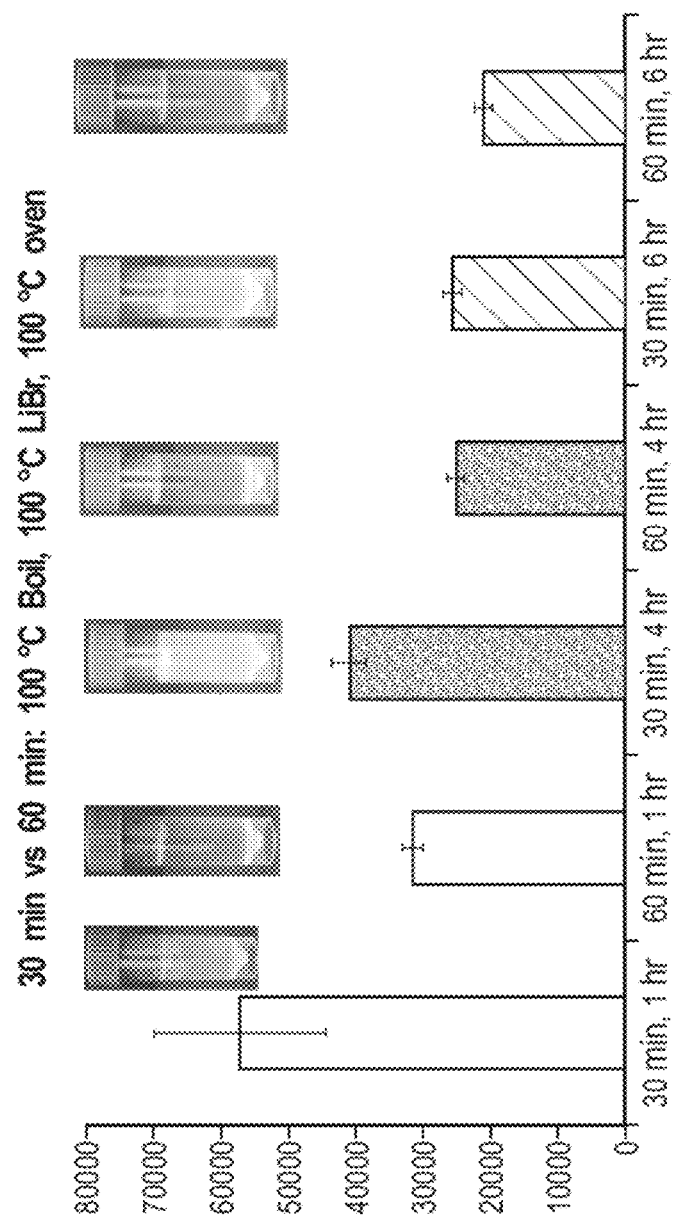
FIG. 9 is a graph summarizing the effect of Extraction Time on Molecular Weight of silk processed under the conditions of 100° C. Extraction Temperature, 100° C. LiBr and 100° C. Oven Dissolution (Oven/Dissolution Time was varied).
Figure 10:
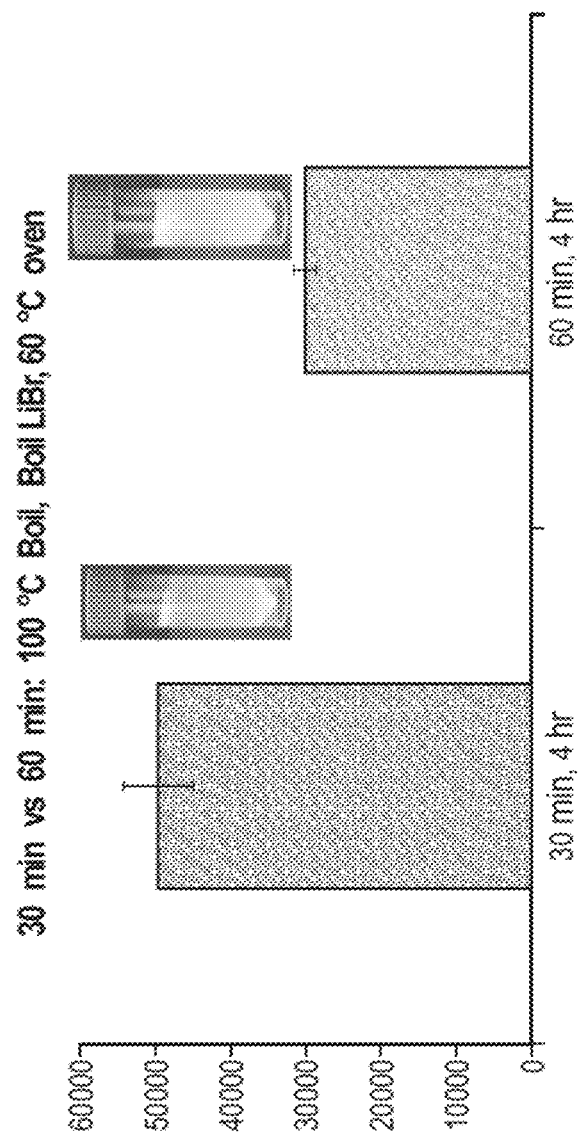
FIG. 10 is a graph summarizing the effect of Extraction Time on Molecular Weight of silk processed under the conditions of 100° C. Extraction Temperature, boiling LiBr and 60° C. Oven Dissolution (Oven/Dissolution Time was varied).
Figure 11:
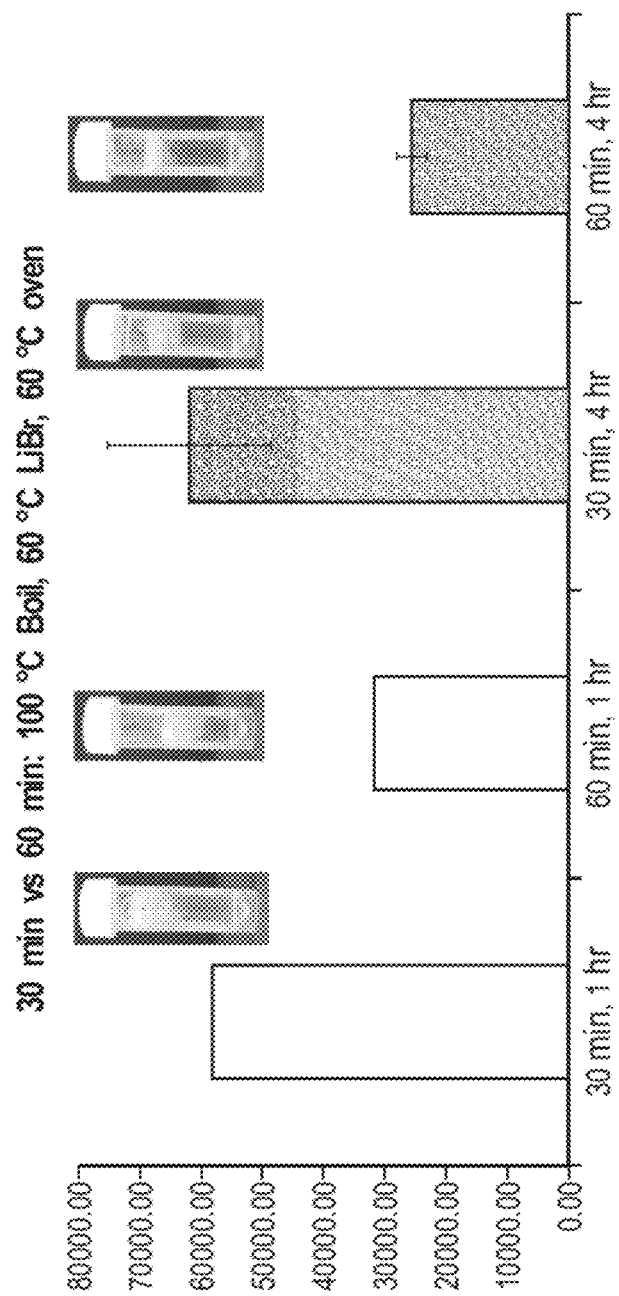
FIG. 11 is a graph summarizing the effect of Extraction Time on Molecular Weight of silk processed under the conditions of 100° C. Extraction Temperature, 60° C. LiBr and 60° C. Oven Dissolution (Oven/Dissolution Time was varied).
Figure 12:
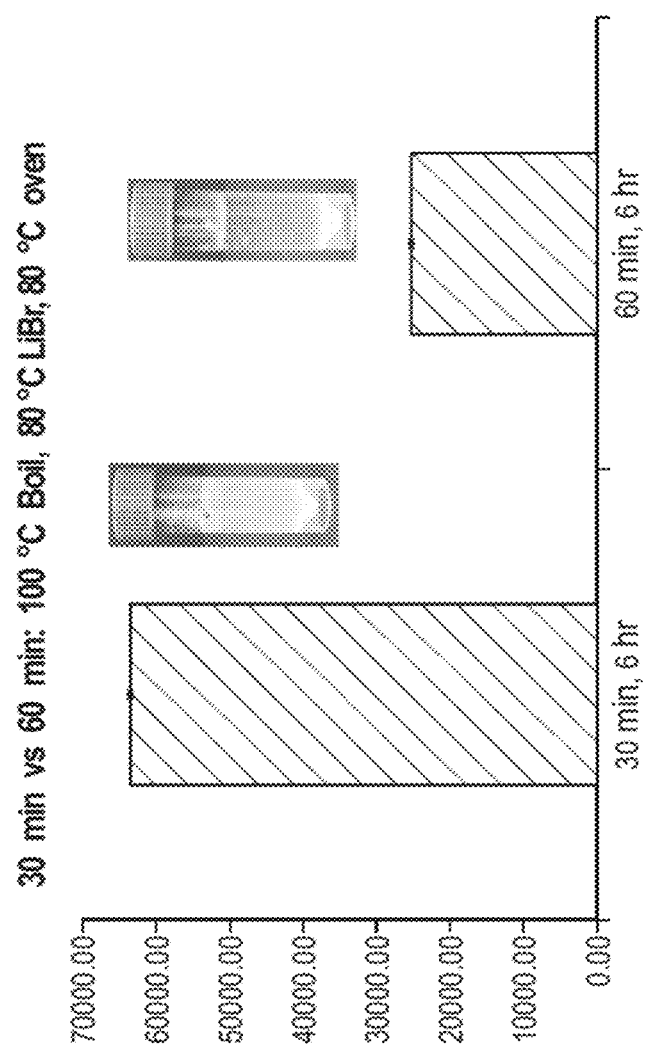
FIG. 12 is a graph summarizing the effect of Extraction Time on Molecular Weight of silk processed under the conditions of 100° C. Extraction Temperature, 80° C. LiBr and 80° C. Oven Dissolution (Oven/Dissolution Time was varied).
Figure 13:
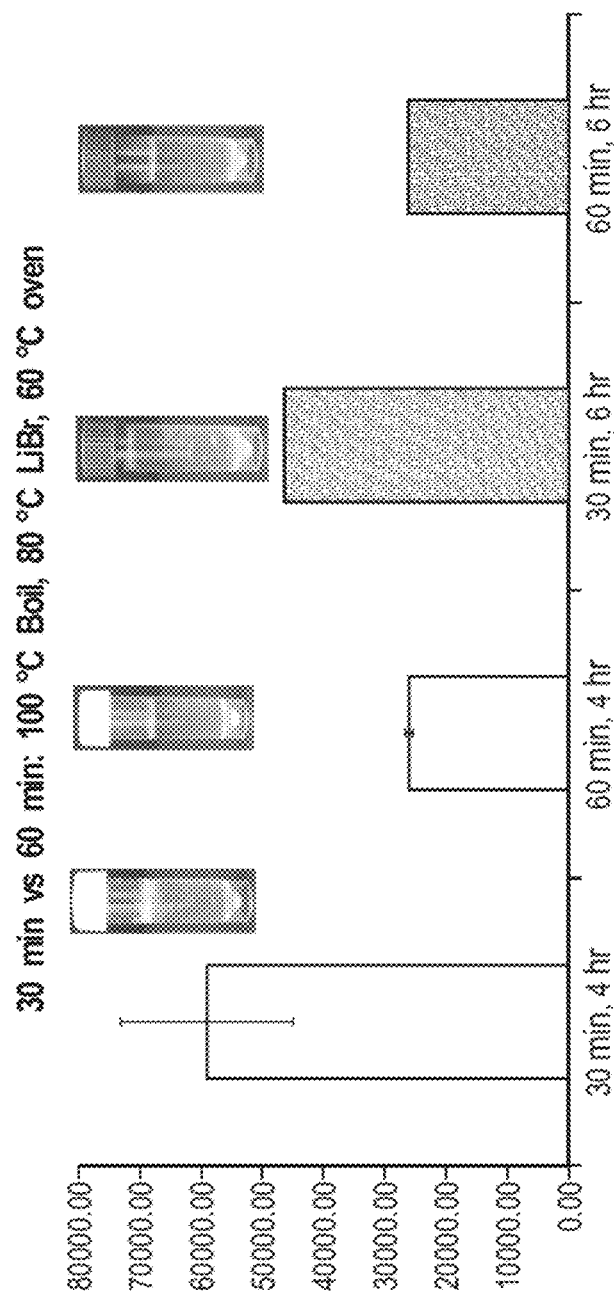
FIG. 13 is a graph summarizing the effect of Extraction Time on Molecular Weight of silk processed under the conditions of 100° C. Extraction Temperature, 80° C. LiBr and 60° C. Oven Dissolution (Oven/Dissolution Time was varied).
Figure 14:
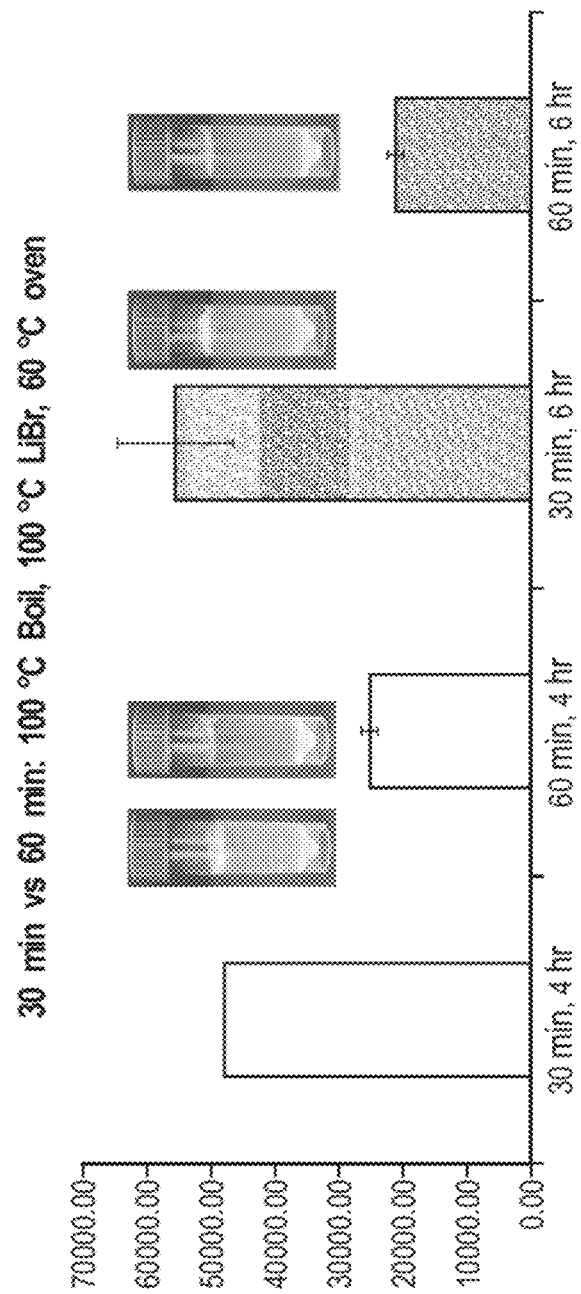
FIG. 14 is a graph summarizing the effect of Extraction Time on Molecular Weight of silk processed under the conditions of 100° C. Extraction Temperature, 100° C. LiBr and 60° C. Oven Dissolution (Oven/Dissolution Time was varied).
Figure 15:
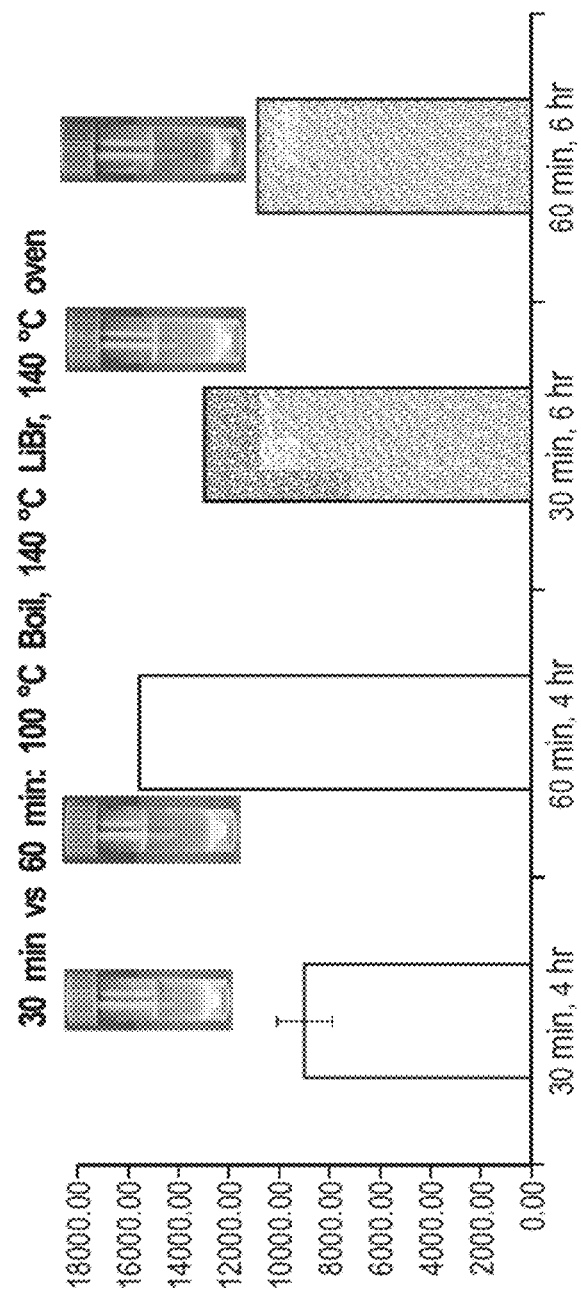
FIG. 15 is a graph summarizing the effect of Extraction Time on Molecular Weight of silk processed under the conditions of 100° C. Extraction Temperature, 140° C. LiBr and 140° C. Oven Dissolution (Oven/Dissolution Time was varied).

Methods of making silk protein fragments used in the compositions of the present disclosure are demonstrated in U.S. Patent Application Publication Nos. 2015/00933340, 2015/0094269, 2016/0193130, 2016/0022560, 2016/0022561, 2016/0022562, 2016/0022563, and 2016/0222579, 2016/0281294, and U.S. Pat. Nos. 9,187,538, 9,522,107, 9,517,191, 9,522,108, 9,511,012, and 9,545,369, the entirety of which are incorporated herein by reference. However, an exemplary method is demonstrated in FIG. 1, which is a flow chart showing various embodiments for producing pure silk fibroin-based protein fragments (SPFs) of the present disclosure. It should be understood that not all of the steps illustrated are necessarily required to fabricate all silk solutions of the present disclosure. As illustrated in FIG. 1, step A, cocoons (heat-treated or non-heat-treated), silk fibers, silk powder or spider silk can be used as the silk source. If starting from raw silk cocoons from *Bombyx mori*, the cocoons can be cut into small pieces, for example pieces of approximately equal size, step B1. The raw silk is then extracted and rinsed to remove any sericin, step C1a. This results in substantially sericin free raw silk. In an embodiment, water is heated to a temperature between 84° C. and 100° C. (ideally boiling) and then $Na_2CO_3$ (sodium carbonate) is added to the boiling water until the $Na_2CO_3$ is completely dissolved. The raw silk is added to the boiling water/$Na_2CO_3$ (100° C.) and submerged for approximately 15-90 minutes, where boiling for a longer time results in smaller silk protein fragments. In an embodiment, the water volume equals about 0.4× raw silk weight and the $Na_2CO_3$ volume equals about 0.848× raw silk weight. In an embodiment, the water volume equals 0.1× raw silk weight and the $Na_2CO_3$ volume is maintained at 2.12 g/L. This is demonstrated in FIG. 6 and FIG. 7: silk mass (x-axis) was varied in the same volume of extraction solution (i.e., the same volume of water and concentration of $Na_2CO_3$) achieving sericin removal (substantially sericin free) as demonstrated by an overall silk mass loss of 26 to 31 percent (y-axis). Subsequently, the water dissolved $Na_2CO_3$ solution is drained and excess water/$Na_2CO_3$ is removed from the silk fibroin fibers (e.g., ring out the fibroin extract by hand, spin cycle using a machine, etc.). The resulting silk fibroin extract is rinsed with warm to hot water to remove any remaining adsorbed sericin or contaminate, typically at a temperature range of about 40° C. to about 80° C., changing the volume of water at least once (repeated for as many times as required). The resulting silk fibroin extract is a substantially sericin-depleted silk fibroin. In an embodiment, the resulting silk fibroin extract is rinsed with water at a temperature of about 60° C. In an embodiment, the volume of rinse water for each cycle equals 0.1 L to 0.2 L× raw silk weight. It may be advantageous to agitate, turn or circulate the rinse water to maximize the rinse effect. After rinsing, excess water is removed from the extracted silk fibroin fibers (e.g., ring out fibroin extract by hand or using a machine). Alternatively, methods known to one skilled in the art such as pressure, temperature, or other reagents or combinations thereof may be used for the purpose of sericin extraction. Alternatively, the silk gland (100% sericin free silk protein) can be removed directly from a worm. This would result in liquid silk protein, without any alteration of the protein structure, free of sericin.

The extracted fibroin fibers are then allowed to dry completely. Once dry, the extracted silk fibroin is dissolved using a solvent added to the silk fibroin at a temperature between ambient and boiling, step C1b. In an embodiment, the solvent is a solution of Lithium bromide (LiBr) (boiling for LiBr is 140° C.). Alternatively, the extracted fibroin fibers are not dried but wet and placed in the solvent; solvent concentration can then be varied to achieve similar concentrations as to when adding dried silk to the solvent. The final concentration of LiBr solvent can range from 0.1 M to 9.3 M. FIG. 8 is a table summarizing the Molecular Weights of silk dissolved from different concentrations of Lithium Bromide (LiBr) and from different extraction and dissolution sizes. Complete dissolution of the extracted fibroin fibers can be achieved by varying the treatment time and temperature along with the concentration of dissolving solvent. Other solvents may be used including, but not limited to, phosphate phosphoric acid, calcium nitrate, calcium chloride solution or other concentrated aqueous solutions of inorganic salts. To ensure complete dissolution, the silk fibers should be fully immersed within the already heated solvent solution and then maintained at a temperature ranging from about 60° C. to about 140° C. for 1-168 hrs. In an embodiment, the silk fibers should be fully immersed within the solvent solution and then placed into a dry oven at a temperature of about 100° C. for about 1 hour.

The temperature at which the silk fibroin extract is added to the LiBr solution (or vice versa) has an effect on the time required to completely dissolve the fibroin and on the resulting molecular weight and polydispersity of the final SPF mixture solution. In an embodiment, silk solvent solution concentration is less than or equal to 20% w/v. In addition, agitation during introduction or dissolution may be used to facilitate dissolution at varying temperatures and concentrations. The temperature of the LiBr solution will provide control over the silk protein fragment mixture molecular weight and polydispersity created. In an embodiment, a higher temperature will more quickly dissolve the silk offering enhanced process scalability and mass production of silk solution. In an embodiment, using a LiBr solution heated to a temperature between 80° C.-140° C. reduces the time required in an oven in order to achieve full dissolution. Varying time and temperature at or above 60° C. of the dissolution solvent will alter and control the MW and polydispersity of the SPF mixture solutions formed from the original molecular weight of the native silk fibroin protein.

Alternatively, whole cocoons may be placed directly into a solvent, such as LiBr, bypassing extraction, step B2. This requires subsequent filtration of silk worm particles from the silk and solvent solution and sericin removal using methods know in the art for separating hydrophobic and hydrophilic proteins such as a column separation and/or chromatography, ion exchange, chemical precipitation with salt and/or pH, and or enzymatic digestion and filtration or extraction, all methods are common examples and without limitation for standard protein separation methods, step C2. Non-heat treated cocoons with the silkworm removed, may alternatively be placed into a solvent such as LiBr, bypassing extraction. The methods described above may be used for sericin separation, with the advantage that non-heat treated cocoons will contain significantly less worm debris.

Dialysis may be used to remove the dissolution solvent from the resulting dissolved fibroin protein fragment solution by dialyzing the solution against a volume of water, step E1. Pre-filtration prior to dialysis is helpful to remove any debris (i.e., silk worm remnants) from the silk and LiBr solution, step D. In one example, a 3 μm or 5 μm filter is used with a flow-rate of 200-300 mL/min to filter a 0.1% to 1.0% silk-LiBr solution prior to dialysis and potential concentration if desired. A method disclosed herein, as described above, is to use time and/or temperature to decrease the concentration from 9.3 M LiBr to a range from 0.1 M to 9.3 M to facilitate filtration and downstream dialysis, particularly when considering creating a scalable process method. Alternatively, without the use of additional time or temperate, a 9.3 M LiBr-silk protein fragment solution may be diluted with water to facilitate debris filtration and dialysis. The result of dissolution at the desired time and temperate filtration is a translucent particle-free room temperature shelf-stable silk protein fragment-LiBr solution of a known MW and polydispersity. It is advantageous to change the dialysis water regularly until the solvent has been removed (e.g., change water after 1 hour, 4 hours, and then every 12 hours for a total of 6 water changes). The total number of water volume changes may be varied based on the resulting concentration of solvent used for silk protein dissolution and fragmentation. After dialysis, the final silk solution maybe further filtered to remove any remaining debris (i.e., silk worm remnants).

Alternatively, Tangential Flow Filtration (TFF), which is a rapid and efficient method for the separation and purification of biomolecules, may be used to remove the solvent from the resulting dissolved fibroin solution, step E2. TFF offers a highly pure aqueous silk protein fragment solution and enables scalability of the process in order to produce large volumes of the solution in a controlled and repeatable manner. The silk and LiBr solution may be diluted prior to TFF (20% down to 0.1% silk in either water or LiBr). Pre-filtration as described above prior to TFF processing may maintain filter efficiency and potentially avoids the creation of silk gel boundary layers on the filter's surface as the result of the presence of debris particles. Pre-filtration prior to TFF is also helpful to remove any remaining debris (i.e., silk worm remnants) from the silk and LiBr solution that may cause spontaneous or long-term gelation of the resulting water only solution, step D. TFF, recirculating or single pass, may be used for the creation of water-silk protein fragment solutions ranging from 0.1% silk to 30.0% silk (more preferably, 0.1%-6.0% silk). Different cutoff size TFF membranes may be required based upon the desired concentration, molecular weight and polydispersity of the silk protein fragment mixture in solution. Membranes ranging from 1-100 kDa may be necessary for varying molecular weight silk solutions created for example by varying the length of extraction boil time or the time and temperate in dissolution solvent (e.g., LiBr). In an embodiment, a TFF 5 or 10 kDa membrane is used to purify the silk protein fragment mixture solution and to create the final desired silk-to-water ratio. As well, TFF single pass, TFF, and other methods known in the art, such as a falling film evaporator, may be used to concentrate the solution following removal of the dissolution solvent (e.g., LiBr) (with resulting desired concentration ranging from 0.1% to 30% silk). This can be used as an alternative to standard HFIP concentration methods known in the art to create a water-based solution. A larger pore membrane could also be utilized to filter out small silk protein fragments and to create a solution of higher molecular weight silk with and/or without tighter polydispersity values. FIG. 5 is a table summarizing Molecular Weights for some embodiments of silk protein solutions of the present disclosure. Silk protein solution processing conditions were as follows: 100° C. extraction for 20 min, room temperature rinse, LiBr in 60° C. oven for 4-6 hours. TFF processing conditions for water-soluble films were as follows: 100° C. extraction for 60 min, 60° C. rinse, 100° C. LiBr in 100° C. oven for 60 min. FIGS. 12-23 further demonstrate manipulation of extraction time, LiBr dissolution conditions, and TFF processing and resultant example molecular weights and polydispersities. These examples are not intended to be limiting, but rather to demonstrate the potential of specifying parameters for specific molecular weight silk fragment solutions.

An assay for LiBr and $Na_2CO_3$ detection was performed using an HPLC system equipped with evaporative light scattering detector (ELSD). The calculation was performed by linear regression of the resulting peak areas for the analyte plotted against concentration. More than one sample of a number of formulations of the present disclosure was used for sample preparation and analysis. Generally, four samples of different formulations were weighed directly in a 10 mL volumetric flask. The samples were suspended in 5 mL of 20 mM ammonium formate (pH 3.0) and kept at 2-8° C. for 2 hours with occasional shaking to extract analytes from the film. After 2 hours the solution was diluted with 20 mM ammonium formate (pH 3.0). The sample solution from the volumetric flask was transferred into HPLC vials and injected into the HPLC-ELSD system for the estimation of sodium carbonate and lithium bromide.

The analytical method developed for the quantitation of $Na_2CO_3$ and LiBr in silk protein formulations was found to be linear in the range 10-165 sg/mL, with RSD for injection precision as 2% and 1% for area and 0.38% and 0.19% for retention time for sodium carbonate and lithium bromide respectively. The analytical method can be applied for the quantitative determination of sodium carbonate and lithium bromide in silk protein formulations.

The final silk protein fragment solution is pure silk protein fragments and water with PPM to undetectable levels of particulate debris and/or process contaminants, including LiBr and $Na_2CO_3$. FIG. 3 and FIG. 4 are tables summarizing LiBr and $Na_2CO_3$ concentrations in solutions of the present disclosure. In FIG. 3, the processing conditions included 100° C. extraction for 60 min, 60° C. rinse, 100° C. LiBr in 100° C. oven for 60 min. TFF conditions including pressure differential and number of dia-filtration volumes were varied. In FIG. 4, the processing conditions included 100° C. boil for 60 min, 60° C. rinse, LiBr in 60° C. oven for 4-6 hours.

Either the silk fragment-water solutions, the lyophilized silk protein fragment mixture, or any other compositions including SPFs, can be sterilized following standard methods in the art not limited to filtration, heat, radiation or e-beam. It is anticipated that the silk protein fragment mixture, because of its shorter protein polymer length, will withstand sterilization better than intact silk protein solutions described in the art. Additionally, silk articles created from the SPF mixtures described herein may be sterilized as appropriate to application. For example, an SPF dermal filler loaded with a molecule to be used in medical applications with an open wound/incision, may be sterilized standard methods such as by radiation or e-beam.

Figure 2:
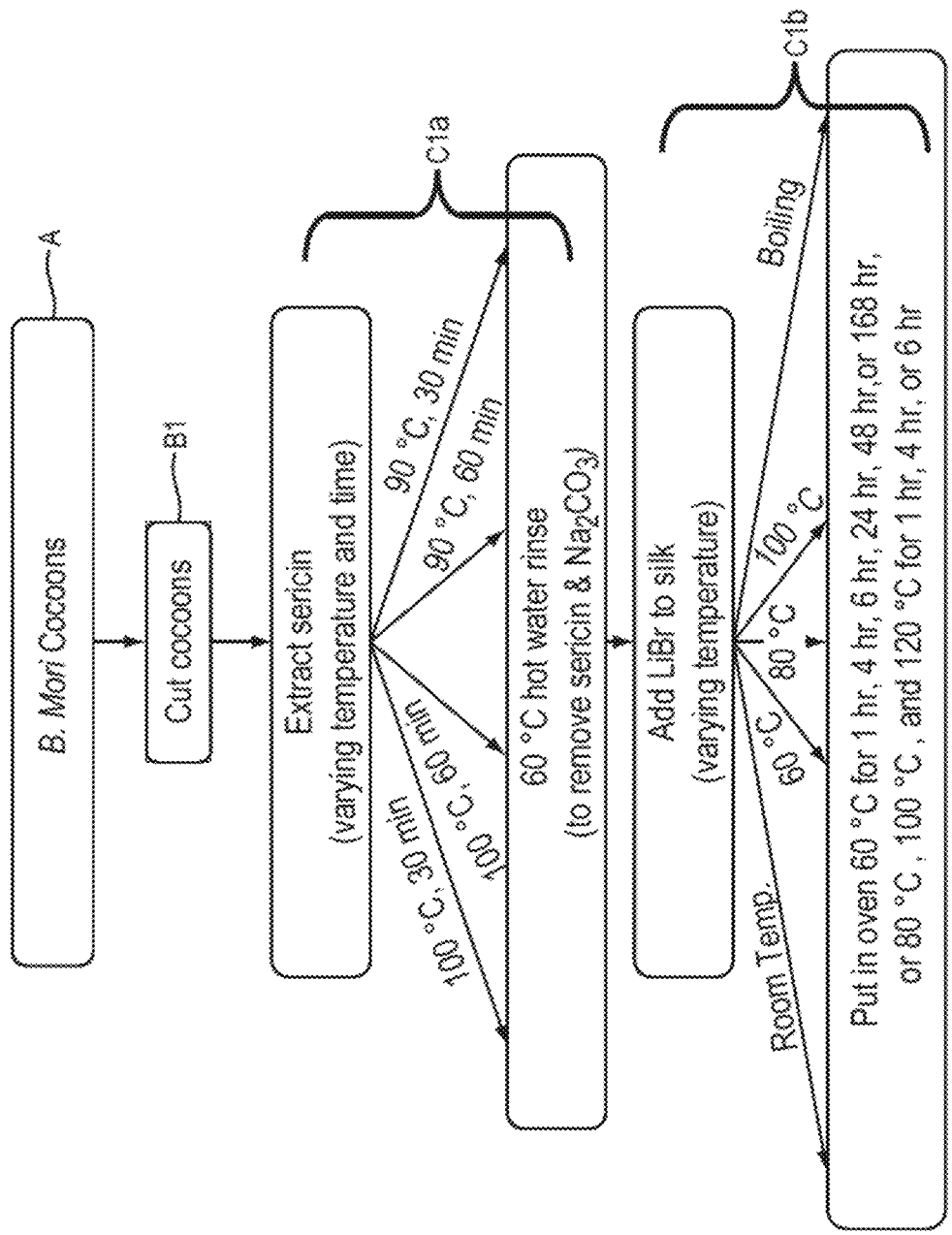
FIG. 2 is a flow chart showing various parameters that can be modified during the process of producing SPFs of the present disclosure during the extraction and the dissolution steps.

FIG. 2 is a flow chart showing various parameters that can be modified during the process of producing a silk protein fragment solution of the present disclosure during the extraction and the dissolution steps. Select method parameters may be altered to achieve distinct final solution characteristics depending upon the intended use, e.g., molecular weight and polydispersity. It should be understood that not all of the steps illustrated are necessarily required to fabricate all silk solutions of the present disclosure.

In an embodiment, a process for producing a silk protein fragment solution of the present disclosure includes forming pieces of silk cocoons from the *Bombyx mori* silk worm; extracting the pieces at about 100° C. in a solution of water and $Na_2CO_3$ for about 60 minutes, wherein a volume of the water equals about 0.4× raw silk weight and the amount of $Na_2CO_3$ is about 0.848× the weight of the pieces to form a silk fibroin extract: triple rinsing the silk fibroin extract at about 60° C. for about 20 minutes per rinse in a volume of rinse water, wherein the rinse water for each cycle equals about 0.2 L× the weight of the pieces; removing excess water from the silk fibroin extract; drying the silk fibroin extract; dissolving the dry silk fibroin extract in a LiBr solution, wherein the LiBr solution is first heated to about 100° C. to create a silk and LiBr solution and maintained; placing the silk and LiBr solution in a dry oven at about 100° C. for about 60 minutes to achieve complete dissolution and further fragmentation of the native silk protein structure into mixture with desired molecular weight and polydispersity; filtering the solution to remove any remaining debris from the silkworm; diluting the solution with water to result in a 1% silk solution; and removing solvent from the solution using Tangential Flow Filtration (TFF). In an embodiment, a 10 kDa membrane is utilized to purify the silk solution and create the final desired silk-to-water ratio. TFF can then be used to further concentrate the pure silk solution to a concentration of 2% silk to water.

Each process step from raw cocoons to dialysis is scalable to increase efficiency in manufacturing. Whole cocoons are currently purchased as the raw material, but pre-cleaned cocoons or non-heat treated cocoons, where worm removal leaves minimal debris, have also been used. Cutting and cleaning the cocoons is a manual process, however for scalability this process could be made less labor intensive by, for example, using an automated machine in combination with compressed air to remove the worm and any particulates, or using a cutting mill to cut the cocoons into smaller pieces. The extraction step, currently performed in small batches, could be completed in a larger vessel, for example an industrial washing machine where temperatures at or in between 60° C. to 100° C. can be maintained. The rinsing step could also be completed in the industrial washing machine, eliminating the manual rinse cycles. Dissolution of the silk in LiBr solution could occur in a vessel other than a convection oven, for example a stirred tank reactor. Dialyzing the silk through a series of water changes is a manual and time intensive process, which could be accelerated by changing certain parameters, for example diluting the silk solution prior to dialysis. The dialysis process could be scaled for manufacturing by using semi-automated equipment, for example a tangential flow filtration system.

Varying extraction (i.e., time and temperature), LiBr (i.e., temperature of LiBr solution when added to silk fibroin extract or vice versa) and dissolution (i.e., time and temperature) parameters results in solvent and silk solutions with different viscosities, homogeneities, and colors. Increasing the temperature for extraction, lengthening the extraction time, using a higher temperature LiBr solution at emersion and over time when dissolving the silk and increasing the time at temperature (e.g., in an oven as shown here, or an alternative heat source) all resulted in less viscous and more homogeneous solvent and silk solutions. While almost all parameters resulted in a viable silk solution, methods that allow complete dissolution to be achieved in fewer than 4 to 6 hours are preferred for process scalability.

Molecular weight of the silk protein fragments may be controlled based upon the specific parameters utilized during the extraction step, including extraction time and temperature; specific parameters utilized during the dissolution step, including the LiBr temperature at the time of submersion of the silk in to the lithium bromide and time that the solution is maintained at specific temperatures; and specific parameters utilized during the filtration step. By controlling process parameters using the disclosed methods, it is possible to create SPF mixture solutions with polydispersity equal to or lower than 2.5 at a variety of different molecular weight ranging from 1 kDa to 250 kDa, 5 kDa to 200 kDa, 5 kDa to 150 kDa, 10 kDa to 150 kDa, or 10 kDa to 80 kDa. By altering process parameters to achieve silk solutions with different molecular weights, a range of fragment mixture end products, with desired polydispersity of equal to or less than 2.5 may be targeted based upon the desired performance requirements. For example, a lower molecular weight silk film containing a drug may have a faster release rate compared to a higher molecular weight SPF preparation. Additionally, SPF mixture solutions with a polydispersity of greater than 2.5 can be achieved. Further, two solutions with different average molecular weights and polydispersities can be mixed to create combination solutions. Alternatively, a liquid silk gland (100% sericin free silk protein) that has been removed directly from a worm could be used in combination with any of the SPF mixture solutions of the present disclosure. Molecular weight of the pure silk fibroin-based protein fragment composition was determined using High Pressure Liquid Chromatography (HPLC) with a Refractive Index Detector (RID). Polydispersity was calculated using Cirrus GPC Online GPC/SEC Software Version 3.3 (Agilent).

Parameters were varied during the processing of raw silk cocoons into silk solution. Varying these parameters affected the MW of the resulting silk solution. Parameters manipulated included (i) time and temperature of extraction, (ii) temperature of LiBr, (iii) temperature of dissolution oven, and (iv) dissolution time. Molecular weight was determined with mass spec as shown in FIGS. 9-25.

Experiments were carried out to determine the effect of varying the extraction time. FIGS. 9-15 are graphs showing these results, and Tables 2-8 summarize the results. Below is a summary:

- A sericin extraction time of 30 minutes resulted in larger MW than a sericin extraction time of 60 minutes
- MW decreases with time in the oven
- 140° C. LiBr and oven resulted in the low end of the confidence interval to be below a MW of 9500 Da
- 30 min extraction at the 1 hour and 4 hour time points have undigested silk
- 30 min extraction at the 1 hour time point resulted in a significantly high molecular weight with the low end of the confidence interval being 35,000 Da
- The range of MW reached for the high end of the confidence interval was 18000 to 216000 Da (important for offering solutions with specified upper limit)

TABLE 2

The effect of extraction time (30 min vs 60 min) on molecular weight of silk processed under the conditions of 100° C. Extraction Temperature, 100° C. Lithium Bromide (LiBr) and 100° C. Oven Dissolution (Oven/Dissolution Time was varied).

| Boil Time | Oven Time | Average Mw | Standard deviation | Confidence Interval | | PD |
|---|---|---|---|---|---|---|
| 30 | 1 | 57247 | 12780 | 35093 | 93687 | 1.63 |
| 60 | 1 | 31520 | 1387 | 11633 | 85407 | 2.71 |
| 30 | 4 | 40973 | 2632 | 14268 | 117658 | 2.87 |
| 60 | 4 | 25082 | 1248 | 10570 | 59803 | 2.38 |
| 30 | 6 | 25604 | 1405 | 10252 | 63943 | 2.50 |
| 60 | 6 | 20980 | 1262 | 10073 | 43695 | 2.08 |

TABLE 3

The effect of extraction time (30 min vs 60 min) on molecular weight of silk processed under the conditions of 100° C. Extraction Temperature, boiling Lithium Bromide (LiBr) and 60° C. Oven Dissolution for 4 hr.

| Sample | Boil Time | Average Mw | Standard deviation | Confidence Interval | | PD |
|---|---|---|---|---|---|---|
| 30 min, 4 hr | 30 | 49656 | 4580 | 17306 | 142478 | 2.87 |
| 60 min, 4 hr | 60 | 30042 | 1536 | 11183 | 80705 | 2.69 |

TABLE 4

The effect of extraction time (30 min vs 60 min) on molecular weight of silk processed under the conditions of 100° C. Extraction Temperature, 60° C. Lithium Bromide (LiBi) and 60° C. Oven Dissolution (Oven/Dissolution Time was varied).

| Sample | Boil Time | Oven Time | Average Mw | Standard deviation | Confidence Interval | | PD |
|---|---|---|---|---|---|---|---|
| 30 min, 1 hr | 30 | 1 | 58436 | | 22201 | 153809 | 2.63 |
| 60 min, 1 hr | 60 | 1 | 31700 | | 11931 | 84224 | 2.66 |
| 30 min, 4 hr | 30 | 4 | 61956.5 | 13337 | 21463 | 178847 | 2.89 |
| 60 min, 4 hr | 60 | 4 | 25578.5 | 2446 | 9979 | 65564 | 2.56 |

TABLE 5

The effect of extraction time (30 min vs 60 min) on molecular weight of silk processed under the conditions of 100° C. Extraction Temperature, 80° C. Lithium Bromide (LiBr) and 80° C. Oven Dissolution for 6 hr.

| Sample | Boil Time | Average Mw | Standard deviation | Confidence Interval | | PD |
|---|---|---|---|---|---|---|
| 30 min, 6 hr | 30 | 63510 | | 18693 | 215775 | 3.40 |
| 60 min, 6 hr | 60 | 25164 | 238 | 9637 | 65706 | 2.61 |

TABLE 6

The effect of extraction time (30 min vs 60 min) on molecular weight of silk processed under the conditions of 100° C. Extraction Temperature, 80° C. Lithium Bromide (LiBr) and 60° C. Oven Dissolution (Oven/Dissolution Time was varied).

| Sample | Boil Time | Oven Time | Average Mw | Standard deviation | Confidence Interval | | PD |
|---|---|---|---|---|---|---|---|
| 30 min, 4 hr | 30 | 4 | 59202 | 14028 | 19073 | 183760 | 3.10 |
| 60 min, 4 hr | 60 | 4 | 26312.5 | 637 | 10266 | 67442 | 2.56 |
| 30 min, 6 hr | 30 | 6 | 46824 | | 18076 | 121293 | 2.59 |
| 60 min, 6 hr | 60 | 6 | 26353 | | 10168 | 68302 | 2.59 |

TABLE 7

The effect of extraction time (30 min vs 60 min) on molecular weight of silk processed under the conditions of 100° C. Extraction Temperature, 100° C. Lithium Bromide (LiBr) and 60° C. Oven Dissolution (Oven/Dissolution Time was varied).

| Sample | Boil Time | Oven Time | Average Mw | Standard deviation | Confidence Interval | | PD |
|---|---|---|---|---|---|---|---|
| 30 min, 4 hr | 30 | 4 | 47853 | | 19758 | 115900 | 2.42 |
| 60 min, 4 hr | 60 | 4 | 25082 | 1248 | 10520 | 59804 | 2.38 |
| 30 min, 6 hr | 30 | 6 | 55421 | 8992 | 19153 | 160366 | 2.89 |
| 60 min, 6 hr | 60 | 6 | 20980 | 1262 | 10073 | 43694 | 2.08 |

TABLE 8

The effect of extraction time (30 min vs 60 min) on molecular weight of silk processed under the conditions of 100° C. Extraction Temperature, 140° C. Lithium Bromide (LiBr) and 140° C. Oven Dissolution (Oven/Dissolution Time was varied).

| Sample | Boil Time | Oven Time | Average Mw | Standard deviation | Confidence Interval | | PD |
|---|---|---|---|---|---|---|---|
| 30 min, 4 hr | 30 | 4 | 9024.5 | 1102 | 4493 | 18127 | 2.00865 |
| 60 min, 4 hr | 60 | 4 | 15548 | | 6954 | 34762 | 2.2358 |
| 30 min, 6 hr | 30 | 6 | 13021 | | 5987 | 28319 | 2.1749 |
| 60 min, 6 hr | 60 | 6 | 10888 | | 5364 | 22100 | 2.0298 |

Figure 16:
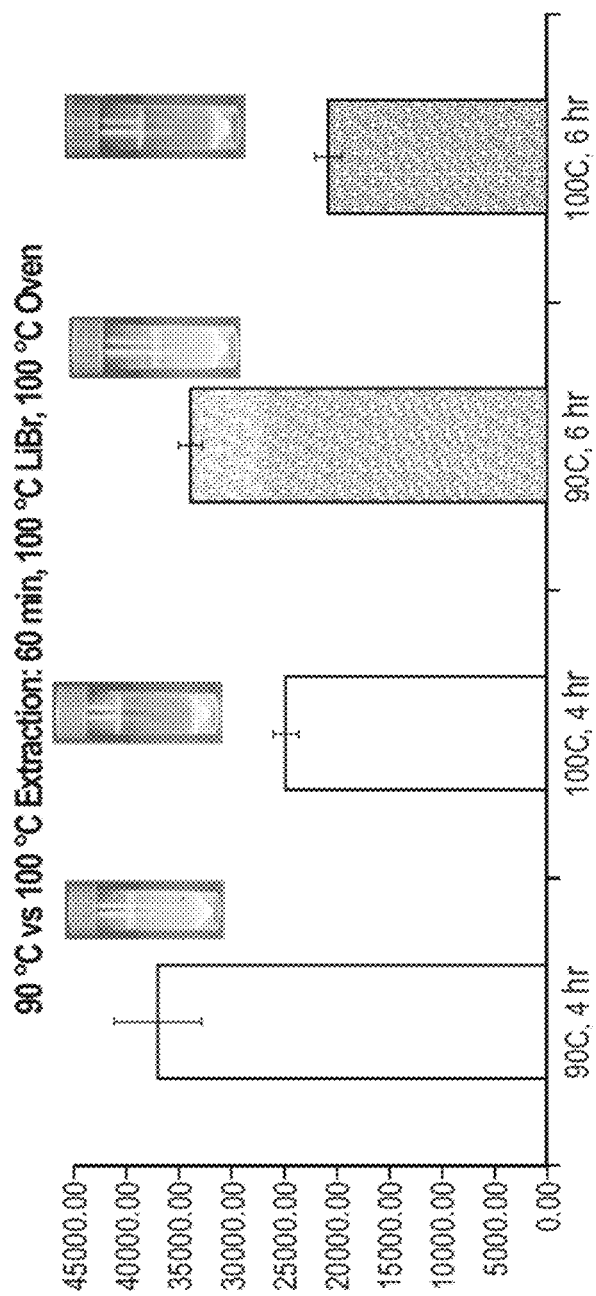
FIG. 16 is a graph summarizing the effect of Extraction Temperature on Molecular Weight of silk processed under the conditions of 60 minute Extraction Time, 100° C. LiBr and 100° C. Oven Dissolution (Oven/Dissolution Time was varied).

Experiments were carried out to determine the effect of varying the extraction temperature. FIG. 16 is a graph showing these results, and Table 9 summarizes the results. Below is a summary:

Sericin extraction at 90° C. resulted in higher MW than sericin extraction at 100° C. extraction Both 90° C. and 100° C. show decreasing MW over time in the oven

TABLE 9

The effect of extraction temperature (90° C. vs. 100° C.) on molecular weight of silk processed under the conditions of 60 min. Extraction Temperature, 100° C. Lithium Bromide (LiBr) and 100° C. Oven Dissolution (Oven/Dissolution Time was varied).

| Sample | Boil Time | Oven Time | Average Mw | Standard deviation | Confidence Interval | | PD |
|---|---|---|---|---|---|---|---|
| 90° C., 4 hr | 60 | 4 | 37308 | 4204 | 13368 | 104119 | 2.79 |
| 100° C., 4 hr | 60 | 4 | 25082 | 1248 | 10520 | 59804 | 2.38 |
| 90° C., 6 hr | 60 | 6 | 34224 | 1135 | 12717 | 92100 | 2.69 |
| 100° C., 6 hr | 60 | 6 | 20980 | 1262 | 10073 | 43694 | 2.08 |

Figure 17:
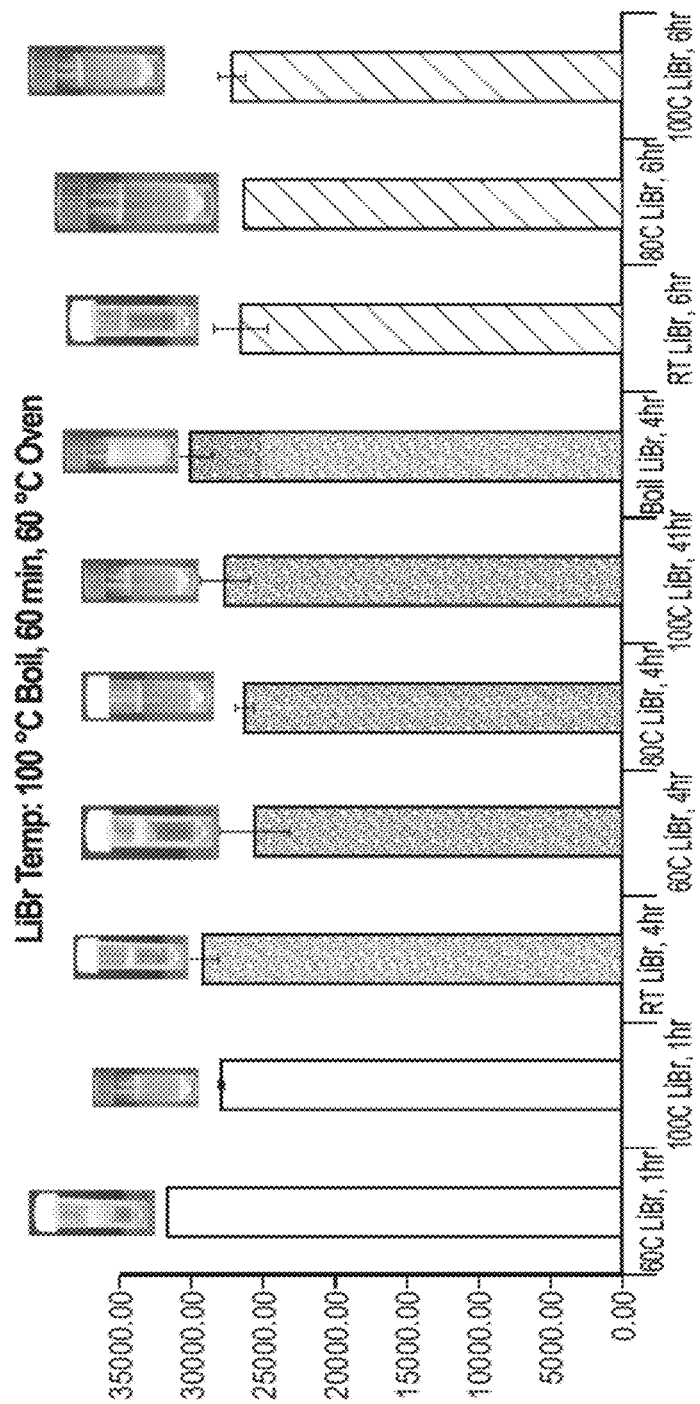
FIG. 17 is a graph summarizing the effect of LiBr Temperature on Molecular Weight of silk processed under the conditions of 60 minute Extraction Time, 100° C. Extraction Temperature and 60° C. Oven Dissolution (Oven/Dissolution Time was varied).
Figure 18:
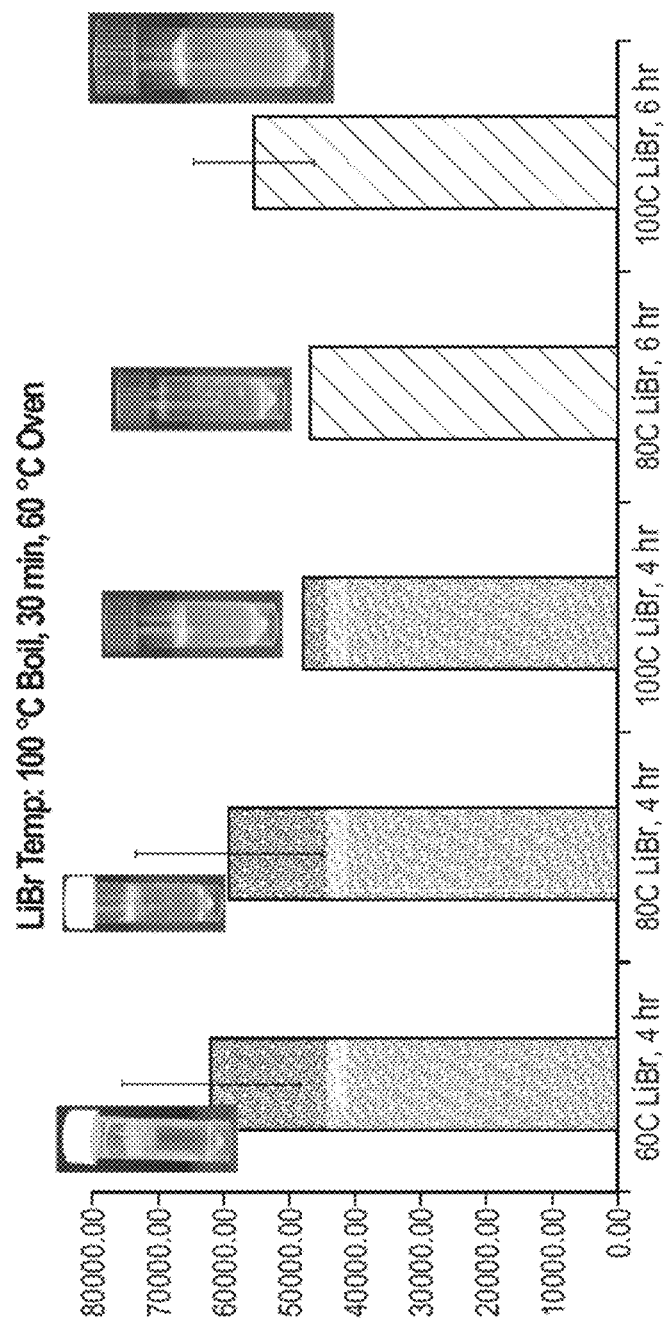
FIG. 18 is a graph summarizing the effect of LiBr Temperature on Molecular Weight of silk processed under the conditions of 30 minute Extraction Time, 100° C. Extraction Temperature and 60° C. Oven Dissolution (Oven/Dissolution Time was varied).
Figure 19:
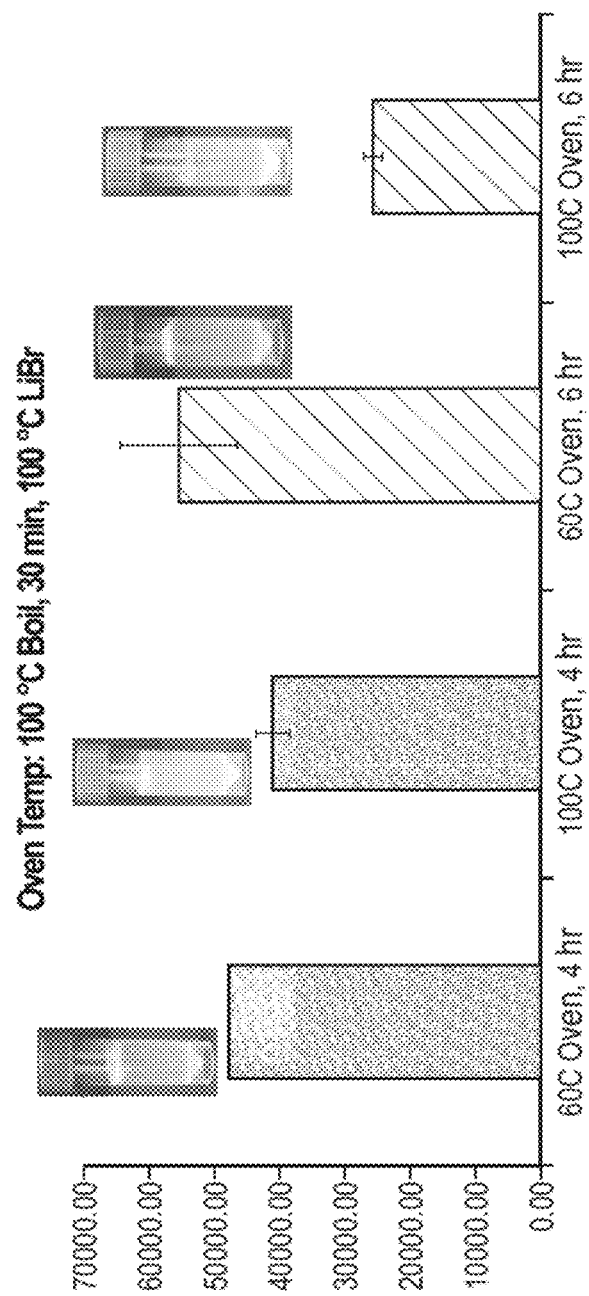
FIG. 19 is a graph summarizing the effect of Oven/Dissolution Temperature on Molecular Weight of silk processed under the conditions of 100° C. Extraction Temperature, 30 minute Extraction Time, and 100° C. Lithium Bromide (Oven/Dissolution Time was varied).
Figure 20:
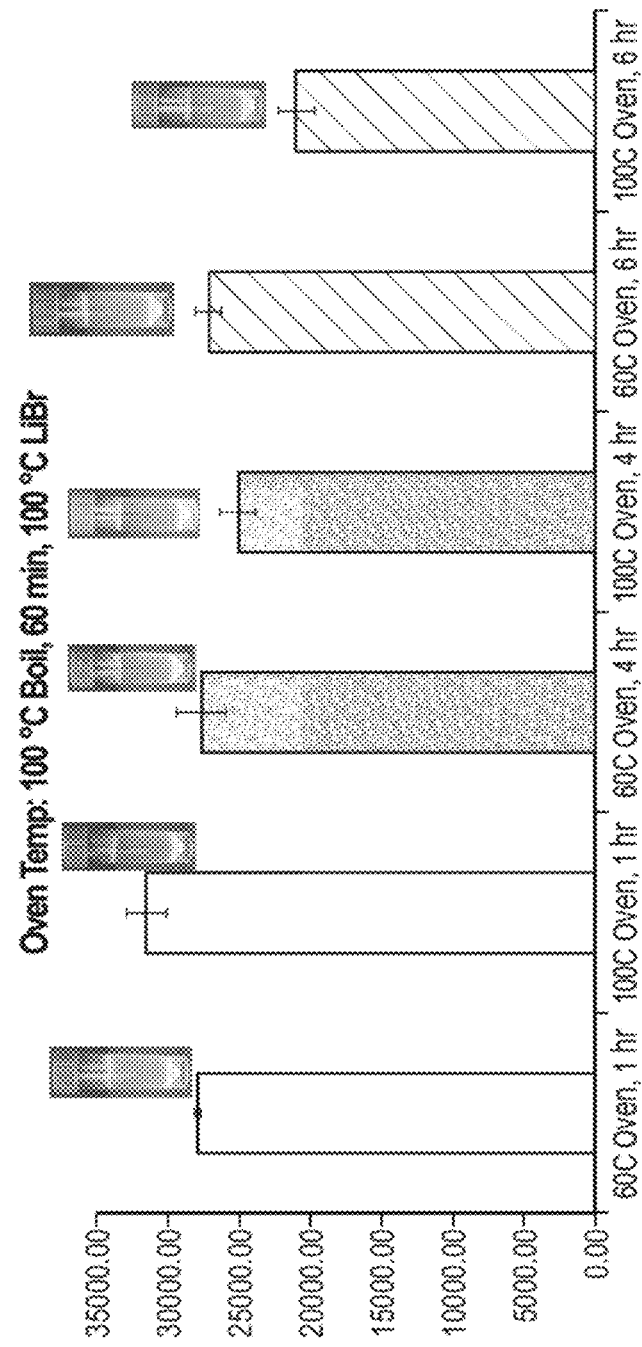
FIG. 20 is a graph summarizing the effect of Oven/Dissolution Temperature on Molecular Weight of silk processed under the conditions of 100° C. Extraction Temperature, 60 minute Extraction Time, and 100° C. Lithium Bromide. (Oven/Dissolution Time was varied).
Figure 21:
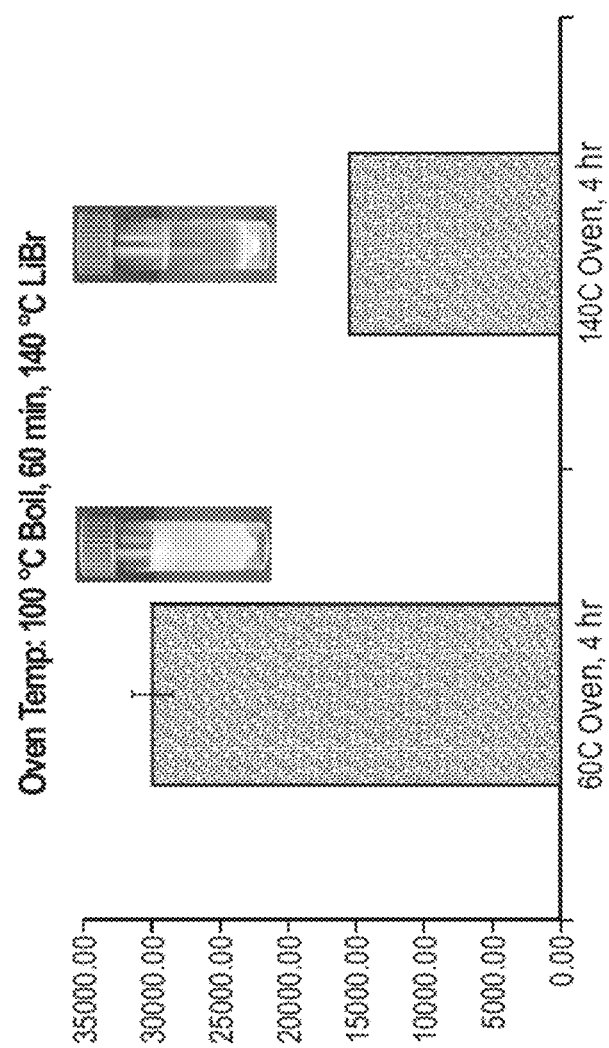
FIG. 21 is a graph summarizing the effect of Oven/Dissolution Temperature on Molecular Weight of silk processed under the conditions of 100° C. Extraction Temperature, 60 minute Extraction Time, and 140° C. Lithium Bromide (Oven/Dissolution Time was varied).
Figure 22:
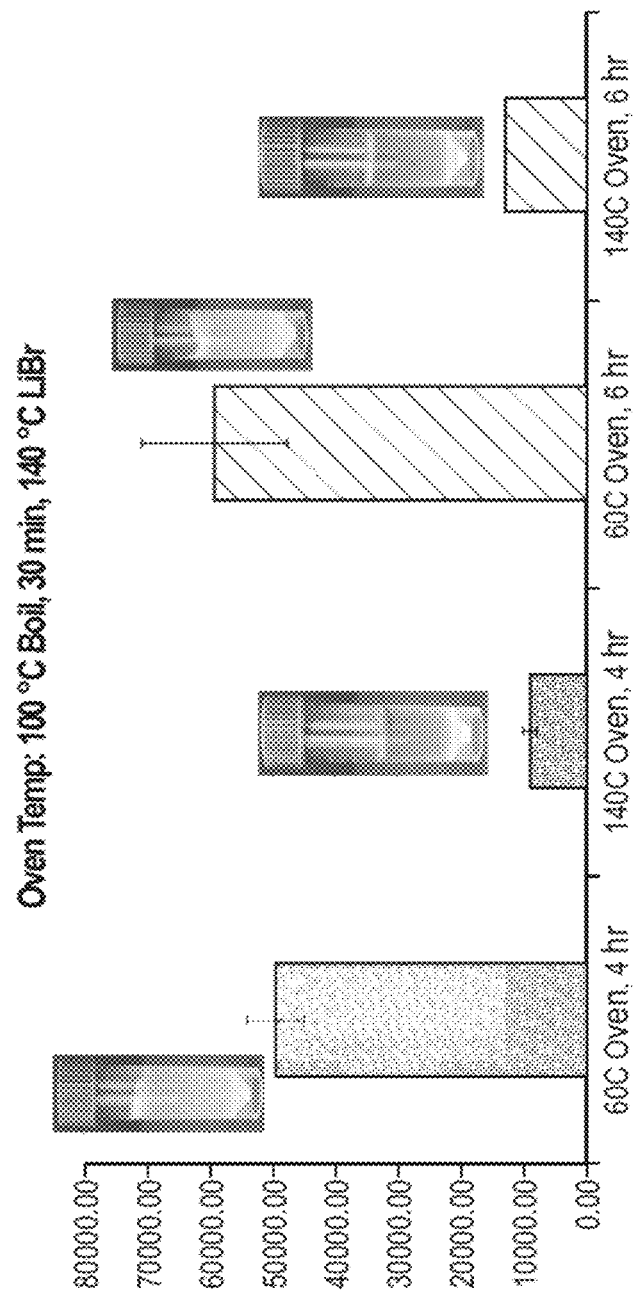
FIG. 22 is a graph summarizing the effect of Oven/Dissolution Temperature on Molecular Weight of silk processed under the conditions of 100° C. Extraction Temperature, 30 minute Extraction Time, and 140° C. Lithium Bromide (Oven/Dissolution Time was varied).
Figure 23:
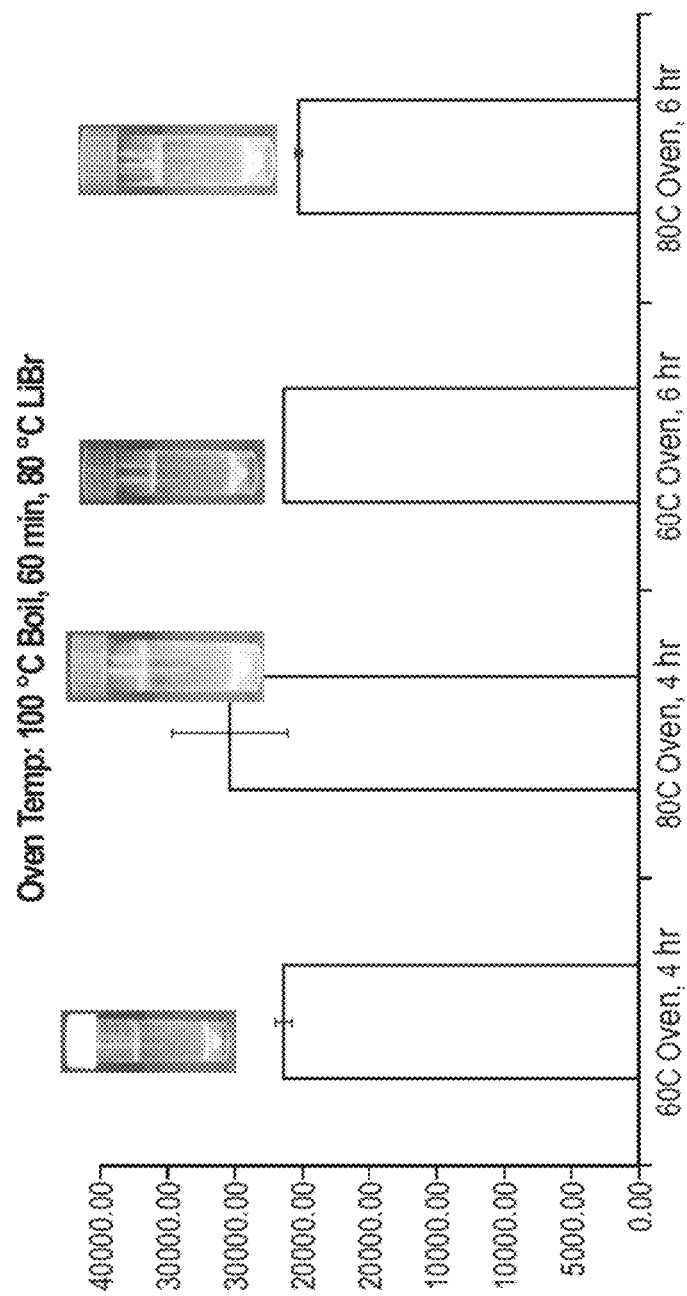
FIG. 23 is a graph summarizing the effect of Oven/Dissolution Temperature on Molecular Weight of silk processed under the conditions of 100° C. Extraction Temperature, 60 minute Extraction Time, and 80° C. Lithium Bromide (Oven/Dissolution Time was varied).
Figure 24:
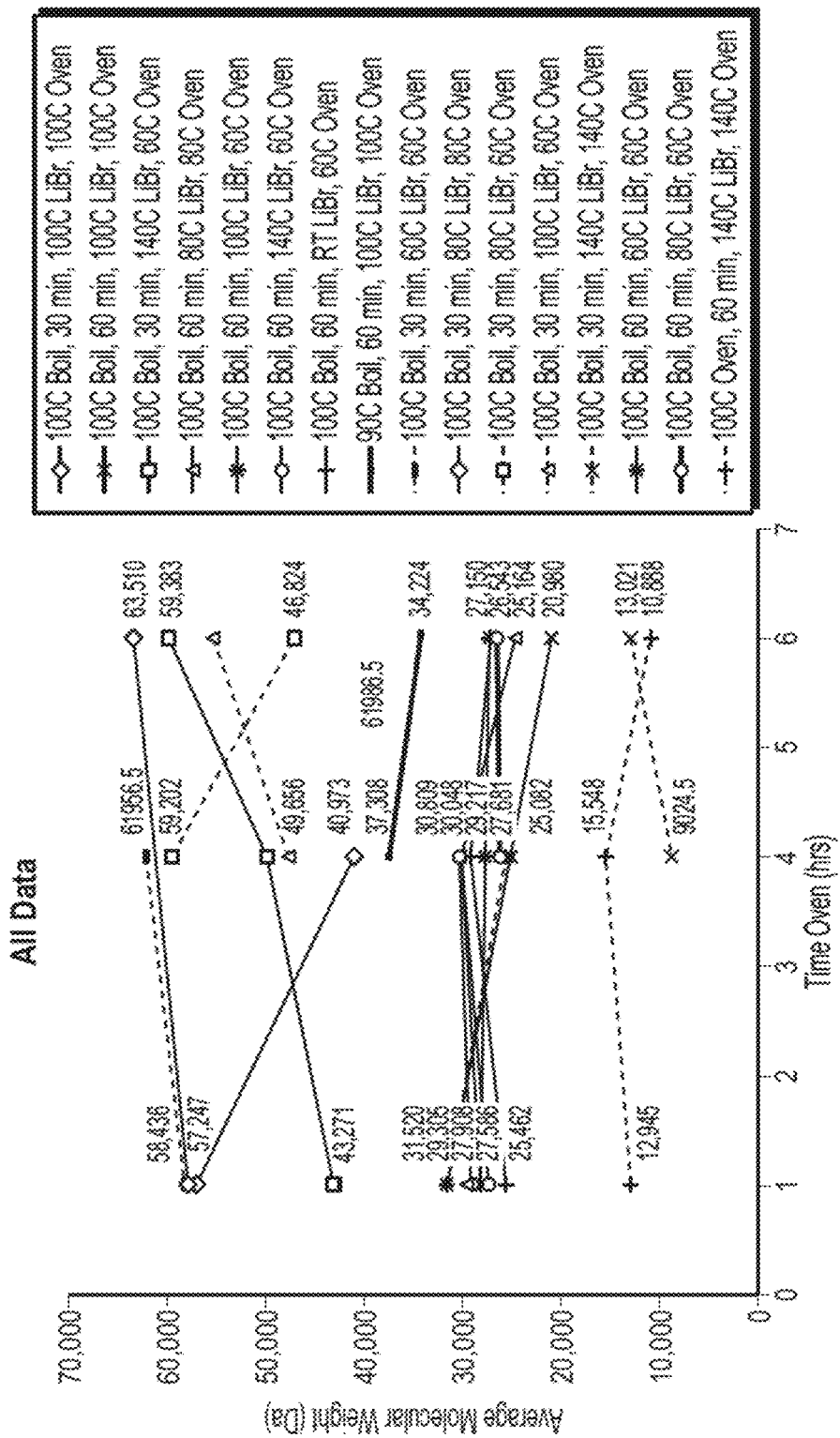
FIG. 24 is a graph summarizing the Molecular Weights of silk processed under varying conditions including Extraction Time, Extraction Temperature, Lithium Bromide (LiBr) Temperature, Oven Temperature for Dissolution, Oven Time for Dissolution.
Figure 25:
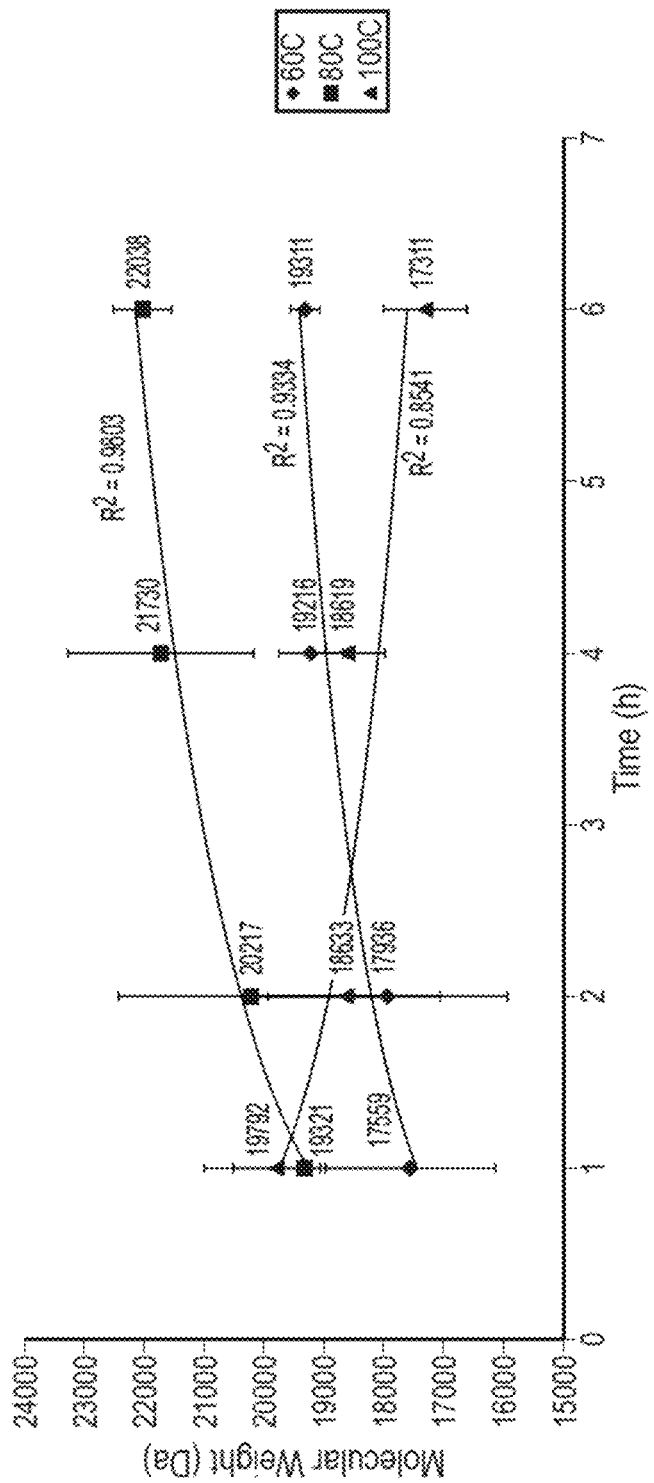
FIG. 25 is a graph summarizing the Molecular Weights of silk processed under conditions in which Oven/Dissolution Temperature is equal to LiBr Temperature.

Experiments were carried out to determine the effect of varying the Lithium Bromide (LiBr) temperature when added to silk. FIGS. 17-18 are graphs showing these results and Tables 10-11 summarize the results. Below is a summary:

No impact on MW or confidence interval (all CI~10500-6500 Da)

Studies illustrated that the temperature of LiBr-silk dissolution, as LiBr is added and begins dissolving, rapidly drops below the original LiBr temperature due to the majority of the mass being silk at room temp

TABLE 10

The effect of Lithium Bromide (LiBr) temperature on molecular weight of silk processed under the conditions of 60 min. Extraction Time., 100° C. Extraction Temperature and 60° C. Oven Dissolution (Oven/Dissolution Time was varied).

| Sample | LiBr Temp (° C.) | Oven Time | Average Mw | Standard deviation | Confidence Interval | | PD |
|---|---|---|---|---|---|---|---|
| 60° C. LiBr, 1 hr | 60 | 1 | 31700 | | 11931 | 84223 | 2.66 |
| 100° C. LiBr, 1 hr | 100 | 1 | 27907 | 200 | 10735 | 72552 | 2.60 |
| RT LiBr, 4 hr | RT | 4 | 29717 | 1082 | 10789 | 79119 | 2.71 |
| 60° C. LiBr, 4 hr | 60 | 4 | 25578 | 2445 | 9978 | 65564 | 2.56 |
| 80° C. LiBr, 4 hr | 80 | 4 | 26312 | 637 | 10265 | 67441 | 2.56 |
| 100° C. LiBr, 4 hr | 100 | 4 | 27681 | 1729 | 11279 | 67931 | 2.45 |
| Boil LiBr, 4 hr | Boil | 4 | 30042 | 1535 | 11183 | 80704 | 2.69 |
| RT LiBr, 6 hr | RT | 6 | 26543 | 1893 | 10783 | 65332 | 2.46 |
| 80° C. LiBr, 6 hr | 80 | 6 | 26353 | | 10167 | 68301 | 2.59 |
| 100° C. LiBr, 6 hr | 100 | 6 | 27150 | 916 | 11020 | 66889 | 2.46 |

TABLE 11

The effect of Lithium Bromide (LiBr) temperature on molecular weight of silk processed under the conditions of 30 min. Extraction Time, 100° C. Extraction Temperature and 60° C. Oven Dissolution (Oven/Dissolution Time was varied).

| Sample | LiBr Temp (° C.) | Oven Time | Average Mw | Standard deviation | Confidence Interval | | PD |
|---|---|---|---|---|---|---|---|
| 60° C. LiBr, 4 hr | 60 | 4 | 61956 | 13336 | 21463 | 178847 | 2.89 |
| 80° C. LiBr, 4 hr | 80 | 4 | 59202 | 14027 | 19073 | 183760 | 3.10 |
| 100° C. LiBr, 4 hr | 100 | 4 | 47853 | | 19757 | 115899 | 2.47 |
| 80° C. LiBr, 6 hr | 80 | 6 | 46824 | | 18075 | 121292 | 2.59 |
| 100° C. LiBr, 6 hr | 100 | 6 | 55421 | 8991 | 19152 | 160366 | 2.89 |

Experiments were carried out to determine the effect of oven/dissolution temperature. FIGS. 19-23 are graphs showing these results, and Tables 12-16 summarize the results. Below is a summary:

Oven temperature has less of an effect on 60 min extracted silk than 30 min extracted silk. Without wishing to be bound by theory, it is believed that the 30 min silk is less degraded during extraction and therefore the oven temperature has more of an effect on the larger MW, less degraded portion of the silk.

For 60° C. vs. 140° C. oven the 30 min extracted silk showed a very significant effect of lower MW at higher oven temp, while 60 min extracted silk had an effect but much less The 140° C. oven resulted in a low end in the confidence interval at ~6000 Da

TABLE 12

The effect of oven/dissolution temperature on molecular weight of silk processed under the conditions of 100° C. Extraction Temperature, 30 min. Extraction Time, and 100° C. Lithium Bromide (LiBr) (Oven/Dissolution Time was varied)

| Boil Time | Oven Temp (° C.) | Oven Time | Average Mw | Standard deviation | Confidence Interval | | PD |
|---|---|---|---|---|---|---|---|
| 30 | 60 | 4 | 47853 | | 19758 | 115900 | 2.42 |
| 30 | 100 | 4 | 40973 | 2632 | 14268 | 117658 | 2.87 |
| 30 | 60 | 6 | 55421 | 8992 | 19153 | 160366 | 2.89 |
| 30 | 100 | 6 | 25604 | 1405 | 10252 | 63943 | 2.50 |

TABLE 13

The effect of oven/dissolution temperature on molecular weight of silk processed under the conditions of 100° C. Extraction Temperature, 60 min. Extraction Time, and 100° C. Lithium Bromide (LiBr) (Oven/Dissolution Time was varied).

| Boil Time | Oven Temp (° C.) | Oven Time | Average Mw | Standard deviation | Confidence Interval | | PD |
|---|---|---|---|---|---|---|---|
| 60 | 60 | 1 | 27908 | 200 | 10735 | 72552 | 2.60 |
| 60 | 100 | 1 | 31520 | 1387 | 11633 | 85407 | 2.71 |
| 60 | 60 | 4 | 27681 | 1730 | 11279 | 72552 | 2.62 |
| 60 | 100 | 4 | 25082 | 1248 | 10520 | 59803 | 2.38 |
| 60 | 60 | 6 | 27150 | 916 | 11020 | 66889 | 2.46 |
| 60 | 100 | 6 | 20980 | 1262 | 10073 | 43695 | 2.08 |

TABLE 14

The effect of oven/dissolution temperature on molecular weight of silk processed under the conditions of 100° C. Extraction Temperature, 60 min. Extraction Time, and 140° C. Lithium Bromide (LiBr) (Oven/Dissolution Time was varied).

| Boil Time | Oven Temp (° C.) | Oven Time | Average Mw | Standard deviation | Confidence Interval | | PD |
|---|---|---|---|---|---|---|---|
| 60 | 60 | 4 | 30042 | 1536 | 11183 | 80705 | 2.69 |
| 60 | 140 | 4 | 15548 | | 7255 | 33322 | 2.14 |

TABLE 15

The effect of oven/dissolution temperature on molecular weight of silk processed under the conditions of 100° C. Extraction Temperature, 30 min. Extraction Time, and 140° C. Lithium Bromide (LiBr) (Oven/Dissolution Time was varied).

| Boil Time | Oven Temp (° C.) | Oven Time | Average Mw | Standard deviation | Confidence Interval | | PD |
|---|---|---|---|---|---|---|---|
| 30 | 60 | 4 | 49656 | 4580 | 17306 | 142478 | 2.87 |
| 30 | 140 | 4 | 9025 | 1102 | 4493 | 18127 | 2.01 |
| 30 | 60 | 6 | 59383 | 11640 | 17641 | 199889 | 3.37 |
| 30 | 140 | 6 | 13021 | | 5987 | 28319 | 2.17 |

TABLE 16

The effect of oven/dissolution temperature on molecular weight of silk processed under the conditions of 100° C. Extraction Temperature, 60 min. Extraction Time, and 80° C. Lithium Bromide (LiBr) (Oven/Dissolution Time was varied).

| Boil Time | Oven Temp (° C.) | Oven Time | Average Mw | Standard deviation | Confidence Interval | | PD |
|---|---|---|---|---|---|---|---|
| 60 | 60 | 4 | 26313 | 637 | 10266 | 67442 | 2.56 |
| 60 | 80 | 4 | 30308 | 4293 | 12279 | 74806 | 2.47 |
| 60 | 60 | 6 | 26353 | | 10168 | 68302 | 2.59 |
| 60 | 80 | 6 | 25164 | 238 | 9637 | 65706 | 2.61 |

In an embodiment, the methods disclosed herein result in a solution with characteristics that can be controlled during manufacturing, including, but not limited to: MW—may be varied by changing extraction and/or dissolution time and temp (e.g., LiBr temperature), pressure, and filtration (e.g., size exclusion chromatography); Structure—removal or cleavage of heavy or light chain of the fibroin protein polymer; Purity—hot water rinse temperature for improved sericin removal or filter capability for improved particulate removal that adversely affects shelf stability of the silk fragment protein mixture solution; Color—the color of the solution can be controlled with, for example, LiBr temp and time; Viscosity; Clarity; and Stability of solution. The resultant pH of the solution is typically about 7 and can be altered using an acid or base as appropriate to storage requirements.

The above-described SPF mixture solutions may be utilized to produce SPF containing tissue fillers, as described herein.

A method for preparing an aqueous solution of pure silk fibroin-based protein fragments having an average weight average molecular weight ranging from about 1 kDa to about 250 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 1 kDa to about 250 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

A method for preparing an aqueous solution of pure silk fibroin-based protein fragments having an average weight average molecular weight ranging from about 5 kDa to about 150 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 5 kDa to about 150 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

A method for preparing an aqueous solution of pure silk fibroin-based protein fragments having an average weight average molecular weight ranging from about 6 kDa to about 17 kDa includes the steps of: degumming a silk source by adding the silk source to a boiling (100° C.) aqueous solution of sodium carbonate for a treatment time of between about 30 minutes to about 60 minutes; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 60° C. to about 140° C.; maintaining the solution of silk fibroin-lithium bromide in an oven having a temperature of about 140° C. for a period of at least 1 hour; removing the lithium bromide from the silk fibroin extract; and producing an aqueous solution of silk protein fragments, the aqueous solution comprising: fragments having an average weight average molecular weight ranging from about 6 kDa to about 17 kDa. and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide. A film may be fabricated from the aqueous solution of pure silk fibroin-based protein fragments produced by this method. The film may comprise from about 1.0 wt. % to about 50.0 wt. % of vitamin C or a derivative thereof. The film may have a water content ranging from about 2.0 wt. % to about 20.0 wt. %. The film may comprise from about 30.0 wt. % to about 99.5 wt. % of pure silk fibroin-based protein fragments. A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

A method for preparing an aqueous solution of pure silk fibroin-based protein fragments having an average weight average molecular weight ranging from about 17 kDa to about 39 kDa includes the steps of: adding a silk source to a boiling (100° C.) aqueous solution of sodium carbonate for a treatment time of between about 30 minutes to about 60 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, wherein the aqueous solution of silk protein fragments comprises sodium carbonate residuals of between about 10 ppm and about 100 ppm, wherein the aqueous solution of pure silk fibroin-based protein fragments comprises fragments having an average weight average molecular weight ranging from about 17 kDa to about 39 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

According to aspects illustrated herein, there is disclosed a method for preparing an aqueous solution of pure silk fibroin-based protein fragments having an average weight average molecular weight ranging from about 39 kDa to about 80 kDa, the method including the steps of: adding a silk source to a boiling (100° C.) aqueous solution of sodium carbonate for a treatment time of about 30 minutes so as to result in degumming; removing sericin from the solution to produce a silk fibroin extract comprising non-detectable levels of sericin; draining the solution from the silk fibroin extract; dissolving the silk fibroin extract in a solution of lithium bromide having a starting temperature upon placement of the silk fibroin extract in the lithium bromide solution that ranges from about 80° C. to about 140° C.; maintaining the solution of silk fibroin-lithium bromide in a dry oven having a temperature in the range between about 60° C. to about 100° C. for a period of at least 1 hour; removing the lithium bromide from the silk fibroin extract; and producing an aqueous solution of pure silk fibroin-based protein fragments, wherein the aqueous solution of pure silk fibroin-based protein fragments comprises lithium bromide residuals of between about 10 ppm and about 300 ppm, sodium carbonate residuals of between about 10 ppm and about 100 ppm, fragments having an average weight average molecular weight ranging from about 40 kDa to about 65 kDa, and wherein the aqueous solution of pure silk fibroin-based protein fragments comprises a polydispersity of between about 1.5 and about 3.0. The method may further comprise drying the silk fibroin extract prior to the dissolving step. The aqueous solution of pure silk fibroin-based protein fragments may comprise lithium bromide residuals of less than 300 ppm as measured using a high-performance liquid chromatography lithium bromide assay. The aqueous solution of pure silk fibroin-based protein fragments may comprise sodium carbonate residuals of less than 100 ppm as measured using a high-performance liquid chromatography sodium carbonate assay. The method may further comprise adding a therapeutic agent to the aqueous solution of pure silk fibroin-based protein fragments. The method may further comprise adding a molecule selected from one of an antioxidant or an enzyme to the aqueous solution of pure silk fibroin-based protein fragments. The method may further comprise adding a vitamin to the aqueous solution of pure silk fibroin-based protein fragments. The vitamin may be vitamin C or a derivative thereof. The aqueous solution of pure silk fibroin-based protein fragments may be lyophilized. The method may further comprise adding an alpha hydroxy acid to the aqueous solution of pure silk fibroin-based protein fragments. The alpha hydroxy acid may be selected from the group consisting of glycolic acid, lactic acid, tartaric acid and citric acid. The method may further comprise adding hyaluronic acid or its salt form at a concentration of about 0.5% to about 10.0% to the aqueous solution of pure silk fibroin-based protein fragments. The method may further comprise adding at least one of zinc oxide or titanium dioxide.

A gel may be fabricated from the aqueous solution of pure silk fibroin-based protein fragments produced by this method. The gel may comprise from about 0.5 wt. % to about 20.0 wt. % of vitamin C or a derivative thereof. The gel may have a silk content of at least 2% and a vitamin content of at least 20%.

Hyaluronic Acid and Hyaluronic Acid Gels

A biodegradable polymer component of the present invention is hyaluronate, also known as hyaluronic acid (HA). HA consists of alternating residues of D-glucuronic acid and N-acetyl-D-glucosamine. This water soluble polymer is naturally found in nearly all tissue, especially in the extracellular matrix, the eyes and synovial fluid of joints. HA is commercially available in pure form. Small gel particle HA fillers may be used stimulate natural collagen production that is presumed to be induced by mechanical stretching of the dermis and activation of dermal fibroblasts.

HA concentration in the resulting dermal fillers of the invention contributes to dermal filler stiffness and longevity. In some embodiments, an increased concentration of HA in the resulting dermal fillers described herein may increase the stiffness and/or longevity of the resulting dermal filler as compared to a dermal filler having a comparatively lesser concentration of HA.

In some embodiments, HA incorporated in the tissue fillers described herein has a molecular weight of 100,000 daltons or greater, 150,000 daltons or greater, 1 million daltons or greater, or 2 million daltons or greater. In some embodiments, HA incorporated in the tissue fillers described herein has a molecular weight of 100,000 daltons or less, 150,000 daltons or less, 1 million daltons or less, or 2 million daltons or less. In some embodiments, the HA incorporated in the tissue fillers described herein has a high molecular weight (e.g., an HA molecular weight of about 1 MDa to about 4 MDa). In some embodiments, the HA incorporated in the tissue fillers described herein has a low molecular weight (e.g., an HA molecular weight of less than about 1 MDa).

In some embodiments, the HA source may be a hyaluronate salt such as, for example, sodium hyaluronate. In some embodiments, the HA is cross-linked. Cross-linked HA can be formulated into a variety of shapes, such as membranes, gels, semi-gels, sponges, or microspheres. In some embodiments, the cross-linked HA is in fluid gel form, i.e., it takes the shape of its container. The viscosity of an HA gel or semi-gel can be altered by the addition of unconjugated HA and/or hyaluronate. Viscosity can also be tuned by varying the degree of SPF-SPF, SPF-HA, and/or HA-HA cross-linking as described herein. In some embodiment, about 4% to about 12% of the HA may be cross-linked as HA-HA or HA-SPF.

In an embodiment, the SPF compositions described herein may be combined with HA to form a tissue filler composition. In an embodiment, the percent HA in the tissue filler composition by weight is less than 99%. In an embodiment, the percent HA in the tissue filler composition by weight is less than 98%. In an embodiment, the percent HA in the tissue filler composition by weight is less than 97%. In an embodiment, the percent HA in the tissue filler composition by weight is less than 96%. In an embodiment, the percent HA in the tissue filler composition by weight is less than 95%. In an embodiment, the percent HA in the tissue filler composition by weight is less than 94%. In an embodiment, the percent HA in the tissue filler composition by weight is less than 93%. In an embodiment, the percent HA in the tissue filler composition by weight is less than 92%. In an embodiment, the percent HA in the tissue filler composition by weight is less than 91%. In an embodiment, the percent HA in the tissue filler composition by weight is less than 90%. In an embodiment, the percent HA in the tissue filler composition by weight is less than 85%. In an embodiment, the percent HA in the tissue filler composition by weight is less than 80%. In an embodiment, the percent HA in the tissue filler composition by weight is less than 75%. In an embodiment, the percent HA in the tissue filler composition by weight is less than 70%. In an embodiment, the percent HA in the tissue filler composition by weight is less than 65%. In an embodiment, the percent HA in the tissue filler composition by weight is less than 600%. In an embodiment, the percent HA in the tissue filler composition by weight is less than 55%. In an embodiment, the percent HA in the tissue filler composition by weight is less than 50%. In an embodiment, the percent HA in the tissue filler composition by weight is less than 45%. In an embodiment, the percent HA in the tissue filler composition by weight is less than 40%. In an embodiment, the percent HA in the tissue filler composition by weight is less than 35%. In an embodiment, the percent HA in the tissue filler composition by weight is less than 30%. In an embodiment, the percent HA in the tissue filler composition by weight is less than 25%. In an embodiment, the percent HA in the tissue filler composition by weight is less than 20%. In an embodiment, the percent HA in the tissue filler composition by weight is less than 19%. In an embodiment, the percent HA in the tissue filler composition by weight is less than 18%. In an embodiment, the percent HA in the tissue filler composition by weight is less than 17%. In an embodiment, the percent HA in the tissue filler composition by weight is less than 16%. In an embodiment, the percent HA in the tissue filler composition by weight is less than 15%. In an embodiment, the percent HA in the tissue filler composition by weight is less than 14%. In an embodiment, the percent HA in the tissue filler composition by weight is less than 13%. In an embodiment, the percent HA in the tissue filler composition by weight is less than 12%. In an embodiment, the percent HA in the tissue filler composition by weight is less than 11%. In an embodiment, the percent HA in the tissue filler composition by weight is less than 10%. In an embodiment, the percent HA in the tissue filler composition by weight is less than 9%. In an embodiment, the percent HA in the tissue filler composition by weight is less than 8%. In an embodiment, the percent HA in the tissue filler composition by weight is less than 7%. In an embodiment, the percent HA in the tissue filler composition by weight is less than 6%. In an embodiment, the percent HA in the tissue filler composition by weight is less than 5%. In an embodiment, the percent HA in the tissue filler composition by weight is less than 4%. In an embodiment, the percent HA in the tissue filler composition by weight is less than 3%. In an embodiment, the percent HA in the tissue filler composition by weight is less than 2%. In an embodiment, the percent HA in the tissue filler composition by weight is less than 1%. In an embodiment, the percent HA in the tissue filler composition by weight is less than 0.9%. In an embodiment, the percent HA in the tissue filler composition by weight is less than 0.8%. In an embodiment, the percent HA in the tissue filler composition by weight is less than 0.7%. In an embodiment, the percent HA in the tissue filler composition by weight is less than 0.6%. In an embodiment, the percent HA in the tissue filler composition by weight is less than 0.5%. In an embodiment, the percent HA in the tissue filler composition by weight is less than 0.4%. In an embodiment, the percent HA in the tissue filler composition by weight is less than 0.3%. In an embodiment, the percent HA in the tissue filler composition by weight is less than 0.2%. In an embodiment, the percent HA in the tissue filler composition by weight is less than 0.1%. In an embodiment, the percent HA in the tissue filler composition by weight is greater than 0.1%. In an embodiment, the percent HA in the tissue filler composition by weight is greater than 0.2%. In an embodiment, the percent HA in the tissue filler composition by weight is greater than 0.3%. In an embodiment, the percent HA in the tissue filler composition by weight is greater than 0.4%. In an embodiment, the percent HA in the tissue filler composition by weight is greater than 0.5%. In an embodiment, the percent HA in the tissue filler composition by weight is greater than 0.6%. In an embodiment, the percent HA in the tissue filler composition by weight is greater than 0.7%. In an embodiment, the percent HA in the tissue filler composition by weight is greater than 0.8%. In an embodiment, the percent HA in the tissue filler composition by weight is greater than 0.9%. In an embodiment, the percent HA in the tissue filler composition by weight is greater than 1%. In an embodiment, the percent HA in the tissue filler composition by weight is greater than 2%. In an embodiment, the percent HA in the tissue filler composition by weight is greater than 3%. In an embodiment, the percent HA in the tissue filler composition by weight is greater than 4%. In an embodiment, the percent HA in the tissue filler composition by weight is greater than 5%. In an embodiment, the percent HA in the tissue filler composition by weight is greater than 6%. In an embodiment, the percent HA in the tissue filler composition by weight is greater than 7%. In an embodiment, the percent HA in the tissue filler composition by weight is greater than 8%. In an embodiment, the percent HA in the tissue filler composition by weight is greater than 9%. In an embodiment, the percent HA in the tissue filler composition by weight is greater than 10%. In an embodiment, the percent HA in the tissue filler composition by weight is greater than 11%. In an embodiment, the percent HA in the tissue filler composition by weight is greater than 12%. In an embodiment, the percent HA in the tissue filler composition by weight is greater than 13%. In an embodiment, the percent HA in the tissue filler composition by weight is greater than 14%. In an embodiment, the percent HA in the tissue filler composition by weight is greater than 15%. In an embodiment, the percent HA in the tissue filler composition by weight is greater than 16%. In an embodiment, the percent HA in the tissue filler composition by weight is greater than 17%. In an embodiment, the percent HA in the tissue filler composition by weight is greater than 18%. In an embodiment, the percent HA in the tissue filler composition by weight is greater than 19%. In an embodiment, the percent HA in the tissue filler composition by weight is greater than 20%. In an embodiment, the percent HA in the tissue filler composition by weight is greater than 25%. In an embodiment, the percent HA in the tissue filler composition by weight is greater than 30%. In an embodiment, the percent HA in the tissue filler composition by weight is greater than 35%. In an embodiment, the percent HA in the tissue filler composition by weight is greater than 40%. In an embodiment, the percent HA in the tissue filler composition by weight is greater than 45%. In an embodiment, the percent HA in the tissue filler composition by weight is greater than 50%. In an embodiment, the percent HA in the tissue filler composition by weight is greater than 55%. In an embodiment, the percent HA in the tissue filler composition by weight is greater than 60%. In an embodiment, the percent HA in the tissue filler composition by weight is greater than 65%. In an embodiment, the percent HA in the tissue filler composition by weight is greater than 70%. In an embodiment, the percent HA in the tissue filler composition by weight is greater than 75%. In an embodiment, the percent HA in the tissue filler composition by weight is greater than 80%. In an embodiment, the percent HA in the tissue filler composition by weight is greater than 85%. In an embodiment, the percent HA in the tissue filler composition by weight is greater than 90%. In an embodiment, the percent HA in the tissue filler composition by weight is greater than 91%. In an embodiment, the percent HA in the tissue filler composition by weight is greater than 92%. In an embodiment, the percent HA in the tissue filler composition by weight is greater than 93%. In an embodiment, the percent HA in the tissue filler composition by weight is greater than 94%. In an embodiment, the percent HA in the tissue filler composition by weight is greater than 95%. In an embodiment, the percent HA in the tissue filler composition by weight is greater than 96%. In an embodiment, the percent HA in the tissue filler composition by weight is greater than 97%. In an embodiment, the percent HA in the tissue filler composition by weight is greater than 98%.

In an embodiment, the percent HA in the tissue filler composition by weight is about 0.1%. In an embodiment, the percent HA in the tissue filler composition by weight is about 0.2%. In an embodiment, the percent HA in the tissue filler composition by weight is about 0.3%. In an embodiment, the percent HA in the tissue filler composition by weight is about 0.4%. In an embodiment, the percent HA in the tissue filler composition by weight is about 0.5%. In an embodiment, the percent HA in the tissue filler composition by weight is about 0.6%. In an embodiment, the percent HA in the tissue filler composition by weight is about 0.7%. In an embodiment, the percent HA in the tissue filler composition by weight is about 0.8%. In an embodiment, the percent HA in the tissue filler composition by weight is about 0.9%. In an embodiment, the percent HA in the tissue filler composition by weight is about 1%. In an embodiment, the percent HA in the tissue filler composition by weight is about 2%. In an embodiment, the percent HA in the tissue filler composition by weight is about 3%. In an embodiment, the percent HA in the tissue filler composition by weight is about 4%. In an embodiment, the percent HA in the tissue filler composition by weight is about 5%. In an embodiment, the percent HA in the tissue filler composition by weight is about 6%. In an embodiment, the percent HA in the tissue filler composition by weight is about 7%. In an embodiment, the percent HA in the tissue filler composition by weight is about 8%. In an embodiment, the percent HA in the tissue filler composition by weight is about 9%. In an embodiment, the percent HA in the tissue filler composition by weight is about 10%. In an embodiment, the percent HA in the tissue filler composition by weight is about 11%. In an embodiment, the percent HA in the tissue filler composition by weight is about 12%. In an embodiment, the percent HA in the tissue filler composition by weight is about 13%. In an embodiment, the percent HA in the tissue filler composition by weight is about 14%. In an embodiment, the percent HA in the tissue filler composition by weight is about 15%. In an embodiment, the percent HA in the tissue filler composition by weight is about 16%. In an embodiment, the percent HA in the tissue filler composition by weight is about 17%. In an embodiment, the percent HA in the tissue filler composition by weight is about 18%. In an embodiment, the percent HA in the tissue filler composition by weight is about 19%. In an embodiment, the percent HA in the tissue filler composition by weight is about 20%. In an embodiment, the percent HA in the tissue filler composition by weight is about 25%. In an embodiment, the percent HA in the tissue filler composition by weight is about 30%. In an embodiment, the percent HA in the tissue filler composition by weight is about 35%. In an embodiment, the percent HA in the tissue filler composition by weight is about 40%. In an embodiment, the percent HA in the tissue filler composition by weight is about 45%. In an embodiment, the percent HA in the tissue filler composition by weight is about 50%. In an embodiment, the percent HA in the tissue filler composition by weight is about 55%. In an embodiment, the percent HA in the tissue filler composition by weight is about 60%. In an embodiment, the percent HA in the tissue filler composition by weight is about 65%. In an embodiment, the percent HA in the tissue filler composition by weight is about 70%. In an embodiment, the percent HA in the tissue filler composition by weight is about 75%. In an embodiment, the percent HA in the tissue filler composition by weight is about 80%. In an embodiment, the percent HA in the tissue filler composition by weight is about 85%. In an embodiment, the percent HA in the tissue filler composition by weight is about 90%. In an embodiment, the percent HA in the tissue filler composition by weight is about 91%. In an embodiment, the percent HA in the tissue filler composition by weight is about 92%. In an embodiment, the percent HA in the tissue filler composition by weight is about 93%. In an embodiment, the percent HA in the tissue filler composition by weight is about 94%. In an embodiment, the percent HA in the tissue filler composition by weight is about 95%. In an embodiment, the percent HA in the tissue filler composition by weight is about 96%. In an embodiment, the percent HA in the tissue filler composition by weight is about 97%. In an embodiment, the percent HA in the tissue filler composition by weight is about 98%.

In an embodiment, the percent HA in the tissue filler composition by weight is between about 0.1% to about 1%.

In an embodiment, the percent HA in the tissue filler composition by weight is between about 0.5% to about 1.5%. In an embodiment, the percent HA in the tissue filler composition by weight is between about 1% to about 5%. In an embodiment, the percent HA in the tissue filler composition by weight is between about 1.5% to about 5.5%. In an embodiment, the percent HA in the tissue filler composition by weight is between about 2% to about 6%. In an embodiment, the percent HA in the tissue filler composition by weight is between about 2.5% to about 6.5%. In an embodiment, the percent HA in the tissue filler composition by weight is between about 3% to about 7%. In an embodiment, the percent HA in the tissue filler composition by weight is between about 3.5% to about 7.5%. In an embodiment, the percent HA in the tissue filler composition by weight is between about 4% to about 8%. In an embodiment, the percent HA in the tissue filler composition by weight is between about 4.5% to about 8.5%. In an embodiment, the percent HA in the tissue filler composition by weight is between about 5% to about 9%. In an embodiment, the percent HA in the tissue filler composition by weight is between about 5.5% to about 9.5%. In an embodiment, the percent HA in the tissue filler composition by weight is between about 6% to about 10%. In an embodiment, the percent HA in the tissue filler composition by weight is between about 6.5% to about 10.5%. In an embodiment, the percent HA in the tissue filler composition by weight is between about 7% to about 11%. In an embodiment, the percent HA in the tissue filler composition by weight is between about 7.5% to about 11.5%. In an embodiment, the percent HA in the tissue filler composition by weight is between about 8% to about 12%. In an embodiment, the percent HA in the tissue filler composition by weight is between about 8.5% to about 12.5%. In an embodiment, the percent HA in the tissue filler composition by weight is between about 9% to about 13%. In an embodiment, the percent HA in the tissue filler composition by weight is between about 9.5% to about 13.5%. In an embodiment, the percent HA in the tissue filler composition by weight is between about 10% to about 14%. In an embodiment, the percent HA in the tissue filler composition by weight is between about 10.5% to about 14.5%. In an embodiment, the percent HA in the tissue filler composition by weight is between about 11% to about 15%. In an embodiment, the percent HA in the tissue filler composition by weight is between about 11.5% to about 15.5%. In an embodiment, the percent HA in the tissue filler composition by weight is between about 12% to about 16%. In an embodiment, the percent HA in the tissue filler composition by weight is between about 12.5% to about 16.5%. In an embodiment, the percent HA in the tissue filler composition by weight is between about 13% to about 17%. In an embodiment, the percent HA in the tissue filler composition by weight is between about 13.5% to about 17.5%. In an embodiment, the percent HA in the tissue filler composition by weight is between about 14% to about 18%. In an embodiment, the percent HA in the tissue filler composition by weight is between about 14.5% to about 18.5%. In an embodiment, the percent HA in the tissue filler composition by weight is between about 15% to about 19%. In an embodiment, the percent HA in the tissue filler composition by weight is between about 15.5% to about 19.5%. In an embodiment, the percent HA in the tissue filler composition by weight is between about 16% to about 20%. In an embodiment, the percent HA in the tissue filler composition by weight is between about 20% to about 30%. In an embodiment, the percent HA in the tissue filler composition by weight is between about 30% to about 40%. In an embodiment, the percent HA in the tissue filler composition by weight is between about 40% to about 50%. In an embodiment, the percent HA in the tissue filler composition by weight is between about 50% to about 60%. In an embodiment, the percent HA in the tissue filler composition by weight is between about 60% to about 70%. In an embodiment, the percent HA in the tissue filler composition by weight is between about 80% to about 90%

In some embodiments, the percent HA, by weight, in the tissue filler compositions described herein is about 1% to about 2%, or about 1% to about 3%, or about 1% to about 4%, or about 1% to about 5%, or about 1% to about 6%, or about 1% to about 7%, or about 1% to about 8%, or about 1% to about 9%, or about 1% to about 10%, or about 1% to about 11%, or about 1% to about 12%, or about 1% to about 13%, or about 1% to about 14%, or about 1% to about 15%, or about 1% to about 16%, or about 1% to about 17%, or about 1% to about 18%, or about 1% to about 19%, or about 1% to about 20%, or about 1% to about 21%, or about 1% to about 22%, or about 1% to about 23%, or about 1% to about 24%, or about 1% to about 25%, or about 1% to about 30%, or about 1% to about 400%, or about 1% to about 50%, or about 1% to about 60% 0, or about 1% to about 70%, or about 1% to about 80%, or about 1% to about 95%; or about 10% to about 20%, or about 10% to about 25%, or about 10% to about 30%, or about 10% to about 35%, or about 10% to about 40%, or about 10% to about 45%, or about 10% to about 50%, or about 10% to about 55%, or about 10% to about 60%, or about 10% to about 65%, or about 10% to about 70%, or about 10% to about 75%, or about 10% to about 80%, or about 10% to about 85%, or about 10% to about 900%, or about 10% to about 95%.

In some embodiments, the HA described herein may be acquired from commercial sources or may be produced by *Streptococcus equi* bacteria.

Tissue fillers described herein that include HA may be characterized for their in vitro biological activities and in vivo biological activities. For example, in vitro assays may be performed on a portion of the tissue fillers described herein for cell toxicity, resistance to enzymatic degradation, syringeability (e.g., solution viscosity, injection flow rate, syringe/needle diameter), and/or particle morphology analysis. See, e.g., Park, et al., J. Eur. Acad. Dermatol. Venerol. (2014) 28:565-568. In vivo assays may be performed to determine initial morphological patterns, total remaining filler present, histological evaluations, and may include the examination of granuloma formation or cutaneous adverse reactions. See, e.g., Park, et al., J. Eur. Acad. Dermatol. Venerol. (2014) 28:565-568; and Ramot, et al., Toxicology Pathology (2015) 43: 267-271.

Gelation

In an embodiment, silk gels may be provided with a gelation aid. In some embodiments, the gelation aid may be an acid, electricity, mixing, and/or sonication.

In an embodiment, when producing a silk gel, an acid can be added to a silk solution described herein to help facilitate gelation. In an embodiment, when producing a silk gel that includes a neutral or a basic molecule and/or therapeutic agent, an acid can be added to facilitate gelation. In an embodiment, when producing a silk gel, increasing the pH (making the gel more basic) increases the shelf stability of the gel. In an embodiment, when producing a silk gel, increasing the pH (making the gel more basic) allows for a greater quantity of an acidic molecule to be loaded into the gel.

In an embodiment, when producing a silk gel, electricity can be passed through a silk solution described herein to help facilitate gelation.

In an embodiment, when producing a silk gel, mixing of a silk solution described herein can be used to help facilitate gelation.

In an embodiment, when producing a silk gel, sonication of a silk solution described herein can be used to help facilitate gelation.

In an embodiment, natural additives may be added to the silk gel to further stabilize additives. For example, trace elements such as selenium or magnesium or L-methionine can be used. Further, light-block containers can be added to further increase stability.

In some embodiments, gelation enhancers can be used to accelerate SPF gelation. In some embodiments, an SPF solution can be mixed with pure alcohol or aqueous alcohol solution at varied volume ratios accompanied by mixing, either through stirring, shaking or any other form of agitation. In some embodiments, this alcohol solution enhancer may then have a quantity of an amphiphilic peptide added as a further enhancer of the final gel outcome. The extent of acceleration may be heightened or lessened as appropriate by adding a larger or smaller enhancer component to the system.

In some embodiments, gelation rate may be enhanced by increasing the concentration of SPF in a solution used for making a gel. Various methods can be used to that end, including but not limited to: dialysis of intermediate SPF solution against a buffer incorporating a hygroscopic species such as polyethylene glycol, a lyophilization step, and/or an evaporation step. Increased temperature may also be used as an enhancer of the gelation process. In addition, manipulation of intermediate silk solution pH by methods including but not limited to direct titration and gas exchange can be used to enhance the gelation process. Introduction of select ionic species including calcium and potassium in particular may also be used to accelerate gelation rate.

In some embodiments, gelation can be helped by the use of nucleating agents, including organic and inorganic species, both soluble and insoluble in an SPF intermediate. Nucleating agents can include but are not limited to peptide sequences which bind silk molecules, previously gelled silk, and poorly soluble β-sheet rich structures. In some embodiments, a further means of accelerating the gelation process is through the introduction of mechanical excitation, which can be imparted through a shearing device, ultrasound device, or mechanical mixer.

The time necessary for complete silk solution gelation may vary from seconds to hours or days, depending on the values of the above mentioned parameters as well as the initial state of aggregation and organization found in the SPF solution. The volume fraction of added enhancer may vary from about 0% to about 99% of the total system volume (i.e., either component may be added to a large excess of the other or in any relative concentration within the interval). The concentration of SPF solution used can range from about 1% (w/v), to about 20% (w/v), and any other appropriate range. The enhancer can be added to SPF solution or the SPF solution can be added to enhancer. The formed SPF hydrogel may be further chemically or physically cross-linked to gain altered mechanical properties.

In some embodiments, an enhancer solution is added to an SPF solution, or vice-versa, the SPF solution having a concentration of SPF of about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), about 12% (w/v), about 15% (w/v), about 18% (w/v), about 20% (w/v), about 25% (w/v), or about 30% (w/v). In some embodiments, an enhancer solution is added to an SPF solution, or vice-versa, the SPF solution having a concentration of SPF of at least 1% (w/v), at least 2% (w/v), at least 3% (w/v), at least 4% (w/v), at least 5% (w/v), at least 6% (w/v), at least 7% (w/v), at least 8% (w/v), at least 9% (w/v), at least 10% (w/v), at least 12% (w/v), at least 15% (w/v), at least 18% (w/v), at least 20% (w/v), at least 25% (w/v), or at least 30% (w/v). In some embodiments, an enhancer solution is added to an SPF solution, or vice-versa, the SPF solution having a concentration of SPF of about 1% (w/v) to about 5% (w/v), about 1% (w/v) to about 10% (w/v), about 1% (w/v) to about 15% (w/v), about 1% (w/v) to about 20% (w/v), about 1% (w/v) to about 25% (w/v), about 1% (w/v) to about 30% (w/v), about 5% (w/v) to about 10% (w/v), about 5% (w/v) to about 15% (w/v), about 5% (w/v) to about 20% (w/v), about 5% (w/v) to about 25% (w/v), about 5% (w/v) to about 30% (w/v), about 10% (w/v) to about 15% (w/v), about 10% (w/v) to about 20% (w/v), about 10% (w/v) to about 25% (w/v), or about 10% (w/v) to about 30% (w/v).

Gels and Hydrogels—Modifying and Cross-Linking

In some embodiments, the invention provides compositions comprising one or more hydrogels comprising one or more cross-linked matrix polymers. As used herein, the term "cross-linked" refers to the intermolecular bonds joining the individual polymer molecules, macromolecules, and/or monomer chains, into a more stable structure like a gel. As such, a cross-linked matrix polymer has at least one intermolecular bond joining at least one individual polymer molecule to another one, where the first individual polymer molecule can be of similar, or different, chemical nature to the other. Matrix polymers disclosed herein may be cross-linked using dialdehydes and disulfides cross-linking agents including, without limitation, multifunctional PEG-based crosslinking agents, divinyl sulfones, diglycidyl ethers, and bis-epoxides. Non-limiting examples of SPF, and/or HA, cross-linking agents include divinyl sulfone (DVS), 1,4-butanediol diglycidyl ether (BDDE), UV light, glutaraldehyde, 1,2-bis(2,3-epoxypropoxy)ethylene (EGDGE), 1,2,7,8-diepoxyoctane (DEO), biscarbodiimide (BCD), pentaerythritol tetraglycidyl ether (PETGE), adipic dihydrazide (ADH), bis(sulfosuccinimidyl)suberate (BS), hexamethylenediamine (HMDA), 1-(2,3-epoxypropyl)-2,3-epoxycyclohexane, or combinations thereof. In some embodiments, the HA cross-linking agent may include BDDE or DVS. In some embodiments, the HA and/or SPF cross-linking agent may be BDDE, DVS, UV light, glutaraldehyde, or a carbodiimide, as described herein.

In some embodiments, the tissue fillers described herein may contain residual cross-linking agent. In some embodiments, the tissue fillers described herein may contain only trace amounts of the cross-linking agent such as, for example, no greater than about 2 ppm, or no greater than about 1.9 ppm, or no greater than about 1.8 ppm, or no greater than about 1.7 ppm, or no greater than about 1.6 ppm, or no greater than about 1.5 ppm, or no greater than about 1.4 ppm, or no greater than about 1.3 ppm, or no greater than about 1.2 ppm, or no greater than about 1.1 ppm, or no greater than about 1.0 ppm, or no greater than about 0.9 ppm, or no greater than about 0.8 ppm, or no greater than about 0.7 ppm, or no greater than about 0.6 ppm, or no greater than about 0.5 ppm, or no greater than about 0.4 ppm, or no greater than about 0.3 ppm, or no greater than about 0.2 ppm, or no greater than about 0.1 ppm. In some embodiments, the tissue fillers described herein may contain trace amounts BDDE, but at a concentration no greater than about 2 ppm, or no greater than about 1.9 ppm, or no greater than about 1.8 ppm, or no greater than about 1.7 ppm, or no greater than about 1.6 ppm, or no greater than about 1.5 ppm, or no greater than about 1.4 ppm, or no greater than about 1.3 ppm, or no greater than about 1.2 ppm, or no greater than about 1.1 ppm, or no greater than about 1.0 ppm, or no greater than about 0.9 ppm, or no greater than about 0.8 ppm, or no greater than about 0.7 ppm, or no greater than about 0.6 ppm, or no greater than about 0.5 ppm, or no greater than about 0.4 ppm, or no greater than about 0.3 ppm, or no greater than about 0.2 ppm, or no greater than about 0.1 ppm. As understood by a person having ordinary skill in the art, the amount of residual cross-linking agent present in a particular tissue filler sample may be determined by gas chromatography-mass spectrometry.

In some embodiments, the tissue fillers described herein may include a matrix that may include an SPF matrix portion and an HA matrix portion, where the SPF matrix portion includes a mixture of cross-linked and non-cross-linked SPF and the HA matrix portion includes a mixture of cross-linked and non-cross-linked HA.

In some embodiments, the tissue fillers of the invention include linker modified HA. In some embodiments, the tissue fillers of the invention include linker modified SPF. Bifunctional cross-linkers can react at both ends to connect two different HA molecules, two different SPF molecules, or an HA molecule with an SPF molecule. In some embodiments, the cross-linker bonds with an HA molecule only at one end, leaving the other end pendant. In some embodiments, the cross-linker bonds with an SPF molecule only at one end, leaving the other end pendant.

As used herein, the degree of modification (MoD) can be defined as (see for example J. Kablik et al., Dermatol Surg, 2009 (35): 302-312):

Total % Degree of Modification=% Crosslink+% Pendant

In order to determine the MoD, it can also be defined as (see for example L. Kenne et al., Carbohydrate Polymers, 2013 (91): 410-418):

$$MoD = \frac{n_{linked\ crosslinkers}}{n_{HA\ disaccharides} + n_{SPF\ repeating\ units}}$$

where $n_{linked\ crosslinkers}$ is the number of linked cross-linker molecules, $n_{HA\ disaccharides}$ is the number or disaccharides in HA, and $n_{SPF\ repeating\ units}$ is the number of repeating units in SPF. These numbers can be determined by NMR using characteristic chemical shifts of crosslinker, HA, and SPF.

In some embodiments, the MoD is between about 1% and 25%, between about 2% and about 20%, or between about 3.5% and about 17.5%. In some embodiments, the MoD is about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, about 5.0%, about 5.1%, about 5.2%, about 5.3%, about 5.4%, about 5.5%, about 5.6%, about 5.7%, about 5.8%, about 5.9%, about 6.0%, about 6.1%, about 6.2%, about 6.3%, about 6.4%, about 6.5%, about 6.6%, about 6.7%, about 6.8%, about 6.9%, about 7.0%, about 7.1%, about 7.2%, about 7.3%, about 7.4%, about 7.5%, about 7.6%, about 7.7%, about 7.8%, about 7.9%, about 8.0%, about 8.1%, about 8.2%, about 8.3%, about 8.4%, about 8.5%, about 8.6%, about 8.7%, about 8.8%, about 8.9%, about 9.0%, about 9.1%, about 9.2%, about 9.3%, about 9.4%, about 9.5%, about 9.6%, about 9.7%, about 9.8%, about 9.9%, about 10.0%, about 10.1%, about 10.2%, about 10.3%, about 10.4%, about 10.5%, about 10.6%, about 10.7%, about 10.8%, about 10.9%, about 11.0%, about 11.1%, about 11.2%, about 11.3%, about 11.4%, about 11.5%, about 11.6%, about 11.7%, about 11.8%, about 11.9%, about 12.0%, about 12.1%, about 12.2%, about 12.3%, about 12.4%, about 12.5%, about 12.6%, about 12.7%, about 12.8%, about 12.9%, about 13.0%, about 13.1%, about 13.2%, about 13.3%, about 13.4%, about 13.5%, about 13.6%, about 13.7%, about 13.8%, about 13.9%, about 14.0%, about 14.1%, about 14.2%, about 14.3%, about 14.4%, about 14.5%, about 14.6%, about 14.7%, about 14.8%, about 14.9%, about 15.0%, about 15.1%, about 15.2%, about 15.3%, about 15.4%, about 15.5%, about 15.6%, about 15.7%, about 15.8%, about 15.9%, about 16.0%, about 16.1%, about 16.2%, about 16.3%, about 16.4%, about 16.5%, about 16.6%, about 16.7%, about 16.8%, about 16.9%, about 17.0%, about 17.1%, about 17.2%, about 17.3%, about 17.4%, about 17.5%, about 17.6%, about 17.7%, about 17.8%, about 17.9%, about 18.0%, about 18.1%, about 18.2%, about 18.3%, about 18.4%, about 18.5%, about 18.6%, about 18.7%, about 18.8%, about 18.9%, about 19.0%, about 19.1%, about 19.2%, about 19.3%, about 19.4%, about 19.5%, about 19.6%, about 19.7%, about 19.8%, about 19.9%, or about 20.0%.

In some embodiments, the tissue fillers of the invention include cross-linked SPF. In some embodiments, the tissue fillers of the invention include cross-linked HA. An SPF fragment can be cross-linked to another SPF fragment, or with HA. SPF-SPF, SPF-HA, and HA-HA cross-linked species can be obtained by using cross-linking agents of various lengths, including zero length.

In some embodiments, the tissue fillers described herein may be provided in the form of a hydrogel having cross-linked HA and/or cross-linked SPF. The cross-linked HA and/or cross-linked SPF (or SPF-HA cross-linked species) may have a measurable degree of cross-linking. As used herein, the term "degree of crosslinking" refers to the number of cross-linking units (or molecules or residues) relative to the number of monomeric units in the polymer macromolecule, which was cross-linked. In some embodiments, the monomeric units are the amino acids in SPF. In some embodiments, the monomeric units are the disaccharide monomer units of HA. Thus, a composition that that has a cross-linked matrix polymer with a 4% degree of cross-linking means that on average there are four crosslinking molecules for every 100 monomeric units. Every other parameter being equal, the greater the degree of crosslinking, the harder the gel becomes. Without being limited to any one theory of the invention, the degree of cross-linking in HA and/or SPF may result in stiffer resulting materials or compositions prepared therefrom. For example, the higher the degree of cross-linking, the longer such materials are likely to persist in the body. Indeed, without being limited to any one theory, biocompatible materials that include cross-linked materials will have varied rates of bioresorption, bioabsorption, and/or biodegradation depending on the degree of crosslinking where degree of cross-linking is inversely proportional to the rate of bioresorption, bioabsorption, and/or biodegradation. Furthermore, greater cross-linking in the tissue fillers described herein may reduce hydrophilicity and the lifting capacity of such tissue fillers.

In a non-limiting example, a cross-linked SPF that has a degree of crosslinking of about 5%, has about 5 cross-linking moieties for every 100 monomeric units, e.g., amino acids, in the cross-linked SPF.

Non-limiting examples of a degree of crosslinking include about 1% to about 15%, or about 2% to about 14%, or about 1% to about 2%, about 1.5% to about 2.5%, or about 2% to about 3%, or about 2.5% to about 3.5%, or about 3% to about 4%, or about 3.5% to about 4.5%, or about 4% to about 5%, or about 4.5% to about 5.5%, or about 5% to about 6%, or about 5.5% to about 6.5%, or about 6% to about 7%, or about 6.5% or about 7.5%, or about 7% to about 8%, or about 7.5% or about 8.5%, or about 8% to about 9%, or about 8.5% to about 9.5%, or about 9% to about 10%, or about 9.5% to about 10.5%, or about 10% to about 11%, or about 10.5% to about 11.5%, or about 11% to about 12%, or about 11.5% to about 12.5%, or about 12% to about 13%, or about 12.5% to about 13.5%, or about 13% to about 14%, or about 13.5% to about 14.5%, or about 14% to about 15%.

In some embodiments, the degree of crosslinking is at least 1%. In some embodiments, the degree of crosslinking is at least 2%. In some embodiments, the degree of crosslinking is at least 3%. In some embodiments, the degree of crosslinking is at least 4%. In some embodiments, the degree of crosslinking is at least 5%. In some embodiments, the degree of crosslinking is at least 6%. In some embodiments, the degree of crosslinking is at least 7%. In some embodiments, the degree of crosslinking is at least 8%. In some embodiments, the degree of crosslinking is at least 9%. In some embodiments, the degree of crosslinking is at least 10%. In some embodiments, the degree of crosslinking is at least 11%. In some embodiments, the degree of crosslinking is at least 12%. In some embodiments, the degree of crosslinking is at least 13%. In some embodiments, the degree of crosslinking is at least 14%. In some embodiments, the degree of crosslinking is at least 15%.

In some embodiments, a composition of the invention comprises cross-linked SPF where the degree of crosslinking is at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%. In some embodiments, a composition comprises cross-linked SPF where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In some embodiments, a composition comprises cross-linked SPF where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%, or about 1% to about 2%, about 1.5% to about 2.5%, or about 2% to about 3%, or about 2.5% to about 3.5%, or about 3% to about 4%, or about 3.5% to about 4.5%, or about 4% to about 5%, or about 4.5% to about 5.5%, or about 5% to about 6%, or about 5.5% to about 6.5%, or about 6% to about 7%, or about 6.5% to about 7.5%, or about 7% to about 8%, or about 7.5% to about 8.5%, or about 8% to about 9%, or about 8.5% to about 9.5%, or about 9% to about 10%, or about 9.5% to about 10.5%, or about 10% to about 11%, or about 10.5% to about 11.5%, or about 11% to about 12%, or about 11.5% to about 12.5%, or about 12% to about 13%, or about 12.5% to about 13.5%, or about 13% to about 14%, or about 13.5% to about 14.5%, or about 14% to about 15%.

In some embodiments, a composition of the invention comprises cross-linked HA where the degree of crosslinking is at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%. In some embodiments, a composition comprises cross-linked HA where the degree of crosslinking is at most 1%, at most 2%, at most 3%, at most 4%, at most 5%, at most 6%, at most 7%, at most 8%, at most 9%, at most 10%, at most 11%, at most 12%, at most 13%, at most 14%, or at most 15%. In some embodiments, a composition comprises cross-linked HA where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%, or about 1% to about 2%, about 1.5% to about 2.5%, or about 2% to about 3%, or about 2.5% to about 3.5%, or about 3% to about 4%, or about 3.5% to about 4.5%, or about 4% to about 5%, or about 4.5% to about 5.5%, or about 5% to about 6%, or about 5.5% to about 6.5%, or about 6% to about 7%, or about 6.5% or about 7.5%, or about 7% to about 8%, or about 7.5% or about 8.5%, or about 8% to about 9%, or about 8.5% to about 9.5%, or about 9% to about 10%, or about 9.5% to about 10.5%, or about 10% to about 11%, or about 10.5% to about 11.5%, or about 11% to about 12%, or about 11.5% to about 12.5%, or about 12% to about 13%, or about 12.5% to about 13.5%, or about 13% to about 14%, or about 13.5% to about 14.5%, or about 14% to about 15%.

In some embodiments, a composition of the invention comprises cross-linked SPF-HA where the degree of crosslinking is at least 1%, at least 2%, at least 3%, at least 4%, at least 5%, at least 6%, at least 7%, at least 8%, at least 9%, at least 10%, at least 11%, at least 12%, at least 13%, at least 14%, or at least 15%. In some embodiments, a composition comprises cross-linked SPF-HA where the degree of crosslinking is at most 1%, at most 2, at most 3%, at most 4%, at most 5%, at most 6%, at most 7%, at most 8%, at most 9%, at most 10%, at most 11%, at most 12%, at most 13%, at most 14%, or at most 15%. In some embodiments, a composition comprises cross-linked SPF-HA where the degree of crosslinking is about 1% to about 15%, about 2% to about 11%, about 3% to about 10%, about 1% to about 5%, about 10% to about 15%, about 11% to about 15%, about 6% to about 10%, or about 6% to about 8%, or about 1% to about 2%, about 1.5% to about 2.5%, or about 2% to about 3%, or about 2.5% to about 3.5%, or about 3% to about 4%, or about 3.5% to about 4.5%, or about 4% to about 5%, or about 4.5% to about 5.5%, or about 5% to about 6%, or about 5.5% to about 6.5%, or about 6% to about 7%, or about 6.5% or about 7.5%, or about 7% to about 8%, or about 7.5% or about 8.5%, or about 8% to about 9%, or about 8.5% to about 9.5%, or about 9% to about 10%, or about 9.5% to about 10.5%, or about 10% to about 11%, or about 10.5% to about 11.5%, or about 11% to about 12%, or about 11.5% to about 12.5%, or about 12% to about 13%, or about 12.5% to about 13.5%, or about 13% to about 14%, or about 13.5% to about 14.5%, or about 14% to about 15%.

For example, 1 mole of SPF to 1 mole of HA may be cross linked wherein the mole of HA could have a molecular weight of about 1 kDa to about 2 M kDa. In some embodiments, 1 mole of SPF to 1 million moles of HA, or vis versa, where SPF can be 100 Da to 350 kDa, whereby any percentage of each mole can be cross-linked or free. A method of cross-linking SPF to other SPF can include one or more steps. In a first step, the epoxide, such as BDDE, is added to an SPF solution in excess and the reaction is allowed to proceed. Epoxides can react with various groups on the SPF macromolecule, such as carboxyl, amine, alcohol, thiol, and the like, resulting in linkages such as esters, secondary or tertiary amines, ethers, thioethers, and the like. Where both epoxides of BDDE have reacted with the functional groups in one or more SPF macromolecules, the SPF becomes cross-linked. In an embodiment, cross-linking of HA may be performed via a reaction with BDDE under alkaline conditions to yield a covalent linkage between HA and the cross-linker as described in Schanté et al., Carbohydrate Polymers (2011) 85:469-489. The degree of modification or crosslinking may be determined by NMR in accordance with methods known in the art (e.g., Edsman et al., Dermatol. Surg. (2012) 38: 1170-1179).

Methods of linking peptides are known in the art. The linking of the individual isolated SPF into oligomeric and/or cross-linked SPF peptides as set forth herein, can be effected by chemical conjugation procedures well known in the art, such as by creating peptide linkages, use of condensation agents, and by employing well known bifunctional cross-linking reagents. The conjugation may be direct, which includes linkages not involving any intervening group, e.g., direct peptide linkages, or indirect, wherein the linkage contains an intervening moiety, such as a protein or peptide, e.g., plasma albumin, or other spacer molecule. For example, the linkage may be via a heterobifunctional or homobifunctional cross-linker, e.g., carbodiimide, glutaraldehyde, N-succinimidyl 3-(2-pyridyldithio)propionate (SPDP) and derivatives, bis-maleimide, 4-(N-maleimidomethyl)cyclohexane-1-carboxylate, and the like.

Cross-linking can also be accomplished without exogenous cross-linkers by utilizing reactive groups on the molecules being conjugated. Methods for chemically cross-linking peptide molecules are generally known in the art, and a number of hetero- and homobifunctional agents are described in, e.g., U.S. Pat. Nos. 4,355,023, 4,657,853, 4,676,980, 4,925,921, and 4,970,156, and Immuno Technology Catalogue and Handbook, Pierce Chemical Co. (1989), each of which is incorporated herein by reference. Such conjugation, including cross-linking, should be performed so as not to substantially affect the desired function of the peptide oligomer or entity conjugated thereto, including therapeutic agents, and moieties capable of binding substances of interest.

It will be understood to one skilled in the art that alternative linkers can be used to link SPF peptides, for example the use of chemical protein cross-linkers. For example a homobifunctional cross-linker such as disuccinimidyl-suberimidate-dihydrochloride; dimethyl-adipimidate-dihydrochloride; 1,5,-2,4 dinitrobenzene or heterobifunctional cross-linkers such as N-hydroxysuccinimidyl 2,3-dibromopropionate; 1-ethyl-3-[3-dimethylaminopropyl]carbodiimide hydrochloride; and succinimidyl-4-[n-maleimidomethyl]-cyclohexane-1-carboxylate.

The present invention also provides compositions including cross-linked SPF to HA. SPF to HA cross-linking can be achieved by various methods, for example by epoxide methods, periodate methods, and/or tresyl chloride methods. In some embodiments, SPF are cross-linked to HA using an epoxide, for example a multifunctional epoxide. For example, a bifunctional epoxide such as 1,4 butanediol diglycidyl ether (BDDE) can be used. Other multifunctional epoxides include, but are not limited to, polyglycerolpolyglycidyl ether (PGPGE), pentaerythriolpolyglycidyl ether (PEPGE) and diglycerolpolyglycidyl ether (DGPGE). Zero-length cross-linking between SPF and HA is also provided using an activating agent.

A method of cross-linking SPF to other macromolecules, for example HA, can include one or more steps. In a first step, the epoxide, such as BDDE, is added to an SPF solution in excess and the reaction is allowed to proceed. Epoxides can react with various groups on the SPF macromolecule, such as carboxyl, amine, alcohol, thiol, and the like, resulting in linkages such as esters, secondary or tertiary amines, ethers, thioethers, and the like. Where only one epoxide has reacted with SPF, there remains a free epoxide attached to the SPF available for cross-linking with another SPF, or a different macromolecule, for example HA, or the like. The order of adding the reagents can be varied. For example BDDE can be added to HA first, and then SPF is added to form cross-linked SPF-HA. In some embodiments, SPF and HA can be mixed first, and then BDDE is added to the mixture. In some embodiments, adding BDDE to a mixture of SPF and HA results in a composition including cross-linked SPF to SPF, cross-linked HA to HA, and cross-linked SPF to HA.

In some embodiments, the cross-linked SPF-HA can be prepared using the tresyl chloride method, including one or more steps. In one step, cross-linked HA and/or non-cross-linked HA can be activated with tresyl chloride, i.e., 2,2,2-trifluoroethanesulfonyl chloride, or any other suitable acid chloride. Tresyl chloride is added for example drop-wise to a base/solvent solution, for example, pyridine/acetone solution, containing cross-linked and/or non-cross-linked HA. In some embodiments, the tresyl chloride is reactive with all four of the hydroxyl groups on the sugar rings of cross-linked and/or non-cross-linked HA. In an optional step, the resulting HA-tresylate is washed. In a step, SPF fragments are added which will react with the HA-tresylate.

In some embodiments, the tresyl chloride method can be used to attach an SPF directly to cross-linked and/or non-cross-linked HA. In other embodiments, the tresyl chloride method can be used to attach an SPF to cross-linked and/or non-cross-linked HA via a spacer, for example 6-amino-1-hexanol. In some embodiments, the spacer can first be coupled to cross-linked or non-cross-linked HA via tresyl activation and coupling. For coupling an SPF to the spacer, the tresyl activation and coupling are thereafter repeated. Any suitable spacer can be used, i.e., spacers having at least some characteristics similar to 6-amino-1-hexanol, i.e., a primary amine for coupling to the HA-tresylate, and a reactive group, for example a hydroxyl group, for activation and coupling of the SPF.

In some embodiments, tresyl chloride does not cross-link HA. The HA matrix used in the tresyl chloride method may, however, be cross-linked for additional stability. The cross-linking can be effected, for example, by using a multifunctional epoxide, such as BDDE, as described above. Cross-linking can be done either before or after peptide coupling.

The tresyl chloride method has advantages over other immobilization methods, including efficient coupling under very mild conditions, no side reactions during activation and coupling, and the RGD peptides can be bound directly to the carbon atoms of the HA support.

In various embodiments, tissue fillers described herein may include gels and hydrogels that are HA-based. HA-based as used herein refers to compositions or materials including cross-linked HA and compositions including cross-linked HA plus one or more other cross-linked polymers. In addition, HA can refer to hyaluronic acid and any of its hyaluronate salts, including, but not limited to, sodium hyaluronate (NaHA), potassium hyaluronate, magnesium hyaluronate, calcium hyaluronate, and combinations thereof. The use of more than one biocompatible polymer is specifically not excluded from the present description. Tissue fillers described herein, which may be in the form gels and hydrogels, can include more than one biocompatible polymer, such as, for example, 2, 3, 4, 5, 6, 7, 8, 9, 10, or more biocompatible polymers in addition to HA and/or SPF. Suitable biocompatible polymers include polysaccharides (e.g., HA, chitosan, chondroitin sulfate, alginate, carboxymethylcellulose), poly(ethyleneglycol), poly(lactic acid), poly(hydroxyethylmethacrylate), poly(methylmethacrylate), proteins other than SPF (e.g., elastin and collagen).

HA described herein may be intermolecularly cross-linked. In some embodiments, the cross-linking stabilizes HA physical properties. In some embodiments, the present invention provides formation of stable cross-linked HA using multifunctional epoxides. As used herein, the term "multifunctional" epoxide means a chemical reagent having two or more epoxides present, such as lower aliphatic epoxides or their corresponding epihalohydrins. Examples of multifunctional epoxides include, but are not limited to, the diepoxide 1,4 butanediol diglycidyl ether (BDDE), polyglycerolpolyglycidyl ether (PGPGE), pentaerythriolpolyglycidyl ether (PEPGE) and diglycerolpolyglycidyl ether (DGPGE). In a preferred embodiment, the diepoxide BDDE is used as the cross-linking agent. The sugar moieties of HA cross-link via the two epoxides of BDDE. In other embodiments, cross-linking agents include alkyldiepoxy bodies such as 1,3-butadiene diepoxide, 1,2,7,8-diepoxyoctane, 1,5-hexadiene diepoxide and the like, diglycidyl ether bodies such as ethylene glycol diglycidyl ether, 1,4-butanediol diglycidyl ether, bisphenol A diglycidyl ether and the like, divinylsulfone, and epichlorohydrin. Among them, particularly, divinylsulfone, 1,4-butanediol diglycidyl ether, and ethylene glycol diglycidyl ether can be suitably used. In the present invention, two or more kinds of crosslinking agents may be used by appropriately combining them.

In some embodiments, HA is cross-linked to HA. A method of cross-linking HA to HA can include one or more steps. In a first step, an epoxide, such as BDDE, is added to an HA solution in excess and the reaction is allowed to proceed. Epoxides can react with from one to four of the hydroxyl groups on the sugar rings of HA to form one to four ether linkages. Alternatively, or in addition to reacting with the hydroxyl groups, the epoxide can react with the carboxylic acid of the polysaccharide to form an ester bond. Where both epoxides of BDDE have reacted with the functional groups in the sugar rings of one or more HA macromolecules, the HA becomes cross-linked.

In some embodiments, the cross cross-linking agent can be a zero length cross-linking agent such as a chemical bond obtained by employing an activating agent such as 1-ethyl-3-(3-dimethylaminopropyl) carbodiimide (EDC), or BCDI. In some embodiments, the zero-length cross-linking activating agent is reacted with the HA in the presence of N-hydroxysuccinimide (NHS), sulfo-NHS (or sulfonyl-NHS) or 4-dimethylaminopyridine (DMAP). In some embodiments, gels and hydrogels described herein are formed by reacting at least one cross-linkable biocompatible polymer, such as HA and/or a protein, e.g. an SPF protein, or any other additional protein, with at least one cross-linking activating agent.

In some embodiments, cross-linked SPF-SPF, cross-linked SPF-HA, and/or cross-linked HA-HA, can have variable residence times after application, for example after being injected as an intra-dermal, subdermal, or generally, as a dermal filler. In some embodiments, residence times can be affected in the sodium periodate method depending on the number of reactive groups in the SPF which are available for attachment to another SPF macromolecule, or to HA. An example of a reactive group in SPF which can attach to HA is a primary amine. An SPF containing two reactive groups, such as two primary amines, can itself cross-link the HA in the periodate method, thereby creating a more stable conjugate. In other embodiments, where only one reactive group is present in the SPF, such as only one primary amine, for example at the amino terminus, SPF-HA cross-linking is reduced resulting in a more biodegradable matrix.

In some embodiments, BDDE cross-linked HA can have a variable residence time after application, for example after being injected as an intra-dermal, subdermal, or generally dermal filler. In some embodiments, BDDE cross-linked HA can persist in dermal tissue anywhere from one to at least thirty days, depending on the amount of cross-linking. The variable residence time of the cross linked HA can be tuned by introducing hydrolyzable bonds during the epoxide cross-linking. In some embodiments, the materials cross-linked with epoxide at a lower pH have a greater amount of ester bond formation and therefore are more rapidly hydrolyzable.

In one embodiment, the cross-linking agent is a zero-length cross-linking activating agent. Generally, zero-length cross-linking activating agents couple polymers without adding any additional spacer arm atoms, and therefore zero-length cross-linking activating agents are not incorporated into the cross-linked polymer matrix. Suitable zero-length cross-linking agents include carbodiimides, such as, for example, 1-ethyl-3-(3-dimethylaminopropyl) carbodiimide (EDC) and BCDI. Non-water soluble carbodiimides include dicyclohexylcarbodiimide (DCC) and diisopropylcarbodiimide (DIC), which may also be suitable.

Carbodiimide-mediated coupling between carboxylates and alcohol or amine functional groups proceeds readily at ambient temperature, neutral pH and under aqueous conditions. Neutral pH can be, for example, between about 6.0 and about 8.0, such as between about 6.5 and about 7.5, such as about 7.0. Typically in water, 1-ethyl-3-(3-dimethylaminopropyl) carbodiimide hydrochloride (EDC) can be used to mediate esterification between carboxylates and alcohols or amidation between carboxylates and amines. Thus, cross-linked HA is formed by exploiting reactive groups present on HA (e.g., carboxylate and alcohol). In addition, by taking advantage of the high reactivity of amine groups on proteins, for example SPF proteins, amidation between lysine side-chains of proteins with carboxylate groups of HA is achieved to form HA-protein cross-linked hydrogels. Cross-linking agents and unreacted polymers can be removed by dialysis.

In some embodiments, EDC is used in conjunction with N-hydroxysuccinimide (NHS) or sulfonyl-NHS (sulfo-NHS), collectively referred to as "NHS" herein. NHS stabilizes reactive intermediates formed by EDC; thus, the addition of NHS can increase the coupling efficiency of EDC. Alternatively, 4-dimethylaminopyridine (DMAP) can be used to catalyze the coupling reaction.

In some embodiments, the HA-based tissue fillers of the invention include cross-linked HA-based compositions and at least partially cross-linked HA-based compositions. Uncross-linked HA as used herein refers to both truly uncross-linked (e.g., "free") HA chains as well as lightly cross-linked chains and fragments thereof that are generally in soluble liquid form.

In some embodiments, the hydrogel compositions of the invention includes at least some cross-linking between HA and SPF.

Non-Limiting Exemplary Embodiments

In one embodiment, the invention relates to a biocompatible dermal filler including silk protein fragments (SPF) having a polydispersity of between about 1.5 and about 3.0 and an average weight average molecular weight ranging from about 1 kDa to about 250 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 5 kDa to about 150 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 6 kDa to about 17 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 17 kDa to about 39 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 39 kDa to about 80 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including low molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100%, w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including medium molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including low molecular weight silk protein fragments (SPF) having a polydispersity of between about 1.5 and about 3.0, medium molecular weight silk protein fragments (SPF) having a polydispersity of between about 1.5 and about 3.0, hyaluronic acid (HA), water, and between about 0.05% to about 0.5% lidocaine. e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%; wherein the w/w ratio between low molecular weight SPF and medium molecular weight SPF is about 3:1.

In one embodiment, the invention relates to a biocompatible dermal filler including high molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking occurring as a result of using an epoxy derived cross-linker, e.g., BDDE, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 1 kDa to about 250 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 5 kDa to about 150 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 6 kDa to about 17 kDa, hyaluronic acid (HA), water, and between about 0.05% to about 0.5% lidocaine. e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent. e.g., BCDI, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 17 kDa to about 39 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent. e.g., BCDI, and with a degree of cross-linking of up to 15%.

In one embodiment, the invention relates to a biocompatible dermal filler including silk protein fragments (SPF) having a polydispersity of between about 1.5 and about 3.0 and an average weight average molecular weight ranging from about 39 kDa to about 80 kDa, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent. e.g., BCDI, and with a degree of cross-linking of up to 15%.

In one embodiment, the invention relates to a biocompatible dermal filler including low molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%.

In one embodiment, the invention relates to a biocompatible dermal filler including medium molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%.

In one embodiment, the invention relates to a biocompatible dermal filler including low molecular weight silk protein fragments (SPF) having a polydispersity of between about 1.5 and about 3.0, medium molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%; wherein the w/w ratio between low molecular weight SPF and medium molecular weight SPF is about 3:1.

In one embodiment, the invention relates to a biocompatible dermal filler including high molecular weight silk protein fragments (SPF) having a polydispersity of between about 1.5 and about 3.0, hyaluronic acid (HA), water, and between about 0.05% to about 0.5% lidocaine, e.g., about 0.3% lidocaine; wherein a portion of up to 100% w/w of SPF are cross-linked, and a portion of up to 100% w/w of HA is cross linked, the cross-linking occurring between one or more of SPF to SPF, SPF to HA, and HA to HA; the cross-linking including zero-length cross-linking occurring as a result of using an activating agent, e.g., BCDI, and with a degree of cross-linking of up to 15%.

Additional Agents

In some embodiments, the tissue fillers described herein include an active agent, such as a drug. In some embodiments, the active agent can be one or more of enzyme inhibitors, anesthetic agents, medicinal neurotoxins, antioxidants, anti-infective agents, anti-inflammatory agents, vasodilators, ultraviolet (UV) light blocking agents, dyes (e.g., tattoo dye, ink or pigment), a reflective agent, hormones, immunosuppressants, and combinations thereof. The tissue fillers described herein can include an active agent selected from the group consisting of enzyme inhibitors, anesthetic agents, medicinal neurotoxins (e.g., botulinum toxin and *clostridium* toxin), antioxidants, anti-infective agents (e.g., antibiotics), vasodilators, dyes (e.g., tattoo ink or pigment, reflective agents, anti-inflammatory agents, ultraviolet (UV) light blocking agents, dyes, hormones, immunosuppressants, and combinations thereof.

In some embodiments, the immunosuppressant is rapamycin, or rapamycin-like compound.

In some embodiments, the active agent may be an antibiotic selected from the group consisting of a penicillin (e.g., penicillin V, amoxicillin), an erythromycin (e.g., erythromycin stearate), a lincosamide (e.g., clindamycin), and a cephalosporin (e.g. cephalexin), and a combination thereof.

In some embodiments, the active agent may be a vasodilator selected from the group consisting of nitroglycerin, labetalol, thrazide, isosorbide dinitrate, pentaerythritol tetranitrate, digitalis, hydralazine, diazoxide, amrinone, L-arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di-isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, xanthinol nicotinate, diazoxide, hydralazine, minoxidil, and sodium nitroprusside, and a combination thereof.

In some embodiments, the tissue fillers described herein may include an active agent at a concentration, by weight, of at least 0.01%, or at least 0.02%, or at least 0.03%, or at least 0.04%, or at least 0.05%, or at least 0.06%, or at least 0.07%, or at least 0.08%, or at least 0.09%, or at least 0.1%, or at least 0.2%, or at least 0.3%, or at least 0.4%, or at least 0.5%, or at least 0.6%, or at least 0.7%, or at least 0.8%, or at least 0.9%, or at least 1.0%, or at least 1.5%, or at least 2.0%, or at least 2.5%, or at least 3.0%, or at least 3.5%, or at least 4.0%, or at least 4.5%, or at least 5.0%, or at least 5.5%, or at least 6.0%, or at least 6.5%, or at least 7.0%, or at least 7.5%, or at least 8.0%, or at least 8.5%, or at least 9.0%, or at least 9.5%, or at least 10%, or at least 15%, or at least 20%, or at least 25%, or at least 30%, or at least 35%, or at least 40%, or at least 45%, or at least 50%.

In some embodiments, the tissue fillers described herein may include an active agent at a concentration, by weight, of at most 0.01%, or at most 0.02%, or at most 0.03%, or at most 0.04%, or at most 0.05%, or at most 0.06%, or at most 0.07%, or at most 0.08%, or at most 0.09%, or at most 0.1%, or at most 0.2%, or at most 0.3%, or at most 0.4%, or at most 0.5%, or at most 0.6%, or at most 0.7%, or at most 0.8%, or at most 0.9%, or at most 1.0%, or at most 1.5%, or at most 2.0%, or at most 2.5%, or at most 3.0%, or at most 3.5%, or at most 4.00%, or at most 4.5%, or at most 5.0%, or at most 5.5%, or at most 6.0%, or at most 6.5%, or at most 7.0%, or at most 7.5%, or at most 8.0%, or at most 8.5%, or at most 9.0%, or at most 9.5%, or at most 10%, or at most 15%, or at most 20%, or at most 25%, or at most 30%, or at most 35%, or at most 40%, or at most 45%, or at most 50%.

In some embodiments, the tissue fillers described herein may include an active agent at a concentration, by weight, of about 0.01% to about 0.1%, or about 0.05% to about 0.15%, or about 0.1% to about 0.2%, or about 0.15% to about 0.25%, or about 0.2% to about 0.3%, or about 0.25% to about 0.35%, or about 0.3% to about 0.4%, or about 0.35% to about 0.45%, or about 0.4% to about 0.5%, or about 0.45% to about 0.55%, or about 0.5% to about 0.6%, or about 0.55% to about 0.65%, or about 0.6% to about 0.7%, or about 0.65% to about 0.75%, or about 0.7% to about 0.8%, or about 0.75% to about 0.85%, or about 0.8% to about 0.9%, or about 0.85% to about 0.95%, or about 1% to about 2%, or about 1.5% to about 2.5%, or about 2% to about 3%, or about 2.5% to about 3.5%, or about 3% to about 4%, or about 3.5% to about 4.5%, or about 4% to about 5%, or about 4.5% to about 5.5%, or about 5% to about 6%, or about 5.5% to about 6.5%, or about 6% to about 7%, or about 6.5% to about 7.5%, or about 7% to about 8%, or about 7.5% to about 8.5%, or about 8% to about 9%, or about 8.5% to about 9.5%, or about 9% to about 10%, or about 10% to about 15%, or about 15% to about 20%, or about 20% to about 25%, or about 25% to about 30%, or about 30% to about 35%, or about 35% to about 40%, or about 40% to about 45%, or about 45% to about 50%.

In some embodiments, the tissue fillers described herein may include an active agent at a concentration, by weight, of about 0.01%, or about 0.02%, or about 0.03%, or about 0.04%, or about 0.05%, or about 0.06%, or about 0.07%, or about 0.08%, or about 0.09%, or about 0.1%, or about 0.2%, or about 0.3%, or about 0.4%, or about 0.5%, or about 0.6%, or about 0.7%, or about 0.8%, or about 0.9%, or about 1.0%, or about 1.5%, or about 2.0%, or about 2.5%, or about 3.0%, or about 3.5%, or about 4.0%, or about 4.5%, or about 5.0%, or about 5.5%, or about 6.0%, or about 6.5%, or about 7.0%, or about 7.5%, or about 8.0%, or about 8.5%, or about 9.0%, or about 9.5%, or about 10%, or about 11%, or about 12%, or about 13%, or about 14%, or about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%, or about 36%, or about 37%, or about 38%, or about 39%, or about 40%, or about 41%, or about 42%, or about 43%, or about 44%, or about 45%, or about 46%, or about 47%, or about 48%, or about 49%, or about 50%.

In some embodiments, the tissue fillers described herein include a fibrosis-inhibiting agent. In some embodiments, tissue fillers described herein may further include a compound that acts to have an inhibitory effect on pathological processes in or around the treatment site. In certain aspects, the active agent may be selected from one of the following classes of compounds: anti-inflammatory agents (e.g., dexamethasone, cortisone, fludrocortisone, prednisone, prednisolone, 6α-methylprednisolone, triamcinolone, betamethasone, and aspirin).

In some embodiments, with the active agent may, but is not limited to, antioxidants and enzymes. In an embodiment, the active agent may include, but is not limited to, selenium, ubiquinone derivatives, thiol-based antioxidants, saccharide-containing antioxidants, polyphenols, botanical extracts, caffeic acid, apigenin, pycnogenol, resveratrol, folic acid, vitamin B12, vitamin B6, vitamin B3, vitamin E, vitamin C and derivatives thereof, vitamin D, vitamin A, astaxathin, lutein, lycopene, essential fatty acids (omegas 3 and 6), iron, zinc, magnesium, flavonoids (soy, curcumin, silymarin, pycnongeol), growth factors, aloe, hyaluronic acid, extracellular matrix proteins, cells, nucleic acids, biomarkers, biological reagents, zinc oxide, benzoyl peroxide, retinoids, titanium, allergens in a known dose (for sensitization treatment), essential oils including, but not limited to, lemongrass or rosemary oil, and fragrances. Considering the active agents more broadly, the active agents may include therapeutic agents such as small molecules, drugs, proteins, peptides and nucleic acids.

In certain embodiments, the tissue fillers described herein can include one or more anesthetic agents in an amount effective to ameliorate or mitigate pain or discomfort at the tissue filler injection site. The local anesthetic can be selected from the group of ambucaine, amolanone, amylocalne, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dicyclomine, ecgonidine, ecgonine, ethyl chloride, etidocaine, beta-eucaine, euprocin, fenalcomine, formocaine, hexylcaine, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine, phenol, piperocaine, piridocaine, polidocanol, pramoxine, prilocalne, procaine, propanocaine, proparacaine, propipocaine, propoxycaine, pseudococaine, pyrrocaine, ropivacaine, salicyl alcohol, tetracaine, tolycaine, trimecaine, zolamine, and salts thereof.

In some embodiments, the tissue fillers described herein may include lidocaine or other anesthetic recited above at a concentration, by weight, of at least 0.01%, or at least 0.02%, or at least 0.03%, or at least 0.04%, or at least 0.05%, or at least 0.06%, or at least 0.07%, or at least 0.08%, or at least 0.09%, or at least 0.1%, or at least 0.2%, or at least 0.3%, or at least 0.4%, or at least 0.5%, or at least 0.6%, or at least 0.7%, or at least 0.8%, or at least 0.9%, or at least 1.0%, or at least 1.5%, or at least 2.0%, or at least 2.5%, or at least 3.0%, or at least 3.5%, or at least 4.0%, or at least 4.5%, or at least 5.0%, or at least 5.5%, or at least 6.0%, or at least 6.5%, or at least 7.0%, or at least 7.5%, or at least 8.0%, or at least 8.5%, or at least 9.0%, or at least 9.5%, or at least 10%.

In some embodiments, the tissue fillers described herein may include lidocaine or other anesthetic recited above at a concentration, by weight, of at most 0.01%, or at most 0.02%, or at most 0.03%, or at most 0.04%, or at most 0.05%, or at most 0.06%, or at most 0.07%, or at most 0.08%, or at most 0.09%, or at most 0.1%, or at most 0.2%, or at most 0.3%, or at most 0.4%, or at most 0.5%, or at most 0.6%, or at most 0.7%, or at most 0.8%, or at most 0.9%, or at most 1.0%, or at most 1.5%, or at most 2.0, or at most 2.5%, or at most 3.0%, or at most 3.5%, or at most 4.0%, or at most 4.5%, or at most 5.0%, or at most 5.5%, or at most 6.0%, or at most 6.5%, or at most 7.0%, or at most 7.5%, or at most 8.0%, or at most 8.5%, or at most 9.0%, or at most 9.5%, or at most 10%.

In some embodiments, the tissue fillers described herein may include lidocaine or other anesthetic recited above at a concentration, by weight, of about 0.01%, or about 0.02%, or about 0.03%, or about 0.04%, or about 0.05%, or about 0.06%, or about 0.07%, or about 0.08%, or about 0.09%, or about 0.1%, or about 0.2%, or about 0.3%, or about 0.4%, or about 0.5%, or about 0.6%, or about 0.7%, or about 0.8%, or about 0.9%, or about 1.0%, or about 1.5%, or about 2.0%, or about 2.5%, or about 3.0%, or about 3.5%, or about 4.0%, or about 4.5%, or about 5.0%, or about 5.5%, or about 6.0%, or about 6.5%, or about 7.0%, or about 7.5%, or about 8.0%, or about 8.5%, or about 9.0%, or about 9.5%, or about 10%.

In some embodiments, the tissue fillers described herein may include lidocaine or other anesthetic recited above at a concentration, by weight, of about 0.01% to about 0.02%, or about 0.03% to about 0.04%, or about 0.05% to about 0.06% to about 0.07%, or about 0.08% to about 0.09%, or about 0.1% to about 0.2%, or about 0.3% to about 0.4%, or about 0.5% to about 0.6%, or about 0.7% to about 0.8%, or about 0.9% to about 1.0%, or about 1% to about 1.5%, or about 1.5% to about 2.0%, or about 2.0% to about 2.5%, or about 2.5% to about 3.0%, or about 3.0% to about 3.5%, or about 3.5% to about 4.0%, or about 4.0% to about 4.5%, or about 4.5% to about 5.0%, or about 5.0% to about 5.5%, or about 5.5% to about 6.0%, or about 6.0% to about 6.5%, or about 6.5% to about 7.0%, or about 7.5% to about 8.0%, or about 8.0% to about 8.5%, or about 8.5% to about 9.0%, or about 9.5% to about 10%.

In one embodiment, the anesthetic agent is lidocaine, such as in the form of lidocaine HCl. The tissue fillers described herein may have a lidocaine or other anesthetic in a concentration of between about 0.1% and about 5% by weight of the composition, for example, about 0.2% to about 1.0% by weight of the tissue filler. In one embodiment, the tissue filler has a lidocaine concentration of about 0.3% by weight (w/w %) of the tissue filler. The concentration of lidocaine in the tissue fillers described herein can be therapeutically effective meaning the concentration is adequate to provide a therapeutic benefit such as, for example, ameliorating or mitigating pain or discomfort at the tissue filler injection site.

Optical Properties

When light encounters a material, it can interact with it in several ways. These interactions depend on the nature of the light, i.e., its wavelength, frequency, energy, etc., and the nature of the material. Light interacts with an object by some combination of reflection, and transmittance with refraction. An optically transparent material allows much of the light that falls on it to be transmitted, with little light being reflected. Materials which do not allow the transmission of light are called optically opaque, or simply opaque.

In some embodiments, the invention provides a tissue filler described herein having transparency and/or translucency. Transparency (also called pellucidity or diaphaneity) is the physical property of allowing light to pass through a material, whereas translucency (also called translucence or translucidity) only allows light to pass through diffusely. The opposite property is opacity. Transparent materials are clear, while translucent ones cannot be seen through clearly. The tissue fillers disclosed herein may, or may not, exhibit optical properties such as transparency and/or translucency. In some embodiments, including methods for superficial line filling, it would be an advantage to have an opaque hydrogel. Factors used to control a tissue filler's optical properties include, without limitation, SPF concentration, degree of crystallinity, and/or hydrogel homogeneity.

In some embodiments, the tissue fillers described herein are opaque.

In an embodiment, a tissue filler described herein is optically transparent. In aspects of this embodiment, a tissue filler described herein transmits, e.g., about 75% of the light, about 80% of the light, about 85% of the light, about 90% of the light, about 95% of the light, or about 100% of the light. In other aspects of this embodiment, a tissue filler described herein, e.g., at least 75% of the light, at least 80% of the light, at least 85% of the light, at least 90% of the light, or at least 95% of the light. In yet other aspects of this embodiment, an a tissue filler described herein transmits, e.g., about 75% to about 100% of the light, about 80% to about 100% of the light, about 85% to about 100° % of the light, about 90% to about 100% of the light, or about 95% to about 100% of the light.

In another embodiment, a tissue filler described herein is optically opaque. In aspects of this embodiment, a tissue filler described herein transmits, e.g., about 0.1% of the light, about 1% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, about 70% of the light, about 75% of the light, about 80% of the light, about 85% of the light, about 90% of the light, about 95% of the light, or about 100% of the light. In other aspects of this embodiment, a tissue filler described herein transmits, e.g., at most 0.1% of the light, at most 1% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a tissue filler described herein transmits, e.g., at least 0.1% of the light, at least 1% of the light, at least 10% of the light, at least 15% of the light, at least 20% of the light, at least 25% of the light, at least 30% of the light, at least 35% of the light, at least 40% of the light, at least 45% of the light, at least 50% of the light, at least 55% of the light, at least 60% of the light, at least 65% of the light, at least 70% of the light, or at least 75% of the light. In other aspects of this embodiment, a tissue filler described herein transmits, e.g., about 0.1% to about 15%, about 0.1% to about 20%, about 0.1% to about 25%, about 0.1% to about 30%, about 0.1% to about 35%, about 0.1% to about 40%, about 0.1% to about 45%, about 0.1% to about 50%, about 0.1% to about 55%, about 0.1% to about 60%, about 0.1% to about 65%, about 0.1% to about 70%, about 0.1% to about 75%, about 1% to about 15%, about 1% to about 20%, about 1% to about 25%, about 1% to about 30%, about 1% to about 35%, about 1% to about 40%, about 1% to about 45%, about 1% to about 50%, about 1% to about 55%, about 1% to about 60%, about 1% to about 65%, about 1% to about 70%/o, about 1% to about 75%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 10% to about 65%, about 10% to about 70%, about 10% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In some embodiments, a tissue filler described herein is optically translucent. In aspects of this embodiments, a tissue filler described herein diffusely transmits, e.g., about 75% of the light, about 80% of the light, about 85% of the light, about 90% of the light, about 95% of the light, or about 100% of the light. In other aspects of these embodiments, a tissue filler diffusely transmits, e.g., at least 0.1% of the light, at least 1% of the light, at least 5% of the light, at least 10% of the light, at least 15% of the light, at least 20% of the light, at least 25% of the light, at least 30% of the light, at least 35% of the light, at least 40% of the light, at least 45% of the light, at least 50% of the light, at least 55% of the light, at least 60% of the light, at least 65% of the light, at least 70% of the light, 75% of the light, at least 80% of the light, at least 85% of the light, at least 90% of the light, or at least 95% of the light. In other aspects of these embodiments, a tissue filler diffusely transmits, e.g., at most 0.1% of the light, at most 1% of the light, at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, 75% of the light, at most 80% of the light, at most 85% of the light, at most 90% of the light, at most 95% of the light, or at most 100% of the light. In yet other aspects of these embodiments, a tissue filler diffusely transmits, e.g., about 0.1% to about 100% of the light, about 1% to about 100% of the light, about 5% to about 100% of the light, about 10% to about 100% of the light, about 15% to about 100% of the light, about 20% to about 100% of the light, about 25% to about 100% of the light, about 30% to about 100% of the light, about 35% to about 100% of the light, about 45% to about 100% of the light, about 50% to about 100% of the light, about 55% to about 100% of the light, about 60% to about 100% of the light, about 65% to about 100% of the light, about 70% to about 100% of the light, about 75% to about 100% of the light, about 80% to about 100% of the light, about 85% to about 100% of the light, about 90% to about 100% of the light, or about 95% to about 100% of the light.

In some embodiments, a tissue filler described herein may be described by its attenuation coefficient, which is defined as a description of material's ability to scatter or absorb light.

Tissue filler and skin properties can influence the manifestation of the adverse Tyndall effect event in skin following delivery of certain tissue fillers known in the art. Fillers with high stiffness and elasticity can be used to correct areas on the face like nasolabial folds, cheeks, and chin without any fear of facial discoloration, as the materials are injected in the mid and deep dermis regions. However, when fillers are used for more superficial applications, for example to correct fine line wrinkles, or mistakenly applied too superficially in the upper regions of the dermis, a bluish discoloration of the skin is often observed. This phenomenon, which is thought to be the result of Tyndall effect, leaves a semi-permanent discoloration of the application sites. In some embodiments, the effect disappears after the administration of enzymes, for example hyaluronidase, in order to degrade the filler material. Consequently, Tyndall effect is more common in patients treated for superficial fine line wrinkles. Prolonged manifestation of Tyndall effect, typically for as long as the filler lasts in the skin, is an undesired side effect and a cause of concern for patients.

In some embodiments, the tissue fillers described herein mitigate the Tyndall effect due to their homogeneity and resulting opacity.

In some embodiments, the tissue fillers described herein do not result in Tyndall effect, or do not result in any visually perceptible blue discoloration resulting from Tyndall effect. In some embodiments, the invention relates to tissue fillers and methods for improving aesthetic appearance, comprising administering, to a dermal region of a patient, a substantially optically transparent dermal filler composition that exhibits no or insignificant Tyndall effect. The appearance of a blue discoloration at the skin site where a tissue filler had been injected, (Tyndall effect) is a significant adverse event experienced by some dermal filler patients. Tyndall effect is more common in patients treated for superficial fine line wrinkles. Embodiments of the present invention have been developed which provide long lasting, translucent fillers which can be injected superficially to treat fine lines and wrinkles, even in regions of relatively thin skin, without any resulting blue discoloration from Tyndall effect. Fine lines or superficial wrinkles are generally understood to be those wrinkles or creases in skin that are typically found in regions of the face (forehead, lateral canthus, vermillion border/perioral lines) where the skin is thinnest, that is, the skin has a dermis thickness of less than 1 mm. On the forehead the average dermal thickness is about 0.95 mm for normal skin and about 0.81 mm for wrinkled skin. Dermis around the lateral canthus is even thinner (e.g., about 0.61 mm for normal skin and about 0.41 mm for wrinkled skin). The average outer diameter of a 30 or 32 gauge needle (needles that are typically used for fine line gel application) is about 0.30 and about 0.24 mm.

In an embodiment, a tissue filler disclosed herein is optically opaque. In aspects of this embodiment, a tissue filler disclosed herein transmits. e.g., about 5% of the light, about 10% of the light, about 15% of the light, about 20% of the light, about 25% of the light, about 30% of the light, about 35% of the light, about 40% of the light, about 45% of the light, about 50% of the light, about 55% of the light, about 60% of the light, about 65% of the light, or about 70% of the light. In other aspects of this embodiment, a tissue filler disclosed herein transmits, e.g., at most 5% of the light, at most 10% of the light, at most 15% of the light, at most 20% of the light, at most 25% of the light, at most 30% of the light, at most 35% of the light, at most 40% of the light, at most 45% of the light, at most 50% of the light, at most 55% of the light, at most 60% of the light, at most 65% of the light, at most 70% of the light, or at most 75% of the light. In other aspects of this embodiment, a tissue filler disclosed herein transmits, e.g., about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 5% to about 65%, about 5% to about 70%, about 5% to about 75%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 15% to about 65%, about 15% to about 70%, about 15% to about 75%, about 25% to about 35%, about 25% to about 40%, about 25% to about 45%, about 25% to about 50%, about 25% to about 55%, about 25% to about 60%, about 25% to about 65%, about 25% to about 70%, or about 25% to about 75%, of the light.

In some embodiments, a tissue filler disclosed herein exhibits, e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% reduction in tyndalling. In other aspects of these embodiments, a tissue filler disclosed herein exhibits, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, reduction in tyndalling. In other aspects of these embodiments, a tissue filler disclosed herein exhibits, e.g., about 20% to about 100%, about 50% to about 100%, about 70% to about 100%, about 15% to about 35%, about 20% to about 40%, about 25% to about 45%, about 30% to about 50%, about 35% to about 55%, about 40% to about 60%, about 45% to about 65%, about 50% to about 70%, about 55% to about 75%, about 60% to about 80%, about 65% to about 85%, about 70% to about 90%, about 75% to about 95%, or about 80% to about 100%, reduction in tyndalling.

Water Content

In an embodiment, the tissue fillers described herein may include water. For example, some tissue fillers described herein may be gels, such as hydrogels, and may include water absorbed, entrapped, or otherwise disposed therein.

In an embodiment, the percent water content, by weight, in the tissue fillers of the present disclosure is 1% to 95%. In an embodiment, the percent water content, by weight, in the tissue fillers described herein is at least 1%, or at least 2%, or at least 3%, or at least 4%, or at least 5%, or at least 6%, or at least 7%, or at least 8%, or at least 9%, or at least 10%, or at least 11%, or at least 12%, or at least 13%, or at least 14%, or at least 15%, or at least 16%, or at least 17%, or at least 18%, or at least 19%, or at least 20%, or at least 21%, or at least 22%, or at least 23%, or at least 24%, or at least 25%, or at least 26%, or at least 27%, or at least 28%, or at least 29%, or at least 30%, or at least 31%, or at least 32%, or at least 33%, or at least 34%, or at least 35%, or at least 36%, or at least 37%, or at least 38%, or at least 39%, or at least 40%, or at least 41%, or at least 42%, or at least 43%, or at least 44%, or at least 45%, or at least 46%, or at least 47%, or at least 48%, or at least 49%, or at least 50%, or at least 51%, or at least 52%, or at least 53%, or at least 54%, or at least 55%, or at least 56%, or at least 57%, or at least 58%, or at least 59%, or at least 60%, or at least 61%, or at least 62%, or at least 63%, or at least 64%, or at least 65%, or at least 66%, or at least 67%, or at least 68%, or at least 69%, or at least 70%, or at least 71%, or at least 72%, or at least 73%, or at least 74%, or at least 75%, or at least 76%, or at least 77%, or at least 78%, or at least 79%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%.

In an embodiment, the percent water content, by weight, in the tissue fillers described herein is at most 1%, or at most 2%, or at most 3%, or at most 4%, or at most 5%, or at most 6%, or at most 7%, or at most 8%, or at most 9%, or at most 10%, or at most 11%, or at most 12%, or at most 13%, or at most 14%, or at most 15%, or at most 16%, or at most 17%, or at most 18%, or at most 19%, or at most 20%, or at most 21%, or at most 22%, or at most 23%, or at most 24%, or at most 25%, or at most 26%, or at most 27%, or at most 28%, or at most 29%, or at most 30%, or at most 31%, or at most 32%, or at most 33%, or at most 34%, or at most 35%, or at most 36%, or at most 37%, or at most 38%, or at most 39%, or at most 40%, or at most 41%, or at most 42%, or at most 43%, or at most 44%, or at most 45%, or at most 46%, or at most 47%, or at most 48%, or at most 49%, or at most 50%, or at most 51%, or at most 52%, or at most 53%, or at most 54%, or at most 55%, or at most 56%, or at most 57%, or at most 58%, or at most 59%, or at most 60%, or at most 61%, or at most 62%, or at most 63%, or at most 64%, or at most 65%, or at most 66%, or at most 67%, or at most 68%, or at most 69%, or at most 700%, or at most 71%, or at most 72%, or at most 73%, or at most 74%, or at most 75%, or at most 76%, or at most 77%, or at most 78%, or at most 79%, or at most 80%, or at most 81%, or at most 82%, or at most 83%, or at most 84%, or at most 85%, or at most 86%, or at most 87%, or at most 88%, or at most 89%, or at most 90%, or at most 91%, or at most 92%, or at most 93%, or at most 94%, or at most 95%.

In an embodiment, the percent water content, by weight, in the tissue fillers described herein is 1% to 2%, or 2% to 3%, or 3% to 4%, or 4% to 5%, or 5% to 6%, or 6% to 7%, or 7% to 8%, or 8% to 9%, or 9% to 10%, or 10% to 11%, or 11% to 12%, or 12% to 13%, or 13% to 14%, or 14% to 15%, or 15% to 16%, or 16% or 17%, or 17% to 18%, or 18% to 19%, or 19% to 20%, or 20% to 21%, or 21% to 22%, or 22% to 23%, or 23% to 24%, or 24% to 25%, or 25% to 26%, or 26% to 27%, or 27% to 28%, or 28% to 29%, or 30% to 31%, or 31% to 32%, or 32% to 33%, or 33% to 34%, or 34% to 35%, or 35% to 36%, or 36% to 37%, or 37% to 38%, or 38% to 39%, or 39% to 40%, or 40% to 41%, or 41% to 42%, or 42% to 43%, or 43% to 44%, or 44% to 45%, or 45% to 46%, or 46% to 47%, or 47% to 48%, or 48% to 49%, or 49% to 500%, or 50% to 51%, or 51% to 52%, or 52% to 53%, or 53% to 54%, or 54% to 55%, or 55% to 56%, or 56% to 57%, or 57% to 58%, or 58% to 59%, or 59% to 60%, or 60% to 61%, or 61% to 62%, or 62% to 63%, or 63% to 64%, or 64% to 65%, or 65% to 66%, or 66% to 67%, or 67% to 68%, or 68% to 69%, or 69% to 70%, or 70% to 71%, or 71% to 72%, or 72% to 73%, or 73% to 74%, or 74% to 75%, or 75% to 76%, or 76% to 77%, or 77% to 78%, or 78% to 79%, or 79% to 80%, or 80% to 81%, or 81% to 82%, or 82% to 83%, or 83% to 84%, or 84% to 85%, or 85% to 86%, or 86% to 87%, or 87% to 88%, or 88% to 89%, or 89% to 90%, or 90% to 91%, or 91% to 92%, or 92% to 93%, or 93% to 94%, or 94% to 95%, or 95% to 96%, or 96% to 97%, or 97% to 98%.

In an embodiment, the percent water content, by weight, in the tissue fillers described herein is about 1%, or about 2%, or about 3%, or about 4%, or about 5%, or about 6%, or about 7%, or about 8%, or about 9%, or about 10%, or about 11%, or about 12%, or about 13%, or about 14%, or about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%, or about 36%, or about 37%, or about 38%, or about 39%, or about 40%, or about 41%, or about 42%, or about 43%, or about 44%, or about 45%, or about 46%, or about 47%, or about 48%, or about 49%, or about 50%, or about 51%, or about 52%, or about 53%, or about 54%, or about 55%, or about 56%, or about 57%, or about 58%, or about 59%, or about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%.

Mechanical Properties

The tissue fillers described herein, or components thereof, may be provided in a number of physical states depending upon the selected therapy and mode of delivery. In some embodiments, the tissue fillers of the invention are fluids, for example liquids. In some embodiments, the tissue fillers of the invention are viscous fluids. In some embodiments, the tissue fillers of the invention are solids. In some embodiments, the tissue fillers of the invention are elastic solids.

A number of rheological properties may be evaluated when examining the tissue fillers described herein, as shown in Table 17:

TABLE 17

| Rheology Terms Used to Describe Tissue Fillers | |
| --- | --- |
| Elasticity | Ability of tissue filler to spring back to its original shape after deformation |
| Elastic Modulus | Measure of stored energy in viscoelastic material represented by symbol G' |
| Viscosity | Flow characteristics of tissue filler (gel thickness) |
| Viscous Modulus | Measure of dissipated energy in viscoelastic material represented by G" |
| Complex Modulus | Total resistance to deformation of tissue tiller determined by vector sum of G' and G" (G*) |
| Complex Viscosity | Viscosity calculated from frequency sweep represented by n* |
| Viscoelastic | Describes tissue fillers which possess elastic and viscous properties |

TABLE 17-continued

| Rheology Terms Used to Describe Tissue Fillers | |
| --- | --- |
| Shear force | External force which is applied parallel to tissue filler by placing between two plates that mist in opposite directions |
| Shear thinning | Decreasing tissue filler viscosity with increasing rate of deformation. |

In some embodiments, the tissue fillers of the invention are viscoelastic materials, which exhibit mechanical properties of both elastic, and viscous materials. In some embodiments, the tissue fillers of the invention may be described as gels. Methods for assessing the mechanical or rheological properties (e.g., viscoelastic properties) of a material are known in the art, such as for example described in U.S. Patent Application Publication No. 2006/0105022 and Stocks, et al., J. Drugs. Dermatol. (2011) 10:974-980, the entirety of which are incorporated herein by reference. Viscoelasticity of a material can be characterized by using dynamic mechanical analysis, for example by applying an oscillatory stress to a sample and measuring the resulting strain. Elastic materials typically exhibit in-phase stress and strain, i.e., application of stress results in immediate strain. In viscous materials, strain is de-phased from the application of stress by 90 degrees. In viscoelastic materials, the phase difference between strain and stress is more than 0, but less than 90 degrees. In some embodiments, the viscoelasticity of SPF materials of the invention can be characterized by means of the complex dynamic modulus G, which includes the storage modulus G' (also referred to as the elastic modulus), and the loss modulus G" (also referred to as the viscous modulus):

$$G = G' + iG''$$

where $i^2 = -1$, $G' = \dfrac{\sigma_0}{\varepsilon_o}\cos\delta$, and $G'' = \dfrac{\sigma_0}{\varepsilon_o}\sin\delta$, $\sigma_0$ is the amplitude of stress, $\varepsilon_0$ is the amplitude of strain, and $\delta$ is the phase shift.

The elastic modulus G' and the loss modulus G" are measured by subjecting an SPF gel sample to an oscillatory stress in a rotational, or shear rheometer. The sample is placed between two plates, one fixed and one being able to rotate, or oscillate with a given frequency. The values of the elastic modulus G' and the loss modulus G" are frequency dependent. Ranges of frequency used in measuring the elastic modulus G' and the loss modulus G" are typically between, but not limited to, 0.1 to 10 Hz. In some embodiments, the elastic modulus G' and the loss modulus G" are measured at an oscillatory frequency of 1 Hz.

In some embodiments, rheological properties of the tissue fillers described herein, e.g., G' and G", can be measured with an oscillatory parallel plate rheometer. A plate of various diameters, for example 25 mm can be used at a gap height between plates of various distances, for example 1 mm. Measurements can be performed at various temperatures. In some embodiments, measurements are performed at a constant temperature of 25° C. In some embodiments, a measurement includes a frequency sweep between two frequency values, for example from 1 to 10 Hz, at a specific strain value, for example at a constant strain of 2%. In some embodiments, measurements include a logarithmic increase of frequency, followed by a strain sweep which can be for example between 1 to 300% at a constant frequency, for example 5 Hz with a logarithmic increase in strain. In some embodiments, the storage modulus G' and the loss modulus G" can be obtained from a strain sweep at a specific percentage strain value, for example at 1% strain.

In some embodiments, the complex modulus (i.e., the sum of G' and iG") provides a comprehensive measure of total resistance to deformation of a particular tissue filler described herein. Complex modulus may be tested using a rheometer where a particular tissue filler (e.g., a gel) may be squeezed between two parallel circular plates and variable rotational strain is provided by rotating one plate at varying frequencies.

In some embodiments, the characteristics of a particular tissue filler may be examined via that tissue filler's percent elasticity, where percent elasticity is equal to $100 \times G'/(G'+G")$.

In some embodiments, the characteristics of a particular tissue filler may be examined via that tissue filler's recovery coefficient:

$$\text{Recovery Coefficient} = \frac{\text{Viscosity value obtained during } increasing \text{ sweep frequency}}{\text{Viscosity value obtained during } decreasing \text{ sweep frequency}}$$

where: a recovery coefficient of about 1 means that the particular tissue filler (e.g., a gel) retained its structure despite applied forces; a recovery coefficient of greater than 1 means that the particular tissue filler (e.g., a gel) experienced structural breakdown; and a recovery coefficient of less than 1 gel experienced increased structural performance.

Without being limited to any one theory of the invention, increasing G' results in a relative increase in a material's ability to better resist alterations in shape and the material may be described as being firmer, harder, or more elastic than a material (e.g., gel tissue filler) with a lower G'. Accordingly, increasing G' may result in a corresponding increase in a material's ability to provide structural support and/or volumization.

Without being limited to any one theory of the invention, increasing G" results in a more viscous material (e.g., gel) as compared to a material having a lower G". Moreover, there is a greater energy loss as dissipated heat for materials with higher G". In some embodiments, G' increases with an increasing degree of cross-linking. In some embodiments, G" increases with an increasing degree of cross-linking. In some embodiments, both G' and G" increase with an increasing degree of cross-linking. In some embodiments, the tissue fillers of the invention have a G' from about less than 50 Pa, to about more than 15000 Pa. In some embodiments, the tissue fillers of the invention have a G' from about 50 Pa to about 500.000 Pa. In some embodiments, the tissue fillers of the invention have a G' from about 100 Pa to about 500.000 Pa. In some embodiments, the tissue fillers of the invention have a G' from about 75 Pa to about 150 Pa. In some embodiments, the tissue fillers of the invention have a G' from about 100 Pa to about 250 Pa. In some embodiments, the tissue fillers of the invention have a G' from about 150 Pa to about 275 Pa. In some embodiments, the tissue fillers of the invention have a G' from about 150 Pa to about 500 Pa. In some embodiments, the tissue fillers of the invention have a G' from about 250 Pa to about 750 Pa. In some embodiments, the tissue fillers of the invention have a G' from about 375 Pa to about 675 Pa. In some embodiments, the tissue fillers of the invention have a G' from about 425 Pa to about 850 Pa. In some embodiments, the tissue fillers of the invention have a G' from about 500 Pa to about 1000 Pa. In some embodiments, the tissue fillers of the invention have a G' from about 650 Pa to about 1050 Pa. In some embodiments, the tissue fillers of the invention have a G' from about 750 Pa to about 1250 Pa. In some embodiments, the tissue fillers of the invention have a G' from about 950 Pa to about 1500 Pa.

In some embodiments, the tissue fillers of the invention have a G' of at least 50 Pa. In some embodiments, the tissue fillers of the invention have a G' of at least 100 Pa. In some embodiments, the tissue fillers of the invention have a G' of at least 150 Pa. In some embodiments, the tissue fillers of the invention have a G' of at least 200 Pa. In some embodiments, the tissue fillers of the invention have a G' of at least 225 Pa. In some embodiments, the tissue fillers of the invention have a G' of at least 250 Pa. In some embodiments, the tissue fillers of the invention have a G' of at least 275 Pa. In some embodiments, the tissue fillers of the invention have a G' of at least 300 Pa. In some embodiments, the tissue fillers of the invention have a G' of at least 325 Pa. In some embodiments, the tissue fillers of the invention have a G' of at least 350 Pa. In some embodiments, the tissue fillers of the invention have a G' of at least 375 Pa. In some embodiments, the tissue fillers of the invention have a G' of at least 400 Pa. In some embodiments, the tissue fillers of the invention have a G' of at least 425 Pa. In some embodiments, the tissue fillers of the invention have a G' of at least 450 Pa. In some embodiments, the tissue fillers of the invention have a G' of at least 475 Pa. In some embodiments, the tissue fillers of the invention have a G' of at least 500 Pa.

In some embodiments, the tissue fillers of the invention have a G' of at least 525 Pa. In some embodiments, the tissue fillers of the invention have a G' of at least 550 Pa. In some embodiments, the tissue fillers of the invention have a G' of at least 575 Pa. In some embodiments, the tissue fillers of the invention have a G' of about at least Pa. In some embodiments, the tissue fillers of the invention have a G' of about 625 Pa. In some embodiments, the tissue fillers of the invention have a G' of at least 650 Pa. In some embodiments, the tissue fillers of the invention have a G' of at least 675 Pa. In some embodiments, the tissue fillers of the invention have a G' of at least 700 Pa. In some embodiments, the tissue fillers of the invention have a G' of at least 725 Pa. In some embodiments, the tissue fillers of the invention have a G' of at least 750 Pa. In some embodiments, the tissue fillers of the invention have a G' of at least 775 Pa. In some embodiments, the tissue fillers of the invention have a G' of at least 800 Pa. In some embodiments, the tissue fillers of the invention have a G' of at least 825 Pa. In some embodiments, the tissue fillers of the invention have a G' of at least 850 Pa. In some embodiments, the tissue fillers of the invention have a G' of at least 875 Pa. In some embodiments, the tissue fillers of the invention have a G' of at least 900 Pa. In some embodiments, the tissue fillers of the invention have a G' of at least 925 Pa. In some embodiments, the tissue fillers of the invention have a G' of at least 950 Pa. In some embodiments, the tissue fillers of the invention have a G' of at least 975 Pa. In some embodiments, the tissue fillers of the invention have a G' of at least 1000 Pa.

In some embodiments, the tissue fillers of the invention have a G' of at least 1050 Pa. In some embodiments, the tissue fillers of the invention have a G' of at least 1100 Pa. In some embodiments, the tissue fillers of the invention have a G' of at least 1150 Pa. In some embodiments, the tissue fillers of the invention have a G' of at least 1200 Pa. In some embodiments, the tissue fillers of the invention have a G' of at least 1250 Pa. In some embodiments, the tissue fillers of the invention have a G' of at least 1300 Pa. In some embodiments, the tissue fillers of the invention have a G' of at least 1350 Pa. In some embodiments, the tissue fillers of the invention have a G' of at least 1400 Pa. In some embodiments, the tissue fillers of the invention have a G' of at least 1450 Pa. In some embodiments, the tissue fillers of the invention have a G' of at least 1500 Pa.

In some embodiments, the tissue fillers of the invention have a G' of at most 50 Pa. In some embodiments, the tissue fillers of the invention have a G' of at most 100 Pa. In some embodiments, the tissue fillers of the invention have a G' of at most 150 Pa. In some embodiments, the tissue fillers of the invention have a G' of at most 200 Pa. In some embodiments, the tissue fillers of the invention have a G' of at most 225 Pa. In some embodiments, the tissue fillers of the invention have a G' of at most 250 Pa. In some embodiments, the tissue fillers of the invention have a G' of at most 275 Pa. In some embodiments, the tissue fillers of the invention have a G' of at most 300 Pa. In some embodiments, the tissue fillers of the invention have a G' of at most 325 Pa. In some embodiments, the tissue fillers of the invention have a G' of at most 350 Pa. In some embodiments, the tissue fillers of the invention have a G' of at most 375 Pa. In some embodiments, the tissue fillers of the invention have a G' of at most 400 Pa. In some embodiments, the tissue fillers of the invention have a G' of at most 425 Pa. In some embodiments, the tissue fillers of the invention have a G' of at most 450 Pa. In some embodiments, the tissue fillers of the invention have a G' of at most 475 Pa, in some embodiments, the tissue fillers of the invention have a G' of at most 500 Pa.

In some embodiments, the tissue fillers of the invention have a G' of at most 525 Pa. In some embodiments, the tissue fillers of the invention have a G' of at most 550 Pa. In some embodiments, the tissue fillers of the invention have a G' of at most 575 Pa. In some embodiments, the tissue fillers of the invention have a G' of at most Pa. In some embodiments, the tissue fillers of the invention have a G' of about 625 Pa. In some embodiments, the tissue fillers of the invention have a G' of at most 650 Pa. In some embodiments, the tissue fillers of the invention have a G' of at most 675 Pa. In some embodiments, the tissue fillers of the invention have a G' of at most 700 Pa. In some embodiments, the tissue fillers of the invention have a G' of at most 725 Pa. In some embodiments, the tissue fillers of the invention have a G' of at most 750 Pa. In some embodiments, the tissue fillers of the invention have a G' of at most 775 Pa. In some embodiments, the tissue fillers of the invention have a G' of at most 800 Pa. In some embodiments, the tissue fillers of the invention have a G' of at most 825 Pa. In some embodiments, the tissue fillers of the invention have a G' of at most 850 Pa. In some embodiments, the tissue fillers of the invention have a G' of at most 875 Pa. In some embodiments, the tissue fillers of the invention have a G' of at most 900 Pa. In some embodiments, the tissue fillers of the invention have a G' of at most 925 Pa. In some embodiments, the tissue fillers of the invention have a G' of at most 950 Pa. In some embodiments, the tissue fillers of the invention have a G' of at most 975 Pa. In some embodiments, the tissue fillers of the invention have a G' of at most 1000 Pa.

In some embodiments, the tissue fillers of the invention have a G' of at most 1050 Pa. In some embodiments, the tissue fillers of the invention have a G' of at most 1100 Pa. In some embodiments, the tissue fillers of the invention have a G' of at most 1150 Pa. In some embodiments, the tissue fillers of the invention have a G' of at most 1200 Pa. In some embodiments, the tissue fillers of the invention have a G' of at most 1250 Pa. In some embodiments, the tissue fillers of the invention have a G' of at most 1300 Pa. In some embodiments, the tissue fillers of the invention have a G' of at most 1350 Pa. In some embodiments, the tissue fillers of the invention have a G' of at most 1400 Pa. In some embodiments, the tissue fillers of the invention have a G' of at most 1450 Pa. In some embodiments, the tissue fillers of the invention have a G' of at most 1500 Pa.

In some embodiments, the tissue fillers of the invention have a G' of about 50 Pa. In some embodiments, the tissue fillers of the invention have a G' of about 100 Pa. In some embodiments, the tissue fillers of the invention have a G' of about 150 Pa. In some embodiments, the tissue fillers of the invention have a G' of about 200 Pa. In some embodiments, the tissue fillers of the invention have a G' of about 225 Pa. In some embodiments, the tissue fillers of the invention have a G' of about 250 Pa. In some embodiments, the tissue fillers of the invention have a G' of about 275 Pa. In some embodiments, the tissue fillers of the invention have a G' of about 300 Pa. In some embodiments, the tissue fillers of the invention have a G' of about 325 Pa. In some embodiments, the tissue fillers of the invention have a G' of about 350 Pa. In some embodiments, the tissue fillers of the invention have a G' of about 375 Pa. In some embodiments, the tissue fillers of the invention have a G' of about 400 Pa. In some embodiments, the tissue fillers of the invention have a G' of about 425 Pa. In some embodiments, the tissue fillers of the invention have a G' of about 450 Pa. In some embodiments, the tissue fillers of the invention have a G' of about 475 Pa. In some embodiments, the tissue fillers of the invention have a G' of about 500 Pa.

In some embodiments, the tissue fillers of the invention have a G' of about 525 Pa. In some embodiments, the tissue fillers of the invention have a G' of about 550 Pa. In some embodiments, the tissue fillers of the invention have a G' of about 575 Pa. In some embodiments, the tissue fillers of the invention have a G' of about 600 Pa. In some embodiments, the tissue fillers of the invention have a G' of about 625 Pa. In some embodiments, the tissue fillers of the invention have a G' of about 650 Pa. In some embodiments, the tissue fillers of the invention have a G' of about 675 Pa. In some embodiments, the tissue fillers of the invention have a G' of about 700 Pa. In some embodiments, the tissue fillers of the invention have a G' of about 725 Pa. In some embodiments, the tissue fillers of the invention have a G' of about 750 Pa. In some embodiments, the tissue fillers of the invention have a G' of about 775 Pa. In some embodiments, the tissue fillers of the invention have a G' of about 800 Pa. In some embodiments, the tissue fillers of the invention have a G' of about 825 Pa. In some embodiments, the tissue fillers of the invention have a G' of about 850 Pa. In some embodiments, the tissue fillers of the invention have a G' of about 875 Pa. In some embodiments, the tissue fillers of the invention have a G' of about 900 Pa. In some embodiments, the tissue fillers of the invention have a G' of about 925 Pa. In some embodiments, the tissue fillers of the invention have a G' of about 950 Pa. In some embodiments, the tissue fillers of the invention have a G' of about 975 Pa. In some embodiments, the tissue fillers of the invention have a G' of about 1000 Pa.

In some embodiments, the tissue fillers of the invention have a G' of about 1050 Pa. In some embodiments, the tissue fillers of the invention have a G' of about 1100 Pa. In some embodiments, the tissue fillers of the invention have a G' of about 1150 Pa. In some embodiments, the tissue fillers of the invention have a G' of about 1200 Pa. In some embodiments, the tissue fillers of the invention have a G' of about 1250 Pa. In some embodiments, the tissue fillers of the invention have a G' of about 1300 Pa. In some embodiments, the tissue fillers of the invention have a G' of about 1350 Pa. In some embodiments, the tissue fillers of the invention have a G' of about 1400 Pa. In some embodiments, the tissue fillers of the invention have a G' of about 1450 Pa. In some embodiments, the tissue fillers of the invention have a G' of about 1500 Pa.

In some embodiments, the tissue fillers of the invention have a G' of at least 2000 Pa. In some embodiments, the tissue fillers of the invention have a G' of at least 2250 Pa. In some embodiments, the tissue fillers of the invention have a G' of at least 2500 Pa. In some embodiments, the tissue fillers of the invention have a G' of at least 2750 Pa. In some embodiments, the tissue fillers of the invention have a G' of at least 3000 Pa. In some embodiments, the tissue fillers of the invention have a G' of at least 3250 Pa. In some embodiments, the tissue fillers of the invention have a G' of at least 3500 Pa. In some embodiments, the tissue fillers of the invention have a G' of at least 3750 Pa. In some embodiments, the tissue fillers of the invention have a G' of at least 4000 Pa. In some embodiments, the tissue fillers of the invention have a G' of at least 4250 Pa. In some embodiments, the tissue fillers of the invention have a G' of at least 4500 Pa. In some embodiments, the tissue fillers of the invention have a G' of at least 4750 Pa. In some embodiments, the tissue fillers of the invention have a G' of at least 5000 Pa.

In some embodiments, the tissue fillers of the invention have a G' of at least 5250 Pa. In some embodiments, the tissue fillers of the invention have a G' of at least 5500 Pa. In some embodiments, the tissue fillers of the invention have a G' of at least 5750 Pa. In some embodiments, the tissue fillers of the invention have a G' of about at least 6000 Pa. In some embodiments, the tissue fillers of the invention have a G' of about 6250 Pa. In some embodiments, the tissue fillers of the invention have a G' of at least 6500 Pa. In some embodiments, the tissue fillers of the invention have a G' of at least 6750 Pa. In some embodiments, the tissue fillers of the invention have a G' of at least 7000 Pa. In some embodiments, the tissue fillers of the invention have a G' of at least 7250 Pa. In some embodiments, the tissue fillers of the invention have a G' of at least 7500 Pa. In some embodiments, the tissue fillers of the invention have a G' of at least 7750 Pa. In some embodiments, the tissue fillers of the invention have a G' of at least 8000 Pa. In some embodiments, the tissue fillers of the invention have a G' of at least 8250 Pa. In some embodiments, the tissue fillers of the invention have a G' of at least 8500 Pa. In some embodiments, the tissue fillers of the invention have a G' of at least 8750 Pa. In some embodiments, the tissue fillers of the invention have a G' of at least 9000 Pa. In some embodiments, the tissue fillers of the invention have a G' of at least 9250 Pa. In some embodiments, the tissue fillers of the invention have a G' of at least 9500 Pa. In some embodiments, the tissue fillers of the invention have a G' of at least 9750 Pa. In some embodiments, the tissue fillers of the invention have a G' of at least 10000 Pa.

In some embodiments, the tissue fillers of the invention have a G' of at least 10500 Pa. In some embodiments, the tissue fillers of the invention have a G' of at least 11000 Pa. In some embodiments, the tissue fillers of the invention have a G' of at least 11500 Pa. In some embodiments, the tissue fillers of the invention have a G' of at least 12000 Pa. In some embodiments, the tissue fillers of the invention have a G' of at least 12500 Pa. In some embodiments, the tissue fillers of the invention have a G' of at least 13000 Pa. In some embodiments, the tissue fillers of the invention have a G' of at least 13500 Pa. In some embodiments, the tissue fillers of the invention have a G' of at least 14000 Pa. In some embodiments, the tissue fillers of the invention have a G' of at least 14500 Pa. In some embodiments, the tissue fillers of the invention have a G' of at least 15000 Pa.

In some embodiments, the tissue fillers of the invention have a G' of at most 2000 Pa. In some embodiments, the tissue fillers of the invention have a G' of at most 2250 Pa. In some embodiments, the tissue fillers of the invention have a G' of at most 2500 Pa. In some embodiments, the tissue fillers of the invention have a G' of at most 2750 Pa. In some embodiments, the tissue fillers of the invention have a G' of at most 3000 Pa. In some embodiments, the tissue fillers of the invention have a G' of at most 3250 Pa. In some embodiments, the tissue fillers of the invention have a G' of at most 3500 Pa. In some embodiments, the tissue fillers of the invention have a G' of at most 3750 Pa. In some embodiments, the tissue fillers of the invention have a G' of at most 4000 Pa. In some embodiments, the tissue fillers of the invention have a G' of at most 4250 Pa. In some embodiments, the tissue fillers of the invention have a G' of at most 4500 Pa. In some embodiments, the tissue fillers of the invention have a G' of at most 4750 Pa. In some embodiments, the tissue fillers of the invention have a G' of at most 5000 Pa.

In some embodiments, the tissue fillers of the invention have a G' of at most 5250 Pa. In some embodiments, the tissue fillers of the invention have a G' of at most 5500 Pa. In some embodiments, the tissue fillers of the invention have a G' of at most 5750 Pa. In some embodiments, the tissue fillers of the invention have a G' of at most 6000 Pa. In some embodiments, the tissue fillers of the invention have a G' of about 6250 Pa. In some embodiments, the tissue fillers of the invention have a G' of at most 6500 Pa. In some embodiments, the tissue fillers of the invention have a G' of at most 6750 Pa. In some embodiments, the tissue fillers of the invention have a G' of at most 7000 Pa. In some embodiments, the tissue fillers of the invention have a G' of at most 7250 Pa. In some embodiments, the tissue fillers of the invention have a G' of at most 7500 Pa. In some embodiments, the tissue fillers of the invention have a G' of at most 7750 Pa. In some embodiments, the tissue fillers of the invention have a G' of at most 8000 Pa. In some embodiments, the tissue fillers of the invention have a G' of at most 8250 Pa. In some embodiments, the tissue fillers of the invention have a G' of at most 8500 Pa. In some embodiments, the tissue fillers of the invention have a G' of at most 8750 Pa. In some embodiments, the tissue fillers of the invention have a G' of at most 9000 Pa. In some embodiments, the tissue fillers of the invention have a G' of at most 9250 Pa. In some embodiments, the tissue fillers of the invention have a G' of at most 9500 Pa. In some embodiments, the tissue fillers of the invention have a G' of at most 9750 Pa. In some embodiments, the tissue fillers of the invention have a G' of at most 10000 Pa.

In some embodiments, the tissue fillers of the invention have a G' of at most 10500 Pa. In some embodiments, the tissue fillers of the invention have a G' of at most 11000 Pa. In some embodiments, the tissue fillers of the invention have a G' of at most 11500 Pa. In some embodiments, the tissue fillers of the invention have a G' of at most 12000 Pa. In some embodiments, the tissue fillers of the invention have a G' of at most 12500 Pa. In some embodiments, the tissue fillers of the invention have a G' of at most 13000 Pa. In some embodiments, the tissue fillers of the invention have a G' of at most 13500 Pa. In some embodiments, the tissue fillers of the invention have a G' of at most 14000 Pa. In some embodiments, the tissue fillers of the invention have a G' of at most 14500 Pa. In some embodiments, the tissue fillers of the invention have a G' of at most 15000 Pa.

In some embodiments, the tissue fillers of the invention have a G' of about 2000 Pa. In some embodiments, the tissue fillers of the invention have a G' of about 2250 Pa. In some embodiments, the tissue fillers of the invention have a G' of about 2500 Pa. In some embodiments, the tissue fillers of the invention have a G' of about 2750 Pa. In some embodiments, the tissue fillers of the invention have a G' of about 3000 Pa. In some embodiments, the tissue fillers of the invention have a G' of about 3250 Pa. In some embodiments, the tissue fillers of the invention have a G' of about 3500 Pa. In some embodiments, the tissue fillers of the invention have a G' of about 3750 Pa. In some embodiments, the tissue fillers of the invention have a G' of about 4000 Pa. In some embodiments, the tissue fillers of the invention have a G' of about 4250 Pa. In some embodiments, the tissue fillers of the invention have a G' of about 4500 Pa. In some embodiments, the tissue fillers of the invention have a G' of about 4750 Pa. In some embodiments, the tissue fillers of the invention have a G' of about 5000 Pa.

In some embodiments, the tissue fillers of the invention have a G' of about 5250 Pa. In some embodiments, the tissue fillers of the invention have a G' of about 5500 Pa. In some embodiments, the tissue fillers of the invention have a G' of about 5750 Pa. In some embodiments, the tissue fillers of the invention have a G' of about 6000 Pa. In some embodiments, the tissue fillers of the invention have a G' of about 6250 Pa. In some embodiments, the tissue fillers of the invention have a G' of about 6500 Pa. In some embodiments, the tissue fillers of the invention have a G' of about 6750 Pa. In some embodiments, the tissue fillers of the invention have a G' of about 7000 Pa. In some embodiments, the tissue fillers of the invention have a G' of about 7250 Pa. In some embodiments, the tissue fillers of the invention have a G' of about 7500 Pa. In some embodiments, the tissue fillers of the invention have a G' of about 7750 Pa. In some embodiments, the tissue fillers of the invention have a G' of about 8000 Pa. In some embodiments, the tissue fillers of the invention have a G' of about 8250 Pa. In some embodiments, the tissue fillers of the invention have a G' of about 8500 Pa. In some embodiments, the tissue fillers of the invention have a G' of about 8750 Pa. In some embodiments, the tissue fillers of the invention have a G' of about 9000 Pa. In some embodiments, the tissue fillers of the invention have a G' of about 9250 Pa. In some embodiments, the tissue fillers of the invention have a G' of about 9500 Pa. In some embodiments, the tissue fillers of the invention have a G' of about 9750 Pa. In some embodiments, the tissue fillers of the invention have a G' of about 10000 Pa.

In some embodiments, the tissue fillers of the invention have a G' of about 1050 Pa. In some embodiments, the tissue fillers of the invention have a G' of about 1100 Pa. In some embodiments, the tissue fillers of the invention have a G' of about 1150 Pa. In some embodiments, the tissue fillers of the invention have a G' of about 1200 Pa. In some embodiments, the tissue fillers of the invention have a G' of about 1250 Pa. In some embodiments, the tissue fillers of the invention have a G' of about 1300 Pa. In some embodiments, the tissue fillers of the invention have a G' of about 1350 Pa. In some embodiments, the tissue fillers of the invention have a G' of about 1400 Pa. In some embodiments, the tissue fillers of the invention have a G' of about 1450 Pa. In some embodiments, the tissue fillers of the invention have a G' of about 1500 Pa.

In some embodiments, the tissue fillers of the invention have a G" from about less than 5 Pa, to about more than 200 Pa. In some embodiments, the tissue fillers of the invention have a G" from about 5 Pa to about 200 Pa. In some embodiments, the tissue fillers of the invention have a G" from about 5 Pa to about 25 Pa. In some embodiments, the tissue fillers of the invention have a G" from about 15 Pa to about 35 Pa. In some embodiments, the tissue fillers of the invention have a G" from about 10 Pa to about 50 Pa. In some embodiments, the tissue fillers of the invention have a G" from about 15 Pa to about 75 Pa. In some embodiments, the tissue fillers of the invention have a G" from about Pa to about 85 Pa. In some embodiments, the tissue fillers of the invention have a G" from about 25 Pa to about 100 Pa. In some embodiments, the tissue fillers of the invention have a G" from about 35 Pa to about 125 Pa. In some embodiments, the tissue fillers of the invention have a G" from about 45 Pa to about 115 Pa. In some embodiments, the tissue fillers of the invention have a G" from about 75 Pa to about 150 Pa. In some embodiments, the tissue fillers of the invention have a G" from about 100 Pa to about 175 Pa. In some embodiments, the tissue fillers of the invention have a G" from about 115 Pa to about 200 Pa.

In some embodiments, the tissue fillers of the invention have a G" of at least 5 Pa. In some embodiments, the tissue fillers of the invention have a G" of at least 10 Pa. In some embodiments, the tissue fillers of the invention have a G" of at least 15 Pa. In some embodiments, the tissue fillers of the invention have a G" of at least 20 Pa. In some embodiments, the tissue fillers of the invention have a G" of at least 25 Pa. In some embodiments, the tissue fillers of the invention have a G" of at least 30 Pa. In some embodiments, the tissue fillers of the invention have a G" of at least 35 Pa. In some embodiments, the tissue fillers of the invention have a G" of at least 40 Pa. In some embodiments, the tissue fillers of the invention have a G" of at least 45 Pa. In some embodiments, the tissue fillers of the invention have a G" of at least 50 Pa. In some embodiments, the tissue fillers of the invention have a G" of at least 55 Pa. In some embodiments, the tissue fillers of the invention have a G" of at least 60 Pa. In some embodiments, the tissue fillers of the invention have a G" of at least 65 Pa. In some embodiments, the tissue fillers of the invention have a G" of at least 70 Pa. In some embodiments, the tissue fillers of the invention have a G" of at least 75 Pa. In some embodiments, the tissue fillers of the invention have a G" of at least 80 Pa. In some embodiments, the tissue fillers of the invention have a G" of at least 85 Pa. In some embodiments, the tissue fillers of the invention have a G" of at least 90 Pa. In some embodiments, the tissue fillers of the invention have a G" of at least 95 Pa. In some embodiments, the tissue fillers of the invention have a G" of at least 100 Pa. In some embodiments, the tissue fillers of the invention have a G" of at least 105 Pa. In some embodiments, the tissue fillers of the invention have a G" of at least 110 Pa. In some embodiments, the tissue fillers of the invention have a G" of at least 115 Pa. In some embodiments, the tissue fillers of the invention have a G" of at least 120 Pa. In some embodiments, the tissue fillers of the invention have a G" of at least 125 Pa. In some embodiments, the tissue fillers of the invention have a G" of at least 130 Pa. In some embodiments, the tissue fillers of the invention have a G" of at least 135 Pa. In some embodiments, the tissue fillers of the invention have a G" of at least 140 Pa. In some embodiments, the tissue fillers of the invention have a G" of at least 145 Pa. In some embodiments, the tissue fillers of the invention have a G" of at least 150 Pa. In some embodiments, the tissue fillers of the invention have a G" of at least 155 Pa. In some embodiments, the tissue fillers of the invention have a G" of at least 160 Pa. In some embodiments, the tissue fillers of the invention have a G" of at least 165 Pa. In some embodiments, the tissue fillers of the invention have a G" of at least 170 Pa. In some embodiments, the tissue fillers of the invention have a G" of at least 175 Pa. In some embodiments, the tissue fillers of the invention have a G" of at least 180 Pa. In some embodiments, the tissue fillers of the invention have a G" of at least 185 Pa. In some embodiments, the tissue fillers of the invention have a G" of at least 190 Pa. In some embodiments, the tissue fillers of the invention have a G" of at least 195 Pa. In some embodiments, the tissue fillers of the invention have a G" of at least 200 Pa.

In some embodiments, the tissue fillers of the invention have a G" of at most 5 Pa. In some embodiments, the tissue fillers of the invention have a G" of at most 10 Pa. In some embodiments, the tissue fillers of the invention have a G" of at most 15 Pa. In some embodiments, the tissue fillers of the invention have a G" of at most 20 Pa. In some embodiments, the tissue fillers of the invention have a G" of at most 25 Pa. In some embodiments, the tissue fillers of the invention have a G" of at most 30 Pa. In some embodiments, the tissue fillers of the invention have a G" of at most 35 Pa. In some embodiments, the tissue fillers of the invention have a G" of at most 40 Pa. In some embodiments, the tissue fillers of the invention have a G" of at most 45 Pa. In some embodiments, the tissue fillers of the invention have a G" of at most 50 Pa. In some embodiments, the tissue fillers of the invention have a G" of at most 55 Pa. In some embodiments, the tissue fillers of the invention have a G" of at most 60 Pa. In some embodiments, the tissue fillers of the invention have a G" of at most 65 Pa. In some embodiments, the tissue fillers of the invention have a G" of at most 70 Pa. In some embodiments, the tissue fillers of the invention have a G" of at most 75 Pa. In some embodiments, the tissue fillers of the invention have a G" of at most 80 Pa. In some embodiments, the tissue fillers of the invention have a G" of at most 85 Pa. In some embodiments, the tissue fillers of the invention have a G" of at most 90 Pa. In some embodiments, the tissue fillers of the invention have a G" of at most 95 Pa. In some embodiments, the tissue fillers of the invention have a G" of at most 100 Pa. In some embodiments, the tissue fillers of the invention have a G" of at most 105 Pa. In some embodiments, the tissue fillers of the invention have a G" of at most 110 Pa. In some embodiments, the tissue fillers of the invention have a G" of at most 115 Pa. In some embodiments, the tissue fillers of the invention have a G" of at most 120 Pa. In some embodiments, the tissue fillers of the invention have a G" of at most 125 Pa. In some embodiments, the tissue fillers of the invention have a G" of at most 130 Pa. In some embodiments, the tissue fillers of the invention have a G" of at most 135 Pa. In some embodiments, the tissue fillers of the invention have a G" of at most 140 Pa. In some embodiments, the tissue fillers of the invention have a G" of at most 145 Pa. In some embodiments, the tissue fillers of the invention have a G" of at most 150 Pa. In some embodiments, the tissue fillers of the invention have a G" of at most 155 Pa. In some embodiments, the tissue fillers of the invention have a G" of at most 160 Pa. In some embodiments, the tissue fillers of the invention have a G" of at most 165 Pa. In some embodiments, the tissue fillers of the invention have a G" of at most 170 Pa. In some embodiments, the tissue fillers of the invention have a G" of at most 175 Pa. In some embodiments, the tissue fillers of the invention have a G" of at most 180 Pa. In some embodiments, the tissue fillers of the invention have a G" of at most 185 Pa. In some embodiments, the tissue fillers of the invention have a G" of at most 190 Pa. In some embodiments, the tissue fillers of the invention have a G" of at most 195 Pa. In some embodiments, the tissue fillers of the invention have a G" of at most 200 Pa.

In some embodiments, the tissue fillers of the invention have a G" of about 5 Pa. In some embodiments, the tissue fillers of the invention have a G" of about 10 Pa. In some embodiments, the tissue fillers of the invention have a G" of about 15 Pa. In some embodiments, the tissue fillers of the invention have a G" of about 20 Pa. In some embodiments, the tissue fillers of the invention have a G" of about 25 Pa. In some embodiments, the tissue fillers of the invention have a G" of about 30 Pa. In some embodiments, the tissue fillers of the invention have a G" of about 35 Pa. In some embodiments, the tissue fillers of the invention have a G" of about 40 Pa. In some embodiments, the tissue fillers of the invention have a G" of about 45 Pa. In some embodiments, the tissue fillers of the invention have a G" of about 50 Pa. In some embodiments, the tissue fillers of the invention have a G" of about 55 Pa. In some embodiments, the tissue fillers of the invention have a G" of about 60 Pa. In some embodiments, the tissue fillers of the invention have a G" of about 65 Pa. In some embodiments, the tissue fillers of the invention have a G" of about 70 Pa. In some embodiments, the tissue fillers of the invention have a G" of about 75 Pa. In some embodiments, the tissue fillers of the invention have a G" of about 80 Pa. In some embodiments, the tissue fillers of the invention have a G" of about 85 Pa. In some embodiments, the tissue fillers of the invention have a G" of about 90 Pa. In some embodiments, the tissue fillers of the invention have a G" of about 95 Pa. In some embodiments, the tissue fillers of the invention have a G" of about 100 Pa. In some embodiments, the tissue fillers of the invention have a G" of about 105 Pa. In some embodiments, the tissue fillers of the invention have a G" of about 110 Pa. In some embodiments, the tissue fillers of the invention have a G" of about 115 Pa. In some embodiments, the tissue fillers of the invention have a G" of about 120 Pa. In some embodiments, the tissue fillers of the invention have a G" of about 125 Pa. In some embodiments, the tissue fillers of the invention have a G" of about 130 Pa. In some embodiments, the tissue fillers of the invention have a G" of about 135 Pa. In some embodiments, the tissue fillers of the invention have a G" of about 140 Pa. In some embodiments, the tissue fillers of the invention have a G" of about 145 Pa. In some embodiments, the tissue fillers of the invention have a G" of about 150 Pa. In some embodiments, the tissue fillers of the invention have a G" of about 155 Pa. In some embodiments, the tissue fillers of the invention have a G" of about 160 Pa. In some embodiments, the tissue fillers of the invention have a G" of about 165 Pa. In some embodiments, the tissue fillers of the invention have a G" of about 170 Pa. In some embodiments, the tissue fillers of the invention have a G" of about 175 Pa. In some embodiments, the tissue fillers of the invention have a G" of about 180 Pa. In some embodiments, the tissue fillers of the invention have a G" of about 185 Pa. In some embodiments, the tissue fillers of the invention have a G" of about 190 Pa. In some embodiments, the tissue fillers of the invention have a G" of about 195 Pa. In some embodiments, the tissue fillers of the invention have a G" of about 200 Pa.

In some embodiments, a tissue filler disclosed herein exhibits dynamic viscosity. Viscosity is resistance of a fluid to shear or flow caused by either shear stress or tensile stress. Viscosity describes a fluid's internal resistance to flow caused by intermolecular friction exerted when layers of fluids attempt to slide by one another and may be thought of as a measure of fluid friction. The less viscous the fluid, the greater its ease of movement (fluidity).

Viscosity can be defined in two ways; dynamic viscosity ($\mu$; $\eta$ is sometimes used) or kinematic viscosity (v). Dynamic viscosity, also known as absolute or complex viscosity, is the tangential force per unit area required to move one horizontal plane with respect to the other at unit velocity when maintained a unit distance apart by the fluid. The SI physical unit of dynamic viscosity is the Pascal-second (Pas), which is identical to $Nm^{-2}s$. Dynamic viscosity can be expressed as $\tau=\mu dvx/dz$, where $\tau$=shearing stress, $\mu$=dynamic viscosity, and $dvx/dz$ is the velocity gradient over time. For example, if a fluid with a viscosity of one Pa·s is placed between two plates, and one plate is pushed sideways with a shear stress of one Pascal, it moves a distance equal to the thickness of the layer between the plates in one second. Kinematic viscosity (v) is the ratio of dynamic viscosity to density, a quantity in which no force is involved and is defined as follows: $v=\mu/\rho$, where $\mu$ is the dynamic viscosity, and $\rho$ is density ($kg/m^3$). Kinematic viscosity is usually measured by a glass capillary viscometer as has an SI unit of $m^2/s$. The viscosity of a fluid is temperature dependent, and thus dynamic and kinematic viscosity are reported in reference to temperature.

In some embodiments, a tissue filler disclosed herein exhibits a dynamic viscosity of, for example, at least 10 Pa·s, at least 20 Pa·s, at least 30 Pa·s, at least 40 Pa·s, at least 50 Pa·s, at least 60 Pa·s, at least 70 Pa·s, at least 80 Pa·s, at least 90 Pa·s, at least 100 Pa·s, at least 125 Pa·s, at least 150 Pa·s, at least 175 Pa·s, at least 200 Pas, at least 225 Pa·s, at least 250 Pa·s, at least 275 Pa·s, at least 300 Pa·s, at least 400 Pa·s, at least 500 Pa·s, at least 600 Pa·s, at least 700 Pa·s, at least 750 Pa·s, at least 800 Pa·s, at least 900 Pa·s, at least 1,000 Pa·s, at least 1,100 Pa·s, or at least 1,200 Pa·s. In some embodiments, a tissue filler disclosed herein exhibits a dynamic viscosity of, for example, at most 10 Pa·s, at most Pa·s, at most 30 Pa·s, at most 40 Pa·s, at most 50 Pa·s, at most 60 Pa·s, at most 70 Pa·s, at most 80 Pa·s, at most 90 Pa·s, at most 100 Pa·s, at most 125 Pa·s, at most 150 Pa·s, at most 175 Pa·s, at most 200 Pa·s, at most 225 Pa·s, at most 250 Pa·s, at most 275 Pa·s, at most 300 Pa·s, at most 400 Pa·s, at most 500 Pa·s, at most 600 Pa·s, at most 700 Pa·s, at most 750 Pa·s, at most 800 Pa·s, at most 900 Pa·s, or at most 1000 Pa·s. In some embodiments, a tissue filler disclosed herein exhibits a dynamic viscosity of, for example, about 10 Pa·s to about 100 Pa·s, about 10 Pa·s to about 150 Pa·s, about 10 Pa·s to about 250 Pa·s, about 50 Pa·s to about 100 Pa·s, about 50 Pa·s to about 150 Pa·s, about 50 Pa·s to about 250 Pa·s, about 100 Pa·s to about 500 Pa·s, about 100 Pa·s to about 750 Pa·s, about 100 Pa·s to about 1,000 Pa·s, about 100 Pa·s to about 1,200 Pa·s, about 300 Pa·s to about 500 Pa·s, about 300 Pa·s to about 750 Pa·s, about 300 Pa·s to about 1,000 Pa·s, or about 300 Pa·s to about 1,200 Pa·s.

In an embodiment, the tissue fillers described herein may substantially maintain their G' and/or G" in vivo for at least 1 day, or at least 2 days, or at least 3 days, or at least 4 days, or at least 5 days, or at least 6 days, or at least 1 week, or at least 2 weeks, or at least 3 weeks, or at least 1 month, or at least 2 months, or at least 3 months, or at least 4 months, or at least 5 months, or at least 6 months, or at least 7 months, or at least 8 months, or at least 9 months, or at least 10 months, or at least 11 months, or at least 1 year.

In an embodiment, the tissue fillers described herein may substantially maintain their G' and/or G" in vivo for at most 1 day, or at most 2 days, or at most 3 days, or at most 4 days, or at most 5 days, or at most 6 days, or at most 1 week, or at most 2 weeks, or at most 3 weeks, or at most 1 month, or at most 2 months, or at most 3 months, or at most 4 months, or at most 5 months, or at most 6 months, or at most 7 months, or at most 8 months, or at most 9 months, or at most 10 months, or at most 11 months, or at most 1 year.

In an embodiment, the tissue fillers described herein may substantially maintain their G' and/or G" in vivo for about 1 day, or about 2 days, or about 3 days, or about 4 days, or about 5 days, or about 6 days, or about 1 week, or about 2 weeks, or about 3 weeks, or about 1 month, or about 2 months, or about 3 months, or about 4 months, or about 5 months, or about 6 months, or about 7 months, or about 8 months, or about 9 months, or about 10 months, or about 11 months, or about 1 year.

In an embodiment, the tissue fillers described herein may substantially maintain their elasticity in vivo for at least 1 day, or at least 2 days, or at least 3 days, or at least 4 days, or at least 5 days, or at least 6 days, or at least 1 week, or at least 2 weeks, or at least 3 weeks, or at least 1 month, or at least 2 months, or at least 3 months, or at least 4 months, or at least 5 months, or at least 6 months, or at least 7 months, or at least 8 months, or at least 9 months, or at least 10 months, or at least 11 months, or at least 1 year.

In an embodiment, the tissue fillers described herein may substantially maintain their elasticity in vivo for at most 1 day, or at most 2 days, or at most 3 days, or at most 4 days, or at most 5 days, or at most 6 days, or at most 1 week, or at most 2 weeks, or at most 3 weeks, or at most 1 month, or at most 2 months, or at most 3 months, or at most 4 months, or at most 5 months, or at most 6 months, or at most 7 months, or at most 8 months, or at most 9 months, or at most 10 months, or at most 11 months, or at most 1 year.

In an embodiment, the tissue fillers described herein may substantially maintain their elasticity in vivo for about 1 day, or about 2 days, or about 3 days, or about 4 days, or about 5 days, or about 6 days, or about 1 week, or about 2 weeks, or about 3 weeks, or about 1 month, or about 2 months, or about 3 months, or about 4 months, or about 5 months, or about 6 months, or about 7 months, or about 8 months, or about 9 months, or about 10 months, or about 11 months, or about 1 year.

In an embodiment, the tissue fillers described herein may substantially maintain their viscosity in vivo for at least 1 day, or at least 2 days, or at least 3 days, or at least 4 days, or at least 5 days, or at least 6 days, or at least 1 week, or at least 2 weeks, or at least 3 weeks, or at least 1 month, or at least 2 months, or at least 3 months, or at least 4 months, or at least 5 months, or at least 6 months, or at least 7 months, or at least 8 months, or at least 9 months, or at least 10 months, or at least 11 months, or at least 1 year.

In an embodiment, the tissue fillers described herein may substantially maintain their viscosity in vivo for at most 1 day, or at most 2 days, or at most 3 days, or at most 4 days, or at most 5 days, or at most 6 days, or at most 1 week, or at most 2 weeks, or at most 3 weeks, or at most 1 month, or at most 2 months, or at most 3 months, or at most 4 months, or at most 5 months, or at most 6 months, or at most 7 months, or at most 8 months, or at most 9 months, or at most 10 months, or at most 11 months, or at most 1 year.

In an embodiment, the tissue fillers described herein may substantially maintain their viscosity in vivo for about 1 day, or about 2 days, or about 3 days, or about 4 days, or about 5 days, or about 6 days, or about 1 week, or about 2 weeks, or about 3 weeks, or about 1 month, or about 2 months, or about 3 months, or about 4 months, or about 5 months, or about 6 months, or about 7 months, or about 8 months, or about 9 months, or about 10 months, or about 11 months, or about 1 year.

In an embodiment, the tissue fillers described herein may substantially maintain their volume in vivo for at least 1 day, or at least 2 days, or at least 3 days, or at least 4 days, or at least 5 days, or at least 6 days, or at least 1 week, or at least 2 weeks, or at least 3 weeks, or at least 1 month, or at least 2 months, or at least 3 months, or at least 4 months, or at least 5 months, or at least 6 months, or at least 7 months, or at least 8 months, or at least 9 months, or at least 10 months, or at least 11 months, or at least 1 year.

In an embodiment, the tissue fillers described herein may substantially maintain their volume in vivo for at most 1 day, or at most 2 days, or at most 3 days, or at most 4 days, or at most 5 days, or at most 6 days, or at most 1 week, or at most 2 weeks, or at most 3 weeks, or at most 1 month, or at most 2 months, or at most 3 months, or at most 4 months, or at most 5 months, or at most 6 months, or at most 7 months, or at most 8 months, or at most 9 months, or at most 10 months, or at most 11 months, or at most 1 year.

In an embodiment, the tissue fillers described herein may substantially maintain their volume in vivo for about 1 day, or about 2 days, or about 3 days, or about 4 days, or about 5 days, or about 6 days, or about 1 week, or about 2 weeks, or about 3 weeks, or about 1 month, or about 2 months, or about 3 months, or about 4 months, or about 5 months, or about 6 months, or about 7 months, or about 8 months, or about 9 months, or about 10 months, or about 11 months, or about 1 year.

Methods of Manufacture

The tissue fillers provided herein may be prepared by combining an SPF based component with an HA based component with or without any additional agents. In certain embodiments, one or both of the SPF and HA may be cross-linked prior to combination. In some embodiments, the SPF and HA may be combined and then cross-linked with a cross-linking agent as described herein. In some embodiments, the SPF may be cross-linked with a cross linking agent and then added to a HA, which may or may not be cross linked, and then the combination thereof may be subjected to additional cross linking. In some embodiments, the HA may be cross-linked with a cross linking agent and then added to a SPF, which may or may not be cross linked, and then the combination thereof may be subjected to additional cross linking.

In some embodiments, the tissue fillers described herein may be prepared by combining an SPF based component, and HA based component, and an additional agent, as described hereinabove. In such embodiments, one or both of the SPF and HA may be cross-linked prior to combination. In some embodiments, the SPF and HA may be combined with the additional agent and then cross-linked with a cross-linking agent as described herein. In some embodiments, the additional agent may be added after combining the SPF and HA.

In some embodiments, the tissue filler described herein may include SPF and HA in a weight ratio (SPF:HA) of 0.1:1 to 0.1:10, or 0.1:1 to 0.1:100, or 0.1:1000; 1:1 to 1:10, or 1:1 to 1:100, or 1:1 to 1:1000.

In some embodiments, the tissue filler described herein may include SPF and HA in a weight ratio (HA:SPF) of 0.1:1 to 0.1:10, or 0.1:1 to 0.1:100, or 0.1:1000; 1:1 to 1:10, or 1:1 to 1:100, or 1:1 to 1:1000.

In some embodiments, a resulting HA/SPF combination (whether cross-linked or non-cross-linked) may be homogenized such as through mechanical blending of initially cross-linked HA and/or SPF.

In some embodiments, a solution of SPF may be provided and cross-linked with a cross linking agent to yield a cross-linked SPF, to which HA may be added in either its cross-linked form, non-cross-linked form, or a mixture thereof. The resulting mixture may then be homogenized and any additional agents (e.g., lidocaine may be added).

In some embodiments, a solution of SPF may be provided and cross-linked with a cross linking agent in the presence of HA to yield a cross-linked SPF-HA composition, to which HA may, or may not, be added in its non-cross-linked form. The resulting mixture may then be homogenized and any additional agents (e.g., lidocaine may be added).

In some embodiments the specific SPF formulations provided herein may be combined with HA, or may utilize the cross-linking procedures, using the preparations set forth in U.S. Pat. No. 8,288,347 or 8,450,475, or U.S. Patent Application Publication Nos. 2006/0105022, 2016/0376382, or 2017/0315828, the entirety of which are incorporated herein by reference.

In some embodiments, the methods described herein may include a sterilization step where the tissue filler or a portion thereof is exposed, for example, to temperatures of 120° C. to about 130° C. and pressures of about 12 to about 20 pounds per square inch for a time of about 1 to about 15 minutes.

In some embodiments, the methods described herein may include a de-gassing step wherein the SPF, HA, or SPF/HA solutions described herein that are used in preparing the resulting tissue fillers are de-gassed.

In some embodiments, the tissue fillers described herein may be prepared according to the general methods described in Examples 5 to 20. In the methods described therein, silk may be prepared in an aqueous solution, an aqueous/alcohol solution, wherein the alcohol may be ethanol or methanol, for example. In the methods described therein, any of the crosslinking agents described herein may be used as applicable to cross link SPF to SPF, SPF to HA, or HA to HA, as would be understood by a person having ordinary skill in art.

Methods of Treatment

In an embodiment, the tissue fillers described herein may be provided in methods of treating one or more conditions in a patient in need thereof. In some embodiments, a therapeutically effective amount of a tissue filler may be delivered into a tissue of a patient in need thereof to treat a condition or other tissue deficiency.

As used herein, the term "treating,", "treat", or "treatment" refers to reducing or eliminating in a patient a cosmetic or clinical symptom of a condition, such as a soft tissue condition, or delaying or preventing in an individual the onset of a cosmetic or clinical symptom of a condition.

In some embodiments, the condition treated by the tissue fillers described herein may include a soft tissue condition. Soft tissue conditions include, without limitation, augmentations, reconstructions, diseases, disorders, defects, or imperfections of a body part, region or area. In one aspect, a soft tissue condition treated by the disclosed tissue fillers include, without limitation, a facial augmentation, a facial reconstruction, a facial disease, a facial disorder, a facial defect, or a facial imperfection. In some embodiments, a soft tissue condition treated by the tissue fillers described herein include, without limitation, skin dehydration, a lack of skin elasticity, skin roughness, a lack of skin tautness, a skin stretch line or mark, skin paleness, a dermal divot, a sunken check, a sunken temple, a thin lip, a urethra defect, a skin defect, a breast defect, a retro-orbital defect, a facial fold, or a wrinkle. In some embodiments, a soft tissue condition treated by the tissue fillers described herein include, without limitation, breast imperfection, defect, disease and/or disorder, such as, e.g., a breast augmentation, a breast reconstruction, mastopexy, micromastia, thoracic hypoplasia, Poland's syndrome, defects due to implant complications like capsular contraction and/or rupture; a facial imperfection, defect, disease or disorder, such as, e.g., a facial augmentation, a facial reconstruction. Parry-Romberg syndrome, lupus erythematosus profundus, dermal divots, sunken cheeks, sunken temples, thin lips, nasal imperfections or defects, retro-orbital imperfections or defects, a facial fold, line and/or wrinkle like a glabellar line, a nasolabial line, a perioral line, and/or a marionette line, and/or other contour deformities or imperfections of the face; a neck imperfection, defect, disease or disorder; a skin imperfection, defect, disease and/or disorder; other soft tissue imperfections, defects, diseases and/or disorders, such as, e.g., an augmentation or a reconstruction of the upper arm, lower arm, hand, shoulder, back, torso including abdomen, buttocks, upper leg, lower leg including calves, foot including plantar fat pad, eye, genitals, or other body part, region or area, or a disease or disorder affecting these body parts, regions or areas; urinary incontinence, fecal incontinence, other forms of incontinence; and gastroesophageal reflux disease (GERD).

In some embodiments, the tissue fillers described herein may be delivered to soft tissues including, without limitation skin, dermal tissues, subdermal tissues, cutaneous tissues, subcutaneous tissues, intradural tissue, muscles, tendons, ligaments, fibrous tissues, fat, blood vessels and arteries, nerves, and synovial (intradermal) tissues.

In some embodiments, the tissue fillers described herein can be placed directly in a wound to aid in healing by providing an artificial biodegradable matrix along with cell attachment, migration, and proliferation signals. In some embodiments, the tissue fillers described herein can be coated on a biodegradable mesh or other implanted material, or it can itself be formed into sheets or other structures, or can be maintained in a hydrated form.

In some embodiments, the amount of a composition used with any of the methods as disclosed herein will be determined based on the alteration and/or improvement desired, the reduction and/or elimination of a condition symptom desired, the clinical and/or cosmetic effect desired by the individual and/or physician, and the body part or region being treated. The effectiveness of composition administration may be manifested by one or more of the following clinical and/or cosmetic measures: altered and/or improved soft tissue shape, altered and/or improved soft tissue size, altered and/or improved soft tissue contour, altered and/or improved tissue function, tissue ingrowth support and/or new collagen deposition, sustained engraftment of the tissue filler, improved patient satisfaction and/or quality of life, and decreased use of implantable foreign material. For example, for breast augmentation procedures, effectiveness of the compositions and methods may be manifested by one or more of the following clinical and/or cosmetic measures: increased breast size, altered breast shape, altered breast contour, sustained engraftment, reduction in the risk of capsular contraction, decreased rate of liponecrotic cyst formation, improved patient satisfaction and/or quality of life, and decreased use of breast implant.

In some embodiments, effectiveness of the tissue fillers and methods in treating a facial soft tissue may be manifested by one or more of the following clinical and/or cosmetic measures: increased size, shape, and/or contour of facial feature like increased size, shape, and/or contour of lip, cheek, temple, or eye region; altered size, shape, and/or contour of facial feature like altered size, shape, and/or contour of lip, cheek, temple, or eye region shape; reduction or elimination of a wrinkle, fold or line in the skin; resistance to a wrinkle, fold or line in the skin; rehydration of the skin; increased elasticity to the skin; reduction or elimination of skin roughness; increased and/or improved skin tautness; reduction or elimination of stretch lines or marks; increased and/or improved skin tone, shine, brightness and/or radiance; increased and/or improved skin color, reduction or elimination of skin paleness; sustained engraftment of composition; decreased side effects; improved patient satisfaction and/or quality of life.

In some embodiments, the invention provides for tissue fillers and methods of treatment involving a dermal region. As used herein, the term "dermal region" refers to the region of skin comprising the epidermal-dermal junction and the dermis including the superficial dermis (papillary region) and the deep dermis (reticular region). The skin is composed of three primary layers: the epidermis, which provides waterproofing and serves as a barrier to infection; the dermis, which serves as a location for the appendages of skin; and the hypodermis (subcutaneous adipose layer). The epidermis contains no blood vessels, and is nourished by diffusion from the dermis. The main type of cells which make up the epidermis are keratinocytes, melanocytes, Langerhans cells, and Merkels cells.

The dermis is the layer of skin beneath the epidermis that consists of connective tissue and cushions the body from stress and strain. The dermis is tightly connected to the epidermis by a basement membrane. It also harbors many mechanoreceptor/nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the stratum basal of the epidermis. The dermis is structurally divided into two areas: a superficial area adjacent to the epidermis, called the papillary region, and a deep thicker area known as the reticular region.

The papillary region is composed of loose areolar connective tissue. It is named for its fingerlike projections called papillae that extend toward the epidermis. The papillae provide the dermis with a "bumpy" surface that interdigitates with the epidermis, strengthening the connection between the two layers of skin. The reticular region lies deep in the papillary region and is usually much thicker. It is composed of dense irregular connective tissue, and receives its name from the dense concentration of collagenous, elastic, and reticular fibers that weave throughout it. These protein fibers give the dermis its properties of strength, extensibility, and elasticity. Also located within the reticular region are the roots of the hair, sebaceous glands, sweat glands, receptors, nails, and blood vessels. Stretch marks from pregnancy are for example located in the dermis.

The hypodermis lies below the dermis. Its purpose is to attach the dermal region of the skin to underlying bone and muscle as well as supplying it with blood vessels and nerves. It consists of loose connective tissue and elastin. The main cell types are fibroblasts, macrophages and adipocytes (the hypodermis contains 50% of body fat). Fat serves as padding and insulation for the body.

In some embodiments, a tissue filler disclosed herein is administered to a skin region of an individual by injection into a dermal region or a hypodermal region. In some embodiments, a tissue filler disclosed herein is administered to a dermal region of an individual by injection into, e.g., an epidermal-dermal junction region, a papillary region, a reticular region, or any combination thereof.

In some embodiments, the invention provides methods of treating a soft tissue condition of an individual, including administering one or more tissue fillers disclosed herein to a site of the soft tissue condition of the individual, wherein the administration of the composition improves the soft tissue condition, thereby treating the soft tissue condition. In some embodiments, a soft tissue condition is a breast tissue condition, a facial tissue condition, a neck condition, a skin condition, an upper arm condition, a lower arm condition, a hand condition, a shoulder condition, a back condition, a torso including abdominal condition, a buttock condition, an upper leg condition, a lower leg condition including calf condition, a foot condition including plantar fat pad condition, an eye condition, a genital condition, or a condition effecting another body part, region or area.

In some embodiments, the invention provides methods of treating a skin condition including administering to an individual suffering from a skin condition one or more tissue fillers disclosed herein, wherein the administration of the tissue filler improves the skin condition, thereby treating the skin condition. In some embodiments, a skin condition includes skin dehydration, and the method of treatment includes administering to an individual suffering from skin dehydration one or more tissue fillers disclosed herein, wherein the administration of the tissue filler rehydrates the skin, thereby treating skin dehydration. In another aspect of these embodiments, a method of treating a lack of skin elasticity includes administering to an individual suffering from a lack of skin elasticity a tissue filler disclosed herein, wherein the administration of the tissue filler increases the elasticity of the skin, thereby treating a lack of skin elasticity. In yet another aspect of these embodiments, a method of treating skin roughness includes administering to an individual suffering from skin roughness a composition disclosed herein, wherein the administration of the composition decreases skin roughness, thereby treating skin roughness. In some embodiments, a method of treating a lack of skin tautness includes administering to an individual suffering from a lack of skin tautness a tissue filler disclosed herein, wherein the administration of the tissue filler makes the skin tauter, thereby treating a lack of skin tautness.

In some embodiments, the invention provides methods of treating a skin stretch line or mark, including administering to an individual suffering from a skin stretch line or mark one or more tissue fillers disclosed herein, wherein the administration of the one or more tissue fillers reduces or eliminates the skin stretch line or mark, thereby treating a skin stretch line or mark. In some embodiments, a method of treating skin paleness includes administering to an individual suffering from skin paleness a tissue filler disclosed herein, wherein the administration of the tissue filler increases skin tone or radiance, thereby treating skin paleness. In some embodiments, a method of treating skin wrinkles includes administering to an individual suffering from skin wrinkles a tissue filler disclosed herein, wherein the administration of the tissue filler reduces or eliminates skin wrinkles, thereby treating skin wrinkles. In yet another aspect of these embodiments, a method of treating skin wrinkles includes administering to an individual a tissue filler disclosed herein, wherein the administration of the tissue filler makes the skin resistant to skin wrinkles, thereby treating skin wrinkles.

In some embodiments, the invention provides administration of a composition disclosed herein wherein such administration promotes new collagen deposition or formation. The tissue fillers described herein may support tissue ingrowth and new deposition or formation of collagen.

Without being limited to any one theory of the invention, the molecular weight of SPFs used in the preparation tissue fillers described herein may be adjusted to provide a mild inflammatory response at a selected tissue in order trigger the deposition or formation of collagen through the resulting tissue proliferation and maturation responses that follow the initial inflammatory response. Indeed, higher molecular weight SPFs may result in an increased inflammatory response while lower molecular weight SPFs may result in little or no inflammatory response.

Without being limited to any one theory of the invention, the tissue fillers described herein provide the unexpected attribute that a resulting inflammatory response, and thereby collagen formation through the proliferation and maturation tissue response, may be tuned because the SPF solutions used herein have narrow rather than broad polydispersities. In an embodiment, administration of a tissue filler disclosed herein increases new collagen deposition.

In some embodiments, administration of a tissue disclosed herein increases new collagen deposition or formation by about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 200%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%, relative to the same or similar tissue filler comprising HA, but lacking SPF.

In some embodiments, administration of a tissue filler disclosed herein increases new collagen deposition or formation by at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 100%, at least 125%, at least 150%, at least 175%, at least 200%, at least 225%, at least 250%, at least 275%, or at least 300%, relative to the same or similar tissue filler comprising HA, but lacking SPF.

In some embodiments, administration of a tissue filler disclosed herein increases new collagen deposition or formation by at most 1%, at most 2%, at most 3%, at most 4%, at most 5%, at most 6%, at most 7%, at most 8%, at most 9%, at most 10%, at most 11%, at most 12%, at most 13%, at most 14%, at most 15%, at most 16%, at most 17%, at most 18%, at most 19%, at most 20%, at most 21%, at most 22%, at most 23%, at most 24%, at most 25%, at most 26%, at most 27%, at most 28%, at most 29%, at most 30%, at most 31%, at most 32%, at most 33%, at most 34%, at most 35%, at most 36%, at most 37%, at most 38%, at most 39%, at most 40%, at most 41%, at most 42%, at most 43%, at most 44%, at most 45%, at most 46%, at most 47%, at most 48%, at most 49%, at most 50%, at most 51%, at most 52%, at most 53%, at most 54%, at most 55%, at most 56%, at most 57%, at most 58%, at most 59%, at most 60%, at most 61%, at most 62%, at most 63%, at most 64%, at most 65%, at most 66%, at most 67%, at most 68%, at most 69%, at most 70%, at most 71%, at most 72%, at most 73%, at most 74%, at most 75%, at most 76%, at most 770%, at most 78%, at most 79%, at most 80%, at most 81%, at most 82%, at most 83%, at most 84%, at most 85%, at most 86%, at most 87%, at most 88%, at most 89%, at most 90%, at most 91%, at most 92%, at most 93%, at most 94%, at most 95%, at most 96%, at most 97%, at most 98%, at most 99%, at most 100%, at most 125%, at most 150%, at most 175%, at most 200%, at most 225%, at most 250%, at most 275%, or at most 300%, relative to the same or similar tissue filler comprising HA, but lacking SPF.

In some embodiments, administration of a tissue filler disclosed herein increases new collagen deposition or formation by about 1% to about 10%, about 10% to about 50%, about 10% to about 100%, about 50% to about 150%, about 100% to about 200%, about 150% to about 250%, about 200% to about 300%, about 350% to about 450%, about 400% to about 500%, about 550% to about 650%, about 600% to about 700%, relative to the same or similar tissue filler comprising HA, but lacking SPF.

In some embodiments, the amount of a tissue filler used with any of the methods disclosed herein will typically be a therapeutically effective amount. As used herein, the term "therapeutically effective amount" is synonymous with "effective amount", "therapeutically effective dose", and/or "effective dose," and refers to the amount of tissue filler that will elicit the expected biological, cosmetic, or clinical response in a patient in need thereof. As a non-limiting example, an effective amount is an amount sufficient to achieve one or more of the clinical and/or cosmetic measures disclosed herein. The appropriate effective amount to be administered for a particular application of the disclosed methods can be determined by those skilled in the art, using the guidance provided herein. For example, an effective amount can be extrapolated from any and all in vitro and in vivo assays as described herein. One skilled in the art will recognize that the condition of the individual can be monitored throughout the course of therapy and that the effective amount of a composition disclosed herein that is administered can be adjusted accordingly.

In some embodiments, the amount of a tissue filler administered is at least 0.001 g, or at least 0.002 g, or at least 0.003 g, or at least 0.004 g, or at least 0.005 g, or at least 0.006 g, or at least 0.007 g, or at least 0.008 g, or at least 0.009 g, or at least 0.01 g, or at least 0.02 g, or at least 0.03 g, or at least 0.04 g, or at least 0.05 g, or at least 0.06 g, or at least 0.07 g, or at least 0.08 g, or at least 0.09 g, or at least 0.1 g, or at least 0.2 g, or at least 0.3 g, or at least 0.4 g, or at least 0.5 g, or at least 0.6 g, or at least 0.7 g, or at least 0.8 g, or at least 0.9 g, or at least 1 g, or at least 2 g, or at least 3 g, or at least 4 g, or at least 5 g, or at least 6 g, or at least 7 g, or at least 8 g, or at least 9 g, or at least 10 g, or at least 11 g, or at least 12 g, or at least 13 g, or at least 14 g, or at least 15 g, or at least 20 g, or at least 25 g, or at least 30 g, or at least 35 g, or at least 40 g, or at least 45 g, or at least 50 g, or at least 55 g, or at least 60 g, or at least 65 g, or at least 70 g, or at least 75 g, or at least 80 g, or at least 85 g, or at least 90 g, or at least 95 g, or at least 100 g.

In some embodiments, the amount of a tissue filler administered is at most 0.001 g, or at most 0.002 g, or at most 0.003 g, or at most 0.004 g, or at most 0.005 g, or at most 0.006 g, or at most 0.007 g, or at most 0.008 g, or at most 0.009 g, or at most 0.01 g, or at most 0.02 g, or at most 0.03 g, or at most 0.04 g, or at most 0.05 g, or at most 0.06 g, or at most 0.07 g, or at most 0.08 g, or at most 0.09 g, or at most 0.1 g, or at most 0.2 g, or at most 0.3 g, or at most 0.4 g, or at most 0.5 g, or at most 0.6 g, or at most 0.7 g, or at most 0.8 g, or at most 0.9 g, or at most 1 g, or at most 2 g, or at most 3 g, or at most 4 g, or at most 5 g, or at most 6 g, or at most 7 g, or at most 8 g, or at most 9 g, or at most 10 g, or at most 11 g, or at most 12 g, or at most 13 g, or at most 14 g, or at most 15 g, or at most 20 g, or at most 25 g, or at most 30 g, or at most 35 g, or at most 40 g, or at most 45 g, or at most 50 g, or at most 55 g, or at most 60 g, or at most 65 g, or at most 70 g, or at most 75 g, or at most 80 g, or at most 85 g, or at most 90 g, or at most 95 g, or at most 100 g.

In some embodiments, the amount of a tissue filler administered is about 0.001 g, or about 0.002 g, or about 0.003 g, or about 0.004 g, or about 0.005 g, or about 0.006 g, or about 0.007 g, or about 0.008 g, or about 0.009 g, or about 0.01 g, or about 0.02 g, or about 0.03 g, or about 0.04 g, or about 0.05 g, or about 0.06 g, or about 0.07 g, or about 0.08 g, or about 0.09 g, or about 0.1 g, or about 0.2 g, or about 0.3 g, or about 0.4 g, or about 0.5 g, or about 0.6 g, or about 0.7 g, or about 0.8 g, or about 0.9 g, or about 1 g, or about 2 g, or about 3 g, or about 4 g, or about 5 g, or about 6 g, or about 7 g, or about 8 g, or about 9 g, or about 10 g, or about 11 g, or about 12 g, or about 13 g, or about 14 g, or about 15 g, or about 20 g, or about 25 g, or about 30 g, or about 35 g, or about 40 g, or about 45 g, or about 50 g, or about 55 g, or about 60 g, or about 65 g, or about 70 g, or about 75 g, or about 80 g, or about 85 g, or about 90 g, or about 95 g, or about 100 g.

In some embodiments, the amount of a tissue filler administered is 0.001 g to 0.01 g, or 0.01 g to 0.1 g, or 0.1 g to 1 g, or 1 g to 10 g, or 10 g to 20 g, or 20 g to 30 g, or 30 g to 40 g, or 40 g to 50 g, or 50 g to 60 g, or 60 g to 70 g, or 70 g to 80 g, or 80 g to 90 g, or 90 g to 100 g.

In some embodiments, the volume of a tissue filler administered is at least 0.01 mL, or at least 0.02 mL, or at least 0.03 mL, or at least 0.04 mL, or at least 0.05 mL, or at least 0.06 mL, or at least 0.07 mL, or at least 0.08 mL, or at least 0.09 mL, or at least 0.10 mL, or at least 0.15 mL, or at least 0.20 mL, or at least 0.25 mL, or at least 0.30 mL, or at least 0.35 mL, or at least 0.40 mL, or at least 0.45 mL, or at least 0.50 mL, or at least 0.55 mL, or at least 0.60 mL, or at least 0.65 mL, or at least 0.70 mL, or at least 0.75 mL, or at least 0.80 mL, or at least 0.85 mL, or at least 0.90 mL, or at least 0.95 mL, or at least 1 mL, or at least 2 mL, or at least 3 mL, or at least 4 mL, or at least 5 mL, or at least 6 mL, or at least 7 mL, or at least, 8 mL, or at least 9 mL, or at least 10 mL, or at least 15 mL, or at least 20 mL, or at least 25 mL, or at least 30 mL, or at least 35 mL, or at least 40 mL, or at least 45 mL, or at least 50 mL, or at least 55 mL, or at least 60 mL, or at least 65 mL, or at least 70 mL, or at least 75 mL, or at least 80 mL, or at least 85 mL, or at least 90 mL, or at least 95 mL, or at least 100 mL, or at least 110 mL, or at least 120 mL, or at least 130 mL, or at least 140 mL, or at least 150 mL, or at least 160 mL, or at least 170 mL, or at least 180 mL, or at least 190 mL, or at least 200 mL, or at least 210 mL, or at least 220 mL, or at least 230 mL, or at least 240 mL, or at least 250 mL, or at least 260 mL, or at least 270 mL, or at least 280 mL, or at least 290 mL, or at least 300 mL, or at least 325, 350 mL, or at least 375 mL, or at least 400 mL, or at least 425 mL, or at least 450 mL, or at least 475 mL, or at least 500 mL, or at least 525 mL, or at least 550 mL, or at least 575 mL, or at least 600 mL, or at least 625 mL, or at least 650 mL, or at least 675 mL, or at least 700 mL, or at least 725 mL, or at least 750 mL, or at least 775 mL, or at least 800 mL, or at least 825 mL, or at least 850 mL, or at least 875 mL, or at least 900 mL, or at least 925 mL, or at least 950 mL, or at least 975 mL, or at least 1000 mL.

In some embodiments, the volume of a tissue filler administered is at most 0.01 mL, or at most 0.02 mL, or at most 0.03 mL, or at most 0.04 mL, or at most 0.05 mL, or at most 0.06 mL, or at most 0.07 mL, or at most 0.08 mL, or at most 0.09 mL, or at most 0.10 mL, or at most 0.15 mL, or at most 0.20 mL, or at most 0.25 mL, or at most 0.30 mL, or at most 0.35 mL, or at most 0.40 mL, or at most 0.45 mL, or at most 0.50 mL, or at most 0.55 mL, or at most 0.60 mL, or at most 0.65 mL, or at most 0.70 mL, or at most 0.75 mL, or at most 0.80 mL, or at most 0.85 mL, or at most 0.90 mL, or at most 0.95 mL, or at most 1 mL, or at most 2 mL, or at most 3 mL, or at most 4 mL, or at most 5 mL, or at most 6 mL, or at most 7 mL, or at most, 8 mL, or at most 9 mL, or at most 10 mL, or at most 15 mL, or at most 20 mL, or at most 25 mL, or at most 30 mL, or at most 35 mL, or at most 40 mL, or at most 45 mL, or at most 50 mL, or at most 55 mL, or at most 60 mL, or at most 65 mL, or at most 70 mL, or at most 75 mL, or at most 80 mL, or at most 85 mL, or at most 90 mL, or at most 95 mL, or at most 100 mL, or at most 110 mL, or at most 120 mL, or at most 130 mL, or at most 140 mL, or at most 150 mL, or at most 160 mL, or at most 170 mL, or at most 180 mL, or at most 190 mL, or at most 200 mL, or at most 210 mL, or at most 220 mL, or at most 230 mL, or at most 240 mL, or at most 250 mL, or at most 260 mL, or at most 270 mL, or at most 280 mL, or at most 290 mL, or at most 300 mL, or at most 325, 350 mL, or at most 375 mL, or at most 400 mL, or at most 425 mL, or at most 450 mL, or at most 475 mL, or at most 500 mL, or at most 525 mL, or at most 550 mL, or at most 575 mL, or at most 600 mL, or at most 625 mL, or at most 650 mL, or at most 675 mL, or at most 700 mL, or at most 725 mL, or at most 750 mL, or at most 775 mL, or at most 800 mL, or at most 825 mL, or at most 850 mL, or at most 875 mL, or at most 900 mL, or at most 925 mL, or at most 950 mL, or at most 975 mL, or at most 1000 mL.

In some embodiments, the volume of a tissue filler administered is about 0.01 mL, or about 0.02 mL, or about 0.03 mL, or about 0.04 mL, or about 0.05 mL, or about 0.06 mL, or about 0.07 mL, or about 0.08 mL, or about 0.09 mL, or about 0.10 mL, or about 0.15 mL, or about 0.20 mL, or about 0.25 mL, or about 0.30 mL, or about 0.35 mL, or about 0.40 mL, or about 0.45 mL, or about 0.50 mL, or about 0.55 mL, or about 0.60 mL, or about 0.65 mL, or about 0.70 mL, or about 0.75 mL, or about 0.80 mL, or about 0.85 mL, or about 0.90 mL, or about 0.95 mL, or about 1 mL, or about 2 mL, or about 3 mL, or about 4 mL, or about 5 mL, or about 6 mL, or about 7 mL, or about, 8 mL, or about 9 mL, or about 10 mL, or about 11 mL, or about 12 mL, or about 13 mL, or about 14 mL, or about 15 mL, or about 16 mL, or about 17 mL, or about 18 mL, or about 19 mL, or about 20 mL, or about 21 mL, or about 22 mL, or about 23 mL, or about 24 mL, or about 25 mL, or about 26 mL, or about 27 mL, or about 28 mL, or about 30 mL, or about 35 mL, or about 36 mL, or about 37 mL, or about 38 mL, or about 39 mL, or about 40 mL, or about 41 mL, or about 42 mL, or about 43 mL, or about 44 mL, or about 45 mL, or about 46 mL, or about 47 mL, or about 48 mL, or about 49 mL, or about 50 mL, or about 51 mL, or about 52 mL, or about 53 mL, or about 54 mL, or about 55 mL, or about 56 mL, or about 57 mL, or about 58 mL, or about 59 mL, or about 60 mL, or about 61 mL, or about 62 mL, or about 63 mL, or about 64 mL, or about 65 mL, or about 66 mL, or about 67 mL, or about 68 mL, or about 69 mL, or about 70 mL, or about 71 mL, or about 72 mL, or about 73 mL, or about 74 mL, or about 75 mL, or about 76 mL, or about 77 mL, or about 78 mL, or about 79 mL, or about 80 mL, or about 81 mL, or about 82 mL, or about 83 mL, or about 84 mL, or about 85 mL, or about 86 mL, or about 87 mL, or about 88 mL, or about 89 mL, or about 90 mL, or about 91 mL, or about 92 mL, or about 93 mL, or about 94 mL, or about 95 mL, or about 96 mL, or about 97 mL, or about 98 mL, or about 99 mL, or about 100 mL, or about 110 mL, or about 120 mL, or about 130 mL, or about 140 mL, or about 150 mL, or about 160 mL, or about 170 mL, or about 180 mL, or about 190 mL, or about 200 mL, or about 210 mL, or about 220 mL, or about 230 mL, or about 240 mL, or about 250 mL, or about 260 mL, or about 270 mL, or about 280 mL, or about 290 mL, or about 300 mL, or about 310 mL, or about 320 mL, or about 330 mL, or about 340 mL, or about 350 mL, or about 360 mL, or about 370 mL, or about 380 mL, or about 390 mL, or about 400 mL, or about 410 mL, or about 420 mL, or about 430 mL, or about 440 mL, or about 450 mL, or about 460 mL, or about 470 mL, or about 480 mL, or about 490 mL, or about 500 mL, or about 510 mL, or about 520 mL, or about 530 mL, or about 540 mL, or about 550 mL, or about 560 mL, or about 570 mL, or about 580 mL, or about 590 mL, or about 600 mL, or about 610 mL, or about 620 mL, or about 630 mL, or about 640 mL, or about 650 mL, or about 660 mL, or about 670 mL, or about 680 mL, or about 690 mL, or about 700 mL, or about 710 mL, or about 720 mL, or about 730 mL, or about 740 mL, or about 750 mL, or about 760 mL, or about 770 mL, or about 780 mL, or about 790 mL, or about 800 mL, or about 810 mL, or about 820 mL, or about 830 mL, or about 840 mL, or about 850 mL, or about 860 mL, or about 870 mL, or about 880 mL, or about 890 mL, or about 900 mL, or about 910 mL, or about 920 mL, or about 930 mL, or about 940 mL, or about 950 mL, or about 960 mL, or about 970 mL, or about 980 mL, or about 990 mL, or about 1000 mL.

In some embodiments, the volume of a tissue filler administered is 0.01 mL to 0.10 mL, or 0.10 mL to 1 mL, or 1 mL to 10 mL, or 10 mL to 100 mL, or 50 mL to 100 mL, or 100 mL to 150 mL, or 150 mL to 200 mL, or 200 mL to 250 mL, or 250 mL to 300 mL, or 300 mL to 350 mL, or 350 mL to 400 mL, or 400 mL to 450 mL, or 450 mL to 500 mL, or 500 mL to 550 mL, or 550 mL to 600 mL, or 600 mL to 650 mL, or 650 mL to 700 mL, or 700 mL to 750 mL, or 750 mL to 800 mL, or 800 mL to 850 mL, or 850 mL to 900 mL, or 900 mL to 950 mL, or 950 mL to 1000 mL, or 1 mL to 25 mL, or 1 mL to 50 mL, or 1 mL to 75 mL, or 1 mL to 100 mL, or 10 mL to 25 mL, or 10 mL 50 mL, or 10 mL to 75 mL, or 100 mL to 250 mL, or 100 mL to 500 mL, or 100 mL to 750 mL, or 100 mL to 1000 mL.

In some embodiments, the invention provides for administering a tissue filler disclosed herein. As used herein, the term "administering" means any delivery mechanism that provides a tissue filler disclosed herein to an individual that potentially results in a clinically, therapeutically, or experimentally beneficial result. The actual delivery mechanism used to administer a tissue filler to an individual can be determined by a person of ordinary skill in the art by taking into account factors, including, without limitation, the type of condition, the location of the condition, the cause of the condition, the severity of the condition, the degree of relief desired, the duration of relief desired, the particular tissue filler used, the rate of biodegradability, bioabsorbability, bioresorbability, and the like, of the particular tissue filler used, the nature of the components included in the particular tissue filler used, the particular route of administration, the particular characteristics, history and risk factors of the patient, such as, e.g., age, weight, general health and the like, or any combination thereof. In an aspect of this embodiment, a tissue filler disclosed herein is administered to a region of a patient by injection, wherein the region may be in the skin, dermal tissues, subdermal tissues, cutaneous tissues, subcutaneous tissues, intradural tissue, muscles, tendons, ligaments, fibrous tissues, fat, blood vessels and arteries, nerves, or synovial (intradermal) tissues.

In some embodiments, the route of administration of a tissue filler administered to a patient will be determined based on the cosmetic and/or clinical effect desired by the patient and/or physician and the body part or region being treated. A tissue filler disclosed herein may be administered by any means known to persons of ordinary skill in the art including, without limitation, syringe with needle, catheter, topically, or by direct surgical implantation. The tissue filler disclosed herein can be administered into a skin region such as, e.g., a dermal region or a hypodermal region. In addition, a tissue filler disclosed herein may be administered once, twice, thrice, or a plurality of times as required by the specific therapy.

In some embodiments, a tissue filler disclosed herein is injectable. As used herein, the term "injectable" refers to a tissue material having the properties necessary to administer the tissue filler into a skin region of an individual using an injection device with a needle such as, for example, a fine needle. As used herein, the term "fine needle" refers to a needle that is 27 gauge or smaller. In some embodiments, a fine needle can be a 27 gauge to 30 gauge needle. Injectability of a tissue filler disclosed herein can be accomplished by varying certain parameters of the tissue filers disclosed herein by, for example, adjusting the degree of cross-linking, otherwise varying G' and/or G" parameters, adding non-cross linked polymers (e.g., SPF or HA), and the like.

In some embodiments, a tissue filler disclosed herein is injectable through a fine needle. In some embodiments, a tissue filler disclosed herein is injectable through a needle of, for example, 20 gauge, or 21 gauge, or 22 gauge, or 23 gauge, or 24 gauge, or 25 gauge, or 26 gauge, or 27 gauge, or 28 gauge, or 29 gauge, or 30 gauge, or 31 gauge, or 32 gauge, or 33 gauge, or 34 gauge. In some embodiments, the tissue filler described herein are injectable through a needle of 20 gauge, or 21 gauge, or 22 gauge, or 23 gauge, or 24 gauge, or 25 gauge, or 26 gauge, or 27 gauge, or 28 gauge, or 29 gauge, or 30 gauge.

In some embodiments, a tissue filler disclosed herein is injectable with a syringe having a volume of about 0.8 to about 1.0 mL.

In some embodiments, the tissue fillers described herein may be delivered to void spaces in or about soft tissues for the purpose of, for example, tissue augmentation (e.g., breast or buttock augmentation). When delivering the tissue fillers described herein to such void spaces, larger syringes and needles may be used (e.g., needles that are 27 gauge or larger).

In some embodiments, the tissue fillers described herein may be applied to a wound without the use of a needle in order to coat the wound or a medical device proximate to the wound.

In some embodiments, the tissue fillers described herein may be applied to a surface of a medical device.

The following examples are put forth so as to provide those of ordinary skill in the art with a complete disclosure and description of how to make and use the described embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1: Tyndall Evaluation of Gels

In order to further support visual observations and carry out comparative performance analysis of dermal fillers, quantitative analysis of Tyndall effect is performed. Based on existing scientific understanding on light scattering and interaction of light with skin, two distinct approaches based on (a) colorimetry, and (b) spectroscopy are employed to quantify Tyndall effect in skin. Based on these techniques three distinct quantitative parameters (outlined below) are defined to measure Tyndall effect in vivo.

Tyndall Effect Visual Score:

The scale has a range of 1 to 5 with increments of 0.5. A score of 1 is given to injection sites with normal skin tone and no blue discoloration. A maximum score of 5 is given to thick and pronounced blue discoloration. Three independent observers are trained on the scale before being blinded to score test samples.

Blue Component of Skin Color—"b": a chromameter is used to quantify the blue color component of light remitted from skin sites injected with the various fillers. This is achieved by using the "b" component of L-a-b color scale.

"% Blue Light" Remitted from Skin: a portable spectrophotometer is used to quantify the % blue light remitted from skin in the total visible light range. This is achieved by integrating the area under the visible light spectrum between 400-490 nm and normalizing it by the total area under the spectrum (400-700 nm).

Gels of the present disclosure and commercially available gels are injected intradermally through an appropriate needle using linear threading technique into the thighs of two months old hairless rats. The gels are implanted superficially to mimic clinical fine line procedures. Tests for Tyndall are performed 48 h after gel implantation. Before performing the Tyndall tests, the animals are humanely euthanized to improve contrast of the Tyndall effect.

A visual score of 1-5 with increments of 0.5, is used to score the injection sites. Injection sites with score of 1 show no skin discoloration, while injections sites with score of 5 show severe blue discoloration of the skin. Spectroscopic analysis are also performed on the injection sites with the aid of a chromatometer. The blue component of skin color "b", and the % of blue light remitted from skin (400-700 nm) are independently measured.

Example 2: In Vivo Tissue Filler Testing

Tissue fillers prepared according to the foregoing description could be tested following intradermal implantation, muscle implantation, and subcutaneous injection.

For example, a dose of a tissue filler could be loaded in a syringe and injected either intradermally, intramuscularly, or subcutaneously using an appropriately sized syringe that permits flow through the needle of the tissue filler to the injection site.

Following initial injection versus a control (e.g., water and/or a marketed HA based tissue filler such as Juvederm), the injection sites may be monitored at 1 week or 2 week intervals where the patients are observed for biocompatibility concerns, including, cytotoxicity, pyrogenicity, endotoxin formation, acute system toxicity, subchronic toxicity, intradermal reactivity, genotoxicity, and skin sensitization.

In addition, the physical attributes of the tissue filler may be monitored by examining presence of Tyndalling or loss in volume, elasticity, or firmness at the injection site.

Example 3: Examination of Tissue Filler Rheology

An oscillatory parallel plate rheometer (Anton Paar Physica MCR 301) could be used to measure the rheological properties of the tissue fillers described herein. A plate diameter of 25 mm could be used at a gap height of 1 mm. Measurements could be performed at a constant temperature of 25° C. Each measurement would consist of a frequency sweep from 1 to 10 Hz at a constant strain of 2% and a logarithmic increase of frequency followed by a strain sweep from 1 to 300% at a constant frequency of 5 Hz with a logarithmic increase in strain. The results of such analyses would provide the Storage Modulus G' and Loss Modulus G' of each tested tissue filler.

Example 4: Examination of Silk/HA Solution Opacity

Solutions of HA and silk were prepared in water or phosphate-buffered saline according to Table 18.

TABLE 18

| Sample | Description |
|---|---|
| 1 | Silk MW: "Mid" <br> Silk Conc: 0.3 mg/mL <br> HA Conc: 22 mg/mL <br> Solvent: Water |
| 2 | Silk MW: "Mid" <br> Silk Conc: 0.6 mg/mL <br> HA Conc: 22 mg/mL <br> Solvent: Water |
| 3 | Silk MW: "Mid" <br> Silk Conc: 3.0 mg/mL <br> HA Conc: 22 mg/mL <br> Solvent: Water |
| 4 | Silk MW: "Mid" <br> Silk Conc: 6.0 mg/mL <br> HA Conc: 22 mg/mL <br> Solvent: Water |

TABLE 18-continued

| Sample | Description |
|---|---|
| 5 | Silk MW: "Mid" <br> Silk Conc: 15.0 mg/mL <br> HA Conc: 22 mg/mL <br> Solvent: Water |
| 6 | Silk MW: "Mid" <br> Silk Conc: 30.0 mg/mL <br> HA Conc.: 22 mg/mL <br> Solvent: Water |
| 7 | Silk MW: "Mid" <br> Silk Conc: 45.0 mg/mL <br> HA Conc: 22 mg/mL <br> Solvent: Water |
| 8 | Silk MW: "Low" <br> Silk Conc: 0.6 mg/mL <br> HA Conc: 22 mg/mL <br> Solvent: Water |
| 9 | Silk MW: "Low" <br> Silk Conc: 15.0 mg/mL <br> HA Conc: 22 mg/mL <br> Solvent: Water |
| 10 | Silk MW: "Low" <br> Silk Conc: 30.0 mg/mL <br> HA Conc: 22 mg/mL <br> Solvent: Water |
| 11 | Silk MW: "Low" <br> Silk Conc: 45.0 mg/mL <br> HA Conc.: 22 mg/mL <br> Solvent: Water |
| 12 | Silk MW: "Mid" <br> Silk Conc: 0.6 mg/mL <br> HA Conc: 22 mg/mL <br> Solvent: PBS |
| 13 | Silk MW: "Mid" <br> Silk Conc: 15 mg/mL <br> HA Conc: 22 mg/mL <br> Solvent: PBS |
| 14 | Silk MW: "Mid" <br> Silk Conc: 30.0 mg/mL <br> HA Conc: 22 mg/mL <br> Solvent: PBS |
| 15 | Silk MW: "Mid" <br> Silk Conc: 45.0 mg/mL <br> HA Conc: 22 mg/mL <br> Solvent: PBS |

Figure 26:
FIG. 26 is a picture of silk/HA formulations in water or phosphate-buffered saline (PBS) at various concentrations, which demonstrate that silk/HA formulations result in homogenous, opaque solutions. The first unmarked vial is a control vial (22 mg/mL HA in water).
Figure 27:
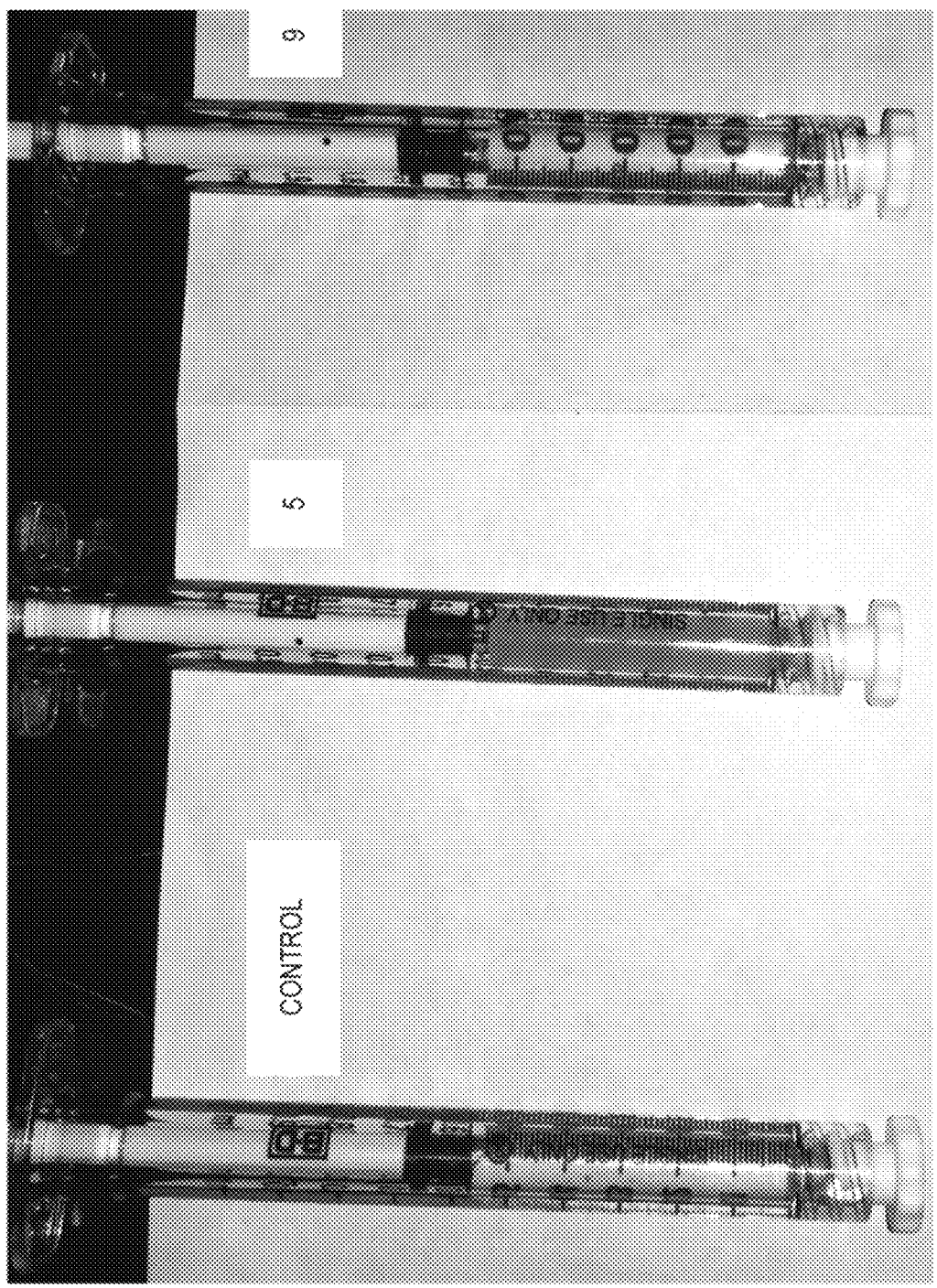
FIG. 27 is a picture of aqueous silk/HA formulations deposited in syringes, which demonstrate that silk/HA formulations result in homogenous, opaque solutions. The control is a solution of 22 mg/mL HA in water.

Low = silk molecular weights of 0 and 25 kDa
Mid = silk molecular weights of 25 kDa to 60 kDa The results the solutions described in the above-table are shown in FIGS. 26 and 27. The control in FIGS. 26 and 27 (unlabeled flask in FIG. 26 and control syringe in FIG. 27) was a solution of HA (22 mg/mL) in water. As illustrated the FIGS. 26 and 27, silk/HA solutions were homogenous and visibly opaque as compared to HA alone.

Example 5: Proposed Tissue Filler Preparation Method

A Silk/HA tissue filler as described herein could be prepared according to the following general method:

Step a: Hyaluronic acid may be dissolved in NaOH solution and added to a solution of silk as described herein;

Step b: Add dissolved BDDE in NaOH to Silk/HA/NaOH solution:

Step c: Cross link by mixing with heat;

Step d: Pass through a metal mesh and allow to swell in water;

Step e: Precipitate swelled gel in ethanol;

Step f: Wash with ethanol, water, and NaOH solution;

Step g: Finalize crosslinking in solution of ethanol/NaOH for about 2 hours with heating (50° C.);

Step h: Neutralize solution pH to 7;

Step i: Precipitate is washed and dried;

Step j: Resulting dry powder allowed to swell into a gel in buffered 0.9% NaCl solution; and Step k: Gel is filled into a syringe and autoclaved provide resulting tissue filler.

Example 6: Proposed Tissue Filler Preparation Method

A Silk/HA tissue filler as described herein could be prepared according to the following general method:

Step a: Hyaluronic acid may be dissolved in NaOH solution;

Step b: Add silk in NaOH solution to a solution of Silk, and then add dissolved BDDE in NaOH to Silk/HA/NaOH solution;

Step c: Cross link by mixing with heat:

Step d: Pass through a metal mesh and allow to swell in water;

Step e: Precipitate swelled gel in ethanol;

Step f: Wash with ethanol, water, and NaOH solution:

Step g: Finalize crosslinking in solution of ethanol/NaOH for about 2 hours with heating (50° C.);

Step h: Neutralize solution pH to 7;

Step i: Precipitate is washed and dried:

Step j: Resulting dry powder allowed to swell into a gel in buffered 0.9% NaCl solution; and Step k: Gel is filled into a syringe and autoclaved provide resulting tissue filler.

Example 7: Proposed Tissue Filler Preparation Method

A Silk/HA tissue filler as described herein could be prepared according to the following general method:

Step a: Hyaluronic acid may be dissolved in NaOH solution;

Step b: Add dissolved BDDE in NaOH to HA/NaOH solution;

Step c: Add silk solution to solution of Step b and cross link by mixing with heat;

Step d: Pass through a metal mesh and allow to swell in water;

Step e: Precipitate swelled gel in ethanol;

Step f: Wash with ethanol, water, and NaOH solution;

Step g: Finalize crosslinking in solution of ethanol/NaOH for about 2 hours with heating (50° C.);

Step h: Neutralize solution pH to 7;

Step i: Precipitate is washed and dried;

Step j: Resulting dry powder allowed to swell into a gel in buffered 0.9% NaCl solution; and Step k: Gel is filled into a syringe and autoclaved provide resulting tissue filler.

Example 8: Proposed Tissue Filler Preparation Method

A Silk/HA tissue filler as described herein could be prepared according to the following general method:

Step a: Hyaluronic acid may be dissolved in NaOH solution;

Step b: Add dissolved BDDE in NaOH to HA/NaOH solution;

Step c: Cross link by mixing with heat;

Step d: Add silk solution to cross-linked HA/NaOH solution, and pass through a metal mesh and allow to swell in water;

Step e: Precipitate swelled gel in ethanol;

Step f: Wash with ethanol, water, and NaOH solution;

Step g: Finalize crosslinking in solution of ethanol/NaOH for about 2 hours with heating (50° C.);

Step h: Neutralize solution pH to 7;

Step i: Precipitate is washed and dried;

Step j: Resulting dry powder allowed to swell into a gel in buffered 0.9% NaCl solution; and Step k: Gel is filled into a syringe and autoclaved provide resulting tissue filler.

Example 9: Proposed Tissue Filler Preparation Method

A Silk/HA tissue filler as described herein could be prepared according to the following general method:

Step a: Hyaluronic acid may be dissolved in NaOH solution;

Step b: Add dissolved BDDE in NaOH to HA/NaOH solution:

Step c: Cross link by mixing with heat;

Step d: Pass through a metal mesh and allow to swell in water:

Step e: Precipitate swelled gel in ethanol;

Step f: Wash with ethanol, water, and NaOH solution:

Step g: Add silk solution to material prepared in Step f and finalize crosslinking in solution of ethanol/NaOH for about 2 hours with heating (50° C.);

Step h: Neutralize solution pH to 7;

Step i: Precipitate is washed and dried:

Step j: Resulting dry powder allowed to swell into a gel in buffered 0.9% NaCl solution;

Step k: Gel is filled into a syringe and autoclaved provide resulting tissue filler.

Example 10: Proposed Tissue Filler Preparation Method

A Silk/HA tissue filler as described herein could be prepared according to the following general method:

Step a: Sodium hyaluronate may be mixed with NaOH solution and a solution of silk as described herein;

Step b: BDDE may be added to the solution of Step a;

Step c: The product of Step b is allowed to react;

Step d: Ammonia is added to the dialyzed mixture of Step c and the mixture is poured into a petri dish;

Step e: The product of Step d is allowed to dry into a film;

Step f: The film of Step e is divided into particles and swelled in saline;

Step g; The product of Step f is added to a syringe and autoclaved;

Step h (optional): The product of Step f can be subjected to a second, final crosslinking procedure with a solution of BDDE, or other crosslinking agent described herein, and washed.

Example 11: Proposed Tissue Filler Preparation Method

A Silk/HA tissue filler as described herein could be prepared according to the following general method:

Step a: Sodium hyaluronate may be mixed with NaOH solution;

Step b: A silk solution may be added to the solution of Step a and BDDE may be added;

Step c: The product of Step b is allowed to react;

Step d: Ammonia is added to the dialyzed mixture of Step c and the mixture is poured into a petri dish:

Step e: The product of Step d is allowed to dry into a film;
Step f: The film of Step e is divided into particles and swelled in saline;
Step g; The product of Step f is added to a syringe and autoclaved;
Step h (optional): The product of Step f can be subjected to a second, final crosslinking procedure with a solution of BDDE, or other crosslinking agent described herein, and washed.

Example 12: Proposed Tissue Filler Preparation Method

A Silk/HA tissue filler as described herein could be prepared according to the following general method:
Step a: Sodium hyaluronate may be mixed with NaOH solution;
Step b: BDDE may be added to the solution of Step a;
Step c: The product of Step b is added to a silk solution and allowed to react;
Step d: Ammonia is added to the dialyzed mixture of Step c and the mixture is poured into a petri dish;
Step e: The product of Step d is allowed to dry into a film;
Step f: The film of Step e is divided into particles and swelled in saline;
Step g: The product of Step f is added to a syringe and autoclaved;
Step h (optional): The product of Step f can be subjected to a second, final crosslinking procedure with a solution of BDDE, or other crosslinking agent described herein, and washed.

Example 13: Proposed Tissue Filler Preparation Method

A Silk/HA tissue filler as described herein could be prepared according to the following general method:
Step a: Sodium hyaluronate may be mixed with NaOH solution;
Step b: BDDE may be added to the solution of Step a;
Step c: The product of Step b is allowed to react;
Step d: The product of Step c is added to a silk solution and then ammonia is added to the dialyzed mixture thereof and the mixture is poured into a petri dish:
Step e: The product of Step d is allowed to dry into a film;
Step f: The film of Step e is divided into particles and swelled in saline;
Step g: The product of Step f is added to a syringe and autoclaved;
Step h (optional): The product of Step f can be subjected to a second, final crosslinking procedure with a solution of BDDE, or other crosslinking agent described herein, and washed.

Example 14: Proposed Tissue Filler Preparation Method

A Silk/HA tissue filler as described herein could be prepared according to the following general method:
Step a: A silk solution may be prepared as described herein, to which BDDE may be added in water:
Step b: HA may be added to the solution of Step a:
Step c: The mixture of Step b may be stirred (e.g., 5 minutes) and allowed to stand for about 1 day;
Step d: The resulting gel from Step c may be allowed to stand in saline for 1 week to provide the resulting tissue filler.

Example 15: Proposed Tissue Filler Preparation Method

A Silk/HA tissue filler as described herein could be prepared according to the following general method:
Step a: BDDE may be added to water:
Step b: A silk solution may be added to the solution of Step a, to which HA may then be added;
Step c: The mixture of Step b may be stirred (e.g., 5 minutes) and allowed to stand for about 1 day;
Step d: The resulting gel from Step c may be allowed to stand in saline for 1 week to provide the resulting tissue filler.

Example 16: Proposed Tissue Filler Preparation Method

A Silk/HA tissue filler as described herein could be prepared according to the following general method:
Step a: BDDE may be added to water;
Step b: HA may be added to the solution of Step a;
Step c: A silk solution may be added to the mixture of Step b and the resulting mixture may be stirred (e.g., 5 minutes) and allowed to stand for about 1 day:
Step d: The resulting gel from Step c may be allowed to stand in saline for 1 week to provide the resulting tissue filler.

Example 17: Proposed Tissue Filler Preparation Method

A Silk/HA tissue filler as described herein could be prepared according to the following general method:
Step a: To a silk solution as described herein may be added HA dissolved (mixed for about 12 hours at 400 rpm) in NaOH solution;
Step b: The solution of Step a may be degassed;
Step c: The solution of Step b may be mixed with a crosslinking agent described herein (e.g., BDDE) at 50° C. for about 10-20 minutes;
Step d: The cross-linked gel is mixed with lidocaine HCl;
Step e: Dialysis of the adjusted cross-linked solution may be carried out for 3 days, then 2 days with PBS, then 1 day with water;
Step f: The filtered resulting product is then lyophilized to obtain solids;
Step g: The solids are dissolved in PBS and then incubated;
Step h (Optional): free HA may be added to the product of Step g;
Step i: The resulting product of Step g or h may be sterilized by steam autoclaving.

Example 18: Proposed Tissue Filler Preparation Method

A Silk/HA tissue filler as described herein could be prepared according to the following general method:
Step a: HA may be dissolved (mixed for about 12 hours at 400 rpm) in NaOH solution;
Step b: A silk solution may be added to the solution of Step a and the resulting mixture may be degassed.
Step c: The solution of Step b may be mixed with a crosslinking agent described herein (e.g., BDDE) at 50° C. for about 10-20 minutes;

Step d: The cross-linked gel is mixed with lidocaine HCl;

Step e: Dialysis of the adjusted cross-linked solution may be carried out for 3 days, then 2 days with PBS, then 1 day with water;

Step f: The filtered resulting product is then lyophilized to obtain solids;

Step g: The solids are dissolved in PBS and then incubated;

Step h (Optional): free HA may be added to the product of Step g;

Step i: The resulting product of Step g or h may be sterilized by steam autoclaving.

Example 19: Proposed Tissue Filler Preparation Method

A Silk/HA tissue filler as described herein could be prepared according to the following general method:

Step a: HA may be dissolved (mixed for about 12 hours at 400 rpm) in NaOH solution;

Step b: The solution of Step a may be degassed;

Step c: A silk solution may be added to the solution of Step b and the resulting mixture may be mixed with a crosslinking agent described herein (e.g., BDDE) at 50° C. for about 10-20 minutes;

Step d: The cross-linked gel is mixed with lidocaine HCl;

Step e: Dialysis of the adjusted cross-linked solution may be carried out for 3 days, then 2 days with PBS, then 1 day with water;

Step f: The filtered resulting product is then lyophilized to obtain solids;

Step g: The solids are dissolved in PBS and then incubated;

Step h (Optional): free HA may be added to the product of Step g;

Step i: The resulting product of Step g or h may be sterilized by steam autoclaving.

Example 20: Proposed Tissue Filler Preparation Method

A Silk/HA tissue filler as described herein could be prepared according to the following general method:

Step a: HA may be dissolved (mixed for about 12 hours at 400 rpm) in NaOH solution;

Step b: The solution of Step a may be degassed;

Step c: The solution of Step b may be mixed with a crosslinking agent described herein (e.g., BDDE) at 50° C. for about 10-20 minutes;

Step d: A silk solution may be added to the product of Step c and mixture may be mixed with lidocaine HCl;

Step e: Dialysis of the adjusted cross-linked solution may be carried out for 3 days, then 2 days with PBS, then 1 day with water;

Step f: The filtered resulting product is then lyophilized to obtain solids;

Step g: The solids are dissolved in PBS and then incubated;

Step h (Optional): free HA may be added to the product of Step g;

Step i: The resulting product of Step g or h may be sterilized by steam autoclaving.

Example 21: Dermal Filler Formulations Composed of Silk and Hyaluronic Acid Cross Linked with BDDE Materials: 1,4-butanediol diglycidyl ether (BDDE; Sigma-Aldrich); sodium hyaluronate (HA; Lifecore); silk, 6% solution (Silk Therapeutics); sodium hydroxide, 0.1 N solution (BDH); hydrochloric acid, 5 N (Ricca Chemical); phosphate buffered saline (PBS; 20×; VWR Life Science).

Formulation variables: Silk Molecular Weight: Medium and Low MW silk solution (6%); HA Molecular Weight: 1.5 MDa and 2.2 MDa; Silk concentration: $1\%_{v/v}$ (0.6 mg/ml), $2\%_{v/v}$ (6 mg/ml) $5\%_{v/v}$ (3 mg/ml) and $20\%_{v/v}$ (12 mg/ml).

Hydrogel crosslinking: (a) add 6% silk solution to 0.1 N sodium hydroxide; (b) gradually add HA powder to above prepared solution under overhead stir at the speed of 200-400 rpm, depending on the silk content; stir gently to avoid generating too much air bubbles; keep stirring until HA is fully dissolved; (c) add $1\%_{w/w}$ of BDDE to the above solution; (d) heat to 50° C. and keep stirring at 100-200 rpm for 30 minutes; (e) let the cross-linked gel cool down below 30° C.; (f) add 5N hydrochloric acid to adjust pH to 7.0-7.4.

Hydrogel dialysis: (a)hydrate the dialysis cassette for 2 minutes; wipe off excessive water and measure the total mass of the empty cassette; (b) add approximately 18 g of hydrogel formulation into the dialysis cassette; measure the total mas of the cassette after is loaded with gel; (c) suspend dialysis cassette in 2 L of 1×PBS buffer and set magnetic stir at 200 rpm; record the time when dialysis starts and change the PBS buffer after 4 hrs, 24 hrs, and 48 hrs of dialysis; collect the gel after 72 hrs.

Characterization: shear storage modulus (G') and viscosity; enzymatic degradation; BDDE residual; crosslinking density; 30-day animal study; cytotoxicity; bacterial endotoxin; turbidity.

Viscoelastic properties: A Discovery HR-1 hybrid rheometer (TA Instruments) was used to determine storage modulus (G') and complex viscosity (η) of dermal filler formulations. Samples were tested by swiping oscillation frequency from 0.1 Hz to 10 Hz with 10 data points per decade interval. Data were recorded and compared at 5 Hz shear rate. The G' and γ data for hydrogel formulations (after dialysis) with constant HA concentration and variable silk concentration are shown in Table 19. In this batch, 1.5 MDa molecular weight HA was used.

TABLE 19

Viscoelastic properties of hydrogels with constant HA concentration

| Sample | HA Conc.* (mg/ml) | Silk. Conc.* (mg/ml) | Silk MW | G' at 5 Hz (Pa) | η at 5 Hz (Pa · s) |
|---|---|---|---|---|---|
| C2 | 24 | 0 | N/A | 46.9 | 2.88 |
| A | 24 | 9.6 | Medium | 105.5 | 4.93 |
| B | 24 | 0.48 | Low | 69.7 | 3.62 |
| C | 24 | 4.8 | Medium | 102.7 | 4.82 |
| D | 24 | 0.48 | Medium | 66.4 | 3.59 |
| E | 24 | 2.4 | Low | 41.4 | 9.56 |
| F | 24 | 0.96 | Low | 42.7 | 2.67 |

*Hydrogel absorbed PBS buffer after dialysis resulting in volume increase. The concentration of HA and silk were recalculated based on the dilution factor.

The G' and γ data for hydrogel formulations (after dialysis) with constant total concentration of 30 mg/ml of HA and silk are summarized in Table 20.

TABLE 20

Viscoelastic properties of hydrogels with constant total concentration

| Sample | HA Conc.* (mg/ml) | HA MW (MDa) | Silk Conc.* (mg/ml) | Silk MW | % Silk | G' at 5 Hz (Pa) | η at 5 Hz (Pa · s) |
|---|---|---|---|---|---|---|---|
| XHA15M01SL17122002 | 23.52 | 1.5 | 0.48 | Low | 1% | 94.1 | 4.52 |
| XHA15M05SL17112002 | 21.60 | 1.5 | 2.4 | Low | 5% | 29.5 | 2.06 |
| XHA15M20SL17122002 | 14.40 | 1.5 | 9.6 | Low | 20% | 31.7 | 1.63 |
| XHA15M01SM17121802 | 23.52 | 1.5 | 0.48 | Medium | 1% | 118.1 | 5.55 |
| XHA15M05SL17111602 | 21.60 | 1.5 | 2.4 | Medium | 5% | 38.4 | 2.35 |
| XHA15M20SM17112702 | 14.40 | 1.5 | 9.6 | Medium | 20% | 15.6 | 1.06 |
| XHA2M01SL171121902 | 23.52 | 2.2 | 0.48 | Low | 1% | 176.3 | 7.50 |
| XHA2M05SL17122002 | 21.60 | 2.2 | 2.4 | Low | 5% | 85.1 | 4.03 |
| XHA2M20SM17122002 | 14.40 | 2.2 | 9.6 | Low | 20% | 36.0 | 1.76 |
| XHA2M01SM17121902 | 23.52 | 2.2 | 0.48 | Medium | 1% | 158.1 | 6.69 |
| XHA2M05SM17122002 | 21.60 | 2.2 | 2.4 | Medium | 5% | 106.7 | 4.76 |
| XHA2M20SM17111302 | 14.40 | 2.2 | 9.6 | Medium | 20% | 11.5 | 0.86 |

*Hydrogel absorbed PBS buffer after dialysis resulting in volume increase. The concentration of HA and silk were recalculated based on the dilution factor.

Figure 28:
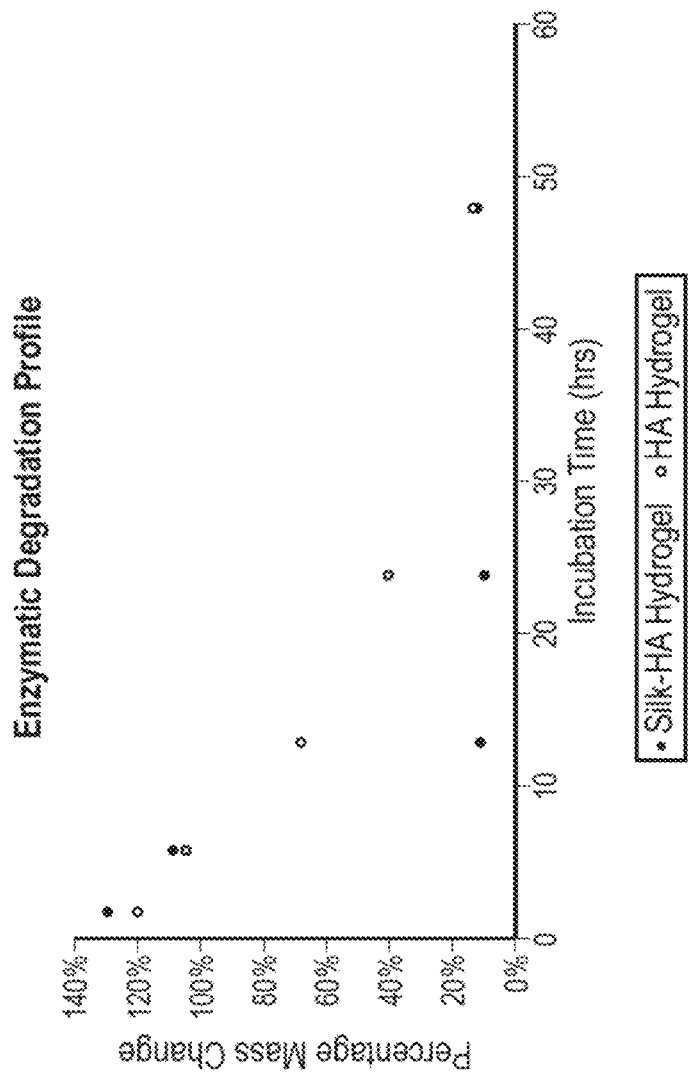
FIG. 28 is a chart depicting the degradation profile of silk-HA and HA hydrogels.

Hydrogel reversibility: Hydrogels with and without silk protein were prepared and dialyzed. The final compositions were 33.3 mg/ml HA+8 mg/ml silk for Silk-HA hydrogel and 33.3 mg/ml of HA for HA hydrogel, respectively. 1 g±100 g of above prepared hydrogels were added to 20 ml glass vial followed by 3 ml of 16 U/ml of hyaluronidase in 1×PBS. Samples were incubated at 37° C. for 3 days. Control samples was also prepared using HA hydrogel without adding hyaluronidase. The degradation profile is shown in FIG. 28. Control samples without hyaluronidase was not degraded during the course of 3 days incubation. Within the first 6 hours of incubation, hydrogels absorbed buffer and swelled resulting in the increase of percentage mass. The Silk-HA hydrogel and HA hydrogel were fully degraded after 3 days incubation. At the presence of silk, the hydrogel was digested faster than the pure HA hydrogel. After 12 hours of incubation, approximately 90% of the Silk-HA hydrogel was digested by enzyme.

Crosslinker (BDDE) residual: Samples listed in Table 19 were tested for BDDE residuals using GC-FID by Millennium Research Laboratories, Inc. (MRL). MRL test report MRL18JAN06 indicated that BDDE residual in all samples were none detectable, meeting the acceptance criteria of equal to or less than 2 ppm.

Crosslinking density: Samples listed in Table 19 were further fully digested by hyaluronidase and analyzed using NMR to determine the crosslinking density in term of percentage modification. The test results are listed in Table 21 (MRL test report MRL18JAN07).

TABLE 21

Percentage modification degree (crosslinking density) for various formulations

| Sample ID | MoD (%) |
|---|---|
| XEIA15M00SX17110202 (C2) | 2.87 |
| XFIA15M205M17103002 (A) | 4.68 |

TABLE 21-continued

Percentage modification degree (crosslinking density) for various formulations

| Sample ID | MoD (%) |
|---|---|
| XHA15M01SL17103002 (B) | 2.58 |
| XFIA15M10SM17103002 (C) | 3.02 |
| XEIA15M01SM17103002 (D) | 7.54 |
| XFIA15M05SL17110202 (E) | 3.76 |

Animal study: A 30-day animal study using guinea pig model was carried out at WuXi AppTec Minneapolis, Minn. facility to address product safety concern. There were 2 termination time points in this study, 7 days and 30 days, to evaluate tissue response. The study was summarized in WuXi AppTec report D28195 (Project C19879). Two control samples (Juvederm Ultra Plus and Sample C2 in Table 19) and 6 formulations (Sample A-F in Table 19) were used for intradermal injection. Samples A-F and control sample C2 were steam sterilized (protocol 201707289) at Nelson Laboratories, LLC prior to injection. The study procedure in brief: twenty-four animals twelve per duration were used in this study. Each animal received six dorsal, intradermal injections using threading technique (injecting a line instead of a bolus): one control site on one side of the spine, the second control site on the contralateral side (with sides alternatively assigned by animal) and four test sites with no more than one injection of a given test article (with right and left sides alternatively assigned among animals). Animals were observed daily throughout the study to assess general health. Animals were humanely euthanized at the scheduled termination dates. The implant sites and surrounding tissue from all animals were excised, placed in formalin, and processed to paraffin blocks followed by histopathological evaluation. The representative histology images and pathological findings were summarized in Table 22. Overall, there was no suggestion of sepsis or immunological response in any of the implant sites.

TABLE 22

Figure 29:
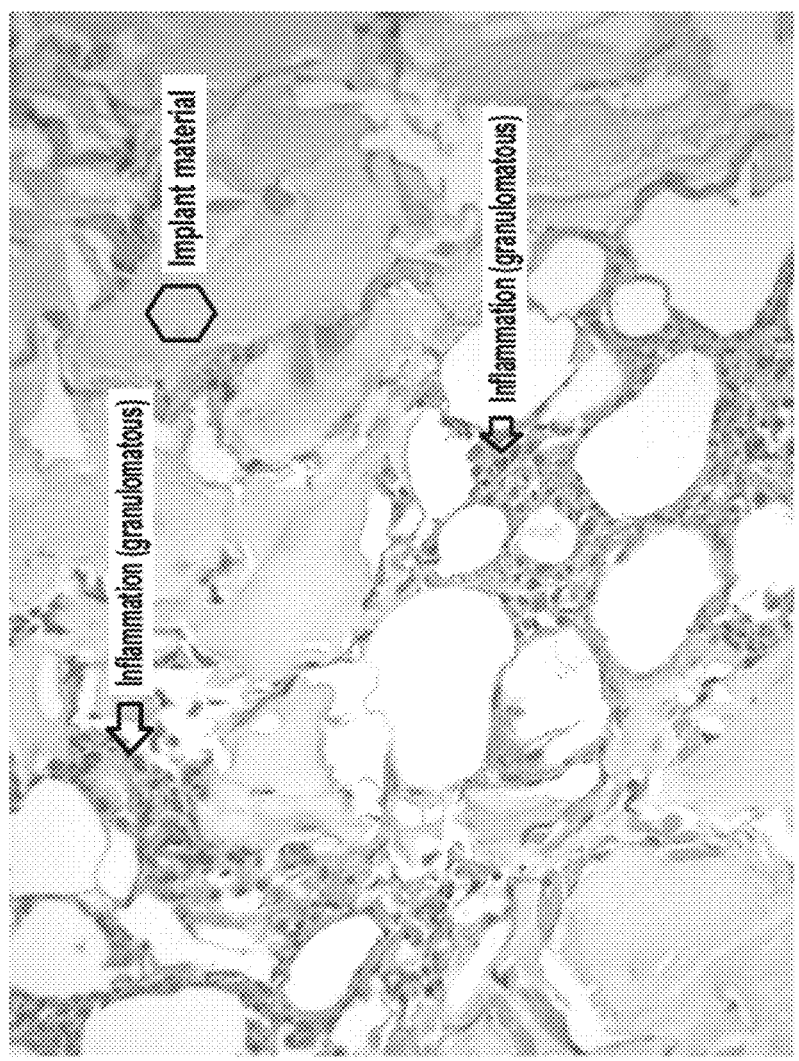
FIG. 29 is a picture of an intradermal area in a guinea pig injected with a control dermal filler (commercially available HA filler including lidocaine); the increased degree of inflammation is reflected by the extent of granulomatous areas. The commercially available filler is noted as blue/gray material. Granulomatous inflammation associated with the material can be observed at 7 days.
Figure 30:
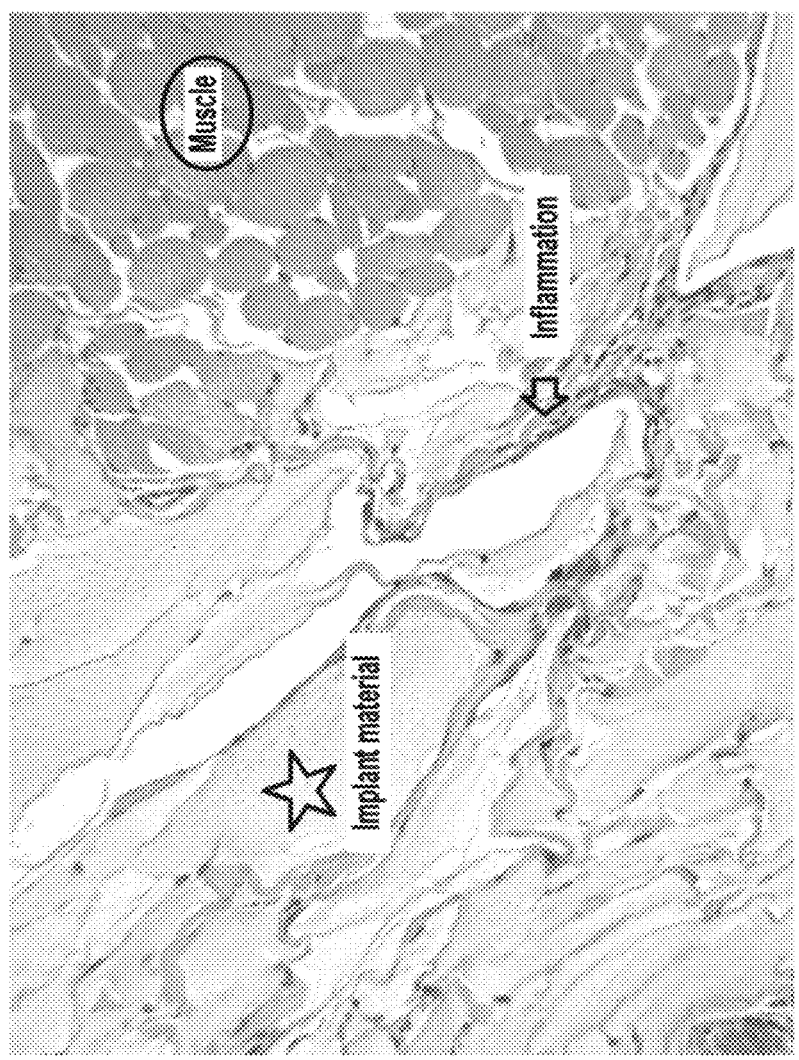
FIG. 30 is a picture of an intradermal area in a guinea pig injected with a control dermal filler (commercially available HA filler including lidocaine); the commercially available product is noted as blue/gray material. At 30 days, inflammation with fibrosis can be observed.

| Summary of histopathological evaluations Samples | 7 Days | 30 Days |
|---|---|---|
| Commercial Control | FIG. 29 The Commercial product is noted in both images as blue/gray material. There is mild granulomatous inflammation | FIG. 30 The Commercial product is noted in both images as blue/gray material. At 30 days, there is a minimal amount of inflammation |

TABLE 22-continued

Summary of histopathological evaluations

Figure 31:
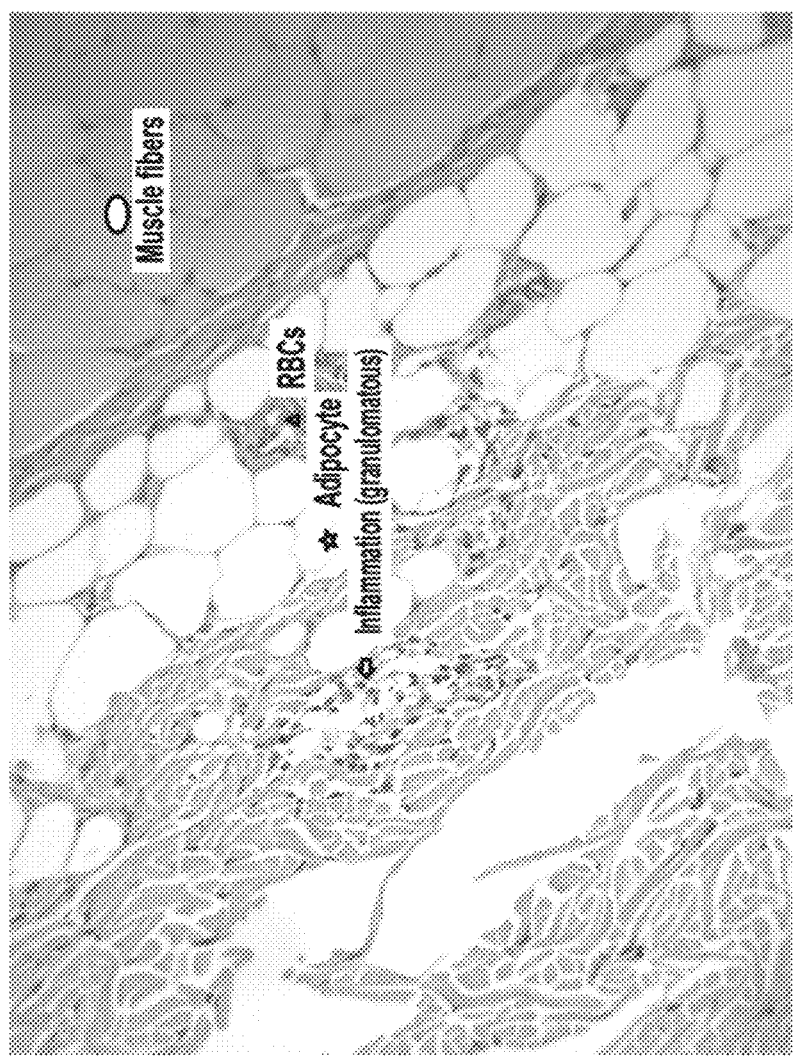
FIG. 31 is a picture of an intradermal area in a guinea pig injected with a silk-HA dermal filler of the invention (24 mg/ml HA, 9.6 mg/ml silk, BDDE cross linked); the reduced granulomatous areas as compared to the control injection indicates negligible acute inflammatory response, and a better biodegradability of the silk-HA filler compared to the control. There is very little inflammation at 7 days. The inflammation is focal and at times hard to find. No implant material is noted.
Figure 32:
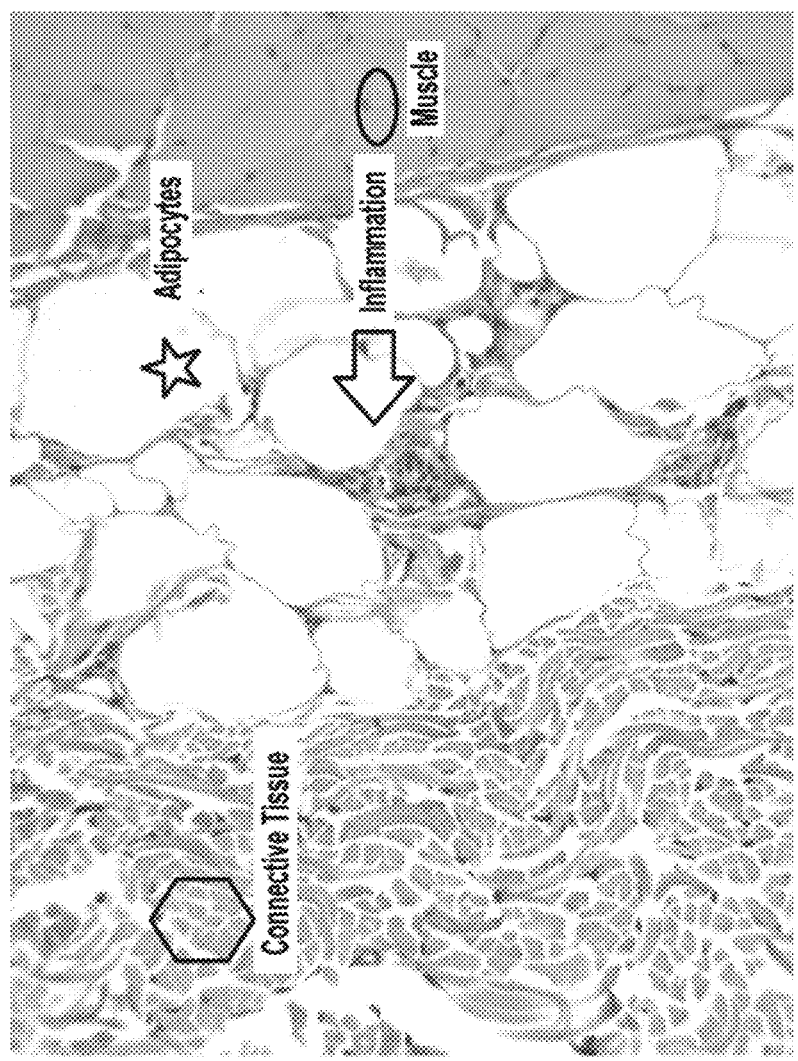
FIG. 32 is a picture of an intradermal area in a guinea pig injected with a silk-HA dermal filler of the invention (24 mg/ml HA, 9.6 mg/ml silk, BDDE cross linked); at 30 days the inflammation is extremely difficult to find and minimal. No implant material is noted.
Figure 33:
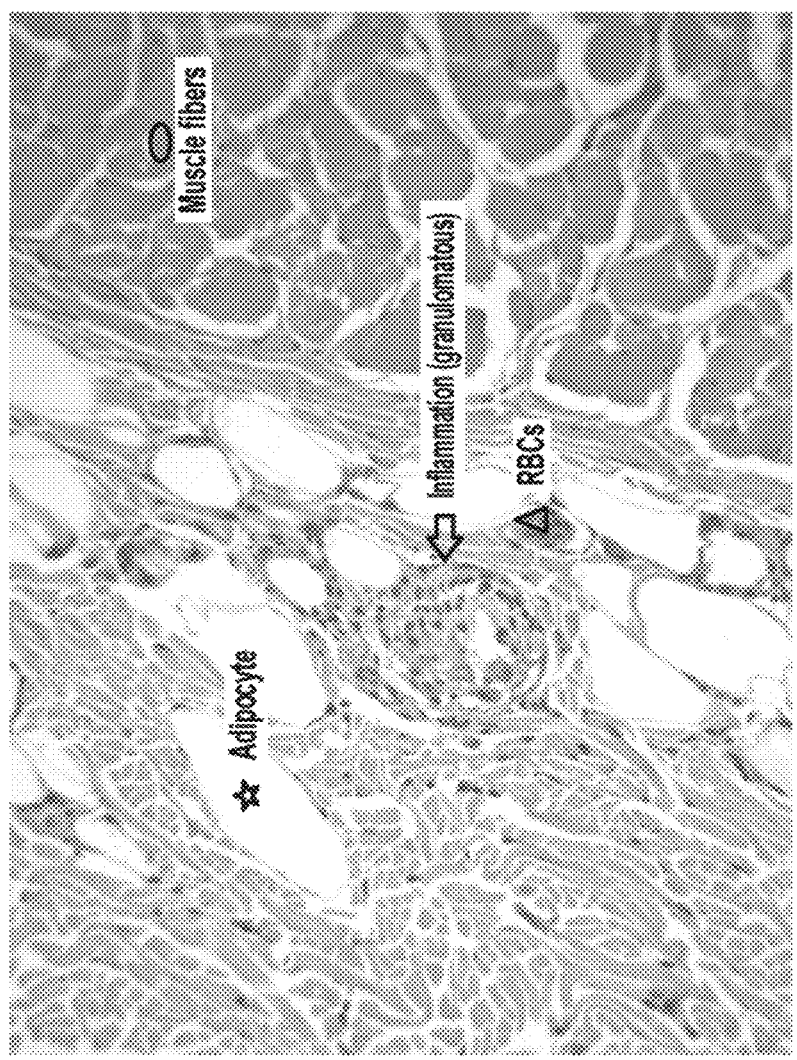
FIG. 33 is a picture of an intradermal area in a guinea pig injected with a silk-HA dermal filler of the invention (24 mg/ml HA, 0.48 mg/ml silk, BDDE cross linked); the filler results in focal mild inflammation in the 7 days. The inflammation is chronic. This inflammation required close evaluation to identify since it was focal and minimal. No implant material is observed.
Figure 34:
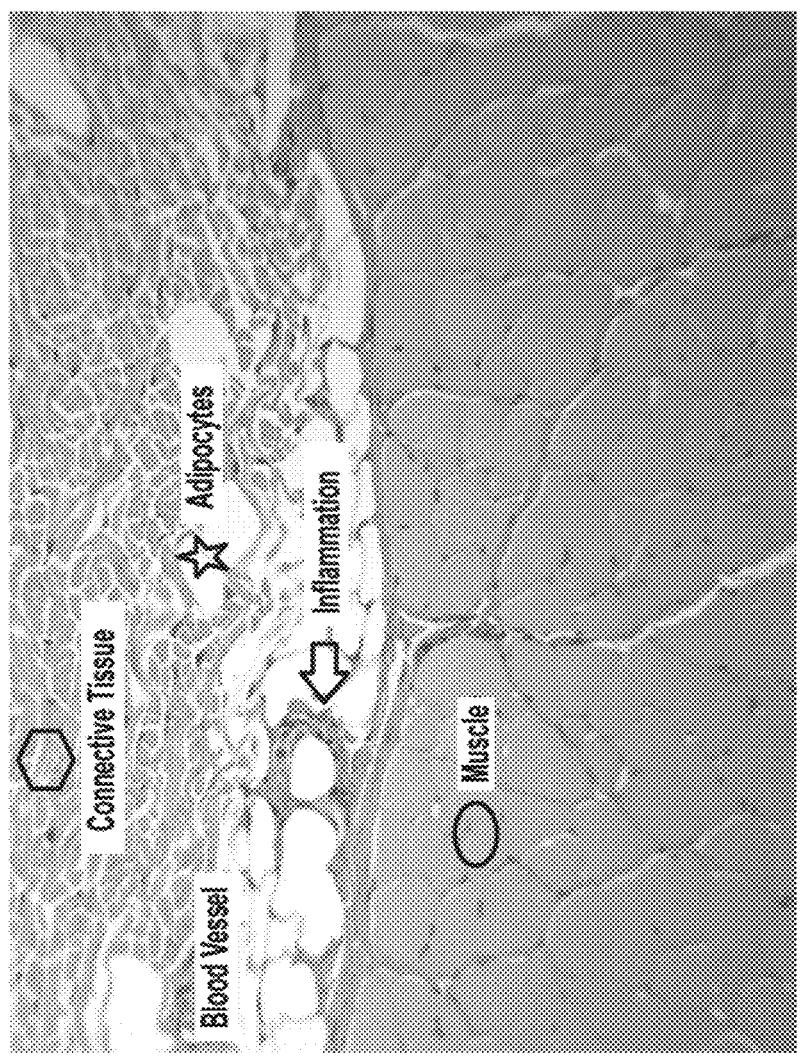
FIG. 34 is a picture of an intradermal area in a guinea pig injected with a silk-HA dermal filler of the invention (24 mg/ml HA, 0.48 mg/ml silk, BDDE cross linked); the 30-day image demonstrates even less inflammation. It was even more difficult to identify as compared to the 7 day implants. No implant material is observed.

| Samples | 7 Days | 30 Days |
|---|---|---|
| | associated with the material at 7 days. | with very mild fibrosis. |
| Product A: 24 mg/ml HA 9.6 ing1n1 silk | FIG. 31 There is very little inflammation at 7 days. The inflammation was focal and at times hard to find. No implant material is noted. | FIG. 32 At 30 days the inflammation is extremely difficult to find and minimal. No implant material is noted. |
| Product B: 24 mg/ml HA 0.48 mg/ml silk | FIG. 33 Product B demonstrates focal mild inflammation in the 7 days. The inflammation is chronic, This inflammation required close evaluation to identify since it was focal and minimal. No implant material is observed. | FIG. 34 The 30-day image demonstrates even less inflammation. It was even more difficult to identify as compared to the 7 day implants. No implant material is observed. |

Overall, there was no suggestion of sepsis or innnunohogic response in any of the implant sites.

Bacterial endotoxin: Three post sterilization samples (Sample A, Sample E and Sample C2) were selected from 7 formulations used in animal study (listed in Table 19) for bacterial endotoxin test. The kinetic Turbidimetric method was used to determine endotoxin level. Test results are listed in Table 23, and are below the acceptance criteria of 20 EU/ml (Nelson Labs study report 1006775-S01).

TABLE 23

Endotoxin test results

| Sample ID | Detected Endotoxin |
|---|---|
| XHA15M20SM17103002 (A) | 0.498 (EU/ml) |
| XHA15M00SX17110202 (C2) | <0.400 (EU/ml) |
| XHA15M05SL17110202 (E) | 1.56 (EU/ml) |

Biocompatibility—Cytotoxicity: Four post sterilization samples (Sample A, Sample B, Sample D and Sample E) were selected from 7 formulations used in animal study (listed in Table 19) for ISO-10993-5 cytotoxicity test (ISO MEM Elution Using L-929 Mouse Fibroblast Cells). These samples represented the highest and lowest silk content of medium molecular weight silk and low molecular weight silk in tested dermal filler formulations. The test reports indicated that all test samples scored grade 0, meaning non-cytotoxic (Wuxi AppTec Reports D28287-1, D28287-2. D28287-3, D28287-4).

Figure 35:
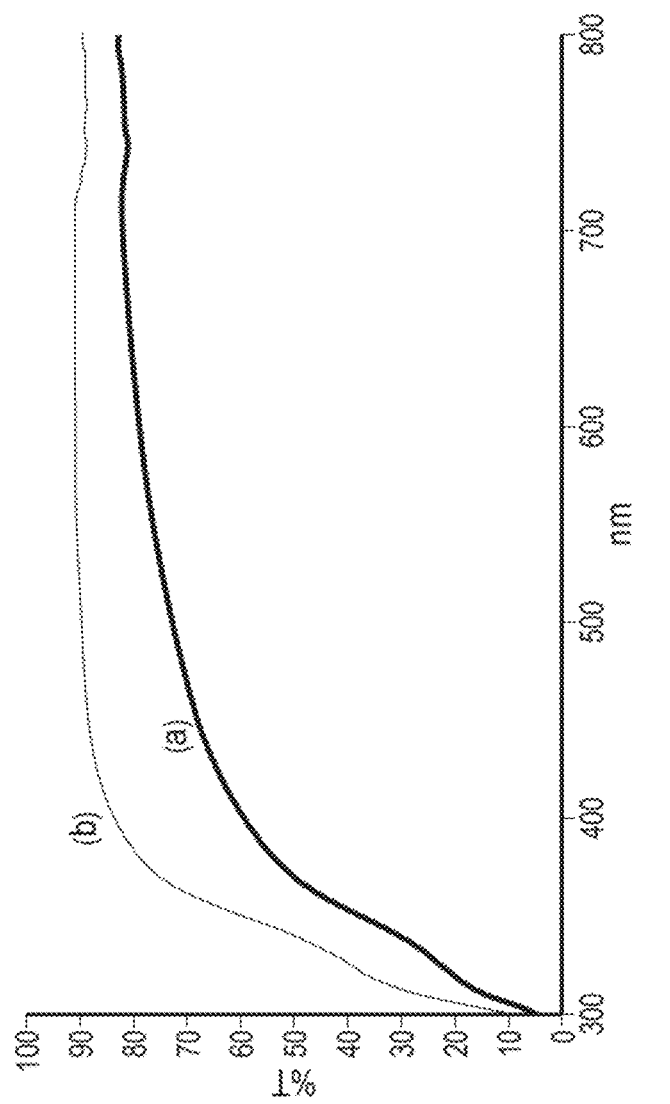
FIG. 35 is a chart depicting turbidity measurement of a silk-HA hydrogel. Black curve (a): standard transmittance; Red curve (b): transmittance plus forward scatter.
Figure 36:
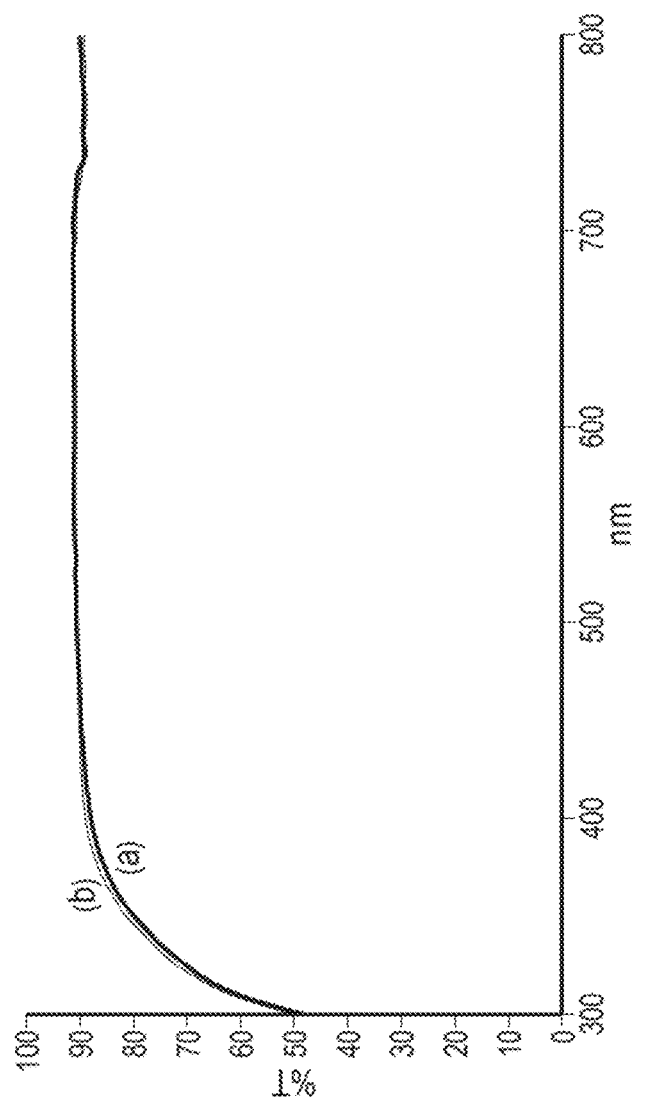
FIG. 36 is a chart depicting turbidity measurement of HA hydrogel without silk. Black curve (a): standard transmittance; Red curve (b): transmittance plus forward scatter.

Turbidity: The pure HA hydrogel is clear under natural light. When HA was cross-linked with silk protein, the hydrogel becomes slightly turbid (cloudy) and the turbidity is dependent on the total silk concentration in the formulation. The turbidity was measured by Lambda X50S UV-Vis spectrophotometer (PerkinElmer) equipped with InGaAs integrating sphere which has the capability to collect forward scattered light in addition to standard transmitted light. The turbidity measurement of Silk-HA hydrogel is shown in FIG. 35. The black curve is the standard transmittance and the red curve was collected by the sphere showing significant forward scatter. The pure HA hydrogel without silk was used as control sample. The curves in FIG. 36 are nearly identical indicating very little scattering of the pure HA gel. The turbidity measurement suggested that the Silk-HA hydrogel has the capability of scattering lights which could eliminate Tyndall effect when used as dermal filler.

Conclusions: Dermal filler formulations were developed based on constant HA concentration with various silk contents and constant total concentration. These formulations provided a broad range of storage modulus, viscosity and crosslinking density which may lead to various applications. The silk-HA hydrogel was enzymatically reversible. The crosslinker residual after dialysis of hydrogel formulations met the acceptance criteria. Cytotoxicity test indicated that silk-HA hydrogels with of silk content ranging from 0.48 mg/ml to 9.6 mg/ml were none cytotoxic and biocompatible. The 30-day animal study demonstrated all formulations with silk content up to 9.6 mg/ml did not cause sepsis and had no immunological response.

Example 22: Dermal Filler Formulations Composed of Silk and Hyaluronic Acid Cross Linked with PEGDE (PEGDGE)

Crosslinker: Poly(ethylene glycol) diglycidyl ether (PEGDE), average molecular weight Mn=500. Reaction conditions: same as BDDE crosslinking (Example 21). The total amount of PEGDE was equivalent to BDDE in moles.

TABLE 24

PEGDE cross linking formulation and test results

| Sample | HA Conc.* (mg/ml) | HA MW (MDa) | Silk Conc.* (mg/ml) | Silk MW | % Silk | Cross-linker | G' at 5 Hz (Pa) | η at 5 Hz (Pa · s) |
|---|---|---|---|---|---|---|---|---|
| XHA15M05SM17111602 | 21.60 | 1.5 | 2.4 | Medium | 10% | BDDE | 38.4 | 2.35 |
| XHA15M05SM18020802P | 20.45 | 1.5 | 2.27 | Medium | 10% | PEG-x | 67.5 | 3.10 |
| XHA15M05SM18020902P | 19.28 | 1.5 | 2.14 | Medium | 10% | PEG-x | 73.5 | 3.40 |

*Hydrogel absorbed PBS buffer after dialysis resulting in volume increase. The concentration of HA and silk were recalculated based on the dilution factor.

Example 23: Animal Study C20419

Formulations and characterization of samples for animal study C20419 are as shown in Table 25:

Sodium hyaluronate (HA), Lifecore; Silk, 6% solution, Silk Inc.; Sodium hydroxide, 0.1 N solution, BDH; Hydrochloric acid, 5 N, Ricca Chemical; Phosphate Buffered Saline (PBS), 20×, VWR Life Science.

TABLE 25

Formulations and characterization of samples for animal study C20419

| Sample | | ID | Cross-linker | HA Conc.* (mg/ml) | Silk Conc.* (mg/ml) | HA MW (Da) | Silk MW | G' at 5 Hz (Pa) | η at 5 Hz (Pa·s) | Injection Force @ 30 G (N) | MoD (%) |
|---|---|---|---|---|---|---|---|---|---|---|---|
| Group 1 | C3 | XHA700K3M00SX180510 | BDDE | 24 | 0 | 700K/3M | n/a | 0.2 | 0.1 | 7.41 | 4.87 |
| | G | XHA700K3M05SX180510 | | 22.8 | 1.2 | 700K/3M | Med | 3.8 | 0.2 | 8.17 | 4.54 |
| | H | XHA700K3M01SL180510 | | 23.76 | 0.24 | 700K/3M | Low | 0 | 0.1 | 6.95 | 5.42 |
| | I | XHA700K3M05SL180510 | | 22.8 | 1.2 | 700K/3M | Low | 0.5 | 0.1 | 7.96 | 6.23 |
| | K | XHA26M05SM180510 | | 22.8 | 1.2 | 2.6M | Med | 0.1 | 0.1 | 8.48 | 2.51 |
| Group 2 | C4 | PXHA700K3M00SX180514 | PEGDE | 24 | 0 | 700K/3M | n/a | 52.3 | 2.4 | 16.19 | 15.14 |
| | L | PXHA700K3M05SX180514 | | 22.8 | 1.2 | 700K/3M | Med | 31.8 | 1.6 | 12.96 | 10.97 |
| | M | PXHA700K3M01SL180514 | | 23.76 | 0.24 | 700K/3M | Low | 32.2 | 1.5 | 15.96 | 11.02 |
| | N | PXHA700K3M05SL180514 | | 22.8 | 1.2 | 700K/3M | Low | 51.9 | 2.1 | 17.82 | 11.23 |
| | O | PXHA26M05SM180514 | | 22.8 | 1.2 | 2.6M | Med | 18.9 | 1.1 | 10.56 | 17.23 |
| Group 3 | C5 | Group 2 + Free HA | | | | 700K/3M | n/a | 63.0 | 2.8 | 19.02 | 8.02 |
| | P | | | | | 700K/3M | Med | 28.3 | 1.4 | 11.22 | 9.71 |
| | Q | | | | | 700K/3M | Low | 42.7 | 1.9 | 16.80 | 10 |
| | R | | | | | 700K/3M | Low | 83.9 | 3.2 | 20.90 | 10.12 |
| | S | | | | | 2.6M | Med | 75.8 | 3.4 | 12.78 | 11.92 |

Figure 37:
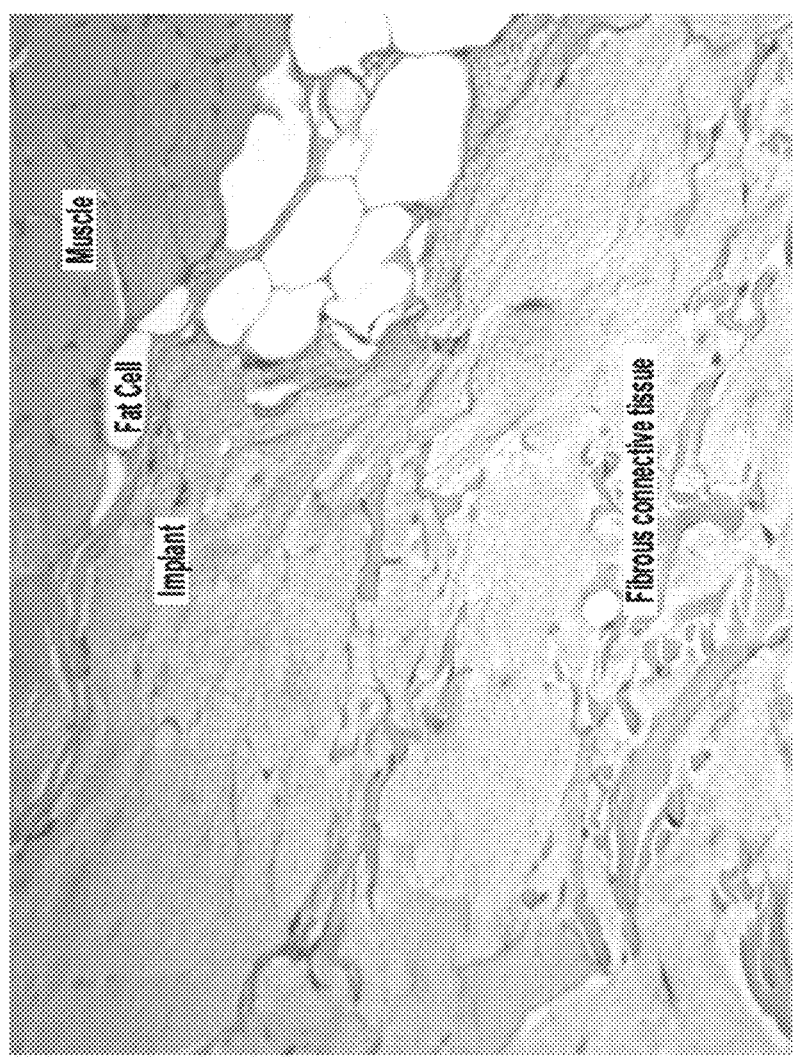
FIG. 37 is a representative histology picture of an intradermal area in a guinea pig injected with a control dermal filler.
Figure 38:
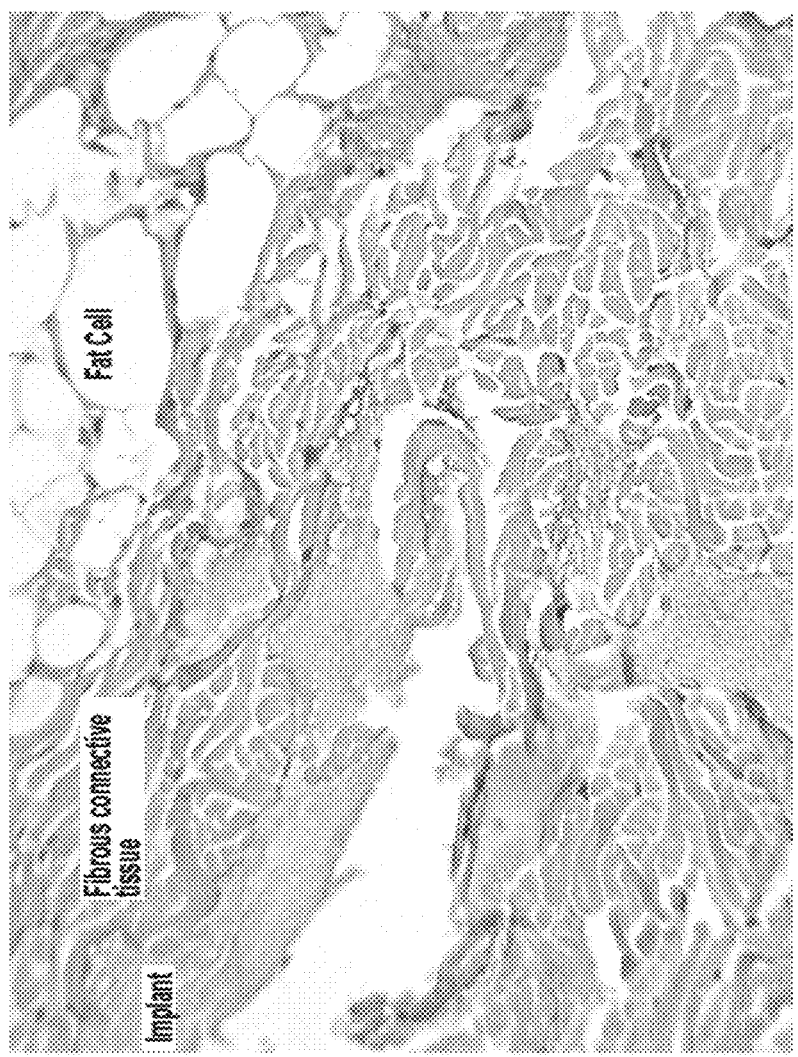
FIG. 38 is a representative histology picture of an intradermal area in a guinea pig injected with an HA dermal filler of the invention (24 mg/ml HA, PEGDE cross linked, Sample C4—Table 25).
Figure 39:
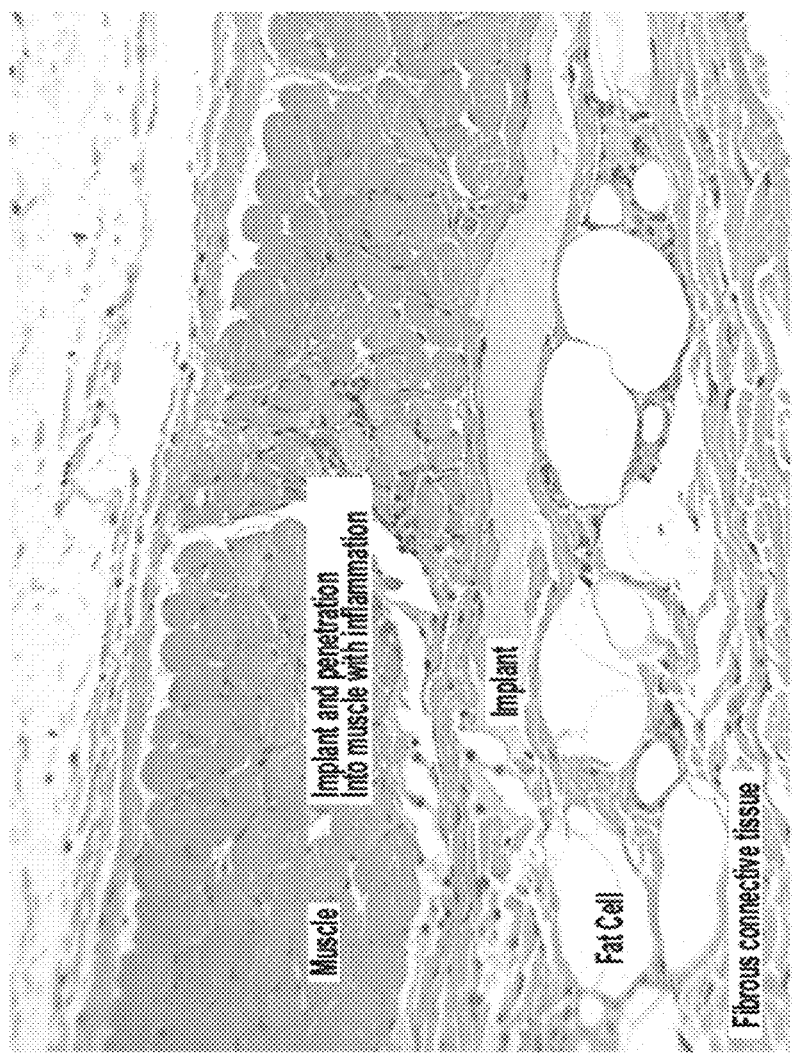
FIG. 39 is a representative histology picture of an intradermal area in a guinea pig injected with a silk-HA dermal filler of the invention (22.8 mg/ml HA, 1.2 mg/ml silk, PEGDE cross linked, Sample L—Table 25).
Figure 40:
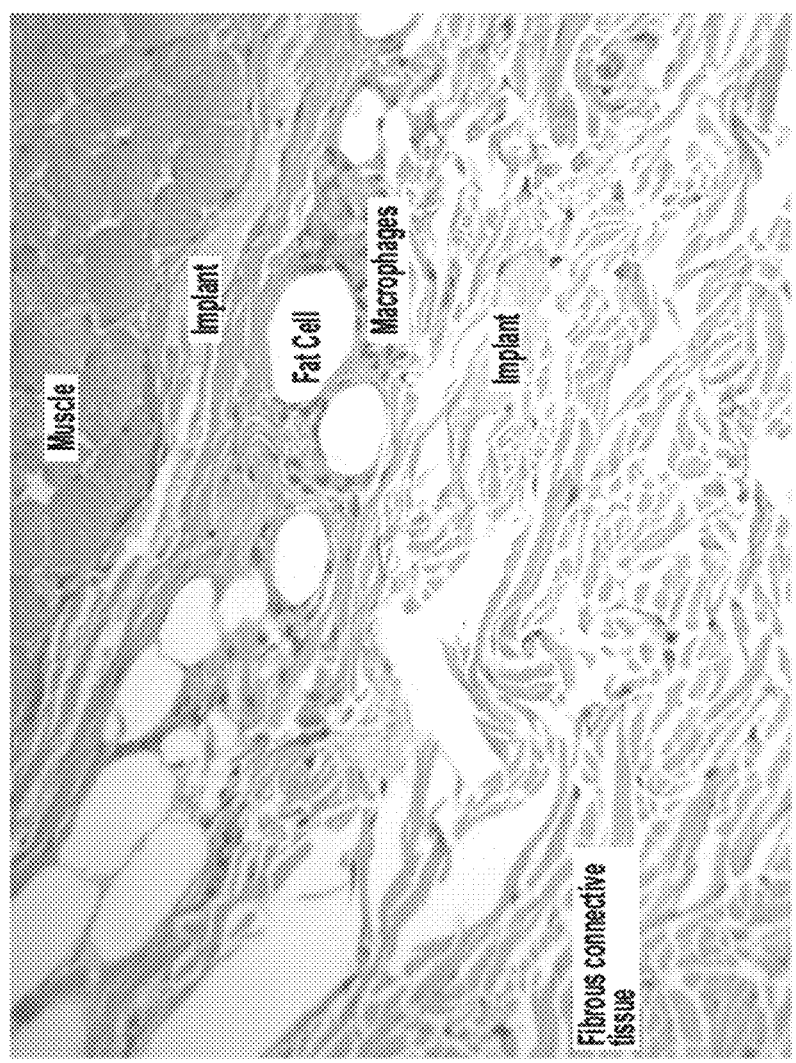
FIG. 40 is a representative histology picture of an intradermal area in a guinea pig injected with a silk-HA dermal filler of the invention (23.76 mg/ml HA, 0.24 mg/ml silk, PEGDE cross linked, Sample M—Table 25).
Figure 41:
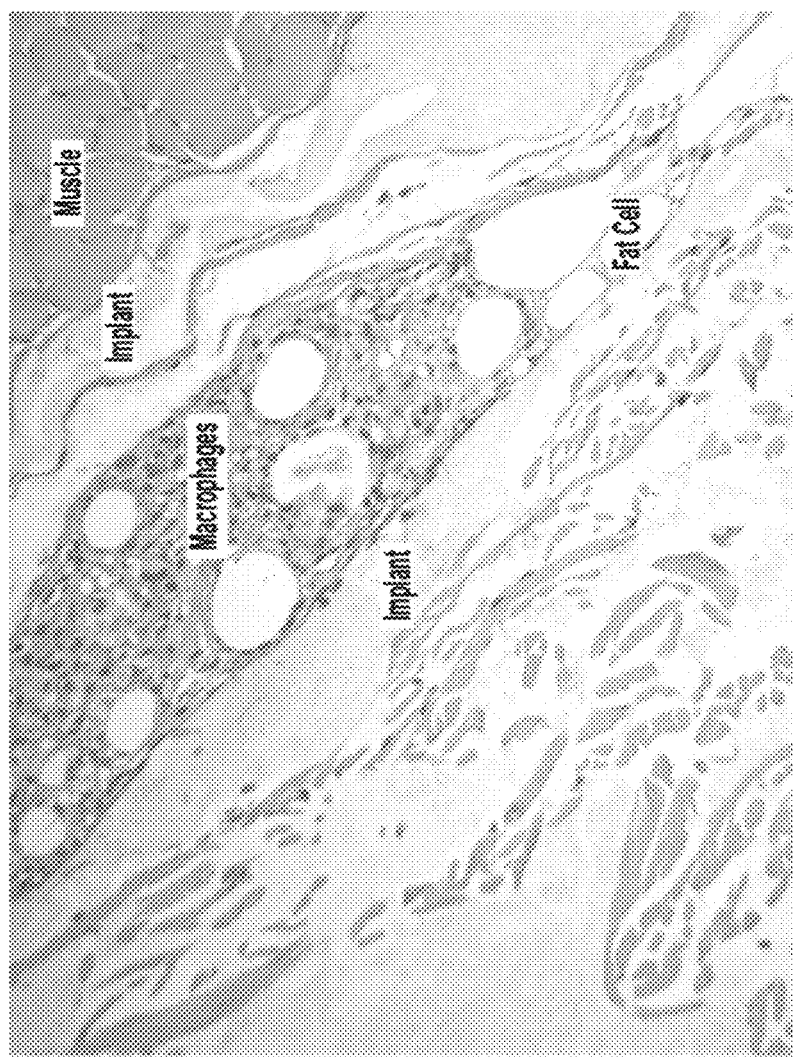
FIG. 41 is a representative histology picture of an intradermal area in a guinea pig injected with a silk-HA dermal filler of the invention (22.8 mg/ml HA, 1.2 mg/ml silk, PEGDE cross linked, Sample N—Table 25).
Figure 42:
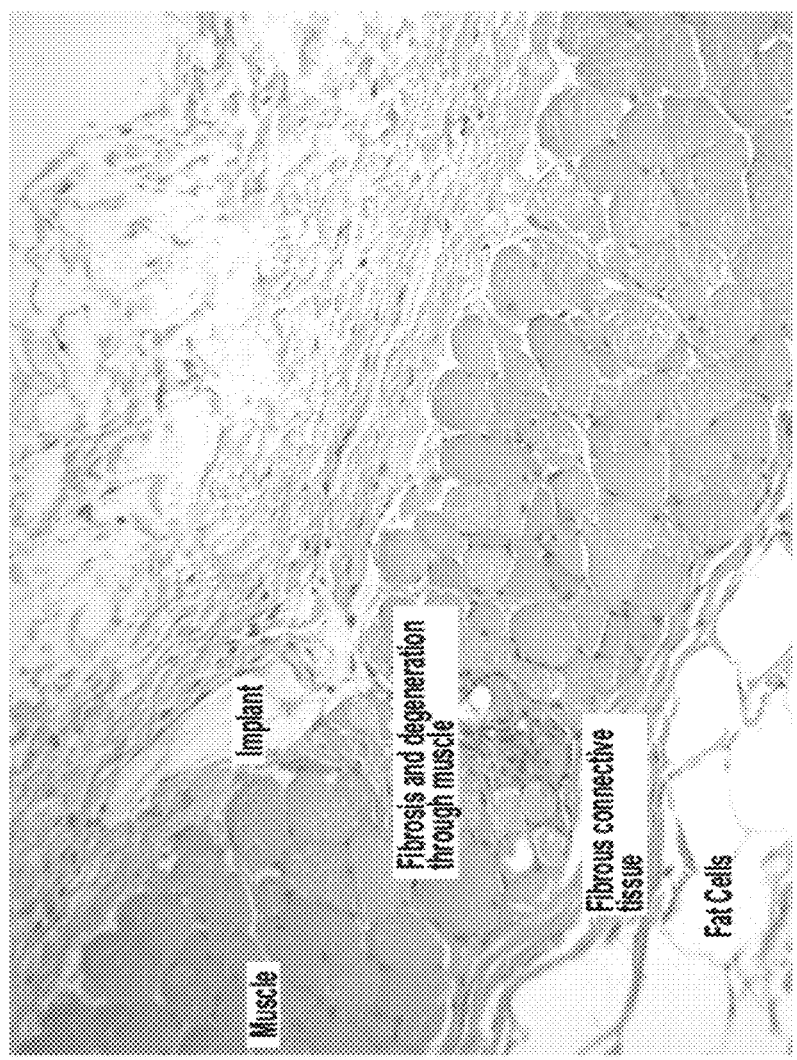
FIG. 42 is a representative histology picture of an intradermal area in a guinea pig injected with a silk-HA dermal filler of the invention (22.8 mg/ml HA, 1.2 mg/ml silk, PEGDE cross linked, Sample O—Table 25).
Figure 43:
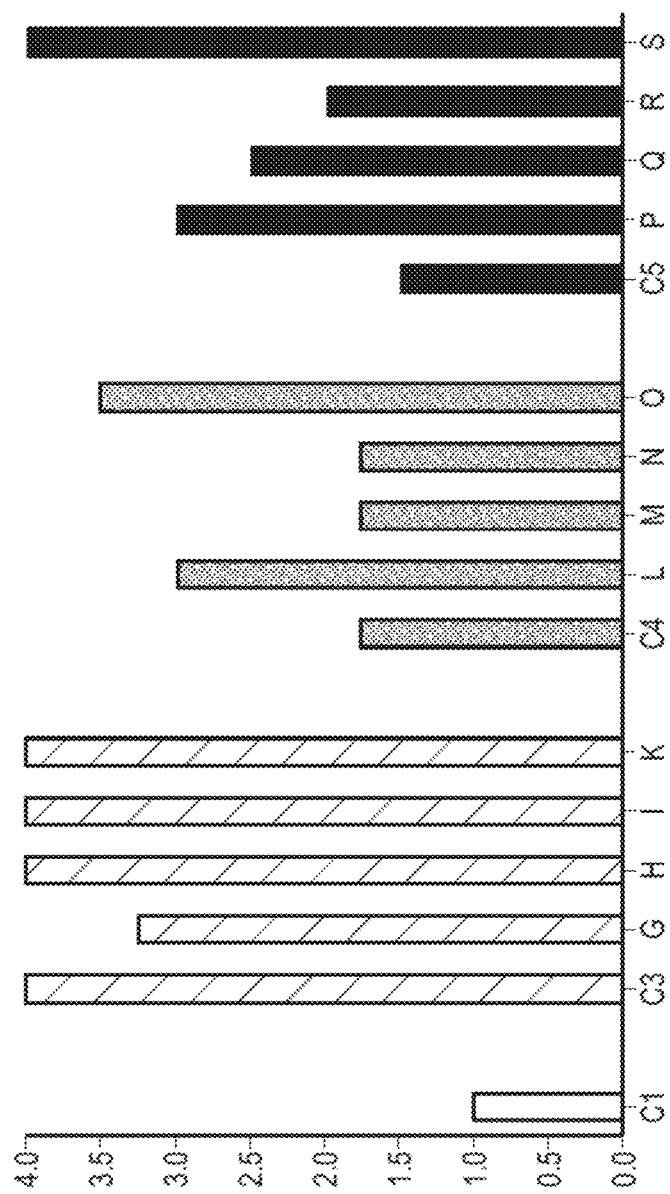
FIG. 43 is a graph showing 7-day post-implantation histology results for gel degradation (Table 25 formulations—BDDE cross-linked formulations are mostly degraded; scoring: 0—normal; 1—minimal; 2—mild; 3—moderate; and 4—severe).
Figure 44:
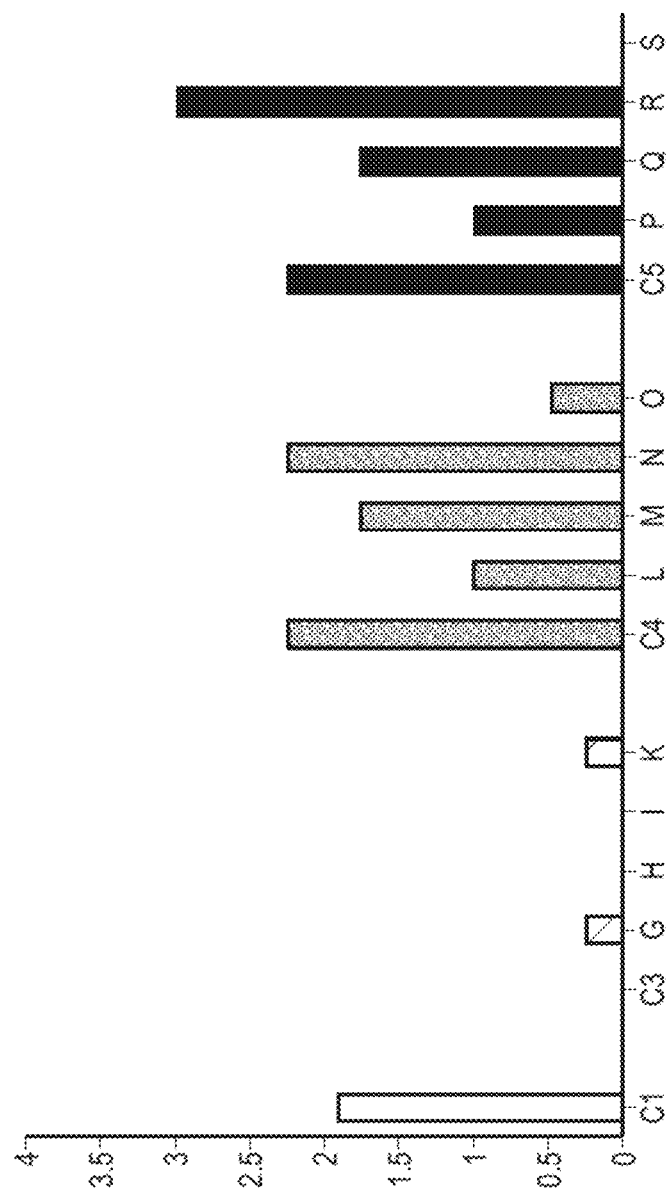
FIG. 44 is a graph showing 7-day post-implantation histology results for gel migration (Table 25 formulations; scoring: 0—normal; 1—minimal; 2—mild; 3—moderate; and 4—severe).
Figure 45:
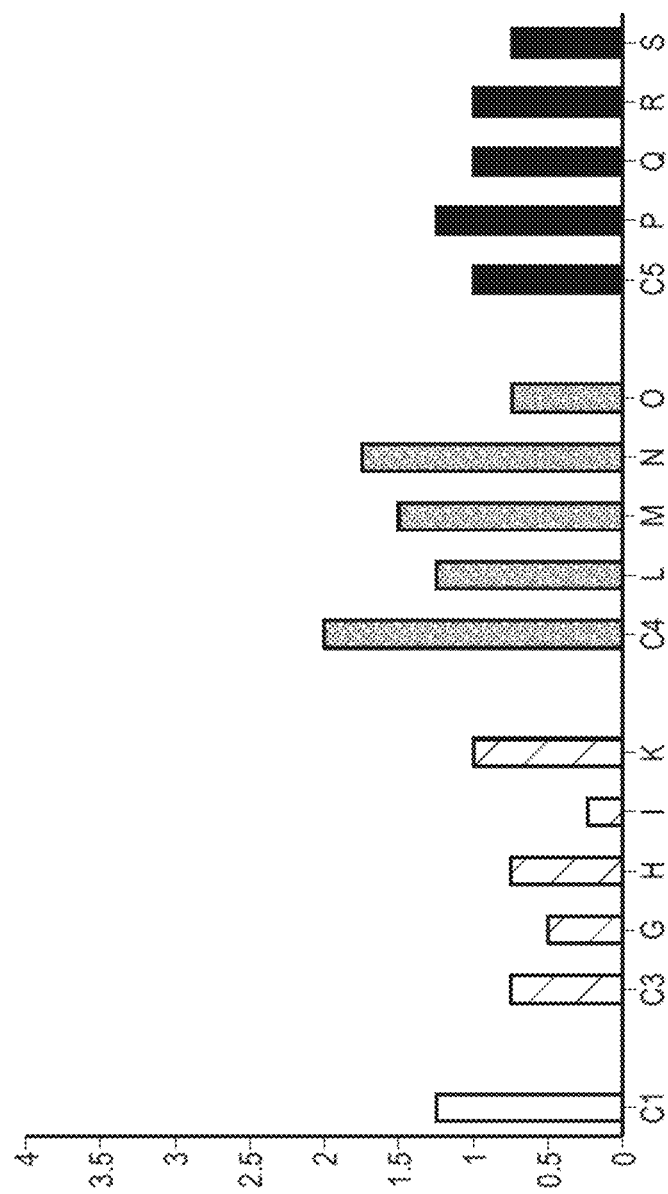
FIG. 45 is a graph showing 7-day post-implantation histology results for inflammation (Table 25 formulations—no tissue necrosis was observed, no blood clotting was observed, and minimal collagen deposition was observed on the control formulation and some of the test formulations; scoring: 0—normal; 1—minimal; 2—mild; 3—moderate; and 4—severe).
Figure 46:
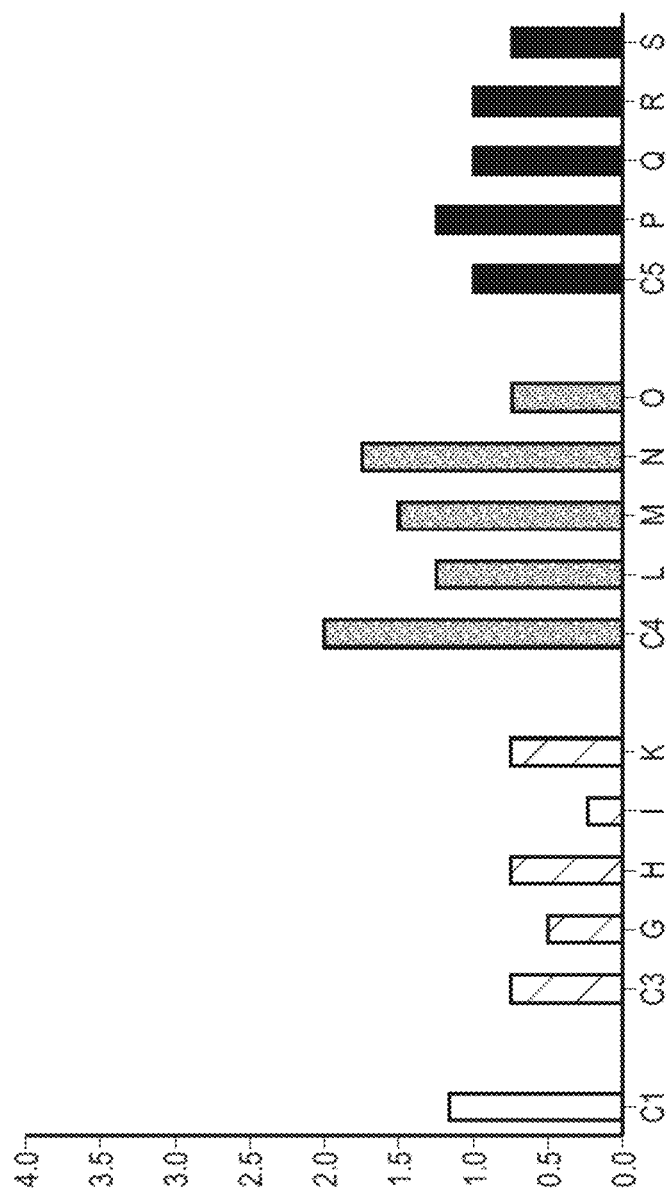
FIG. 46 is a graph showing 7-day post-implantation histology results for macrophages (Table 25 formulations; scoring: 0—normal; 1—minimal; 2—mild; 3—moderate; and 4—severe).

FIGS. 37-46 show the results of the study. FIG. 37 is a representative histology picture of an intradermal area in a guinea pig injected with a control dermal filler. FIG. 38 is a representative histology picture of an intradermal area in a guinea pig injected with an HA dermal filler of the invention (24 mg/ml HA, PEGDE cross linked. Sample C4—Table 25). FIG. 39 is a representative histology picture of an intradermal area in a guinea pig injected with a silk-HA dermal filler of the invention (22.8 mg/ml HA, 1.2 mg/ml silk, PEGDE cross linked, Sample L—Table 25). FIG. 40 is a representative histology picture of an intradermal area in a guinea pig injected with a silk-HA dermal filler of the invention (23.76 mg/ml HA, 0.24 mg/ml silk, PEGDE cross linked, Sample M—Table 25). FIG. 41 is a representative histology picture of an intradermal area in a guinea pig injected with a silk-HA dermal filler of the invention (22.8 mg/ml HA, 1.2 mg/ml silk, PEGDE cross linked, Sample N—Table 25). FIG. 42 is a representative histology picture of an intradermal area in a guinea pig injected with a silk-HA dermal filler of the invention (22.8 mg/ml HA, 1.2 mg/ml silk, PEGDE cross linked, Sample O—Table 25). FIGS. 43-46 are graphical representations of histology results for Table 25 formulations 7-day post-implantation (scoring: 0—normal: 1—minimal; 2—mild; 3—moderate; and 4-severe). FIG. 43 is a graph showing 7-day post-implantation histology results for gel degradation; BDDE cross-linked formulations are mostly degraded. FIG. 44 is a graph showing 7-day post-implantation histology results for gel migration. FIG. 45 is a graph showing 7-day post-implantation histology results for inflammation; no tissue necrosis was observed, no blood clotting was observed, and minimal collagen deposition was observed on the control formulation and some of the test formulations. FIG. 46 is a graph showing 7-day post-implantation histology results for macrophages.

Example 24: Properties of PEGDE Cross-Linked Silk-HA Hydrogels: 1) Shear Storage Modulus (G'), and 2) Swelling Ratio During Dialysis Dermal Filler Preparation, Materials: Poly(ethylene glycol) diglycidyl ether (PEGDE), Mn=500, Sigma-Aldrich;

Dermal Filler Formulation variables: Silk Molecular Weight: Medium and Low MW silk solution (6%); HA Molecular Weight: 700 KDa and 1.5 MDa; Silk concentration (Initial): 0-15 mg/ml.

Hydrogel crosslinking at high concentration: add 6% silk solution to 0.1 N sodium hydroxide; gradually add 100 mg/ml of mixed molecular weight HA (700 KDa/1.51 MDa=90/10) to the above prepared solution under gentle stirring until HA is fully dissolved, add PEGDE to the above solution; heat water bath to 40° C. and maintain the crosslinking in water bath for 45 minutes; let the cross-linked gel cool down below 30° C.; add 5N hydrochloric acid to 1×PBS, dilute the gel to 40 mg/ml and adjust the final pH to 7.0-7.4.

Hydrogel crosslinking at low concentration: add 6% silk solution to 0.1 N sodium hydroxide; gradually add 25 mg/ml of 1.5 MDa HA to above prepared solution under gentle stirring until HA is fully dissolved; add PEGDE to the above solution; heat water bath to 40° C. and maintain the crosslinking in water bath for 45 minutes; let the cross-linked gel cool down below 30° C.; add 5N hydrochloric acid to the cross-linked gel and adjust the final pH to 7.0-7.4.

Hydrogel dialysis: hydrate the dialysis cassette (20 KDa MWCO) for 2 minutes; wipe off excessive water and measure the total mass of the empty cassette; add approximately 18 g of hydrogel into dialysis cassette; measure the total mass of the cassette after loaded with gel; suspend dialysis cassette in 2 L of 1×PBS buffer and set magnetic stir at 200 rpm; collect gel after 72 hrs of dialysis.

Viscoelastic Properties

Figure 47A:
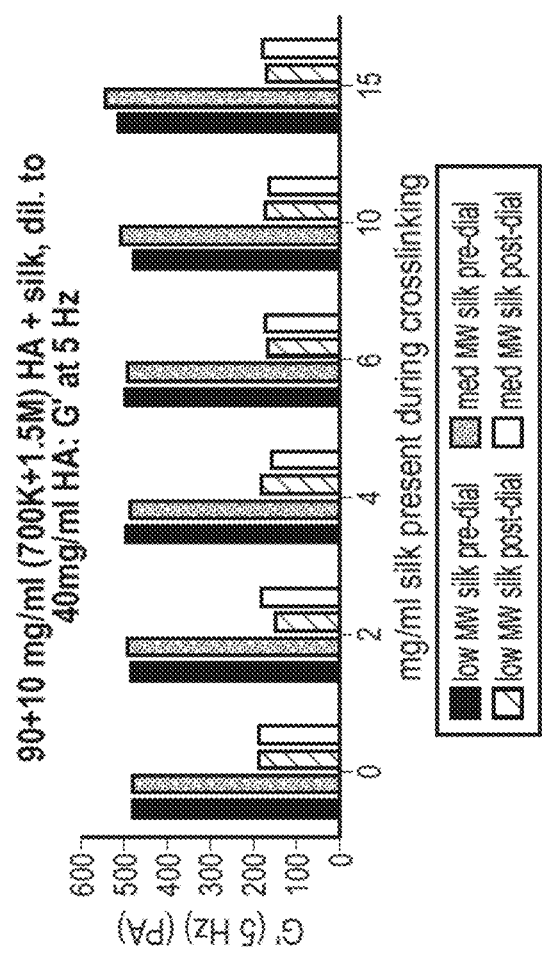
FIGS. 47A and 47B show the G' of hydrogels with various silk concentrations before and after dialysis.
Figure 47B:
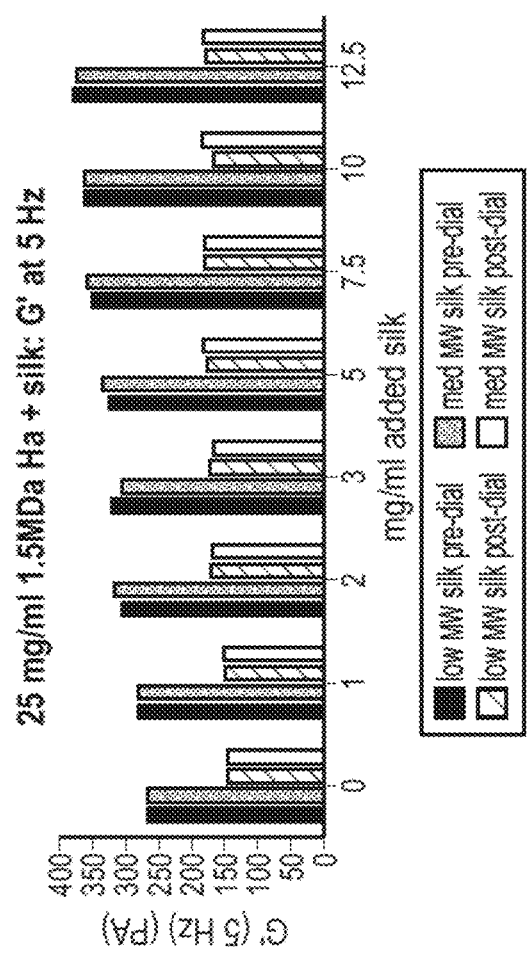

A Discovery HR-1 hybrid rheometer (TA Instruments) was used to determine the storage modulus (G') of the hydrogel formulations. Samples were tested by swiping oscillation frequency from 0.1 Hz to 10 Hz with 10 data points per decade interval. Data were recorded and compared at 5 Hz shear rate. The G' of hydrogel formulations before and after dialysis with constant HA concentration and variable silk concentration are shown in FIGS. 47A and 47B. For the hydrogel cross-linked by PEGDE at high initial HA concentration, the impact of silk concentration to the G' is minimal due to the relatively low ratio of silk to total HA. It may also be contributed to the mixed HA containing 90% of low molecular weight (700 KDa) which is not sensitive to the changes of silk concentration. For the hydrogel cross-linked by PEGDE at low initial HA concentration, the G' increased as more silk was added to the formulation. The changes in silk concentration had more impact to G' when the initial HA concentration was low and also had more impact to the high molecular weight HA (1.5 MDa). No substantial impact of silk molecular weight to the G' was observed for both crosslinking procedures.

Figure 48A:
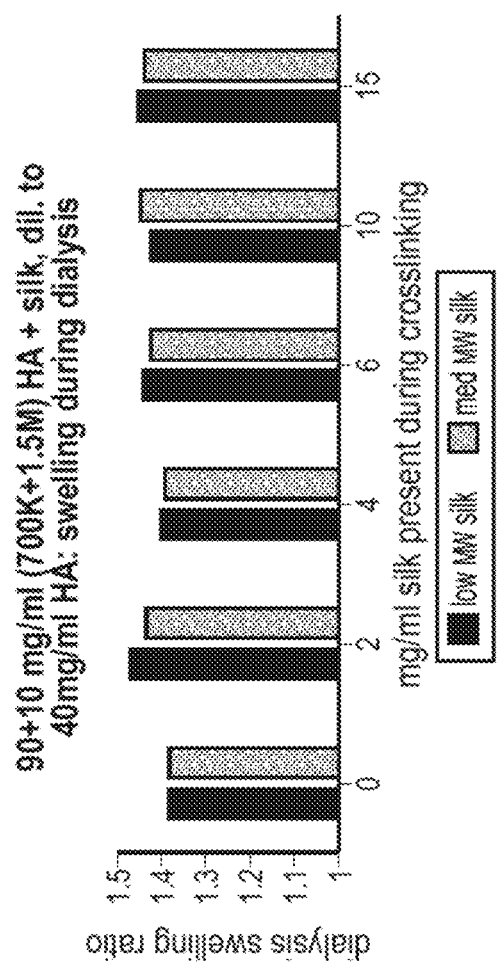
FIGS. 48A and 48B show the swelling ratio of hydrogel with various silk concentrations during dialysis.
Figure 48B:
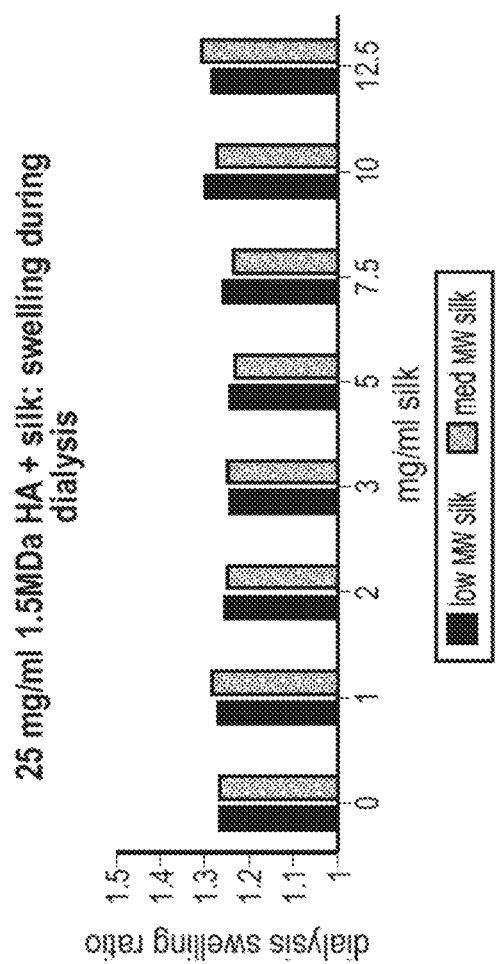

Swelling ratio during dialysis: there was no clear trend showing the amount of silk added to the hydrogel formulation had any impact to the gel swelling during dialysis for both cross-linking procedures and no substantial difference between medium molecular weight and low molecular weight silk (FIGS. 48A and 48B).

The silk concentration in hydrogel formulations had minimal impact to G' if mixed HA was cross-linked by PEGDE at high initial HA concentration, but was proportional to G' if single high MW HA was cross-linked at low initial HA concentration. The molecular weight of silk in the gel formulations had no substantial difference when comparing the contribution to G' and swelling if the HA was cross-linked by PEGDE.

Example 25: Silk Concentration in Silk-HA Dermal Filler Formulations

Materials: silk, 6% solution, Silk, Inc.; phosphate buffered saline (PBS), 20×, VWR Life Science; cross-linked hyaluronic acid (HA) gel.

Equipment: moisture analyzer HE53, Mettler Toledo; Cary 100 UV/Vis Spectrophotometer.

Calibration Standard Curve: measure the dry content for both medium and low molecular weight 6% silk solutions to determine the actual dry content (mg/ml) of the silk solutions; create a series of standard silk solutions by diluting the 6% silk solution using 1×PBS (for example, 1 mg/ml silk, 0.75 mg/ml silk, 0.5 mg/ml silk, 0.25 mg/ml silk, and 0 mg/ml silk); measure the absorbance of each standard solution at 275 nm in a quartz cuvette—absorbance measurements can be performed with a scan from 200-800 nm, data interval of 5 nm, and an average collection of 0.1 seconds; Plot the absorbance at 275 nm against the silk concentration (mg/ml) to create a standard curve.

Measurement of Silk Concentration: dilute HA gel samples with 1×PBS such that absorbance at 275 nm is between 0 and 1.0 (for example, the samples can be diluted with a 1:12 ratio of gel to 1×PBS, i.e., 1200% dilution); perform a scan for absorbance for the silk-HA gel sample against a 1×PBS reference between 200 nm-800 nm, measure the absorbance peak at 275 nm for each gel sample; the absorption signals for the gel samples are corrected by the difference between the absorption signal for the sample with no silk and the intercept of the calibration curve, setting the sample with no silk to have a silk concentration of 0 mg/ml; the silk concentration in the silk-HA gel samples can be calculated from the calibration curve and dilution factor.

Figure 49A:
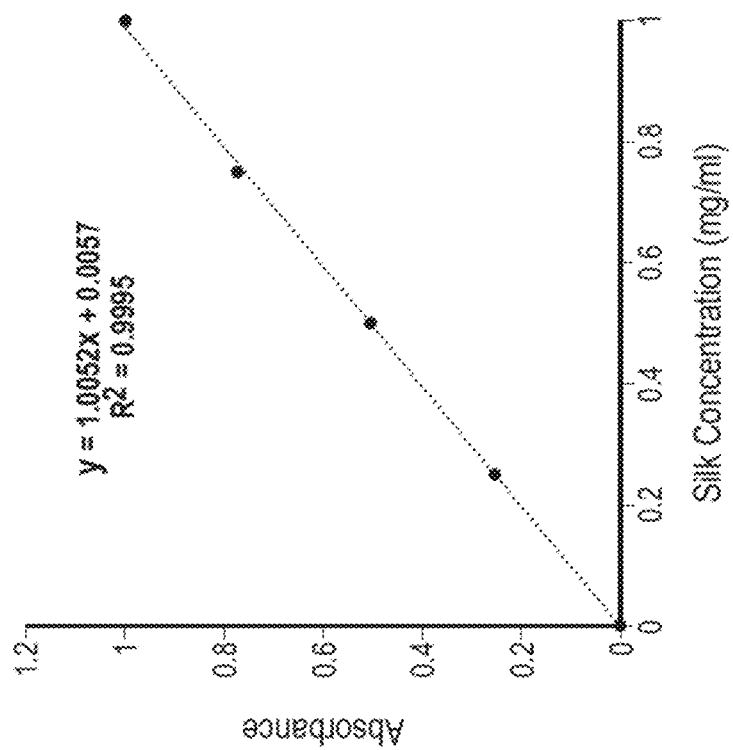
FIGS. 49A and 49B show the calibration curves for medium and low molecular weight silk solutions, respectively.
Figure 49B:
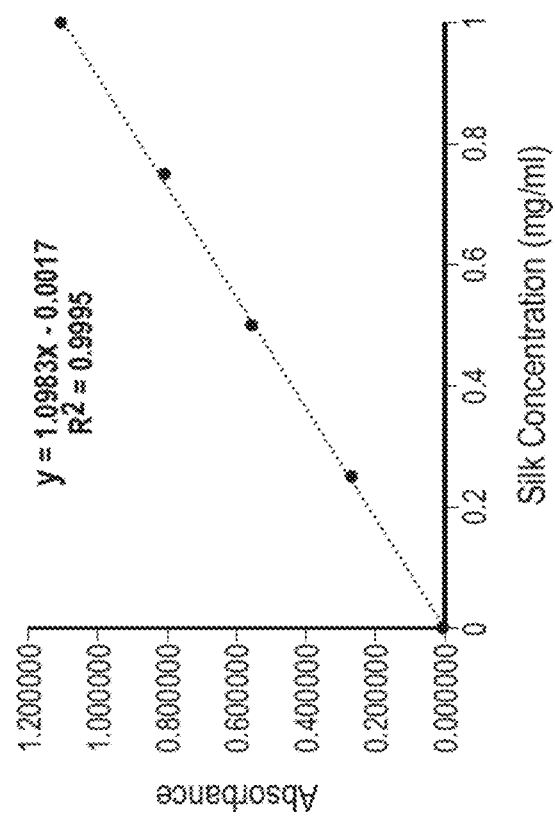

Calibration curves were created by measuring the absorption at 275 nm for a series of standard samples with different concentrations of silk ranging from 0 mg/ml to 1 mg/ml. The calibration curves for the medium and low molecular weight silk solutions are shown in FIGS. 49A and 49B. The $R^2$ values of 0.99947 for medium molecular weight silk and 0.99949 for low molecular weight silk demonstrate that the calibration curves are linear within the working range of 0-1 mg/ml of silk concentration. These curves can be used to determine the silk concentrations in gel samples.

Figure 50A:
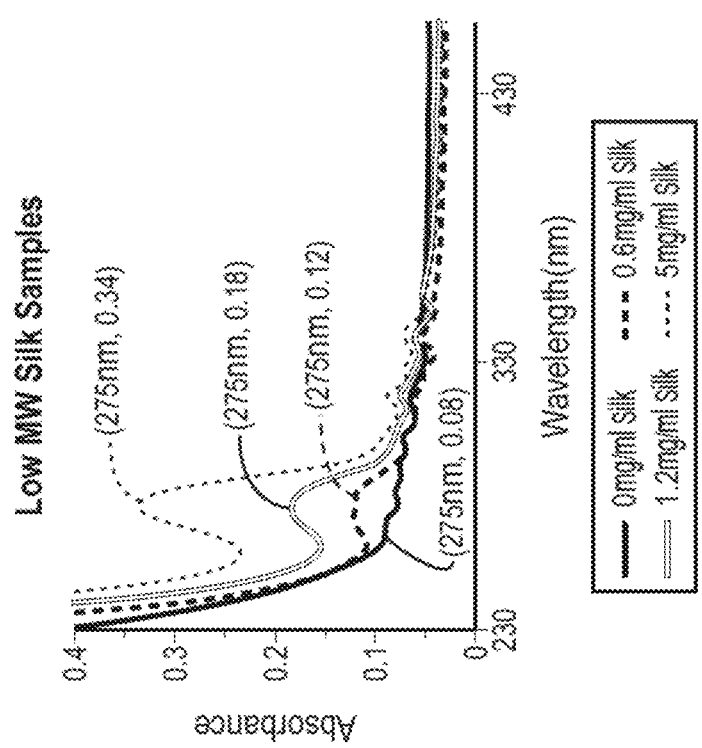
FIGS. 50A and 50B show the absorbance spectra of diluted silk-HA gels with unknown silk concentration; the theoretical silk concentration (mg/ml) is shown for each silk-HA gel sample in Table 26.
Figure 50B:
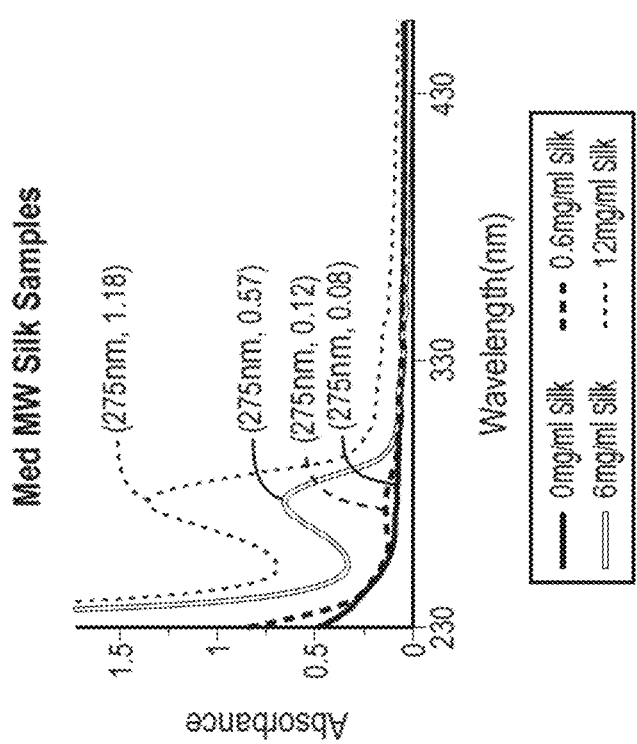

Determining Silk Concentration of HA-Silk hydrogels: the absorption at 275 nm of diluted silk-HA hydrogels was measured for each sample as shown in FIGS. 50A and 50B. The silk concentration of each sample was calculated with the calibration curve and dilution factor, summarized in Table 26.

TABLE 26

Calculated silk concentrations for silk-HA gels with an unknown silk concentration from the calibration curve

| Gel Sample | Theoretical Silk Concentration (mg/ml) | Calculated Silk Concentration (mg/ml) |
| --- | --- | --- |
| XTIA15M00SX17110201 | 0 | 0 |
| XHA1511401SL17103001 | 0.6 | 0.49 |
| XHA15M02SL17110201 | 1.2 | 1.26 |
| XHA15M05SL17110201 | 3 | 3.08 |
| XHA15N401SM17103001 | 0.6 | 0.57 |
| XHA15M10SM17103001 | 6 | 6.21 |
| XHA15M20SM17103001 | 12 | 13.83 |

Example 26: Silk-HA Dermal Filler Formulations: Gel Opacity

Materials: cross-linked hyaluronic acid (HA) gel; phosphate buffered saline (PBS), 20×. VWR Life Science.

Equipment: Cary 100 UV/Vis Spectrophotometer.

Sample Preparation: inject about 2 mL of HA gel into a clean quartz cuvette such that there is a minimal amount of air bubbles in the sample; injection using an 18 G needle may help reduce the amount of bubbles in the sample: a blank reference sample of 1×PBS can be added to a second clean quartz cuvette (Note: for opacity measurements, a plastic cuvette can be used since the plastic cuvette does not have absorption in the visible range, 400 nm-800 nm).

Measurement of Gel Opacity: set the X-scanning range from 200 nm to 800 nm with a data interval of 5 nm and average time of 0.1 seconds; select the Y-mode to be % T for the measurement of transmitted light (Note: Absorption can also be measured and % T can be calculated from Absorption values); perform a scan on the gel sample against the 1×PBS reference standard; the data can be saved as a csv file and the spectrum can be plotted.

Figure 51:
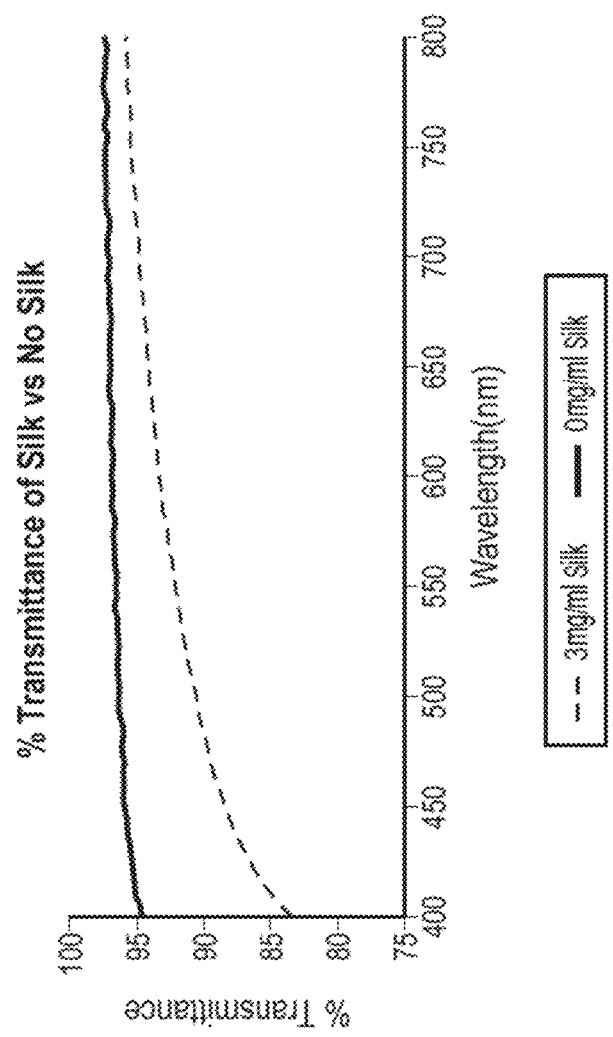
FIG. 51 shows turbidity measurement of HA hydrogel without silk (red; higher transmittance across the entire wavelength interval) and with 3 mg/ml silk (blue; lower transmittance across the entire wavelength interval); a higher % transmittance indicates a less turbid sample, with less optical opacity.

Gel Opacity can be measured using the UV/Vis spectrophotometer for standard transmitted light. An optically clear sample will transmit 100%/o of light, whereas a slightly turbid or cloudy sample may only transmit a portion of that light. FIG. 51 shows the turbidity measurement of an HA hydrogel with and without silk. The blue curve shows the % transmittance for the transmitted light for a Silk-HA gel sample with 3 mg/mL silk and 26 mg/ml HA. The red curve shows the transmitted light for a sample with no silk and 20 mg/ml HA, and shows more transmission of light than the sample with silk. The turbidity measurements suggest that the Silk-HA gel has an ability to scatter visible light more than the HA gel without silk.

Example 27: Degree of Modification (MoD) of the HA Hydrogel Determined by NMR

Degree of Modification (MoD) is defined as the stoichiometric ratio of all linked cross-linker molecules to the moles of HA repeating units. Both cross- and mono-linked linkers are included in MoD. MoD is determined from $^1$H NMR spectrum by integrating the signal from the N-acetyl group in HA at 2.1 ppm and the BDDE cross-linker at 1.7 ppm, or the PEGDE cross-linker at 3.0-4.5 ppm.

Prior to enzymatic degradation, the HA hydrogel was first dialyzed again PBS (1×, 2 L×5) solution to remove the free cross-linker. A Slide-A-Lyzer dialysis cassette (MWCO 3.5 K, Thermo Scientific, Rockford, Ill.) was used, and the PBS solution was stirred at RT for 72 h. After the dialysis, 1 mL of the HA hydrogel solution was taken out and lyophilized with a Labconco FreeZone lyophilizer (2.5 L) to obtain the dry powder.

To prepare the NMR sample, 10 mg of the dry powder was placed into the NMR tube (5 mm, Wilmad-LabGlass) and 0.6 mL of hyaluronidase (MP Biomedicals. Solon, Ohio) solution in deuterium oxide (D$_2$O, Alfa Aesar, Ward Hill, Mass.) was added. The amount of the hyaluronidase was 5 U per 1 mg of HA. The NMR tube was incubated at 37° C. overnight to make all the HA degraded. The NMR spectra were recorded on a Varian MR 400 MHz Automated NMR System. The relaxation delay time is 1 s and the number of scans is 256. All the data was processed using a MestReNova software (Edition 12.0.2).

Example 28: Silk-HA 2-Step Cross-Linking Process

A silk-HA hydrogel can be formed a 2-step crosslinking process to improve the efficiency of silk binding to HA. For a given formulation, at the first step, all silk protein and a small portion of low molecular weight HA are added to NaOH solution at pH 10, and then reacted with a portion of crosslinker. Without wishing to be bound by any particular theory, it is believed that during this step, as much silk as possible reacts with the crosslinker. At the second step, NaOH solution is added to dilute the product from step-1 and increase the pH to 13. The remaining low molecular weight HA, all high molecular weight HA, and the remaining crosslinker are then added to the solution, and the crosslinking reaction is completed.

Example 29: HA Hydrogel Synthesis

HA hydrogel has been synthesized by using different HA molecular weight, crosslinker, reaction time, reaction temperature, HA concentration, crosslinker ratio, mixing process and stirring method. Tables 27 and 28 show the various reaction conditions employed, and the various hydrogels obtained.

TABLE 27

| | |
|---|---|
| HA MW | 700k, 1.5M. 2.2M, 3M, or mixture with different MW at any ratio |
| Crosslinker | PEG500DE, and BDDE |
| Reaction time | 30 min, 60 min, 90 min, 120 min, or 240 min |
| Reaction Temperature | 40° C., or 50° C. |
| HA concentration | 30 mg/ml, 90 mg/ml 100 mg/ml, and 140 mg/ml |
| Crosslinker Ratio | 7 Wt. % or 10 Wt. % |
| Mixing process | Pre-mix HA and crosslinker together or adding crosslinker into the HA solution portion wise |
| Stirring | With or without mechanical stirring |

TABLE 28

| Sample | HA/Cross-linker | Cross-linker ratio (Wt. %) | HA Concentration (mg/mL) | Mixing | Stirring | Reaction time (min) | Temp ° C. | G' (After Dialysis) | MoD (%) |
|---|---|---|---|---|---|---|---|---|---|
| PXHA2M00SX18042541 | 2.2M/PEG500DE | 10 | 30 | Portion wise | Y | 30 | 40 | 163 | 13.02 |
| PXHA2M00SX18042543 | 2.2M/PEG500DE | 10 | 30 | Portion wise | Y | 60 | 40 | 106 | 9.55 |
| PXHA2M00SX18042545 | 2.2M/PEG500DE | 10 | 30 | Portion wise | Y | 120 | 40 | 95 | 11.73 |
| PXHA2M00SX18042547 | 2.2M/PEG500DE | 10 | 30 | One pot | Y | 240 | 40 | 10.6 | 15.6 |
| PXHA2M00SX18051041 | 2.2M/PEG500DE | 10 | 30 | One pot | N | 30 | 40 | 148.67 | 5.3 |
| PXHA2M00SX18051043 | 2.2M/PEG500DE | 10 | 30 | One pot | N | 60 | 40 | 134.61 | 7.88 |
| PXHA2M00SX18051045 | 2.2M/PEG500DE | 10 | 30 | One pot | N | 120 | 40 | 46.53 | 9.44 |
| PXHA2M00SX18051047 | 2.2M/PEG500DE | 10 | 30 | One pot | N | 240 | 40 | 28.9 | 11.2 |
| BXHA700K00SX18050141 | 700K/BDDE | 10 | 30 | Drop-wise | Y | 30 | 40 | 42 | 0 |
| BXHA700K00SX18050143 | 700K/BDDE | 10 | 30 | Drop-wise | Y | 60 | 40 | 38 | 0 |
| BXHA700K00SX18050145 | 700K/BDDE | 10 | 30 | Drop-wise | Y | 120 | 40 | 15 | 0.54 |
| PXHA2M00SX18051641 | 2.2M/PEG500DE | 10 | 30 | One pot/overnight | N | 30 | 40 | 182.91 | 4.62 |
| PXHA2M00SX18051643 | 2.2M/PEG500DE | 10 | 30 | One pot/overnight | N | 60 | 40 | 129.76 | 8.87 |
| BXHA700K00SX18052941 | 700K/BDDE | 10 | 30 | Portion wise | N | 30 | 40 | 17.99 | 0 |
| BXHA700K00SX18052943 | 700K/BDDE | 10 | 30 | Portion wise | N | 60 | 40 | 33.76 | 0.48 |
| BXHA2M00SX18052941 | 2.2M/BDDE | 10 | 30 | Portion wise | N | 30 | 40 | 295.6 | 0.52 |
| BXHA2M00SX18052943 | 2.2M/BDDE | 10 | 30 | Portion wise | N | 60 | 40 | 222.28 | 0.66 |

TABLE 28-continued

| Sample | HA/Cross-linker | Cross-linker ratio (Wt. %) | HA Concentration (mg/mL) | Mixing | Stirring | Reaction time (min) | Temp °C. | G' (After Dialysis) | MoD (%) |
|---|---|---|---|---|---|---|---|---|---|
| BXHA15M00SX18060851 | 1.5M/BDDE | 10 | 90 | Mixed separately | N | 30 | 50 | 261.86 | 3.26 |
| BXHA15M00SX18060853 | 1.5M/BDDE | 10 | 90 | Mixed separately | N | 60 | 50 | 196.8 | 3.4 |
| BXHA15M00SX18060855 | 1.5M/BDDE | 10 | 90 | Mixed separately | N | 90 | 50 | 93.6 | 4.84 |
| BXHA15M00SX18060857 | 1.5M/BDDE | 10 | 90 | Mixed separately | N | 120 | 50 | 72.98 | 4.51 |
| PXHA15M00SX18061351 | 1.5M/PEGDE | 10 | 90 | Mixed separately | N | 30 | 50 | 151.65 | undergoing |
| PXHA15M00SX18061351 | 1.5M/PEGDE | 10 | 90 | Mixed separately | N | 60 | 50 | 71.87 | undergoing |
| BXHA15M00SX18061551 | 1.5M/BDDE | 10 | 100 | One pot | N | 30 | 50 | 234.69 | 4.6 |
| BXHA15M00SX18061553 | 1.5M/BDDE | 10 | 100 | One pot | N | 60 | 50 | 219.43 | 6.1 |
| BXHA3M00SX18061951 | 3M/BDDE | 10 | 100 | One pot | N | 60 | 50 | 268.41 | undergoing |
| BXHA3M00SX18061953 | 3M/BDDE | 7 | 100 | One pot | N | 60 | 50 | 189.13 | undergoing |

All patents, patent applications, and published references cited herein are hereby incorporated by reference in their entirety. While the methods of the present disclosure have been described in connection with the specific embodiments thereof, it will be understood that it is capable of further modification. Further, this application is intended to cover any variations, uses, or adaptations of the methods of the present disclosure, including such departures from the present disclosure as come within known or customary practice in the art to which the methods of the present disclosure pertain.

What is claimed is:

1. A biocompatible tissue filler, comprising hyaluronic acid (HA), an anesthetic agent, and silk fibroin protein fragments (SPF), wherein a portion of the HA or SPF is modified or crosslinked by one or more linker moieties comprising one or more of an alkane or alkyl chain, an ether group, and a secondary alcohol, wherein the linker moieties are covalently attached to the modified or crosslinked HA or SPF,
   wherein the one or more linker moieties comprise a polyethylene glycol (PEG) chain, and
   wherein the tissue filler has a storage modulus (G') of from about 25 Pa to about 1500 Pa.

2. The tissue filler of claim 1, wherein the SPF have an average weight average molecular weight ranging from about 1 kDa to about 250 kDa.

3. The tissue filler of claim 1, wherein the SPF have an average weight average molecular weight ranging from about 5 kDa to about 150 kDa.

4. The tissue filler of claim 1, wherein the SPF have an average weight average molecular weight selected from about 6 kDa to about 17 kDa, from about 17 kDa to about 39 kDa, and from about 39 kDa to about 80 kDa.

5. The tissue filler of claim 1, wherein the silk fibroin protein fragments (SPF) have a polydispersity of selected from between about 1.5 and about 3.0.

6. The tissue filler of claim 1, wherein the degree of modification or cross-linking of the modified or cross-linked HA or SPF is between about 1% and about 15%.

7. The tissue filler of claim 1, wherein the tissue filler is a gel.

8. The tissue filler of claim 1, wherein the tissue filler is a hydrogel.

9. The tissue filler of claim 1, wherein the total concentration of SPF in the tissue filler is from about 0.1 mg/mL to about 15 mg/mL.

10. The tissue filler of claim 1, wherein the tissue filler is injectable.

11. The tissue filler of claim 1, wherein the tissue filler has a storage modulus (G') of from about 50 Pa to about 100 Pa.

12. The tissue filler of claim 1, wherein the tissue filler has a storage modulus (G') of from about 100 Pa to about 200 Pa.

13. The tissue filler of claim 1, wherein the tissue filler has a storage modulus (G') of from about 200 Pa to about 300 Pa.

14. The tissue filler of claim 1, wherein the tissue filler has a complex viscosity from about 1 Pa·s to about 10 Pa·s.

* * * * *